(12) United States Patent
Robinson et al.

(10) Patent No.: US 11,896,657 B2
(45) Date of Patent: Feb. 13, 2024

(54) **REPLICATION-DEFICIENT MODIFIED VACCINIA ANKARA (MVA) EXPRESSING *MARBURG VIRUS* GLYCOPROTEIN (GP) AND MATRIX PROTEIN (VP40)**

(71) Applicant: GeoVax, Inc., Smyrna, GA (US)

(72) Inventors: Harriet Robinson, Palo Alto, CA (US);
Arban Domi, Atlanta, GA (US);
Michael Hellerstein, Atlanta, GA (US)

(73) Assignee: Geovax, Inc., Smyrna, GA (US)

( * ) Notice: Subject to any disclaimer, the term of this patent is extended or adjusted under 35 U.S.C. 154(b) by 77 days.

(21) Appl. No.: 17/584,231

(22) Filed: Jan. 25, 2022

(65) Prior Publication Data

US 2022/0152190 A1    May 19, 2022

Related U.S. Application Data

(63) Continuation of application No. 15/543,139, filed as application No. PCT/US2016/013021 on Jan. 12, 2016, now Pat. No. 11,701,418.
(Continued)

(51) Int. Cl.
*A61K 39/12* (2006.01)
*C12N 15/863* (2006.01)
(Continued)

(52) U.S. Cl.
CPC .............. *A61K 39/12* (2013.01); *C12N 15/86* (2013.01); *C12N 15/863* (2013.01);
(Continued)

(58) Field of Classification Search
CPC ............ A61K 39/12; A61K 2039/5256; C12N 15/863; C12N 2710/24141; C12N 2760/14234
See application file for complete search history.

(56) References Cited

U.S. PATENT DOCUMENTS

| 6,440,422 B1 | 8/2002 | Sutter et al. |
| 2003/0215794 A1 | 11/2003 | Kawaoka et al. |

(Continued)

FOREIGN PATENT DOCUMENTS

| WO | WO 2004/048582 A1 | 6/2004 |
| WO | WO 2015/066715 A1 | 5/2015 |

(Continued)

OTHER PUBLICATIONS

Marzi, A., and H. Feldmann, 2014, Ebola virus vaccines: an overview of current approaches, Expert Rev. Vaccines 13(4):521-531.*

(Continued)

*Primary Examiner* — Jeffrey S Parkin
(74) *Attorney, Agent, or Firm* — Knowles Intellectual Property Strategies, LLC

(57) ABSTRACT

The compositions and methods are described for generating an immune response to a hemorrhagic fever virus such as ebolavirus, Marburgvirus, or arenavirus. The compositions and methods described herein relate to a modified vaccinia Ankara (MVA) vector encoding one or more viral antigens for generating a protective immune response to a member of genus *Ebolavirus* (such as a member of species *Zaire ebolavirus*), a member of genus *Marburgvirus* (such as a member of species *Marburg marburgvirus*), or a member of genus *Arenavirus* (such as a member of species *Lassa virus*) in the subject to which the vector is administered. The compositions and methods of the present invention are useful both prophylactically and therapeutically and may be used to prevent and/or treat an infection caused by ebolavirus, Marburgvirus, or arenavirus.

11 Claims, 14 Drawing Sheets

Specification includes a Sequence Listing.

Related U.S. Application Data

(60) Provisional application No. 62/102,425, filed on Jan. 12, 2015, provisional application No. 62/213,819, filed on Sep. 3, 2015, provisional application No. 62/215,536, filed on Sep. 8, 2015.

(51) Int. Cl.
  *C12N 15/86* (2006.01)
  *A61K 39/00* (2006.01)

(52) U.S. Cl.
  CPC ............ *A61K 2039/5256* (2013.01); *A61K 2039/5258* (2013.01); *C12N 2710/24141* (2013.01); *C12N 2710/24143* (2013.01); *C12N 2760/10034* (2013.01); *C12N 2760/14134* (2013.01); *C12N 2760/14234* (2013.01)

(56) References Cited

U.S. PATENT DOCUMENTS

| | | |
|---|---|---|
| 2006/0088909 A1 | 4/2006 | Compans et al. |
| 2006/0099225 A1 | 5/2006 | Bavari et al. |
| 2006/0153874 A1 | 7/2006 | Howley |
| 2006/0159706 A1 | 7/2006 | Panicali et al. |
| 2006/0188961 A1 | 8/2006 | Howley et al. |
| 2006/0216702 A1 | 9/2006 | Compans et al. |
| 2008/0019483 A1 | 8/2008 | Moss et al. |
| 2010/0047277 A1 | 2/2010 | Compans et al. |
| 2010/0143402 A1 | 6/2010 | Moss et al. |
| 2010/0196419 A1 | 8/2010 | Compans et al. |
| 2010/0330190 A1 | 12/2010 | Compans et al. |
| 2011/0104199 A1 | 5/2011 | Moss et al. |
| 2011/0262483 A1 | 10/2011 | Haynes et al. |
| 2012/0052082 A1 | 3/2012 | Compans et al. |
| 2012/0219576 A1 | 8/2012 | Branco et al. |
| 2012/0263750 A1 | 10/2012 | Moss et al. |
| 2012/0289760 A1 | 11/2012 | Hill et al. |
| 2013/0078276 A1 | 3/2013 | Robinson et al. |
| 2013/0101618 A1 | 4/2013 | Sullivan et al. |
| 2014/0255441 A1 | 9/2014 | Compans et al. |
| 2014/0322265 A1 | 10/2014 | Chaplin et al. |
| 2016/0318985 A1 | 11/2016 | Wang et al. |
| 2019/0117758 A1 | 4/2019 | Robinson et al. |
| 2020/0171141 A1 | 6/2020 | Guirakhoo et al. |

FOREIGN PATENT DOCUMENTS

| | | | |
|---|---|---|---|
| WO | WO 2015/175340 A1 | | 11/2015 |
| WO | WO 2016/034678 | * | 3/2016 |
| WO | WO 2016/034678 A2 | | 3/2016 |

OTHER PUBLICATIONS

Reynolds, P, and A. Marzi, 2017, Ebola and Marburg virus vaccines, Virus Genes 53:501-515.*
Meyer, M., et al., Jan. 2019, Can Ebola virus vaccines have universal immune correlates of protection? Trends Microbiol. 27(1):8-16.*
Falzarano, D., et al., 2011, Progress in filovirus vaccine development: evaluation potential for clinical use, Exp. Rev. Vaccines 10(1):63-77.*
Domi, A., et al., 2018, A Single Dose of Modified Vaccinia Ankara expressing Ebola Virus-Like Particles Protects Nonhuman Primates from Lethal Ebola Virus Challenge, Sci. Reports 8:864, pp. 1-9.*
Malherbe, D.C. et al. A single immunization with a modified vaccinia Ankara vectored vaccine producing Sudan virus-like particles protects from lethal infection. NPJ Vaccines. Jul. 25, 2022;7(1):83.
Hashiguchi, T. et al. Structural Basis for Marburg Virus Neutralization by a Cross-Reactive Human Antibody. Feb. 26, 2015. Cell. 160(5):904-12.
Adu-Gyamfi et al., "The Ebola Virus Matrix Protein Penetrates into the Plasma Membrane," The Journal of Biological Chemistry vol. 288, No. 8 pp. 5779-5789, Feb. 22, 2013.
Baize S. et al., "Lassa virus infection of human dendritic cells and macrophages is productive but fails to activate cells", Journal of Immunology, 2004, 172(5), 2861-2869.
Biedenkopf N et al., "Phosphorylation of Ebola Virus VP30 Influences the Composition of the Viral Nucleocapsid Complex", J. Biol. Chem., 2013, 288(16), 11165-11174.
Cao W et al., "Identification of dystrolycan as a receptor for lymphocytic choriomeningitis virus and lassa fever virus", Science, 1998, 282(5396), 2079-2081.
Carroll et al., "Molecular evolution of viruses of the family Filoviridae based on 97 whole-genome sequences", J. Virol., 2013, 87(5), 2608-2616.
Cornu T.I et al., "Ring Finger Z protein of lymphocytic choriomeningitis virus (LCMV inhibits transcription and RNA replication of an LCMV S-segment minigenome", Journal of Virology, 2001, 75(19), 9415-9426.
Djavani, M. et al., "Completion of a lassa fever virus sequence and identification of a ring finger open reading frame at the L RNA 5' end", Virology, 1997, 235(2), 414-418.
Domi, A, et al. A single dose of modified vaccina Ankara expressing Ebola virus like particles protects nonhuman primates from lethal Ebola virus challenge, Scientific Report 8:864, pp. 1-9, 2018.
GenBank Accession AFV312002, glycoprotein [Marburg Marburgvirus], Protein—NCBI; 3 pages; 2013.
International Search Report from PCT/US2016/013021, dated Mar. 21, 2016.
Kuhn et al., "Filovirus Ref Seq Entries: Evaluation and Selection of Filovirus Type Variants, Type Sequences, and Names", Viruses, 2014, 6(9), 3663-3682.
Kyei et al., "Imported Lassa fever: a report of 2 cases in Ghana", BMC Infectious Diseases, 2015, 15, 217.
Lashley, F.R and Jerry Durham., Emerging Infectious Diseases: Trends and Issues, Emerg Infect Dis., 2003, 9(12), 1660; 2002, New York Springer Pub.
Mahanty S et al., "Cutting edge: Impairment of dendritic cells and adaptive immunity by Ebola and Lassa viruses", Journal of Immunology, 2003, 170(6), 2797-2801.
Manuel E.R. et al. "Intergenic region 3 of modified vaccinia ankara is a functional site for insert gene expression and allows for potent antigen-specific immune responses", Virology, Elsevier, Amsterdam, NL, vol. 403, No. 2, Aug. 2010 (Aug. 1, 2010), pp. 155-162.
Mehedi M. et al., "A New Ebola Virus Nonstructural Glycoprotein Expressed through RNA Editing", J. Virol. 2011, 85(11), 5406-5414.
Mittler et al., "The Cytoplasmic Domain of Marburg Virus GP Modulates Early Steps of Viral Infection," Journal of Virology, Aug. 2011, vol. 85, No. 16, pp. 8188-8196.
Moss, Bernard E.D et al. "Reflections on the early development of poxvirus vectors", Vaccine, vol. 31, No. 39, pp. 4220-4222.
Nanbo A et al., "The spatio-temporal distribution dynamics of Ebola virus proteins and RNA in infected cells", Scientific Reports, 2013, 3, 1206; doi: 10.1038/srep01206.
Orubu et al., "Expression and cellular immunogenicity of a transgenic antigen driven by endogenous poxviral early promoters at their authentic loci in MVA", PLOS One, 2012, 7(6), e40167; doi: 10.1371/journal.pone.0040167.
Radoshitzky S.R. et al., "Ebolavirus Δ-Peptide Immunoinhibits Inhibit Marburgvirus and Ebolavirus Cell Entry," J. Virol., 2011, 85(17), 8502-8513.
Salvato, Maria et al. "A Single Dose of Modified Vaccinia Ankara Expressing Lassa Virus-like Particles Protects Mice from Lethal Intra-cerebral Virus Challenge," Pathogens 2019, 8, 133.
Sanchez A et al., "The virion glycoproteins of Ebola viruses are encoded in two reading frames and are expressed through transcriptional editing", PNAS USA, 1996, 93(8), 3602-3607.
Swenson, D.L. et al. Generation of Marburg virus-like particles by co-expression of glycoprotein and matrix protein, FEMS Immunol. Med. Microbiol. 40:27:31, pp. 27-31, 2004.

(56) References Cited

OTHER PUBLICATIONS

Urata, S.; Yasuda, J., "Cis- and cell-type-dependent trans-requirements for Lassa virus-like particle production", J. Gen. Virol., 2015, 96 Pt 7, 1626-1635.

Wang et al., "Modified H5 promoter improves stability of insert genes while maintaining immunogenicity during extended passage of genetically engineered MVA vaccines", Vaccine, Feb. 1, 20100; 28(6): 1547. doi:10.1016/j.vaccine.2009.11.056.

Ye, L. et al. Ebola Virus-like particles produced in inspect cells exhibit dendritic cell stimulating activity and induce neutralizing antibodies, Virol. 351:260-270; 2006.

Malherbe, D.C. et al. Modified vaccinia Ankara vaccine expressing Marburg virus-like particles protects guinea pigs from lethal Marburg virus infection NPJ Vaccines, 2020, 78.

* cited by examiner

FIG. 11A

Guinea Pig EBOV GP ab titer

FIG. 11B

Hamster EBOV GP ab titer

Guinea pigs

Hamsters

FIG. 13D

REPLICATION-DEFICIENT MODIFIED VACCINIA ANKARA (MVA) EXPRESSING *MARBURG VIRUS* GLYCOPROTEIN (GP) AND MATRIX PROTEIN (VP40)

CROSS REFERENCE TO RELATED APPLICATIONS

This application is a continuation of U.S. patent application Ser. No. 15/543,139, filed May 17, 2018, which is a national stage application under 35 U.S.C. § 371 of International Application No. PCT/US2016/013021, filed Jan. 12, 2016, which claims the benefit of and priority to U.S. provisional patent application U.S. 62/102,425 filed Jan. 12, 2015, U.S. provisional patent application 62/213,819 filed Sep. 3, 2015, and U.S. provisional patent application 62/215,536 filed Sep. 8, 2015. The entirety of each of these applications is hereby incorporated by reference herein for all purposes.

FIELD OF THE INVENTION

The present invention is directed to compositions, including vaccine compositions, for generating an immune response to a hemorrhagic fever virus, as well as methods of manufacture and methods of use thereof. Hemorrhagic fever viruses include filoviruses (members of family Filoviridae), such as members of genera *Ebolavirus* and *Marburgvirus*; and arenaviruses (members of family Arenaviridae) such as members of genus *Arenavirus*. More specifically, the compositions and methods described herein relate to a modified vaccinia Ankara (MVA) vector encoding one or more viral antigens for generating a protective immune response in the subject to which the vector is inhibited to a member of genus *Ebolavirus* (such as a member of species *Zaire ebolavirus*), a member of genus *Marburgvirus* (such as a member of species *Marburg marburgvirus*), or a member of genus *Arenavirus* (such as a member of species *Lassa virus*). The compositions and methods of the present invention are useful both prophylactically and therapeutically.

INCORPORATION BY REFERENCE

The contents of the text file named "19101-015US2_SEQ_TXT" which was created on Jan. 25, 2022, and is 76.1 KB in size, are hereby incorporated by reference in their entirety.

BACKGROUND OF THE INVENTION

The Filoviridae family is composed of three genera, *Ebolavirus*, *Marburgvirus*, and *Cuevavirus*. Genera *Ebolavirus* and *Marburgvirus* include highly pathogenic and virulent viruses causing rapidly fatal hemorrhagic fever in humans and non-human primates. Genus *Marburgvirus* has only one known species (*Marburg marburgvirus*), whereas genus *Ebolavirus* is more variable and has five known species.

The five distinct species of genus *Ebolavirus* include *Zaire ebolavirus*, *Sudan ebolavirus*, *Taï Forest ebolavirus*, *Bundibugyo ebolavirus*, and *Reston ebolavirus*. (Carroll et al., J. Virol., 87(5):2608-2616 (2013). Four of these species (*Zaire ebolavirus*, *Sudan ebolavirus*, *Taï Forest ebolavirus*, and *Bundibugyo ebolavirus*), cause fatal disease in humans.

Known viruses belonging to species *Zaire ebolavirus* are commonly referred to as Ebola viruses. Ebola virus is abbreviated as EBOV. Known viruses belonging to species *Sudan ebolavirus* are commonly referred to as Sudan viruses. Sudan virus is abbreviated as SUDV. Known viruses belonging to species *Taï Forest ebolavirus* are commonly referred to as Taï Forest viruses. Taï Forest virus is abbreviated as TAFV. Known viruses belonging to species *Bundibugyo ebolavirus* are commonly referred to as Bundibugyo viruses. Bundibugyo virus is abbreviated as BDBV. Known viruses belonging to species *Marburg marburgvirus* include Marburg virus (MARV) and Ravn virus (RAVV). (Kuhn et al., Viruses, 6:3663-3682 [2014]) Various forms of filovirus nomenclature and abbreviation have been used in the past. Other known abbreviations for members of this group include ZEBOV for Ebola virus, SEBOV for Sudan virus, CIEBOV for Taï Forest virus, BEBOV for Bundibugyo virus, and REBOV for Reston virus.

In this application, the terms "ebolavirus" or "*Ebolavirus*" (single word, not italicized) will be used to refer to any member of genus *Ebolavirus*, while the terms "marburgvirus" or "Marburgvirus" will be used to refer to any member of genus *Marburgvirus*.

The genetic organization of filoviruses is similar, each containing seven genes in a linear, single-stranded, negative-sense RNA genome. Among the viral proteins expressed from the ebolavirus genome, the envelope glycoprotein exists in three alternative forms: a 50-70 kilodalton (kDa) secreted protein encoded by the viral genome (sGP), a 130 kDa transmembrane glycoprotein (GP), and a small secreted glycoprotein (ssGP), which is a smaller (approximately 50 kDa) version of the secreted glycoprotein. Transcripts for the full-length glycoprotein and ssGP are generated by RNA editing. The functions of sGP and ssGP are unknown, while the transmembrane protein mediates viral entry. (Mehedi, M. et al., J. Virol. 85:5406-5414 (2011); Peters, C. J. et al., Filoviridae: Marburg and Ebola Viruses. in Fields Virology. (eds., Fields, B. N., Knipe, D. M. & Howley, P. M.) 1161-1176 (Philadelphia, Lippincott-Raven, 1996); Sanchez, A. et al., PNAS (USA) 93:3602-3607 (1996). Other gene products include the nucleoprotein (NP), matrix proteins VP24 and VP40, the transcription factor VP30, the polymerase cofactor VP35, and the viral polymerase L (Biedenkopf, N. et al., J. Biol. Chem. 288:11165-11174 (2013); Nanbo, A. et al., Scientific Reports 3, doi: 10.1038/srep01206 (2013); reviewed in Peters, C. J. et al., Filoviridae: Marburg and Ebola Viruses. in Fields Virology. (eds., Fields, B. N., Knipe, D. M. & Howley, P. M.) 1161-1176 (Philadelphia, Lippincott-Raven, 1996)). Proteins expressed by marburgviruses are very similar, but marburgvirus does not express sGP or ssGP (Radoshitzsky, S. R. et al.; J. Virol. 85:8502-8513 (2011)).

Although spontaneous variation of their RNA sequence does occur in nature, there appears to be less nucleotide polymorphism within ebolavirus subtypes than among other RNA viruses (Sanchez, A. et al., PNAS (USA) 93:3602-3607 (1996)).

Since Ebola virus was discovered in 1976, more than 20 outbreaks have occurred (source: cdc.gov). The development of countermeasures against filoviruses have largely focused on SUDV and EBOV, the two species that have historically been responsible for nearly all ebolavirus outbreaks. To date, however, no approved vaccine or therapeutic product is available for Filovirus infections. As such, medical professionals have no means to prevent infection other than the traditional methods of isolation and sanitation, and no means to treat infected patients.

Arenaviridae comprises a family of viruses whose members are generally associated with rodent-transmitted diseases in humans. Arenaviruses are divided into two groups:

the New World or Tacaribe complex and the Old World or LCM/Lassa complex. Arenavirus infections are relatively common in humans in some areas of the world and can cause severe illnesses.

Lassa virus (LASV) is an arenavirus that causes Lassa hemorrhagic fever, a type of viral hemorrhagic fever (VHF), in human and non-human primates. Lassa virus is an emerging virus and a select agent, requiring containment under Biosafety Level 4 or an equivalent standard. LASV is endemic in West African countries, especially Sierra Leone, the Republic of Guinea, Nigeria, and Liberia, where the annual incidence of infection is between 300,000 and 500,000 cases, resulting in 5,000 deaths per year (Kyei et al. (2015), BMC Infectious Diseases 15:217).

Lassa viruses are enveloped, single-stranded, bisegmented, ambisense RNA viruses (Lashley, Felissa R., and Jerry D. Durham. *Emerging Infectious Diseases: Trends and Issues*. New York: Springer Pub., 2002). Their genome is contained in two RNA segments that code for two proteins each, one in each sense, for a total of four viral proteins (Ridley, Matt. *Genome: The Autobiography of a Species in 23 Chapters*. New York: HarperCollins, 1999). The large segment encodes a small zinc-binding protein (Z) that regulates transcription and replication, and the RNA polymerase (L). The small segment encodes the nucleoprotein (NP) and the surface glycoprotein precursor (GP, also known as the viral spike), which is proteolytically cleaved into the envelope glycoproteins GP1 and GP2 that bind to the alpha-dystroglycan receptor and mediate host cell entry (Cornu, T. I.; De La Torre, J. C. (2001). RING Finger Z Protein of Lymphocytic Choriomeningitis Virus (LCMV) Inhibits Transcription and RNA Replication of an LCMV S-Segment Minigenome". *Journal of Virology* 75 (19): 9415-9426; Djavani M, et al. (September 1997). "Completion of the Lassa fever virus sequence and identification of a RING finger open reading frame at the L RNA 5' End.". *Virology* 235 (2): 414-8; Cao, W.; Henry, M. D.; Borrow, P.; Yamada, H.; Elder, J. H.; Ravkov, E. V.; Nichol, S. T.; Compans, R. W.; Campbell, K. P.; Oldstone, M. B. (1998). "Identification of -Dystroglycan as a Receptor for Lymphocytic Choriomeningitis Virus and Lassa Fever Virus". *Science* 282 (5396): 2079-2081)
The pathogenesis of the Lassa virus remains unclear, but it has been shown that the main targets of the virus are antigen-presenting cells (mainly dendritic cells) and endothelial cells (Mahanty, S.; Hutchinson, K.; Agarwal, S.; McRae, M.; Rollin, P. E.; Pulendran, B. (2003). "Cutting edge: Impairment of dendritic cells and adaptive immunity by Ebola and Lassa viruses". *Journal of immunology*, 170 (6): 2797-2801; Baize, S.; Kaplon, J.; Faure, C.; Pannetier, D.; Georges-Courbot, M. C.; Deubel, V. (2004). "Lassa virus infection of human dendritic cells and macrophages is productive but fails to activate cells". *Journal of immunology* (Baltimore, Md.: 1950) 172 (5): 2861-2869). Also, it is reported that *Lassa virus* prevents a host's innate immune system by NP activity. NP encoded in *Lassa virus* is essential in viral replication and transcription, but it also suppresses host innate interferon (IFN) response by inhibiting translocation of IRF-3. NP of Lassa virus is reported to have an exonuclease activity to only dsRNAs. dsRNA exonuclease activity of the NP leads to counteract IFN responses by digesting the PAMP which leads to the evasion of host immune responses.

Currently there is no US licensed vaccine for humans against the Lassa virus. Lassa fever is one of the most prevalent viral hemorrhagic fevers in West Africa responsible for thousands of deaths annually.

What is therefore needed are vaccine compositions and methods of use to prevent and treat disease caused by hemorrhagic fever virus infection, such as an ebolavirus, marburgvirus, or Lassa virus infection.

SUMMARY OF THE INVENTION

The compositions and methods of the invention described herein are useful for generating an immune response to at least one hemorrhagic fever virus in a subject in need thereof. Advantageously, the compositions and methods may be used prophylactically to immunize a subject against ebolavirus, marburgvirus or Lassa virus infection, or used therapeutically to prevent, treat or ameliorate the onset and severity of disease.

In a first aspect, the present invention is a recombinant modified vaccinia Ankara (MVA) vector comprising a glycoprotein sequence and a matrix protein sequence, wherein both the glycoprotein sequence and matrix protein sequence are inserted into the MVA vector under the control of promoters compatible with poxvirus expression systems.

In one embodiment, the glycoprotein sequence and the matrix protein sequence are inserted into one or more deletion sites of the MVA vector.

In one embodiment, the glycoprotein sequence and the matrix protein sequence are inserted into the MVA vector in a natural deletion site, a modified natural deletion site, or between essential or non-essential MVA genes.

In another embodiment, the glycoprotein sequence and the matrix protein sequence are inserted into the same natural deletion site, a modified natural deletion site, or between the same essential or non-essential MVA genes In another embodiment, the glycoprotein sequence and the matrix protein sequence are inserted into a deletion site selected from I, II, III, IV, V or VI and the matrix protein sequence is inserted into a deletion site selected from I, II, III, IV, V or VI.

In another embodiment, the glycoprotein sequence and the matrix protein sequence are inserted into different natural deletion sites, modified deletion sites, or between different essential or non-essential MVA genes.

In another embodiment, the glycoprotein sequence is inserted in a first deletion site and matrix protein sequence is inserted into a second deletion site.

In a particular embodiment, the glycoprotein sequence is inserted between two essential and highly conserved MVA genes; and the matrix protein sequence is inserted into a restructured and modified deletion III.

In one embodiment, the deletion III is modified to remove non-essential sequences and insert the matrix protein sequence between essential genes.

In a particular embodiment, the matrix protein sequence is inserted between MVA genes, I8R and G1L.

In a particular embodiment, the glycoprotein sequence is inserted between two essential and highly conserved MVA genes to limit the formation of viable deletion mutants.

In a particular embodiment, the glycoprotein protein sequence is inserted between MVA genes, I8R and G1L.

In one embodiment, the promoter is selected from the group consisting of Pm2H5, Psyn II, and mH5 promoters or combinations thereof.

In one embodiment, the glycoprotein sequence is optimized. In a particular embodiment, the glycoprotein sequence is optimized by changing selected codons to other synonymous codons that are optimal for protein expression by MVA, interrupting homopolymer stretches using silent mutations, interrupting transcription terminator motifs using silent mutations, or leading to expression of the transmembrane (rather than secreted) form of glycoprotein, and combinations thereof.

In one embodiment, the recombinant MVA viral vector expresses glycoprotein and matrix proteins that assemble into VLPs.

In one embodiment, the glycoprotein sequence and the matrix protein sequence are from a Filovirus species selected from the group of consisting of *Zaire ebolavirus, Sudan ebolavirus, Taï forest ebolavirus, Bundibugyo ebolavirus, Reston ebolavirus,* and *Marburg marburgvirus,* or a combination thereof.

In a particular embodiment, the glycoprotein sequence and the matrix protein sequence are from a *Zaire ebolavirus.*

In a particular embodiment, the glycoprotein sequence and the matrix protein sequence are from a 2014 epidemic strain of *Zaire ebolavirus.*

In a particular embodiment, the glycoprotein sequence and the matrix protein sequence are from a *Sudan ebolavirus.*

In a particular embodiment, the glycoprotein sequence and the matrix protein sequence are from a *Bundibugyo ebolavirus.*

In a particular embodiment, the glycoprotein sequence is from *Zaire ebolavirus* and the matrix protein sequence is from a *Sudan ebolavirus.*

In a particular embodiment, the glycoprotein sequence is from *Zaire ebolavirus* and the matrix protein sequence is from *Bundibugyo ebolavirus.*

In a particular embodiment, the glycoprotein sequence is from *Sudan ebolavirus* and the matrix protein sequence is from a *Zaire ebolavirus.*

In a particular embodiment, the glycoprotein sequence is from a *Sudan ebolavirus* and the matrix protein sequence is from a *Bundibugyo ebolavirus.*

In a particular embodiment, the glycoprotein sequence is from a *Bundibugyo ebolavirus* and the matrix protein sequence is from a *Sudan ebolavirus.*

In a particular embodiment, the glycoprotein sequence is from a *Bundibugyo ebolavirus* and the matrix protein sequence is from a *Zaire ebolavirus.*

In a particular embodiment, the glycoprotein sequence and the matrix protein sequence are from a *Marburg marburgvirus.*

In a particular embodiment, the glycoprotein sequence and the matrix protein sequence are from a *Lassa virus.*

In one embodiment, the recombinant MVA viral vector expresses *Lassa virus* glycoprotein and Z proteins that assemble into VLPs.

In one embodiment, the recombinant MVA viral vector expresses *Lassa virus* glycoprotein, NP and Z proteins that assemble into VLPs.

In a second aspect, the present invention is a pharmaceutical composition comprising the recombinant MVA vector of the present invention and a pharmaceutically acceptable carrier.

In one embodiment, the recombinant MVA vector is formulated for intraperitoneal, intramuscular, intradermal, epidermal, mucosal or intravenous administration.

In a third aspect, the present invention is a pharmaceutical composition comprising a first recombinant MVA vector and a second recombinant MVA vector, each comprising a glycoprotein sequence and a matrix protein sequence, wherein (i) the glycoprotein sequence of the first recombinant MVA vector is different than the glycoprotein sequence of the second recombinant MVA vector and/or (ii) the matrix protein sequence of the first recombinant MVA vector is different than the matrix protein sequence of the second recombinant MVA vector.

In a particular embodiment, the glycoprotein sequence of the first recombinant MVA vector is from a different species than the glycoprotein sequence of the second recombinant MVA vector.

In a particular embodiment, the glycoprotein sequences of the recombinant MVA vectors are from a *Zaire ebolavirus* and a *Bundibugyo ebolavirus.*

In a particular embodiment, the glycoprotein sequences of the recombinant MVA vectors are from a *Zaire ebolavirus* and a *Sudan ebolavirus.*

In a particular embodiment, the glycoprotein sequences of the recombinant MVA vectors are from a *Sudan ebolavirus* and a *Bundibugyo ebolavirus.*

In a particular embodiment, the glycoprotein sequences of the recombinant MVA vectors are from a *Zaire ebolavirus* and a *Marburg marburgvirus.*

In a particular embodiment, the glycoprotein sequences of the recombinant MVA vectors are from a *Sudan ebolavirus* and a *Marburg marburgvirus.*

In a particular embodiment, the glycoprotein sequences of the recombinant MVA vectors are from a *Bundibugyo ebolavirus* and a *Marburg marburgvirus.*

In a particular embodiment, the glycoprotein sequences of the recombinant MVA vectors are from a *Zaire ebolavirus* and a *Lassa virus.*

In a particular embodiment, the glycoprotein sequences of the recombinant MVA vectors are from a *Sudan ebolavirus* and a *Lassa virus.*

In a particular embodiment, the glycoprotein sequences of the recombinant MVA vectors are from a *Bundibugyo ebolavirus* and a *Lassa virus.*

In a particular embodiment, the glycoprotein sequences of the recombinant MVA vectors are from a *Marburg marburgvirus* and a *Lassa virus.*

In another particular embodiment, the matrix protein sequence of the first recombinant MVA vector is from a different species than the matrix protein sequence of the second recombinant MVA vector.

In a particular embodiment, the matrix protein sequences of the recombinant MVA vectors are from a *Zaire ebolavirus* and a *Bundibugyo ebolavirus.*

In a particular embodiment, the matrix protein sequences of the recombinant MVA vectors are from a *Zaire ebolavirus* and a *Sudan ebolavirus.*

In a particular embodiment, the matrix protein sequences of the recombinant MVA vectors are from a *Sudan ebolavirus* and a *Bundibugyo ebolavirus.*

In a particular embodiment, the matrix protein sequences of the recombinant MVA vectors are from a *Zaire ebolavirus* and a *Marburg marburgvirus.*

In a particular embodiment, the matrix protein sequences of the recombinant MVA vectors are from a *Sudan ebolavirus* and a *Marburg marburgvirus.*

In a particular embodiment, the matrix protein sequences of the recombinant MVA vectors are from a *Bundibugyo ebolavirus* and a *Marburg marburgvirus.*

In a particular embodiment, the matrix protein sequences of the recombinant MVA vectors are from a *Zaire ebolavirus* and a *Lassa virus.*

In a particular embodiment, the matrix protein sequences of the recombinant MVA vectors are from a *Sudan ebolavirus* and a *Lassa virus.*

In a particular embodiment, the matrix protein sequences of the recombinant MVA vectors are from a *Bundibugyo ebolavirus* and a *Lassa virus*.

In a particular embodiment, the matrix protein sequences of the recombinant MVA vectors are from a *Marburg marburgvirus* and a *Lassa virus*.

In a fourth aspect, the present invention is a pharmaceutical composition comprising three or more recombinant MVA vectors each comprising a glycoprotein sequence and a matrix protein sequence, wherein (i) the three or more recombinant MVA vectors contain different glycoprotein sequences and/or (ii) the three recombinant MVA vectors contain different matrix protein sequences.

In a particular embodiment, the glycoprotein sequence and matrix sequence of each recombinant vector are from the same species.

In a particular embodiment, the glycoprotein sequences of the three or more recombinant MVA vectors are from different species.

In a particular embodiment, the glycoprotein sequences of the three or more recombinant MVA vectors are from a *Zaire ebolavirus*, a *Sudan ebolavirus*, and a *Bundibugyo ebolavirus*.

In a particular embodiment, the glycoprotein sequences of the three or more recombinant MVA vectors are from a *Zaire ebolavirus*, a *Sudan ebolavirus*, and a *Marburg marburgvirus*.

In a particular embodiment, the glycoprotein sequences of the three or more recombinant MVA vectors are from a *Zaire ebolavirus*, a *Sudan ebolavirus*, and a *Lassa virus*.

In a particular embodiment, the glycoprotein sequences of the three or more recombinant MVA vectors are from a *Zaire ebolavirus*, a *Bundibugyo ebolavirus*, and a *Marburg marburgvirus*.

In a particular embodiment, the glycoprotein sequences of the three or more recombinant MVA vectors are from a *Zaire ebolavirus*, a *Bundibugyo ebolavirus*, and a *Lassa virus*.

In a particular embodiment, the glycoprotein sequences of the three or more recombinant MVA vectors are from a *Zaire ebolavirus*, a *Marburg marburgvirus*, and a *Lassa virus*.

In a particular embodiment, the glycoprotein sequences of the three or more recombinant MVA vectors are from a *Sudan ebolavirus*, a *Bundibugyo ebolavirus*, and a *Marburg marburgvirus*.

In a particular embodiment, the glycoprotein sequences of the three or more recombinant MVA vectors are from a *Sudan ebolavirus*, a *Bundibugyo ebolavirus*, and a *Lassa virus*.

In a particular embodiment, the glycoprotein sequences of the three or more recombinant MVA vectors are from a *Sudan ebolavirus*, a *Marburg marburgvirus*, and a *Lassa virus*.

In a particular embodiment, the glycoprotein sequences of the three or more recombinant MVA vectors are from a *Bundibugyo ebolavirus*, a *Marburg marburgvirus*, and a *Lassa virus*.

In a particular embodiment, the glycoprotein sequences of the three or more recombinant MVA vectors are from a *Zaire ebolavirus*, a *Sudan ebolavirus*, a *Bundibugyo ebolavirus*, and a *Marburg marburgvirus*.

In a particular embodiment, the glycoprotein sequences of the three or more recombinant MVA vectors are from a *Zaire ebolavirus*, a *Sudan ebolavirus*, a *Bundibugyo ebolavirus*, and a *Lassa virus*.

In a particular embodiment, the glycoprotein sequences of the three or more recombinant MVA vectors are from a *Sudan ebolavirus*, a *Bundibugyo ebolavirus*, a *Marburg marburgvirus*, and a *Lassa virus*.

In a particular embodiment, the glycoprotein sequences of the three or more recombinant MVA vectors are from a *Zaire ebolavirus*, a *Bundibugyo ebolavirus*, a *Marburg marburgvirus*, and a *Lassa virus*.

In a particular embodiment, the glycoprotein sequences of the three or more recombinant MVA vectors are from a *Zaire ebolavirus*, a *Sudan ebolavirus*, a *Bundibugyo ebolavirus*, a *Marburg marburgvirus*, and a *Lassa virus*.

In a particular embodiment, the matrix protein sequences of the three or more recombinant MVA vectors are from different species.

In a particular embodiment, the matrix protein sequences of the three or more recombinant MVA vectors are from a *Zaire ebolavirus*, a *Sudan ebolavirus*, and a *Bundibugyo ebolavirus*.

In a particular embodiment, the matrix protein sequences of the three or more recombinant MVA vectors are from a *Zaire ebolavirus*, a *Sudan ebolavirus*, and a *Marburg marburgvirus*.

In a particular embodiment, the matrix protein sequences of the three or more recombinant MVA vectors are from a *Zaire ebolavirus*, a *Sudan ebolavirus*, and a *Lassa virus*.

In a particular embodiment, the matrix protein sequences of the three or more recombinant MVA vectors are from a *Zaire ebolavirus*, a *Bundibugyo ebolavirus*, and a *Marburg marburgvirus*.

In a particular embodiment, the matrix protein sequences of the three or more recombinant MVA vectors are from a *Zaire ebolavirus*, a *Bundibugyo ebolavirus*, and a *Lassa virus*.

In a particular embodiment, the matrix protein sequences of the three or more recombinant MVA vectors are from a *Zaire ebolavirus*, a *Marburg marburgvirus*, and a *Lassa virus*.

In a particular embodiment, the matrix protein sequences of the three or more recombinant MVA vectors are from a *Sudan ebolavirus*, a *Bundibugyo ebolavirus*, and a *Marburg marburgvirus*.

In a particular embodiment, the matrix protein sequences of the three or more recombinant MVA vectors are from a *Sudan ebolavirus*, a *Bundibugyo ebolavirus*, and a *Lassa virus*.

In a particular embodiment, the matrix protein sequences of the three or more recombinant MVA vectors are from a *Sudan ebolavirus*, a *Marburg marburgvirus*, and a *Lassa virus*.

In a particular embodiment, the matrix protein sequences of the three or more recombinant MVA vectors are from a *Bundibugyo ebolavirus*, a *Marburg marburgvirus*, and a *Lassa virus*.

In a particular embodiment, the matrix protein sequences of the three or more recombinant MVA vectors are from a *Zaire ebolavirus*, a *Sudan ebolavirus*, a *Bundibugyo ebolavirus*, and a *Marburg marburgvirus*.

In a particular embodiment, the matrix protein sequences of the three or more recombinant MVA vectors are from a *Zaire ebolavirus*, a *Sudan ebolavirus*, a *Bundibugyo ebolavirus*, and a *Lassa virus*.

In a particular embodiment, the matrix protein sequences of the three or more recombinant MVA vectors are from a *Sudan ebolavirus*, a *Bundibugyo ebolavirus*, a *Marburg marburgvirus*, and a *Lassa virus*.

In a particular embodiment, the matrix protein sequences of the three or more recombinant MVA vectors are from a *Zaire ebolavirus*, a *Bundibugyo ebolavirus*, a *Marburg marburgvirus*, and a *Lassa virus*.

In a particular embodiment, the matrix protein sequences of the three or more recombinant MVA vectors are from a *Zaire ebolavirus*, a *Sudan ebolavirus*, a *Bundibugyo ebolavirus*, a *Marburg marburgvirus*, and a *Lassa virus*.

In a fifth aspect, the present invention is a method of inducing an immune response in a subject in need thereof, said method comprising administering the composition of the present invention to the subject in an amount sufficient to induce an immune response.

In one embodiment, the immune response is a humoral immune response, a cellular immune response or a combination thereof.

In a particular embodiment, the immune response comprises production of binding antibodies against the ebolavirus, marburgvirus, or Lassa virus.

In a particular embodiment, the immune response comprises production of neutralizing antibodies against the ebolavirus, marburgvirus, or Lassa virus.

In a particular embodiment, the immune response comprises production of non-neutralizing antibodies against the ebolavirus, marburgvirus, or Lassa virus.

In a particular embodiment, the immune response comprises production of a cell-mediated immune response against the ebolavirus, marburgvirus, or Lassa virus.

In a particular embodiment, the immune response comprises production of neutralizing and non-neutralizing antibodies against the ebolavirus, marburgvirus, or Lassa virus.

In a particular embodiment, the immune response comprises production of neutralizing antibodies and cell-mediated immunity against the ebolavirus, marburgvirus, or Lassa virus.

In a particular embodiment, the immune response comprises production of non-neutralizing antibodies and cell-mediated immunity against the ebolavirus, marburgvirus, or Lassa virus.

In a particular embodiment, the immune response comprises production of neutralizing antibodies, non-neutralizing antibodies, and cell-mediated immunity against the ebolavirus, marburgvirus, or Lassa virus.

In a sixth aspect, the present invention is a method of preventing a hemorrhagic fever virus infection in a subject in need thereof, said method comprising administering the recombinant MVA vector of the present invention to the subject in a prophylactically effective amount.

In one embodiment, the hemorrhagic fever infection is an ebolavirus, marburgvirus, or Lassa virus infection.

In one embodiment, the method prevents infection by a *Zaire ebolavirus*.

In another embodiment, the method prevents infection by a *Sudan ebolavirus*.

In another embodiment, the method prevents infection by a *Bundibugyo ebolavirus*.

In another embodiment, the method prevents infection by a *Marburg marburgvirus*.

In another embodiment, the method prevents infection by a *Lassa virus*.

In yet another embodiment, the method prevents infection by more than one species of hemorrhagic fever virus, e.g., a *Zaire ebolavirus* and a *Sudan ebolavirus* or a *Zaire ebolavirus* and a *Marburg marburgvirus* or a *Zaire ebolavirus* and a *Lassa virus*.

In a seventh aspect, the present invention is a method of inducing an immune response in a subject in need thereof, said method comprising administering the recombinant MVA vector of the present invention to the subject in a prophylactically effective amount.

In one embodiment, the immune response is considered a surrogate marker for protection.

In one embodiment, the method induces an immune response against a *Zaire ebolavirus*.

In another embodiment, the method induces an immune response against a *Sudan ebolavirus*.

In another embodiment, the method induces an immune response to a *Bundibugyo ebolavirus*.

In another embodiment, the method induces an immune response to a *Marburg marburgvirus*.

In another embodiment, the method induces an immune response to a *Lassa virus*.

In yet another embodiment, the method induces an immune response to more than one species of hemorrhagic fever virus, e.g., a *Zaire ebolavirus* and a *Sudan ebolavirus* or a *Zaire ebolavirus* and a *Marburg marburgvirus* or a *Sudan ebolavirus* and a *Lassa virus*

In an eighth aspect, the present invention is a method of treating hemorrhagic fever virus infection in a subject in need thereof, said method comprising administering the recombinant MVA vector in a therapeutically effective amount to the subject.

In one embodiment, the hemorrhagic fever virus infection is caused by an ebolavirus, an marburgvirus or Lassa virus.

In one embodiment, the subject is exposed to hemorrhagic fever virus, but not yet symptomatic of hemorrhagic fever virus infection. In a particular embodiment, treatment results in prevention of a symptomatic infection.

In another embodiment, the subject was recently exposed but exhibits minimal symptoms of infections.

In another embodiment, the method results in amelioration of at least one symptom of infection.

In one embodiment, the symptom of infection is fever and/or hemorrhagic bleeding.

In another embodiment, the method results in reduction or elimination of the subject's ability to transmit the infection to an uninfected subject.

In one embodiment, the method prevents or ameliorates a *Zaire ebolavirus* infection.

In another embodiment, the method prevents or ameliorates a *Sudan ebolavirus* infection.

In one embodiment, the method prevents or ameliorates a *Bundibugyo ebolavirus* infection.

In another embodiment, the method prevents or ameliorates a *Marburg marburgvirus* infection.

In another embodiment, the method prevents or ameliorates a *Lassa virus* infection.

In yet another embodiment, the method prevents or ameliorates infections resulting from more than one species of hemorrhagic fever virus, e.g., *Zaire ebolavirus* and *Sudan ebolavirus* infections or *Zaire ebolavirus* and *Marburg marburgvirus* infections or *Bundibugyo ebolavirus* and *Lassa virus* infections.

In a ninth aspect, the present invention is a method manufacturing a recombinant modified vaccinia Ankara (MVA) vector comprising inserting at least one glycoprotein sequence and at least one matrix protein sequence into the MVA vector operably linked to promoters compatible with poxvirus expression systems.

In one embodiment, the matrix sequence is VP40, and the GP sequence and the VP40 sequence are from a Filovirus species selected from the group consisting of *Zaire ebola-* virus, *Sudan ebolavirus*, *Taï forest ebolavirus*, *Bundibugyo ebolavirus*, *Reston ebolavirus*, and *Marburg marburgvirus*, or a combination thereof.

In a particular embodiment, the GP sequence and the VP40 sequence are from a *Zaire ebolavirus*.

In a particular embodiment, the GP sequence and the VP40 sequence are from a 2014 epidemic strain of *Zaire ebolavirus*.

In a particular embodiment, the GP sequence and the VP40 sequence are from a *Sudan ebolavirus*.

In a particular embodiment, the GP sequence and the VP40 sequence are from a *Bundibugyo ebolavirus*.

In a particular embodiment, the GP sequence is from *Zaire ebolavirus* and the VP40 sequence is from a *Sudan ebolavirus*.

In a particular embodiment, the GP sequence is from *Zaire ebolavirus* and the VP40 sequence is from *Bundibugyo ebolavirus*.

In a particular embodiment, the GP sequence is from *Sudan ebolavirus* and the VP40 sequence is from a *Zaire ebolavirus*.

In a particular embodiment, the GP sequence is from a *Sudan ebolavirus* and the VP40 sequence is from a *Bundibugyo ebolavirus*.

In a particular embodiment, the GP sequence is from a *Bundibugyo ebolavirus* and the VP40 sequence is from a *Sudan ebolavirus*.

In a particular embodiment, the GP sequence is from a *Bundibugyo ebolavirus* and the VP40 sequence is from a *Zaire ebolavirus*.

In a particular embodiment, the GP sequence and the VP40 sequence are from a *Marburg marburgvirus*.

In a particular embodiment, the GP sequence is from a *Lassa virus*, and the matrix protein sequence is a Z sequence from a *Lassa virus*.

In a particular embodiment, the GP sequence is from a Lassa virus, the matrix protein sequence is a Z sequence from a Lassa virus and further comprises a nucleoprotein (NP) sequence from Lassa virus.

In one embodiment, the recombinant MVA viral vector expresses *Lassa virus* glycoprotein and matrix proteins that assemble into VLPs.

The numbering illustrates the positions (in kilobase pairs) of the various elements in the genome of the MVA vaccine vector. For clarity and brevity, the diagram is not to scale; pairs of diagonal lines indicate a section of the MVA genome that is not illustrated because its contents are not relevant to the invention. Arrows labeled "gp" and "vp40" illustrate the positions of the genes encoding GP and VP40, respectively for use with ebolavirus or Marburgvirus sequences. Rectangles labeled "I8R" and "G1L" indicate the positions of the two MVA genetic elements flanking the gene encoding GP. Rectangles labeled "A50R" and "B1R" indicate the positions of the two MVA genetic elements flanking the gene encoding VP40.

Figure 1:
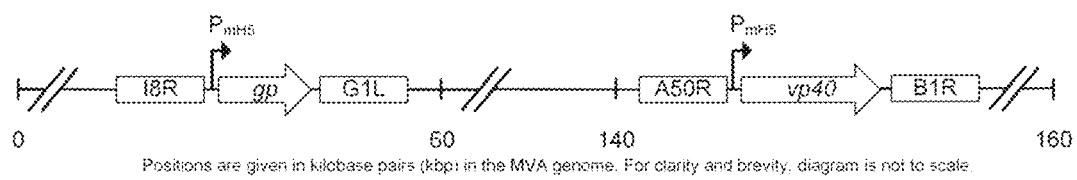
FIG. 1 is a simple line drawing illustrating the design of the MVA vectors.

The design for vectors containing EBOV, SUDV, BDBV, MARV and LASV genes is highly similar; therefore, the diagram in FIG. 1 may apply to the recombinant MVA vaccine vectors described in this application. The "GP" annotation in FIG. 1 indicates a GP sequence from EBOV, SUDV, BDBV, or MARV. The "VP40" annotation in FIG. 1 indicates a VP40 sequence from EBOV, SUDV, BDBV, or MARV. Other embodiments may deviate from this general design and are described herein.

In other embodiments for expressing LASV sequences, this illustration may represent a vector expressing LASV sequences where the GP sequence of FIG. 1 may instead represent the Lassa virus GP sequence and the "VP40" sequence of FIG. 1 may instead represent the Lassa virus Z sequence. In another embodiment, the "VP40" in FIG. 1 represents the Lassa virus Z sequence and NP sequence in reverse orientation each operably linked to a promoter compatible with poxvirus expression systems.

Figure 2:
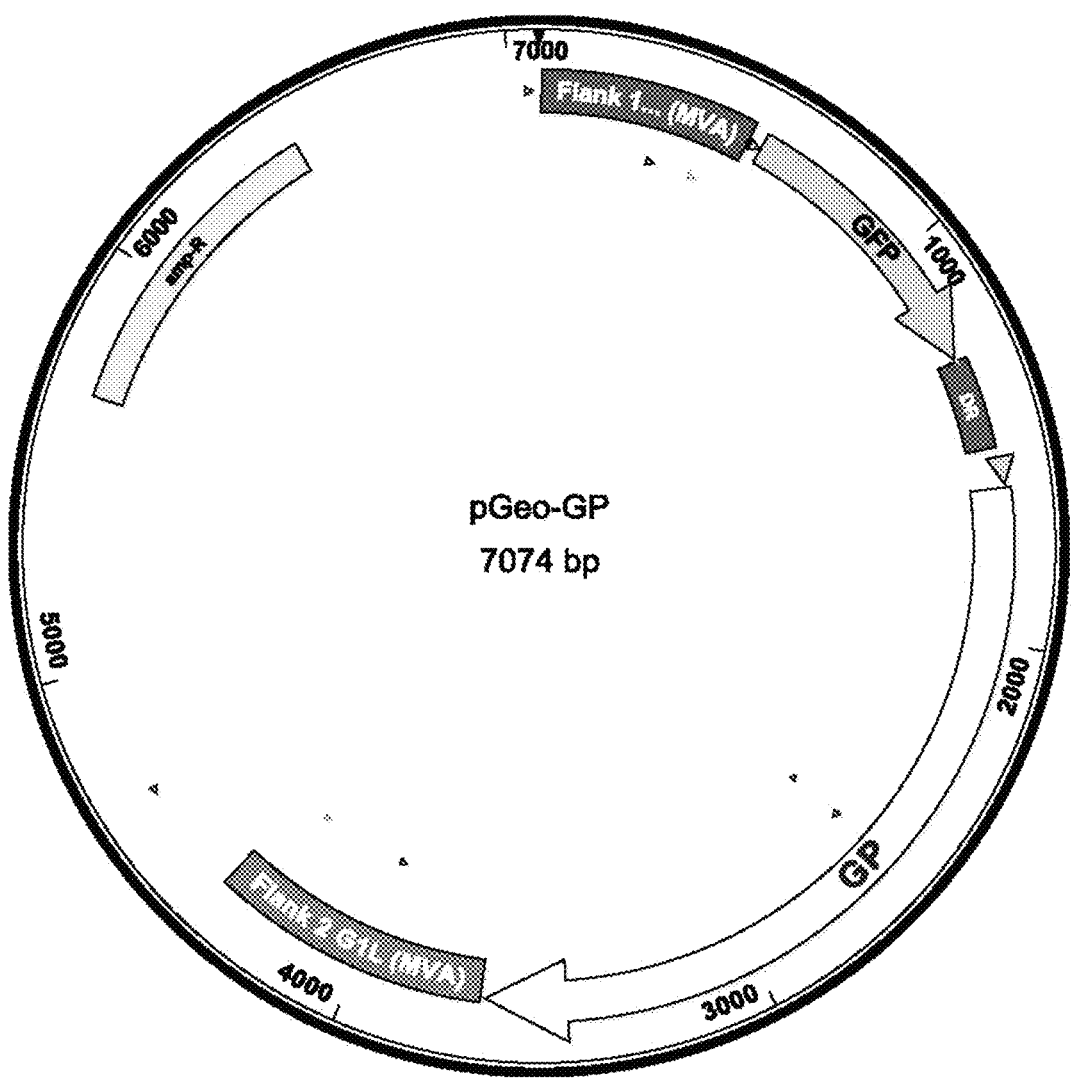

FIG. 2 is a schematic for the shuttle vector for filovirus or Marburg virus GP.

The ampicillin resistance marker, allowing the vector to replicate in bacteria, is illustrated with a block labeled "amp-R." The two flanking sequences, allowing the vector to recombine with the MVA genome, are illustrated with a block and a block labeled "Flank 1" and "Flank 2" respectively. The green fluorescent protein (GFP) selection marker, allowing the selection of recombinant MVAs, is illustrated with an arrow labeled "GFP." The block labeled "DR" illustrates the location of a sequence homologous to part of Flank 1 of the MVA sequence. DR enables removal of the GFP sequence from the MVA vector after insertion of GP into the MVA genome. The modified H5 (mH5) promoter, which enables transcription of the inserted heterologous gene, is illustrated with a triangle between the DR and GP elements. The filovirus GP gene is illustrated with a white arrow labeled "GP."

The shuttle vectors for EBOV, SUDV, BDBV, MARV and LASV glycoproteins use a highly similar design; therefore, FIG. 2 provides a single diagram that applies universally to the MVA vaccine vectors described in this application. FIG. 2 illustrates the design of all glycoprotein shuttle vectors of the invention. The "GP" annotation in FIG. 2 applies to glycoprotein sequences from EBOV, SUDV, BDBV, MARV and LASV.

The shuttle vectors for the various species differ in two principal ways. First, the glycoprotein sequences vary by species. Second, the restriction sites used to insert the glycoprotein sequences into the shuttle vector may vary by species. Neither of these differences affects the orientation of the elements of the shuttle vector.

Figure 3:
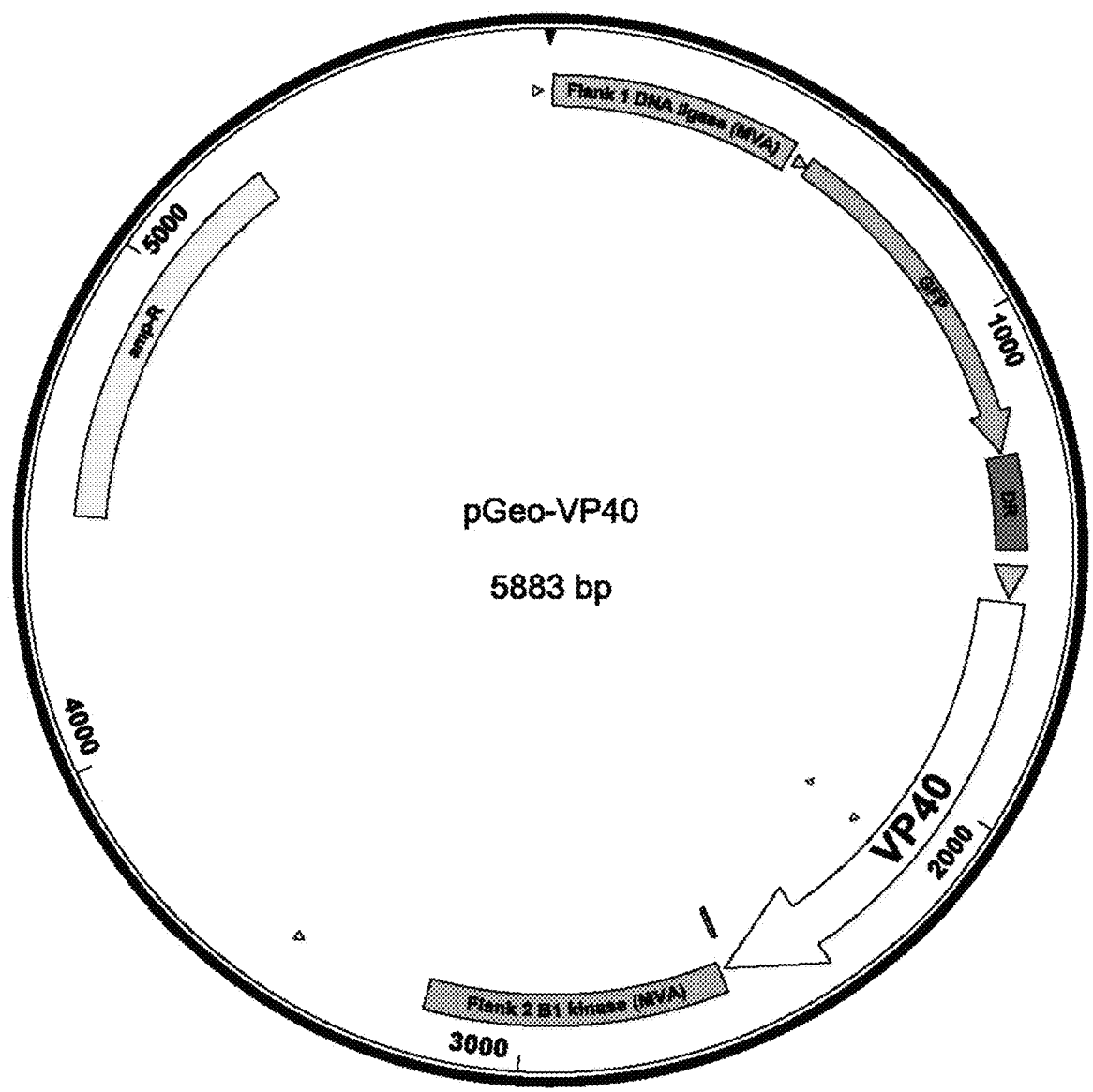

FIG. 3 is a schematic for the shuttle vector for filovirus or Marburg virus VP40.

The ampicillin resistance marker, allowing the vector to replicate in bacteria, is illustrated with a block labeled "amp-R." The two flanking sequences, allowing the vector to recombine with the MVA genome, are illustrated with blocks labeled "Flank 1" and "Flank 2." The green fluorescent protein (GFP) selection marker, allowing the selection of recombinant MVAs, is illustrated with an arrow labeled "GFP." The block labeled "DR" illustrates the location of a sequence homologous to part of Flank 1 of the MVA sequence. DR enables removal of the GFP sequence from the MVA vector after insertion of VP40 into the MVA genome. The modified H5 (mH5) promoter, which enables transcription of the inserted heterologous gene, is illustrated with a triangle between the DR and VP40 elements. The filovirus VP40 gene is illustrated with a white arrow labeled "VP40."

The shuttle vectors for EBOV, SUDV, BDBV, and MARV VP40s use a highly similar design and naming convention; therefore, FIG. 3 provides a single diagram that applies universally to the MVA vaccine vectors described in this application. FIG. 3 illustrates the design of all VP40 shuttle vectors of the invention. The "VP40" annotation in FIG. 3 applies to VP40 sequences from EBOV, SUDV, BDBV, and MARV.

The shuttle vectors for the various species differ in two principal ways. First, the VP40 sequences vary by species. Second, the restriction sites used to insert the VP40 sequences into the shuttle vector may vary by species. Neither of these differences affects the orientation of the elements of the shuttle vector.

Figure 4A:
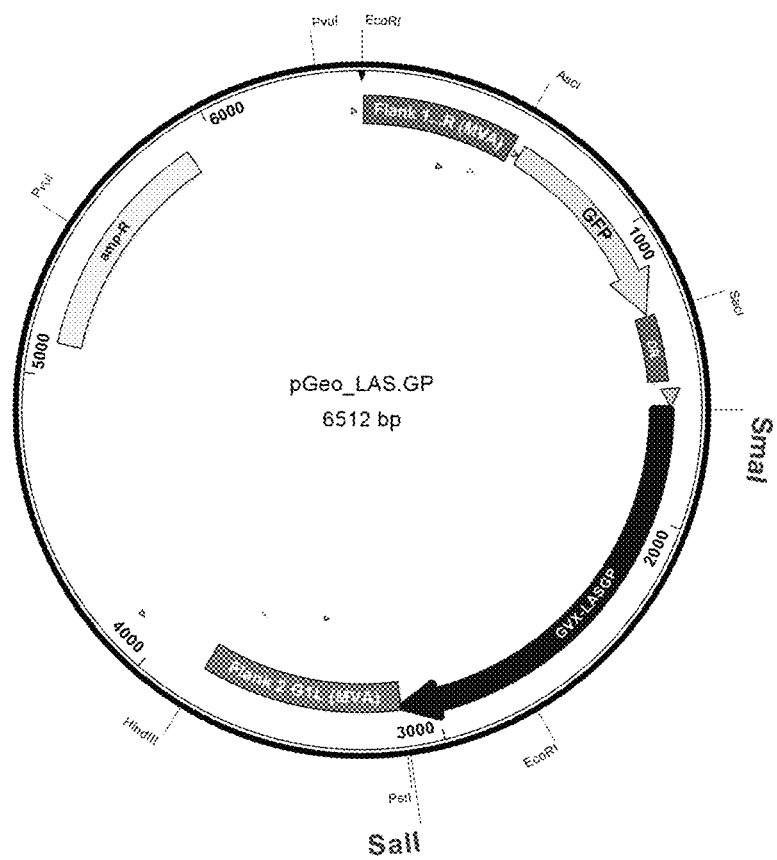
Figure 4B:
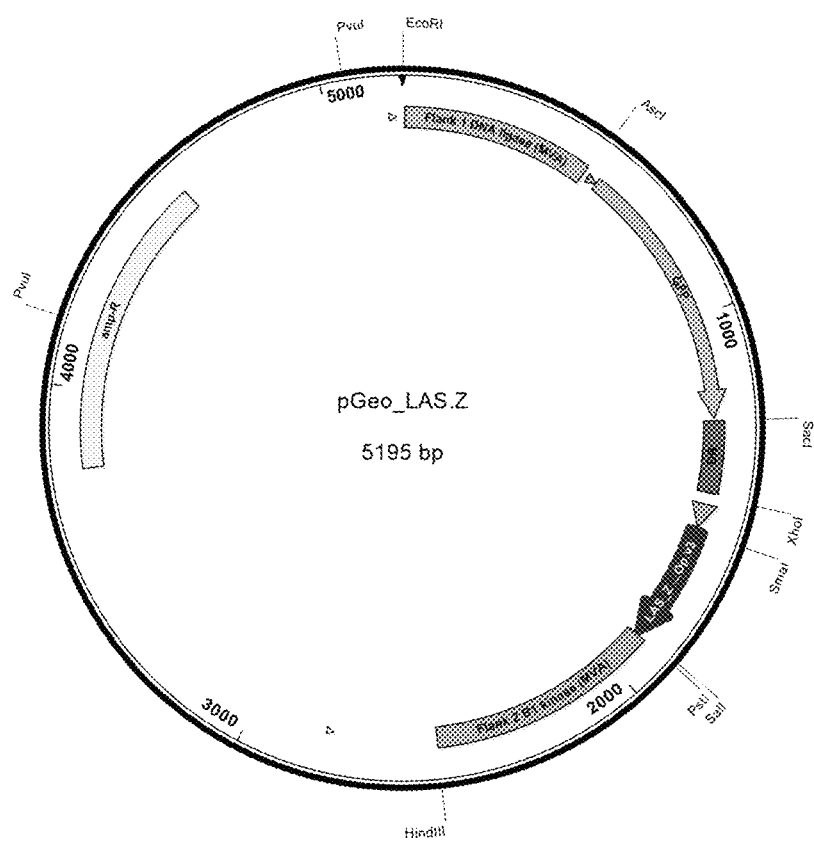

FIG. 4A and FIG. 4B provide a schematic for the shuttle vector for Lassa GP(4A) and Z (4B) genes. The ampicillin resistance marker, allowing the vector to replicate in bacteria, is illustrated with a block labeled "amp-R." The two flanking sequences, allowing the vector to recombine with the MVA genome, are illustrated with blocks labeled "Flank 1" and "Flank 2." The green fluorescent protein (GFP) selection marker, allowing the selection of recombinant MVAs, is illustrated with an arrow labeled "GFP." The block labeled "DR" illustrates the location of a sequence homologous to part of Flank 1 of the MVA sequence. DR enables removal of the GFP sequence from the MVA vector after insertion of GP and Z into the MVA genome. The modified H5 (mH5) promoter and P7.5 promoter, which enable transcription of the inserted heterologous gene, GP and Z respectively, are illustrated with a triangle between the DR and GP or Z elements.

Figure 5:
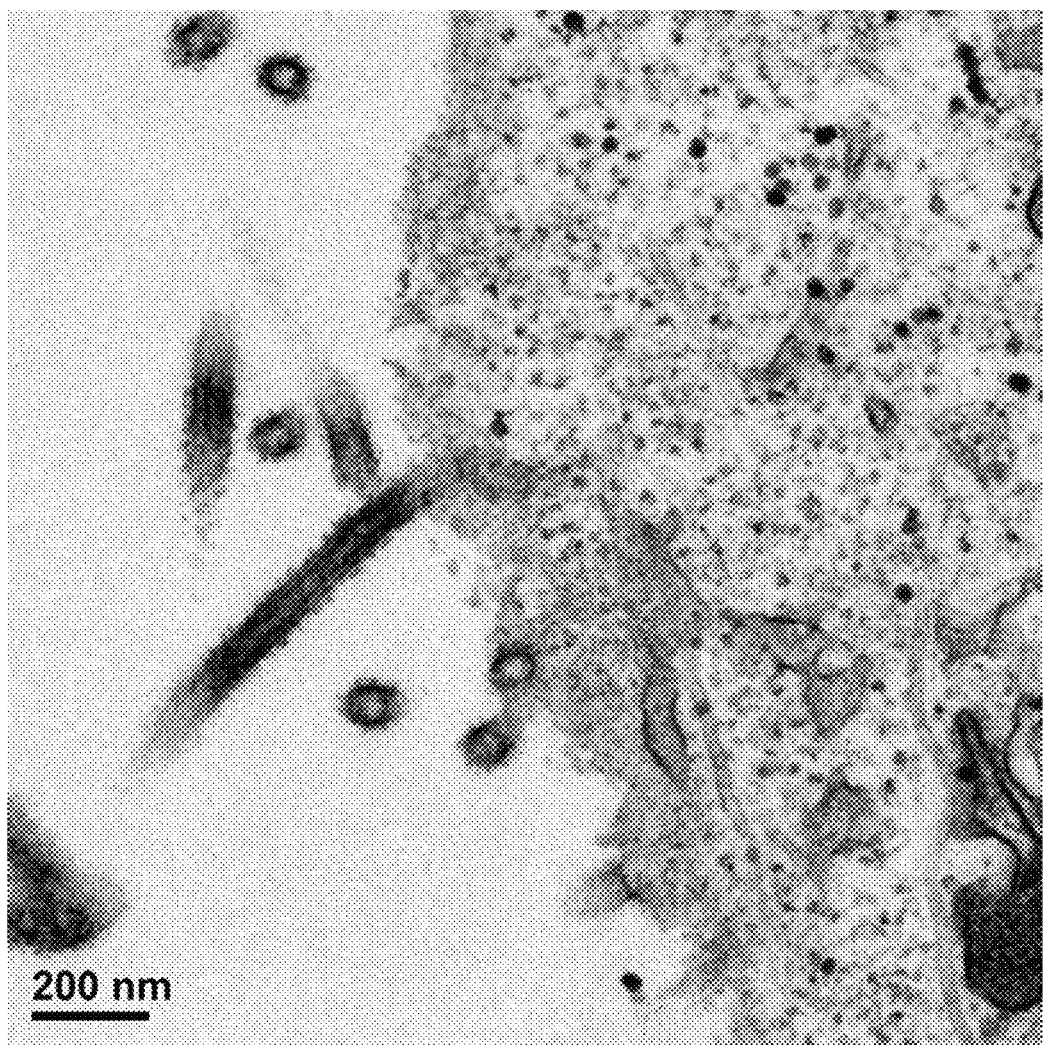

FIG. 5 is an electron micrograph showing virus-like particle (VLP) production by cells transfected with plasmid DNA vectors encoding EBOV GP and VP40 proteins. The sequences of the GP and VP40 in these plasmid DNA vectors are identical to the sequences of the GP and VP40 genes that are used in the MVA vaccine vector that expresses GP and VP40 from the 2014 strain of EBOV. This experiment demonstrated that the 2014 EBOV antigen sequences of this invention are capable of forming VLPs when introduced into cultured cells.

Figure 6:
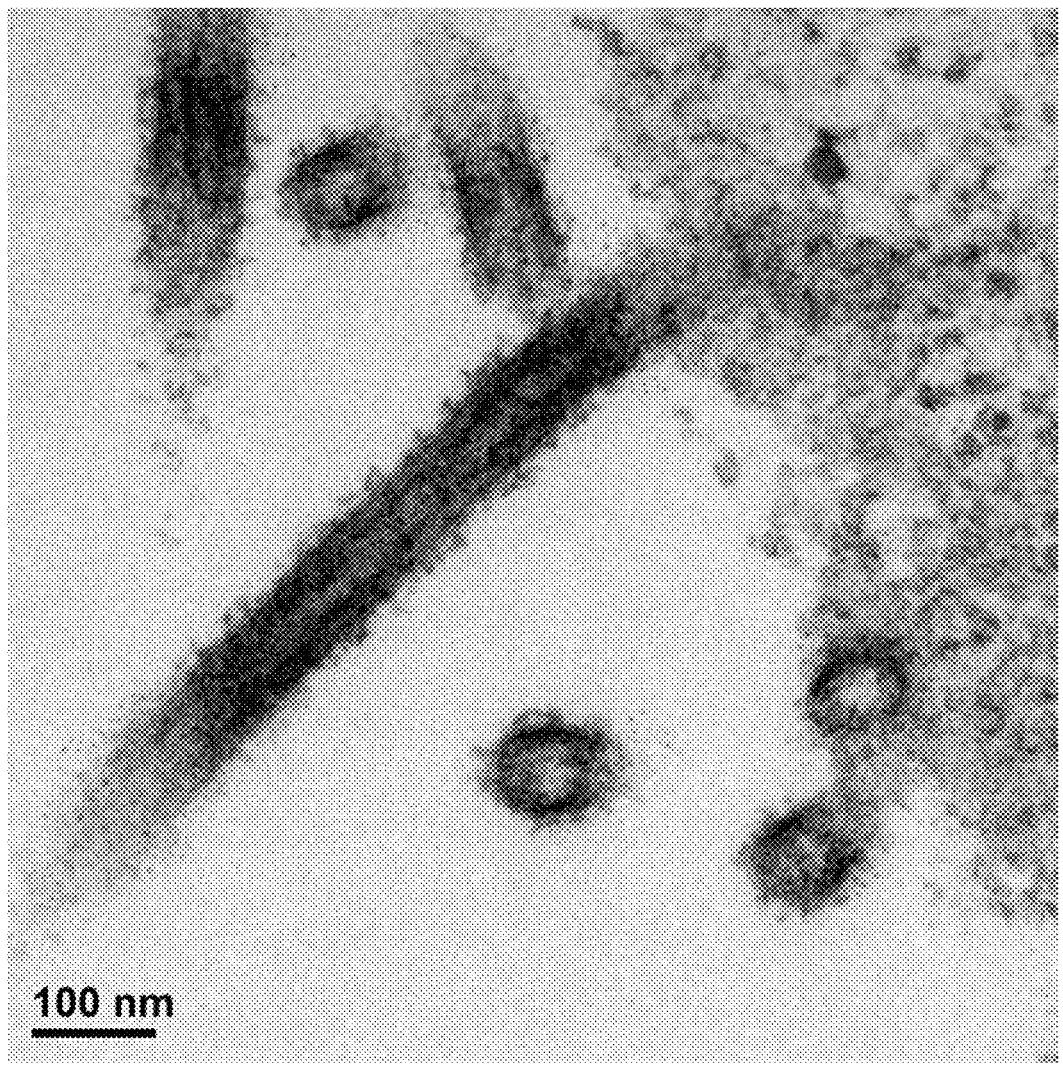

FIG. 6 is a higher magnification of the VLP in FIG. 5 to show the display of ebolavirus GP spikes on the VLP.

Figure 7:
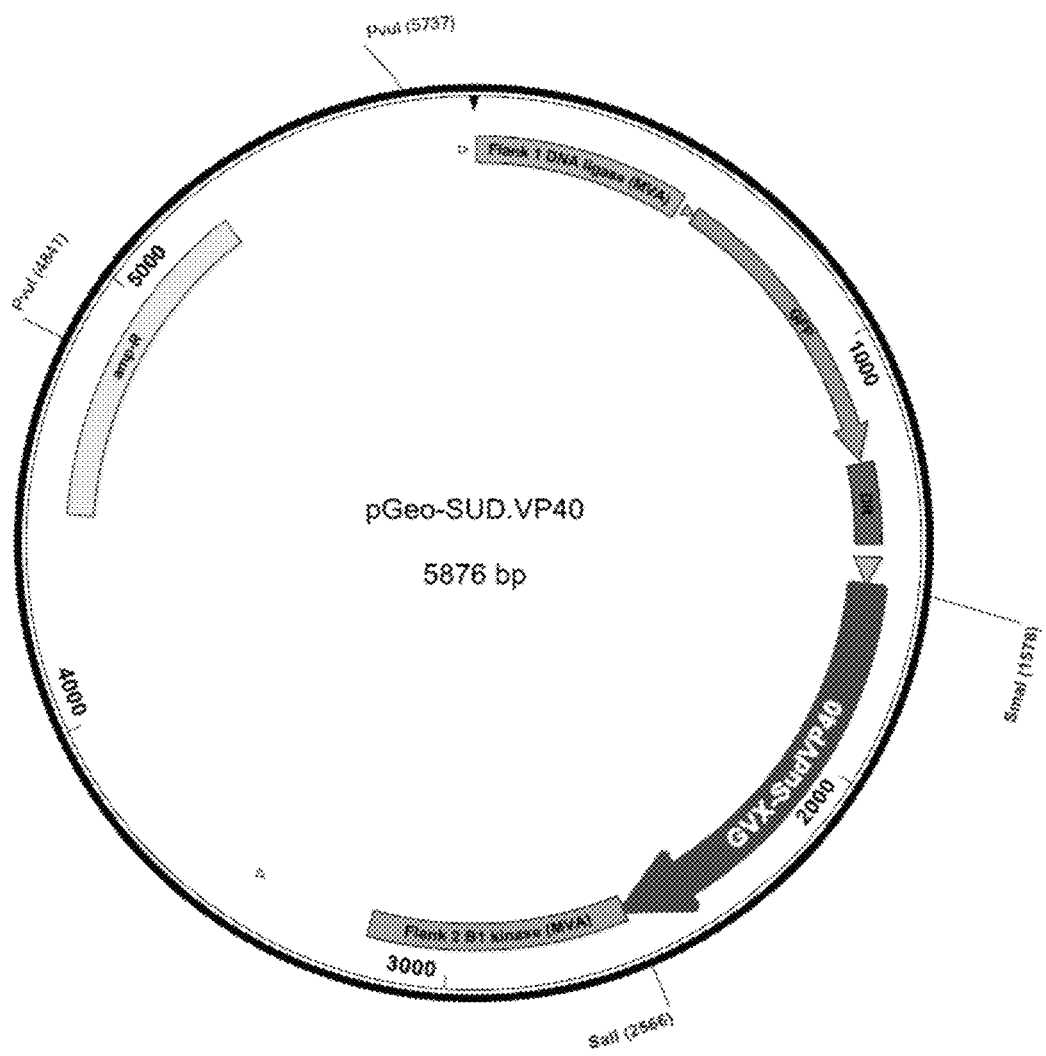

FIG. 7 is a schematic for the shuttle vector for pGEO-.SUD.VP40.

Figure 8:
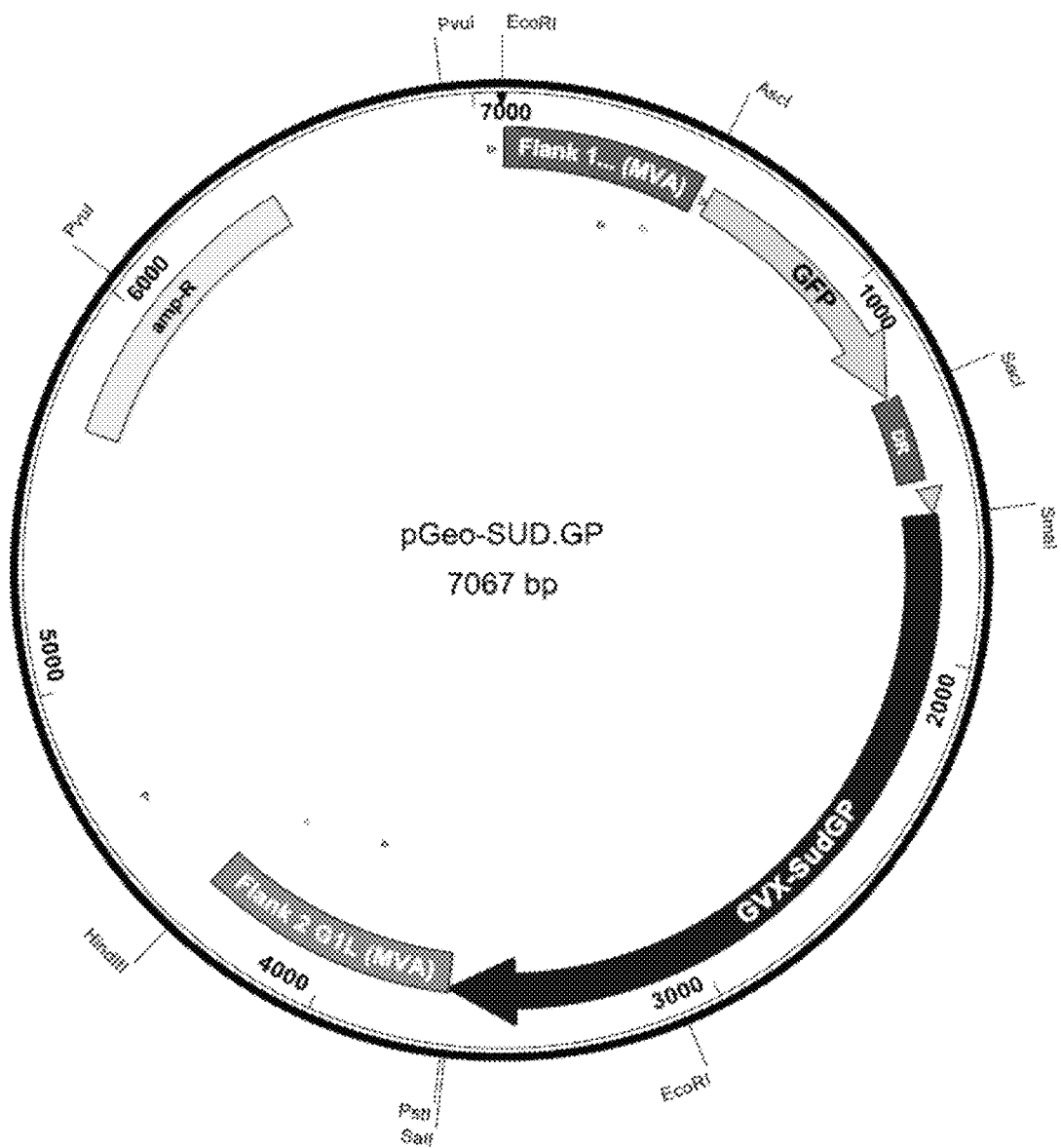

FIG. 8 is a schematic for the shuttle vector for pGEO-.SUD.GP.

Figure 9:
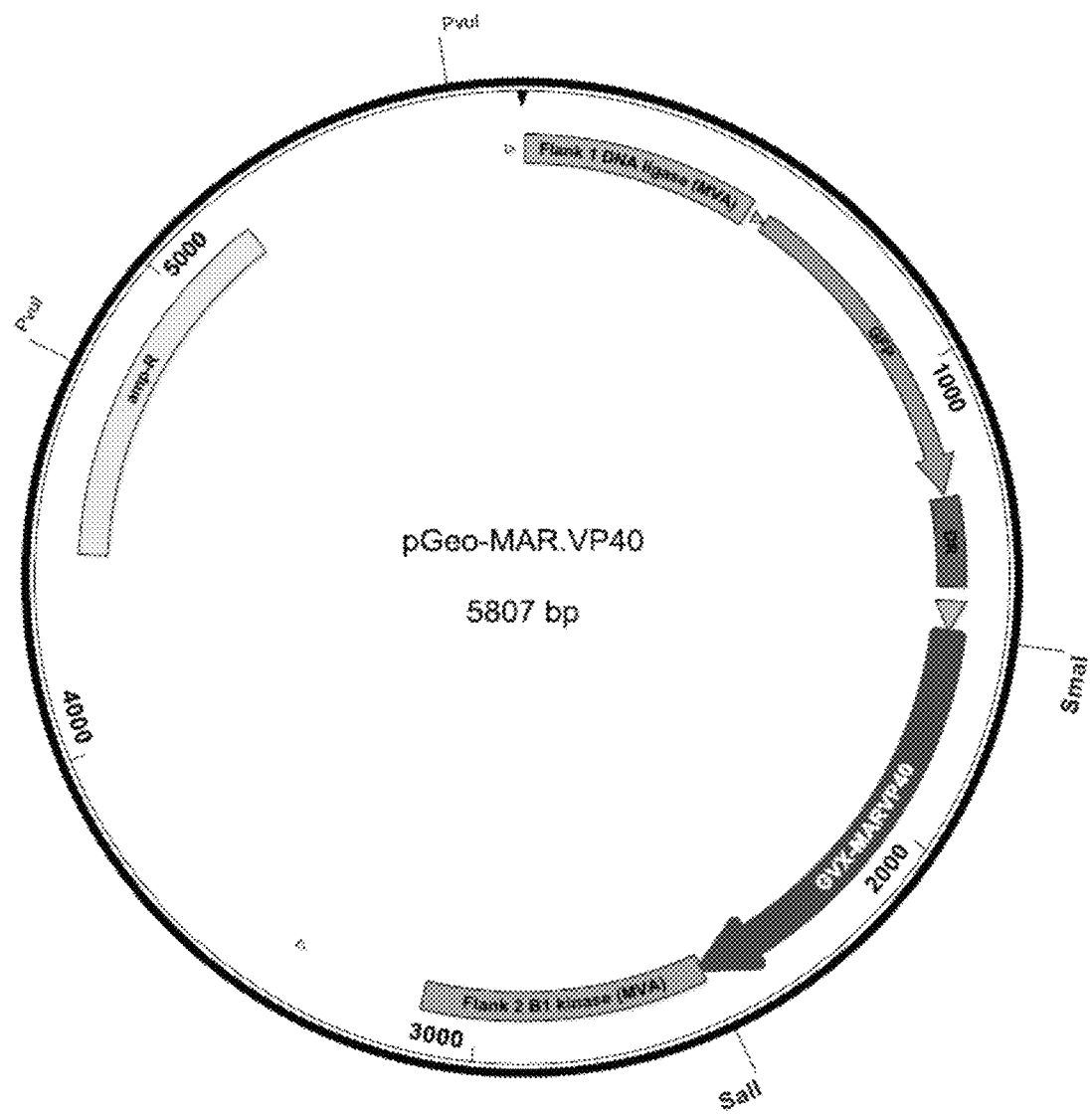

FIG. 9 is a schematic for the shuttle vector for pGEO-.MAR.VP40.

Figure 10:
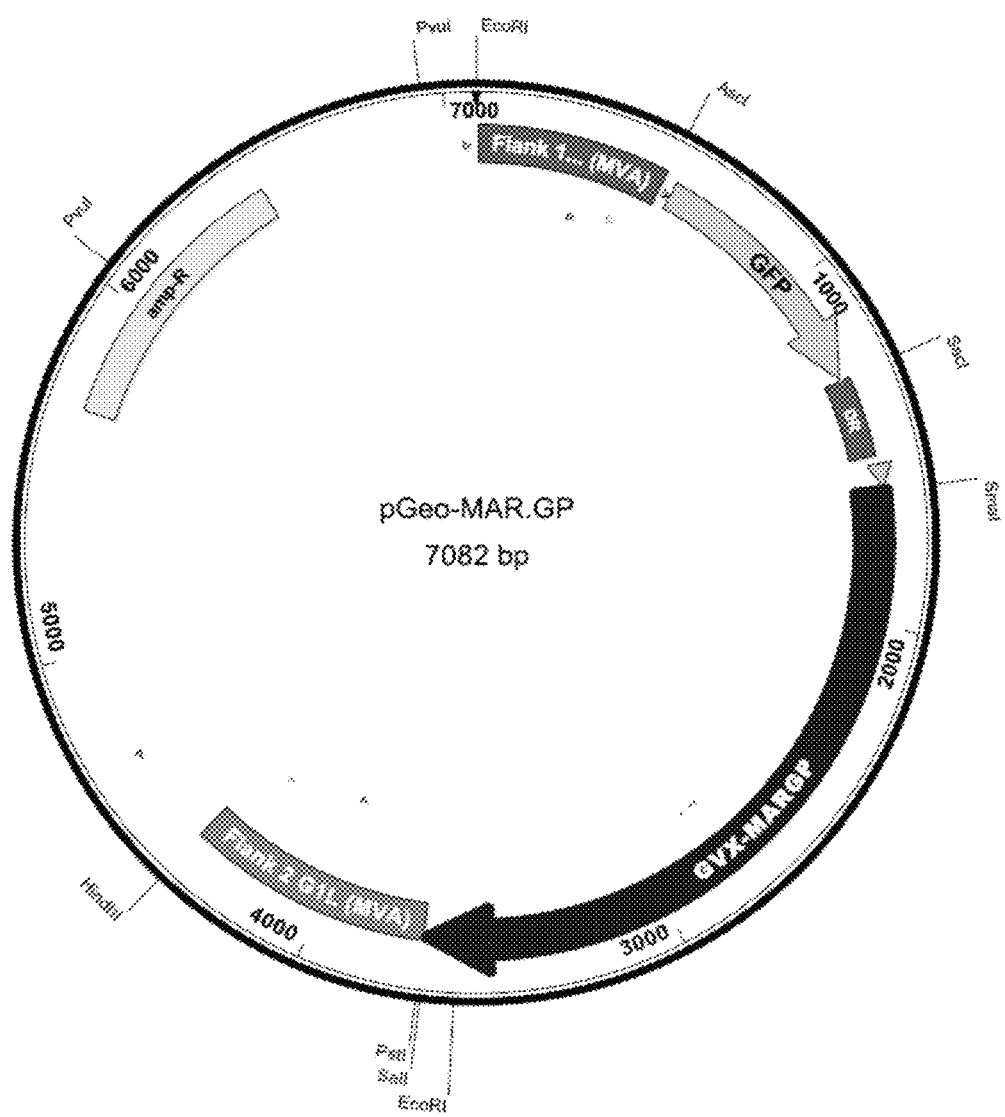

FIG. 10 is a schematic for the shuttle vector for pGEO-.MAR.GP.

FIG. 11A and FIG. 11B show binding antibody responses to the Ebola virus glycoprotein (GP) elicited by the vaccinations and specifically the results for binding Ab elicited by the MVA/Z-VLP vaccine. Guinea pig sera are shown on the left (FIG. 11A) and Syrian golden hamster sera on the right (FIG. 11B). The closed symbols are for animals receiving MVA/Z-VLP vaccine and the open symbols for animals vaccinated with the parental MVA (no vaccine inserts). The horizontal line in the left panel indicates the titer of binding Ab in sera pooled from six guinea pigs vaccinated with a chimeric vesicular stomatitis virus (VSV) expressing GP. Prebleed is prior to first MVA inoculation; MVA1wk4, four weeks after the first MVA inoculation and MVA2wk2, two weeks after the second MVA inoculation.

Figures 12A, 12B:
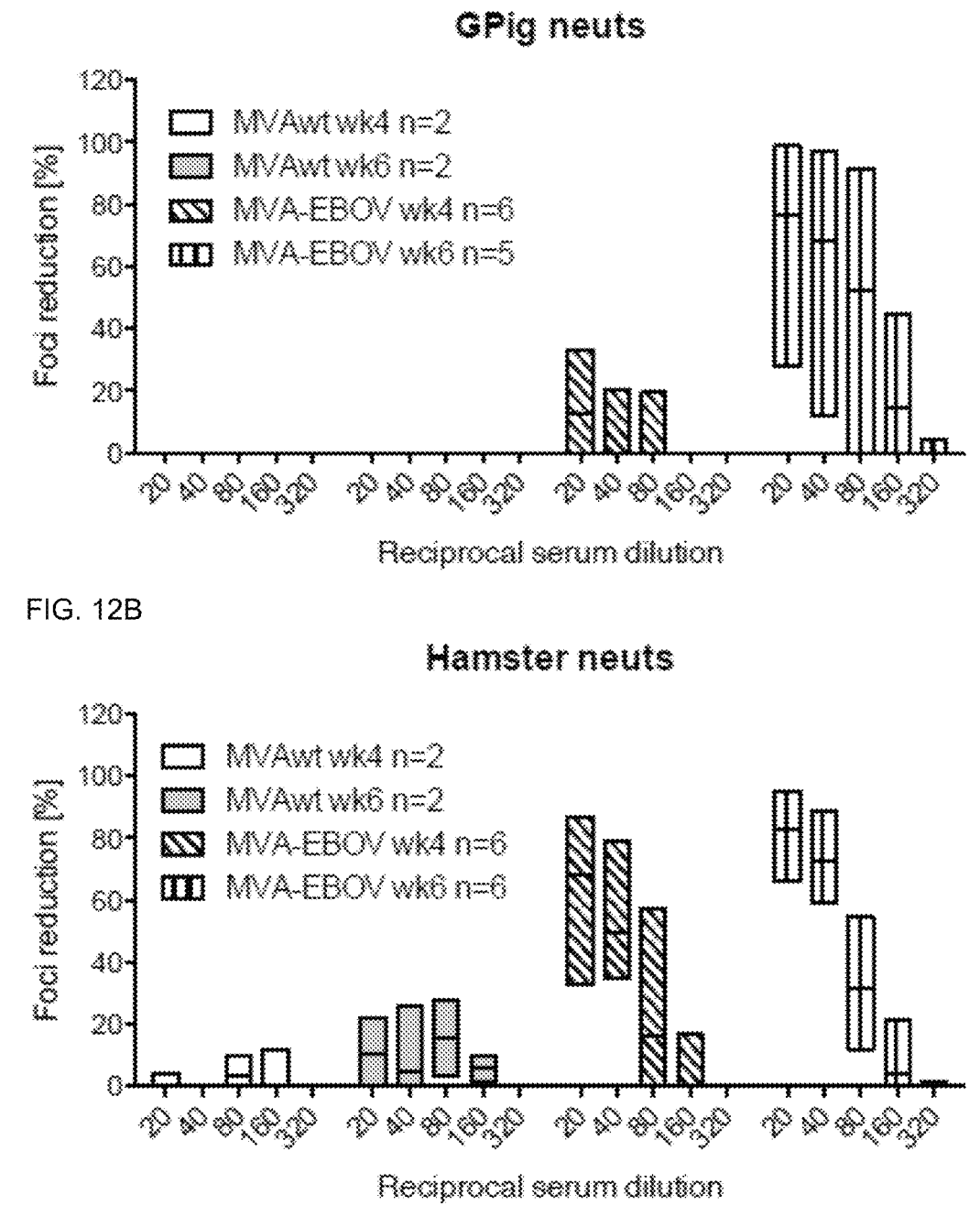

FIG. 12A and FIG. 12B shows neutralizing Ab responses to Ebola virus elicited by the vaccinations and specifically shows the results for neutralizing Ab elicited by the MVA/Z-VLP vaccine. The upper panel (FIG. 12A), GPig shows neutralizing titers elicited in guinea pigs and the bottom panel (FIG. 12B) shows neutralizing titers elicited in SGH.

MVAwt are data for animals infected with parental MVA. MVA-EBOV are data for animals vaccinated with MVA/Z-VLP.

Figures 13A, 13B, 13C, 13D:
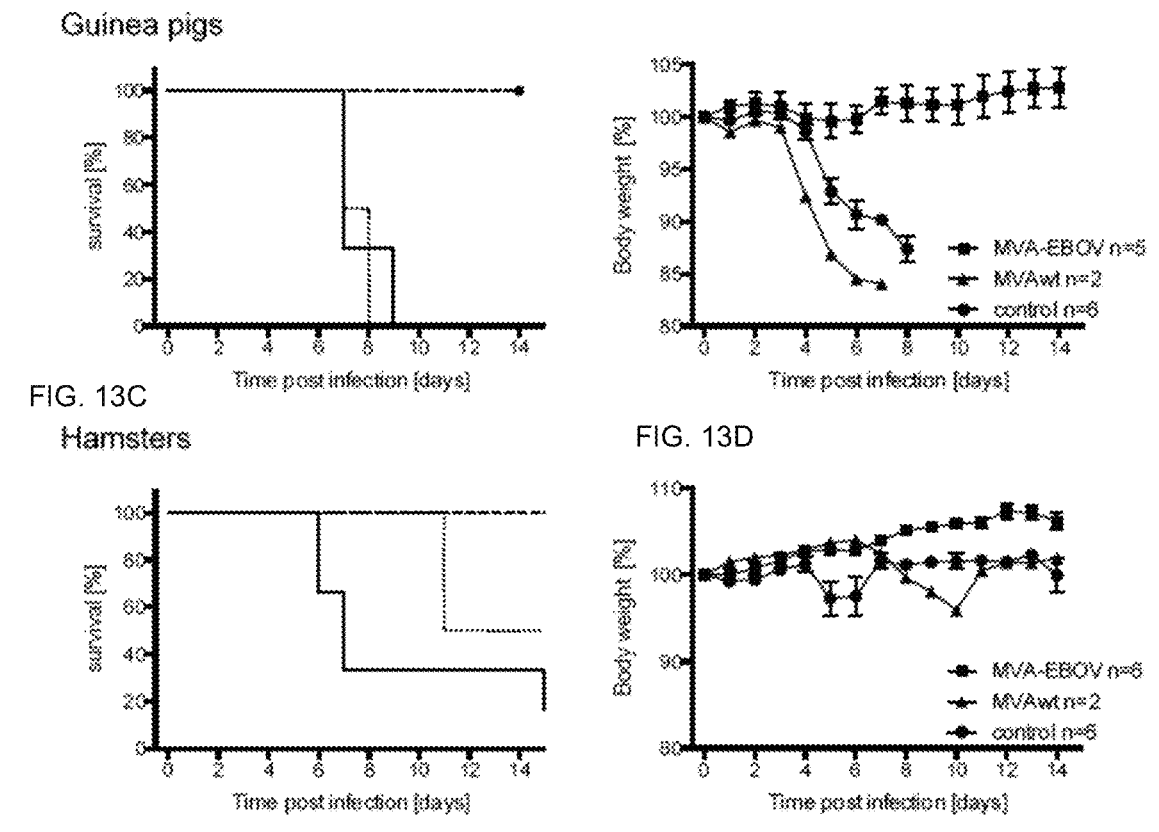

FIG. 13A-FIG. 13B show post challenge survival (left panel FIG. 13A) and body weight charts (right panel FIG. 13B) for guinea pig. FIG. 13C-FIG. 13D show presents post challenge survival (left panel FIG. 13C) and body weight charts (right panel FIG. 13D) for Syrian golden hamster (SGHs). Vaccination with MVA/Z-VLP clearly demonstrates protection against a highly virulent challenge. All of the vaccinated guinea pigs and SGHs survived the challenge.

DETAILED DESCRIPTION OF THE INVENTION

Compositions and methods are provided to produce an immune response to a hemorrhagic fever virus, such as a member of the genus *Ebolavirus, Marburgvirus*, or *Arenavirus*, in a subject in need thereof. The compositions and methods of the present invention can be used to prevent infection in an unexposed person or to treat disease in a subject exposed to a hemorrhagic fever virus who is not yet symptomatic or has minimal symptoms. In one embodiment, treatment limits an infection and/or the severity of disease.

Ideal immunogenic compositions or vaccines have the characteristics of safety, efficacy, scope of protection and longevity, however, compositions having fewer than all of these characteristics may still be useful in preventing viral infection or limiting symptoms or disease progression in an exposed subject treated prior to the development of symptoms. In one embodiment the present invention provides a vaccine that permits at least partial, if not complete, protection after a single immunization.

In one embodiment, the composition is a recombinant vaccine that comprises one or more genes from a hemorrhagic fever virus selected from the group consisting of EBOV, SUDV, BDBV, TAFV, MARV, LASV, and combinations thereof.

In exemplary embodiments, the immune responses are long-lasting and durable so that repeated boosters are not required, but in one embodiment, one or more administrations of the compositions provided herein are provided to boost the initial primed immune response.

I. Definitions

Where a term is provided in the singular, the inventors also contemplate aspects of the invention described by the plural of that term. As used in this specification and in the appended claims, the singular forms "a", "an" and "the" include plural references unless the context clearly dictates otherwise, e.g., "a peptide" includes a plurality of peptides. Thus, for example, a reference to "a method" includes one or more methods, and/or steps of the type described herein and/or which will become apparent to those persons skilled in the art upon reading this disclosure.

The term "antigen" refers to a substance or molecule, such as a protein, or fragment thereof, that is capable of inducing an immune response.

The term "arenavirus" refers to any virus that is a member of the family Arenaviridae.

The term "binding antibody" or "bAb" refers to an antibody which either is purified from, or is present in, a body fluid (e.g., serum or a mucosal secretion) and which recognizes a specific antigen. As used herein, the antibody can be a single antibody or a plurality of antibodies. Binding antibodies comprise neutralizing and non-neutralizing antibodies.

The term "Bundibugyo virus" or "BDBV" refers to a virus belonging to species *Bundibugyo ebolavirus*.

The term "cell-mediated immune response" refers to the immunological defense provided by lymphocytes, such as the defense provided by sensitized T cell lymphocytes when they directly lyse cells expressing foreign antigens and secrete cytokines (e.g., IFN-gamma.), which can modulate macrophage and natural killer (NK) cell effector functions and augment T cell expansion and differentiation. The cellular immune response is the $2^{nd}$ branch of the adaptive immune response.

The term "conservative amino acid substitution" refers to substitution of a native amino acid residue with a non-native residue such that there is little or no effect on the size, polarity, charge, hydrophobicity, or hydrophilicity of the amino acid residue at that position, and without resulting in substantially altered immunogenicity. For example, these may be substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Conservative amino acid modifications to the sequence of a polypeptide (and the corresponding modifications to the encoding nucleotides) may produce polypeptides having functional and chemical characteristics similar to those of a parental polypeptide.

The term "deletion" in the context of a polypeptide or protein refers to removal of codons for one or more amino acid residues from the polypeptide or protein sequence. The term deletion in the context of a nucleic acid refers to removal of one or more bases from a nucleic acid sequence.

The term "Ebola virus" or "EBOV" refers to a virus belonging to species *Zaire ebolavirus*.

The term "*Ebolavirus*" refers to the genus of the family Filoviridae, order Mononegavirales, which includes the five known species: *Zaire ebolavirus, Sudan ebolavirus, Taï Forest ebolavirus* (also known as Ivory Coast ebolavirus or Cote d'Ivoire ebolavirus (CIEBOV)), *Bundibugyo ebolavirus*, and *Reston ebolavirus*.

The term "ebolavirus" or "Ebolavirus" refers to any member of the genus *Ebolavirus*.

The term "filovirus" refers collectively to members of the Filoviridae family of single stranded (–) RNA viruses including ebolaviruses and Marburg viruses.

The term "fragment" in the context of a proteinaceous agent refers to a peptide or polypeptide comprising an amino acid sequence of at least 2 contiguous amino acid residues, at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino acid residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a peptide, polypeptide or protein. In one embodiment, a fragment of a full-length protein retains activity of the full-length protein. In another embodiment, the fragment of the full-length protein does not retain the activity of the full-length protein.

The term "fragment" in the context of a nucleic acid refers to a nucleic acid comprising an nucleic acid sequence of at least 2 contiguous nucleotides, at least 5 contiguous nucleotides, at least 10 contiguous nucleotides, at least 15 contiguous nucleotides, at least 20 contiguous nucleotides, at least 25 contiguous nucleotides, at least 30 contiguous nucleotides, at least 35 contiguous nucleotides, at least 40 contiguous nucleotides, at least 50 contiguous nucleotides, at least 60 contiguous nucleotides, at least 70 contiguous nucleotides, at least contiguous 80 nucleotides, at least 90 contiguous nucleotides, at least 100 contiguous nucleotides, at least 125 contiguous nucleotides, at least 150 contiguous nucleotides, at least 175 contiguous nucleotides, at least 200 contiguous nucleotides, at least 250 contiguous nucleotides, at least 300 contiguous nucleotides, at least 350 contiguous nucleotides, or at least 380 contiguous nucleotides of the nucleic acid sequence encoding a peptide, polypeptide or protein. In a preferred embodiment, a fragment of a nucleic acid encodes a peptide or polypeptide that retains activity of the full-length protein. In another embodiment, the fragment encodes a peptide or polypeptide that of the full-length protein does not retain the activity of the full-length protein.

As used herein, the term "GP" refers to the ebolavirus or marburgivirus surface glycoprotein, or the gene or transcript encoding the ebolavirus or marburgvirus surface glycoprotein.

As used herein, the phrase "heterologous sequence" refers to any nucleic acid, protein, polypeptide or peptide sequence which is not normally associated in nature with another nucleic acid or protein, polypeptide or peptide sequence of interest.

As used herein, the phrase "heterologous gene insert" refers to any nucleic acid sequence that has been, or is to be inserted into the recombinant vectors described herein. The heterologous gene insert may refer to only the gene product encoding sequence or may refer to a sequence comprising a promoter, a gene product encoding sequence (such as GP, VP or Z), and any regulatory sequences associated or operably linked therewith.

The term "homopolymer stretch" refers to a sequence comprising at least four of the same nucleotides uninterrupted by any other nucleotide, e.g., GGGG or TTTTTTT.

The term "humoral immune response" refers to the stimulation of Ab production. Humoral immune response also refers to the accessory proteins and events that accompany antibody production, including T helper cell activation and cytokine production, affinity maturation, and memory cell generation. The humoral immune response is one of two branches of the adaptive immune response.

The term "humoral immunity" refers to the immunological defense provided by antibody, such as neutralizing Ab that can directly block infection; or, binding Ab that identifies a virus or infected cell for killing by such innate immune responses as complement (C')-mediated lysis, phagocytosis, and natural killer cells.

The term "immune response" refers to any response to an antigen or antigenic determinant by the immune system of a subject (e.g., a human). Exemplary immune responses include humoral immune responses (e.g., production of antigen-specific antibodies) and cell-mediated immune responses (e.g., production of antigen-specific T cells).

The term "improved therapeutic outcome" relative to a subject diagnosed as infected with a particular virus (e.g., an ebolavirus) refers to a slowing or diminution in the growth of virus, or viral load, or detectable symptoms associated with infection by that particular virus; or a reduction in the ability of the infected subject to transmit the infection to another, uninfected subject.

The term "inducing an immune response" means eliciting a humoral response (e.g., the production of antibodies) or a cellular response (e.g., the activation of T cells) directed against a virus (e.g., ebolavirus) in a subject to which the composition (e.g., a vaccine) has been administered.

The term "insertion" in the context of a polypeptide or protein refers to the addition of one or more non-native amino acid residues in the polypeptide or protein sequence. Typically, no more than about from 1 to 6 residues (e.g. 1 to 4 residues) are inserted at any one site within the polypeptide or protein molecule.

The term "lassavirus," "Lassa virus," or "LASV" refers to an arenavirus that is any member of the species *Lassa virus*.

The term "marburgvirus" or "Marburgvirus" refers to a filovirus that is any member of the genus *Marburgvirus*.

The term "modified vaccinia Ankara," "modified vaccinia ankara," "Modified Vaccinia Ankara," or "MVA" refers to a highly attenuated strain of vaccinia virus developed by Dr. Anton Mayr by serial passage on chick embryo fibroblast cells; or variants or derivatives thereof. MVA is reviewed in (Mayr, A. et al. 1975 Infection 3:6-14; Swiss Patent No. 568,392).

The term "neutralizing antibody" or "NAb" is meant an antibody which either is purified from, or is present in, a body fluid (e.g., serum or a mucosal secretion) and which recognizes a specific antigen and inhibits the effect(s) of the antigen in the subject (e.g., a human). As used herein, the antibody can be a single antibody or a plurality of antibodies.

The term "non-neutralizing antibody" or "nnAb" refers to a binding antibody that is not a neutralizing antibody.

The term "prevent", "preventing" and "prevention" refers to the inhibition of the development or onset of a condition (e.g., an ebolavirus infection or a condition associated therewith), or the prevention of the recurrence, onset, or development of one or more symptoms of a condition in a subject resulting from the administration of a therapy or the administration of a combination of therapies.

The term "prophylactically effective amount" refers to the amount of a composition (e.g., the recombinant MVA vector or pharmaceutical composition) which is sufficient to result in the prevention of the development, recurrence, or onset of a condition or a symptom thereof (e.g., an ebolavirus infection or a condition or symptom associated therewith or to enhance or improve the prophylactic effect(s) of another therapy.

The term "recombinant" means a polynucleotide of semi-synthetic, or synthetic origin that either does not occur in nature or is linked to another polynucleotide in an arrangement not found in nature.

The term "recombinant," with respect to a viral vector, means a vector (e.g., a viral genome that has been manipulated in vitro, e.g., using recombinant nucleic acid techniques to express heterologous viral nucleic acid sequences.

The term "regulatory sequence" "regulatory sequences" refers collectively to promoter sequences, polyadenylation signals, transcription termination sequences, upstream regulatory domains, origins of replication, internal ribosome entry sites ("IRES"), enhancers, and the like, which collectively provide for the transcription and translation of a coding sequence. Not all of these control sequences need always be present so long as the selected gene is capable of being transcribed and translated.

The term "shuttle vector" refers to a genetic vector (e.g., a DNA plasmid) that is useful for transferring genetic material from one host system into another. A shuttle vector can replicate alone (without the presence of any other vector) in at least one host (e.g., *E. coli*). In the context of MVA vector construction, shuttle vectors are usually DNA plasmids that can be manipulated in *E. coli* and then introduced into cultured cells infected with MVA vectors, resulting in the generation of new recombinant MVA vectors.

The term "silent mutation" means a change in a nucleotide sequence that does not cause a change in the primary structure of the protein encoded by the nucleotide sequence, e.g., a change from AAA (encoding lysine) to AAG (also encoding lysine).

The term "subject" is means any mammal, including but not limited to, humans, domestic and farm animals, and zoo, sports, or pet animals, such as dogs, horses, cats, cows, rats, mice, guinea pigs and the like.

The term "Sudan virus" or SUDV refers to a virus belonging to species *Sudan ebolavirus*.

The term "surrogate endpoint" means a clinical measurement other than a measurement of clinical benefit that is used as a substitute for a measurement of clinical benefit.

The term "surrogate marker" means a laboratory measurement or physical sign that is used in a clinical or animal trial as a substitute for a clinically meaningful endpoint that is a direct measure of how a subject feels, functions, or survives and is expected to predict the effect of the therapy (Katz, R., NeuroRx 1:189-195 (2004); New drug, antibiotic, and biological drug product regulations; accelerated approval—FDA. Final rule. Fed Regist 57: 58942-58960, 1992.)

The term "surrogate marker for protection" means a surrogate marker that is used in a clinical or animal trial as a substitute for the clinically meaningful endpoint of prevention of ebolavirus or marburgvirus infection.

The term "synonymous codon" refers to the use of a codon with a different nucleic acid sequence to encode the same amino acid, e.g., AAA and AAG (both of which encode lysine). Codon optimization changes the codons for a protein to the synonymous codons that are most frequently used by a vector or a host cell.

The term "Taï forest virus" or "TAFV" refers to a virus belonging to species *Taï forest ebolavirus*.

The term "therapeutically effective amount" means the amount of the composition (e.g., the recombinant MVA vector or pharmaceutical composition) that, when administered to a mammal for treating an infection, is sufficient to effect such treatment for the infection.

The term "treating" or "treat" refer to the eradication or control of a filovirus, a reduction in the titer of the filovirus, a reduction in the numbers of the filovirus, the reduction or amelioration of the progression, severity, and/or duration of a condition or one or more symptoms caused by the filovirus resulting from the administration of one or more therapies, or the reduction or elimination of the subject's ability to transmit the infection to another, uninfected subject.

The term "vaccine" means material used to provoke an immune response and confer immunity after administration of the material to a subject. Such immunity may include a cellular or humoral immune response that occurs when the subject is exposed to the immunogen after vaccine administration.

The term "vaccine insert" refers to a nucleic acid sequence encoding a heterologous sequence that is operably linked to a promoter for expression when inserted into a recombinant vector. The heterologous sequence may encode a glycoprotein or matrix protein described here.

The term "viral infection" means an infection by a viral pathogen (e.g., a member of genus *Ebolavirus*) wherein there is clinical evidence of the infection based on symptoms or based on the demonstration of the presence of the viral pathogen in a biological sample from the subject.

The term "virus-like particles" or "VLP" refers to a structure which resembles the native virus antigenically and morphologically.

The term "VP40" refers to the ebolavirus or marburgvirus large matrix protein, or the gene or transcript encoding the ebolavirus or marburgvirus large matrix protein.

II. Filoviruses

The compositions of the present invention are useful for inducing an immune response to a filovirus. The Filoviridae family includes genera *Marburgvirus, Ebolavirus* and *Cuevavirus*. Filoviruses are enveloped, negative strand RNA viruses having a thread-like appearance.

Members of genera *Ebolavirus* and *Marburgvirus* are among the most pathogenic viruses in humans and non-human primates (Feldman and Klenk, 1996, Adv. Virus Res. 47, 1), both causing severe hemorrhagic fever (HF) (Johnson et al., 1997, Lancet 1, no. 8011, P. 569).

Both are zoonotic agents, where human outbreaks initially occur as a result of direct contact with infected wildlife, with subsequent person-to-person transmission through contact with bodily fluids. Although the ecology of these agents remains incompletely understood, several species of African fruit bats may be reservoirs for members of genera *Ebolavirus* and *Marburgvirus*. Filovirus outbreaks are sporadic, sometimes interspersed by years or even decades of no apparent disease activity.

A. Ebolavirus Species and Sequences

The term *Ebolavirus* refers to a genus within the family Filoviridae. Like other filoviruses, species within the *Ebolavirus* genus consist of a single strand of negative sense RNA that is approximately 19 kb in length. The RNA contains seven sequentially arranged genes that produce 8 mRNAs upon infection. Ebolavirus virions, like virions of other filoviruses, contain seven proteins: (1) a surface glycoprotein (GP), (2) a nucleoprotein (NP), (3-6) four virion structural proteins (VP40, VP35, VP30, and VP24), and an (7) RNA-dependent RNA polymerase (L). The glycoprotein of an ebolavirus is unlike other filoviruses in that it is encoded in two open reading frames. Transcriptional editing is needed to express the transmembrane form that is incorporated into the virion. The unedited form produces a nonstructural secreted glycoprotein (sGP) that is synthesized in large amounts early during the course of infection.

Based on nucleotide sequence and outbreak location, isolates in genus *Ebolavirus* are classified into five antigenically distinct species: *Zaire ebolavirus, Sudan ebolavirus, Taï Forest ebolavirus* (also known as Ivory Coast ebolavirus or Cote d'Ivoire ebolavirus (CIEBOV)), *Bundibugyo ebolavirus*, and *Reston ebolavirus*. Known viruses belonging to species *Zaire ebolavirus* are commonly referred to as Ebola viruses(EBOV). Known viruses belonging to species *Sudan ebolavirus* are commonly referred to as Sudan viruses (SUDV). Known viruses belonging to species *Taï Forest ebolavirus* are commonly referred to as Tai Forest viruses (TAFV). Known viruses belonging to species *Bundibugyo ebolavirus* are commonly referred to as Bundibugyo viruses (BDBV). Known viruses belonging to species *Marburg marburgvirus* include Marburg virus (MARV) and Ravn virus (RAVV).

Of these, EBOV and SUDV are the most pathogenic, and are the only two that have been associated with recurring outbreaks. Together, EBOV and SUDV account for 94% of EBOV-related deaths.

Infection by a member of genus *Ebolavirus* can lead to Ebola Hemorrhagic Fever (EHF), also known as Ebola Virus Disease (EVD) the clinical manifestations of which are severe. The incubation period varies between 2 to 21 days after exposure to the virus, but the average is 8 to 10 days. The different species in genus *Ebolavirus* are believed to cause somewhat different clinical syndromes. Even within a single species, variation among strains can cause differences in clinical symptoms. However, opportunities for close observation of the diseases under good conditions have been rare.

The initial symptoms of EHF are generally a severe frontal and temporal headache, generalized aches and pains, malaise, and by the second day the victim will often have a fever. The subsequent signs and symptoms indicate multi-system involvement and include systemic (prostration), gastrointestinal (anorexia, nausea, vomiting, abdominal pain, diarrhea), respiratory (chest pain, shortness of breath, cough, nasal discharge), vascular (conjunctival injection, postural hypotension, oedema) and neurological (headache, confusion, coma) manifestations. Hemorrhagic manifestations arise during the peak of the illness and include petechiae, ecchymoses, uncontrolled oozing from venipuncture sites, mucosal hemorrhages, and post-mortem evidence of visceral hemorrhagic effusions. A macropapular rash associated with varying severity of erythema and desquamate can often be noted by day 5-7 of the illness; this symptom is a valuable differential diagnostic feature and is usually followed by desquamation in survivors. Abdominal pain is sometimes associated with hyperamylasaemia and true pancreatitis. In later stages, shock, convulsions, severe metabolic disturbances, and, in more than half the cases, diffuse coagulopathy supervene. See Sanchez A, Geisbert T W, Feldmann H. Filoviridae: Marburg and Ebola viruses. In: Knipe D M, Howley P M, eds. Fields virology. Philadelphia: Lippincott Williams & Wilkins, 2006: 1409-1448; Pattyn S R. Ebola virus haemorrhagic fever. Amsterdam: Elsevier, North-Holland, 1978; Peters C J, LeDuc L W. Ebola: the virus and the disease. J Infect Dis 1999; 179 (suppl 1): S1-S288; Feldmann H, Geisbert T, Kawaoka Y. Filoviruses: recent advances and future challenges. J Infect Dis 2007; 196 (suppl 2): S129-S443.

Patients with fatal disease develop clinical signs early during infection and typically die between day 6 and 16 as a result of hypovolaemic shock and multiorgan failure. Hemorrhages can be severe but are only present in fewer than half of patients. In non-fatal cases, patients typically have a fever for several days and improve around day 6-11, about the time that the humoral antibody response is noted. Patients with non-fatal or asymptomatic disease mount specific IgM and IgG responses that seem to be associated with a temporary early and strong inflammatory response, including interleukin β, interleukin 6, and tumour necrosis factor α (TNFα).

While case fatality rates vary between outbreaks and among the *Ebolavirus* species, *Zaire ebolavirus* has been associated with up to 90% mortality, while *Sudan ebolavirus* has been associated with up to 60% mortality.

Using current methodology, ebolavirus is detectable in blood only after onset of symptoms, which accompany the rise in circulating virus. It may take up to three days after symptoms start for the virus to reach detectable levels. Laboratory tests used in diagnosis include, for example, antigen-capture enzyme-linked immunosorbent assay (ELISA) testing, IgM ELISA, polymerase chain reaction (PCR), virus isolation, and—later in the course of infection or recovery—detection of IgM and IgG antibodies.

No vaccine or therapeutic has been approved by the FDA for ebolavirus, for either prophylactic or therapeutic use. Present treatment strategies are primarily symptomatic and supportive. In developing countries, these strategies typically include isolation, malaria treatment, broad spectrum antibiotics, and antipyretics before diagnosis. Fluid substitution, preferentially intravenous administration, and analgesics may also be provided. In developed countries with facilities having appropriate isolation units, intensive care treatment is provided and directed towards maintenance of effective blood volume and electrolyte balance. Shock, cerebral edema, renal failure, coagulation disorders, and secondary bacterial infection must also be managed. Organ failure is also addressed, e.g., by dialysis for kidney failure and extracorporeal membrane oxygenation for lung failure.

B. Marburg Virus Species and Sequences

Marburgviruses are substantially identical structurally to ebolaviruses. The marburgvirus genome consists of a single strand of negative sense RNA that is approximately 19.1 kb in length and which encodes a series of polypeptides that correspond in sequence and function to those of ebolaviruses, although the exact intergenic regions are different between the two genera. Thus, a marburgvirus consists of seven polypeptides, which are (as in ebolaviruses) the envelope glycoprotein (GP), the nucleoprotein (NP), matrix proteins VP24 and VP40, the transcription factor VP30, the polymerase cofactor VP35, and the viral polymerase.

Only one species of marburgvirus has been reported, *Marburg marburgvirus* (formerly Lake Victoria marburgvirus), and two individual viruses, Marburg virus (MARV) and Ravn virus (RAVN), within this species.

Marburg hemorrhagic fever (MHF) may affects both humans and non-human primates. After an incubation period of 5-10 days, the onset of the disease is sudden and is marked by fever, chills, headache, and myalgia. Around the fifth day after the onset of symptoms, a maculopapular rash, most prominent on the trunk (chest, back, stomach), may occur. Nausea, vomiting, chest pain, a sore throat, abdominal pain, and diarrhea may then appear. Symptoms become increasingly severe and may include jaundice, inflammation of the pancreas, severe weight loss, delirium, shock, liver failure, massive hemorrhaging, and multi-organ dysfunction.

There is no vaccine for marburgvirus approved by the FDA, either prophylactic or therapeutic. As with EHF, current treatment generally currently consists of supportive therapy, including maintenance of blood volume and electrolyte balance, as well as analgesics and standard nursing care.

C. Lassa Virus Species and Sequences

Lassa virus is an arenavirus belonging to genus *Arenavirus*, family Arenaviridae. The arenavirus genome consists of two single-stranded negative-sense RNAs, one approximately 7.2 kb in length and the other approximately 3.5 kb in length. Each of the RNAs encodes two proteins. The gene sequences for the proteins are oriented in opposite directions; this arrangement is referred to as an ambisense coding strategy. The large (7.2 kb) genomic RNA encodes the RNA-dependent RNA polymerase (L) protein and the matrix (Z) protein. The small (3.5 kb) genomic RNA encodes the nucleoprotein (NP) and the glycoprotein precursor (GP). On each genomic RNA, the two genes are separated by an intergenic region (IGR) The ambisense coding strategy results in different mechanisms of transcription for the four proteins. The NP and L mRNAs are transcribed directly from the genomic RNA. The GP and Z mRNAs, on the other hand, are translated from anti-genomic RNAs. The IGR is believed to serve as a signal for termination of transcription. (Shao et al. (2015), Pathogens 4: 283-306).

Lassa fever is the acute hemorrhagic fever caused by Lassa virus. Symptoms typically appear 6-21 days after infection. Approximately 80% of cases are mild, involving mild fever, general malaise, weakness, and headache. In approximately 20% of cases, Lassa fever causes more severe symptoms including high fever, sore throat, mucosal bleeding, respiratory distress, vomiting, swelling, severe pain, and shock. Certain neurological problems may also occur. Of patients hospitalized for Lassa fever, approximately 15%-20% die from the infection (Kyei et al. (2015), BMC Infectious Diseases 15:217). Unlike filoviruses, which cause sporadic outbreaks, Lassa virus is a common human pathogen that causes endemic disease in a large area of West Africa (Andersen et al. (2015), Cell 162:738-750). Official estimates indicate 300,000-500,000 cases of Lassa fever each year with approximately 5,000-10,000 deaths; however, other measures indicate that the disease may be much more serious, accounting for as many as 3 million cases and 67,000 deaths annually (Leski et al. (2015) Emerging Infectious Diseases 21(4):609-618). Several experimental vaccines against LASV have been tested in animal models. To date, however, no Lassa fever vaccine has yet been approved for sale (Falzarano and Feldmann (2015), Current Opinion in Virology 3:343-351). Other than supportive care, there are few options for treatment of Lassa virus infection. Only the broad-spectrum antiviral drug ribavirin has shown efficacy, and it must be used early in the course of the disease in order to be effective (Ölschläger and Flatz (2013), PLoS Pathogens 9(4):e1003212).

III. Recombinant Viral Vectors

In one aspect, the present invention is a recombinant viral vector comprising one or more genes of a hemorrhagic fever virus, such as an *Ebolavirus*, a *Marburgvirus*, or an *Arenavirus*. In certain embodiments, the recombinant viral vector is a vaccinia viral vector, and more particularly, an MVA vector, comprising one or more genes of a hemorrhagic fever virus, such as an *Ebolavirus*, a *Marburgvirus*, or an *Arenavirus*.

Vaccinia viruses have also been used to engineer viral vectors for recombinant gene expression and for the potential use as recombinant live vaccines (Mackett, M. et al 1982 PNAS USA 79:7415-7419; Smith, G. L. et al. 1984 Biotech Genet Engin Rev 2:383-407). This entails DNA sequences (genes) which code for foreign antigens being introduced, with the aid of DNA recombination techniques, into the genome of the vaccinia viruses. If the gene is integrated at a site in the viral DNA which is non-essential for the life cycle of the virus, it is possible for the newly produced recombinant vaccinia virus to be infectious, that is to say able to infect foreign cells and thus to express the integrated DNA sequence (EP Patent Applications No. 83,286 and No. 110,385). The recombinant vaccinia viruses prepared in this way can be used, on the one hand, as live vaccines for the prophylaxis of infectious diseases, on the other hand, for the preparation of heterologous proteins in eukaryotic cells.

Several such strains of vaccinia virus have been developed to avoid undesired side effects of smallpox vaccination. Thus, a modified vaccinia Ankara (MVA) has been generated by long-term serial passages of the Ankara strain of vaccinia virus (CVA) on chicken embryo fibroblasts (for review see Mayr, A. et al. 1975 Infection 3:6-14; Swiss Patent No. 568,392). The MVA virus is publicly available from American Type Culture Collection as ATCC No.: VR-1508. MVA is distinguished by its great attenuation, as demonstrated by diminished virulence and reduced ability to replicate in primate cells, while maintaining good immunogenicity. The MVA virus has been analyzed to determine alterations in the genome relative to the parental CVA strain. Six major deletions of genomic DNA (deletion I, II, III, IV, V, and VI) totaling 31,000 base pairs have been identified (Meyer, H. et al. 1991 J Gen Virol 72:1031-1038). The resulting MVA virus became severely host cell restricted to avian cells.

Furthermore, MVA is characterized by its extreme attenuation. When tested in a variety of animal models, MVA was proven to be avirulent even in immunosuppressed animals. More importantly, the excellent properties of the MVA strain have been demonstrated in extensive clinical trials (Mayr A. et al. 1978 Zentralbl Bakteriol [B] 167:375-390; Stickl et al. 1974 Dtsch Med Wschr 99:2386-2392). During these studies in over 120,000 humans, including high-risk patients, no side effects were associated with the use of MVA vaccine. MVA replication in human cells was found to be blocked late in infection preventing the assembly to mature infectious virions. Nevertheless, MVA was able to express viral and recombinant genes at high levels even in non-permissive cells and was proposed to serve as an efficient and exceptionally safe gene expression vector (Sutter, G. and Moss, B. 1992 PNAS USA 89:10847-10851). Additionally, novel vaccinia vector vaccines were established on the basis of MVA having foreign DNA sequences inserted at the site of deletion III within the MVA genome (Sutter, G. et al. 1994 Vaccine 12:1032-1040).

Recombinant MVA vaccinia viruses can be prepared as set out hereinafter. A DNA-construct which contains a DNA-sequence which codes for a foreign polypeptide flanked by MVA DNA sequences adjacent to a predetermined insertion site (e.g. between two conserved essential MVA genes such as I8R/G1L; in restructured and modified deletion III; or at other non-essential sites within the MVA genome) is introduced into cells infected with MVA, to allow homologous recombination. Once the DNA-construct has been introduced into the eukaryotic cell and the foreign DNA has recombined with the viral DNA, it is possible to isolate the desired recombinant vaccinia virus in a manner known per se, preferably with the aid of a marker. The DNA-construct to be inserted can be linear or circular. A plasmid or polymerase chain reaction product is preferred. Such methods of making recombinant MVA vectors are described in PCT publication WO/2006/026667 incorporated by reference herein. The DNA-construct contains sequences flanking the left and the right side of a naturally occurring deletion. The foreign DNA sequence is inserted between the sequences flanking the naturally occurring deletion. For the expression of a DNA sequence or gene, it is necessary for regulatory sequences, which are required for the transcription of the gene, to be present on the DNA. Such regulatory sequences (called promoters) are known to those skilled in the art, and include for example those of the vaccinia 11 kDa gene as are described in EP-A-198,328, and those of the 7.5 kDa gene (EP-A-110,385). The DNA-construct can be introduced into the MVA infected cells by transfection, for example by means of calcium phosphate precipitation (Graham et al. 1973 Virol 52:456-467; Wigler et al. 1979 Cell 16:777-785), by means of electroporation (Neumann et al. 1982 EMBO J. 1:841-845), by microinjection (Graessmann et al. 1983 Meth Enzymol 101:482-492), by means of liposomes (Straubinger et al. 1983 Meth Enzymol 101:512-527), by means of spheroplasts (Schaffher 1980 PNAS USA 77:2163-2167) or by other methods known to those skilled in the art.

The MVA vectors described and tested herein were unexpectedly found to be effective after a single prime or a homologous prime/boost regimen. Other MVA vector designs require a heterologous prime/boost regimen while still other published studies have been unable to induce effective immune responses with MVA vectors. Conversely, the present MVA vector design and methods of manufacture are useful in producing effective MVA vaccine vectors for eliciting effective T-cell and antibody immune responses. Furthermore, the utility of an MVA vaccine vector capable of eliciting effective immune responses and antibody production after a single homologous prime boost is significant for considerations such as use, commercialization and transport of materials especially to affected third world locations.

In one embodiment, the present invention is a recombinant viral vector (e.g., an MVA vector) comprising one or more heterologous gene inserts of a filovirus (e.g., an ebolavirus or marburgvirus). The viral vector (e.g., an MVA vector) may be constructed using conventional techniques known to one of skill in the art. The one or more heterologous gene inserts encode a polypeptide having desired immunogenicity, i.e., a polypeptide that can induce an immune reaction, cellular immunity and/or humoral immunity, in vivo by administration thereof. The gene region of the viral vector (e.g., an MVA vector) where the gene encoding a polypeptide having immunogenicity is introduced is flanked by regions that are indispensable. In the introduction of a gene encoding a polypeptide having immunogenicity, an appropriate promoter may be operatively linked upstream of the gene encoding a polypeptide having desired immunogenicity.

The one or more genes may be selected from any species of hemorrhagic fever virus. In one embodiment, the one more genes are selected from an *Ebolavirus, Marburgvirus* or *Arenavirus* species, and more particularly, a hemorrhagic fever virus selected from the group consisting of EBOV, SUDV, TAFV, BDBV, RESTV, MARV, and LASV, or a combination thereof. In exemplary embodiments, the gene encodes a polypeptide or protein capable of inducing an immune response in the subject to which it is administered, and more particularly, an immune response capable of providing a protective and/or therapeutic benefit to the subject. In one embodiment, the one or more genes encode the virus glycoprotein (GP), the secreted GP (sGP), the major nucleoprotein (NP), RNA-dependent RNA polymerase (L), or one or more virion structural proteins (e.g., Z, VP40, VP35, VP30, or VP24)). The heterologous gene inserts are inserted into one or more deletion sites of the vector under the control of promoters compatible with poxvirus expression systems.

In one embodiment, the deletion III site is restructured and modified to remove non-essential flanking sequences.

In exemplary embodiments, the vaccine is constructed to express an ebolavirus GP for example EBOV GP, which is inserted between two conserved essential MVA genes (I8R and G1L) using shuttle vector pGeo-GP; and to express EBOV VP40, which is inserted into deletion III using shuttle vector pGeo-VP40. pGeo-GP and pGeo-VP40 are constructed with an ampicillin resistance marker, allowing the vector to replicate in bacteria; with two flanking sequences, allowing the vector to recombine with a specific location in the MVA genome; with a green fluorescent protein (GFP) selection marker, allowing the selection of recombinant MVAs; with a sequence homologous to part of Flank 1 of the MVA sequence, enabling removal of the GFP sequence from the MVA vector after insertion of VP40 into the MVA genome; with a modified H5 (mH5) promoter, which enables transcription of the inserted heterologous gene insert; and with a filovirus gene. pGeo-GP and pGeo-VP40 differ in that pGeo-GP contains the GP sequence, whereas pGeo-VP40 contains the VP40 sequence; and in that pGeo-GP recombines with sequences of MVA I8R and G1L (two essential genes) and pGeo-VP40 recombines with regions flanking the restructured and modified Deletion III of MVA.

In exemplary embodiments, the present invention provides a recombinant MVA vector comprising a gene encoding the glycoprotein (GP) gene and a gene encoding VP40, in each case, from an ebolavirus, marburgvirus, or Lassa virus.

In certain embodiments, the polypeptide, or the nucleic acid sequence encoding the polypeptide, may have a mutation or deletion (e.g., an internal deletion, truncation of the amino- or carboxy-terminus, or a point mutation).

The one or more genes introduced into the recombinant viral vector are under the control of regulatory sequences that direct its expression in a cell.

The nucleic acid material of the viral vector may be encapsulated, e.g., in a lipid membrane or by structural proteins (e.g., capsid proteins), that may include one or more viral polypeptides.

In exemplary embodiments, the present invention is a recombinant viral vector (e.g., a recombinant MVA vector) comprising one or more genes, or one or more polypeptides encoded by the gene or genes, from an ebolavirus, marburgvirus, or Lassa virus. The ebolavirus, marburgvirus, or Lassa virus gene may encode a polypeptide or protein capable of inducing an immune response in the subject to which it is administered, and more particularly, an immune response capable of providing a protective and/or therapeutic benefit to the subject, e.g., the ebolavirus, marburgvirus, or Lassa virus glycoprotein. As used herein, the term "ebolavirus, marburgvirus, or Lassa virus glycoprotein" refers to the glycoprotein polypeptide encoded by the ebolavirus, marburgvirus, or Lassa virus genome, whether in secreted or transmembrane bound form, or any fragment or mutation of the glycoprotein polypeptide, that is encoded by the ebolavirus, marburgvirus, or Lassa virus genome so long as it has the ability to induce or enhance an immune response or confer a protective or therapeutic benefit to the subject, e.g., against one or more of SUDV, EBOV, TAFV, BDBV, MARV, or LASV. The nucleic acid sequences of ebolavirus, marburgvirus, or Lassa virus glycoproteins are published and are available from a variety of sources, including, e.g., GenBank and PubMed. Exemplary GenBank references including ebolavirus, marburgvirus, or Lassa virus glycoprotein sequences include those corresponding to accession numbers KM233103 (EBOV, 2014 strain), KC242798 (EBOV, central sequence), KC545390 (SUDV), KC545396 (BDBV), NC 001608 (MARV), and JN650517 (LASV GP and NP) and JN650518 (LASV Z).

In certain embodiments, the one or more genes encodes a polypeptide, or fragment thereof, that is substantially identical (e.g., at least 60%, 65%, 70%, 75%, 80%, 85%, 90%, 95%, 98%, 99%, or even 100% identical) to the selected ebolavirus, marburgvirus, or Lassa virus glycoprotein over at least 20, 25, 30, 35, 40, 45, 50, 55, 60, 65, or 70 contiguous residues of the selected ebolavirus, marburgvirus, or Lassa virus glycoprotein that retain immunogenic activity.

In exemplary embodiments, the recombinant viral vector may also include an ebolavirus, marburgvirus, or Lassa virus glycoprotein present on its surface. The ebolavirus, marburgvirus, or Lassa virus glycoprotein may be obtained by any suitable means, including, e.g., application of genetic engineering techniques to a viral source, chemical synthesis techniques, recombinant production, or any combination thereof.

In another embodiments, the present invention is a recombinant MVA vector comprising at least one heterologous gene insert from an ebolavirus, marburgvirus, or Lassa virus, wherein the gene is selected from the group encoding the glycoprotein (GP), the secreted GP (sGP), the major nucleoprotein (NP), RNA-dependent RNA polymerase (L), or one or more other viral proteins (e.g., Z, VP40, VP35, VP30, or VP24)).

In a particular embodiment, the present invention is a recombinant MVA vector comprising a gene encoding GP and a gene encoding VP40. In another embodiment, the present invention is a recombinant MVA vector comprising genes encoding GP, Z, and NP. The heterologous gene inserts are inserted into one or more deletion sites of the MVA vector under the control of promoters compatible with poxvirus expression systems.

In one embodiment, the GP is inserted into deletion site I, II, III, IV, V or VI of the MVA vector, and the VP40 is inserted into deletion site I, II, III, IV, V or VI of the MVA vector.

In one embodiment, the GP is inserted between I8R and G1L of the MVA vector, or into restructured and modified deletion III of the MVA vector; and the VP40 is inserted between I8R and G1L of the MVA vector, or into restructured and modified deletion site III of the MVA vector.

In one embodiment relating to LASV, the GP is inserted into deletion site I, II, III, IV, V or VI of the MVA vector, and the Z is inserted into deletion site I, II, III, IV, V or VI of the MVA vector.

In one embodiment, the recombinant vector comprises in a first deletion site, a gene encoding GP operably linked to a promoter compatible with poxvirus expression systems, and in a second deletion site, genes encoding Z and NP in reverse orientation each operably linked to a promoter compatible with poxvirus expression systems.

In one embodiment relating to LASV, the GP is inserted between I8R and G1L of the MVA vector, or into restructured and modified deletion III of the MVA vector; and the Z is inserted between I8R and G1L of the MVA vector, or into restructured and modified deletion site III of the MVA vector.

In another embodiment relating to LASV, the GP and Z are inserted into different deletion sites. For example, the GP sequence is inserted between two essential and highly conserved MVA genes, I8R/G1L, to limit the formation of viable deletion mutants; and, the Z sequence is inserted into a restructured and modified deletion III site.

In exemplary embodiments, the present invention is a recombinant MVA vector comprising at least one heterologous gene insert (e.g., one or more gene inserts) from an ebolavirus or a marburgvirus which is under the control of regulatory sequences that direct its expression in a cell. The gene may be, for example, under the control of a promoter selected from the group consisting of Pm2H5, Psyn II, or mH5 promoters.

The recombinant viral vector of the present invention can be used to infect cells of a subject, which, in turn, promotes the translation into a protein product of the one or more viral genes of the viral vector (e.g., an ebolavirus, marburgvirus, or Lassa virus glycoprotein). As discussed further herein, the recombinant viral vector can be administered to a subject so that it infects one or more cells of the subject, which then promotes expression of the one or more viral genes of the viral vector and stimulates an immune response that is protective against infection by an ebolavirus, marburgvirus, or Lassa virus (e.g., EBOV) or that reduces or prevents infection by an ebolavirus, marburgvirus, or Lassa virus (e.g., EBOV).

In one embodiment, the recombinant MVA vaccine expresses proteins that assemble into virus-like particles (VLPs) comprising the GP (glycoprotein), and VP40 (matrix protein). While not wanting to be bound by any particular theory, it is believed that the GP is provided to elicit a protective immune response and the VP40 (matrix protein) is provided to enable assembly of VLPs and as a target for T cell immune responses, thereby enhancing the protective immune response and providing cross-protection.

Similarly relating to LASV, in one embodiment, the recombinant MVA vaccine expresses proteins that assemble into virus-like particles (VLPs) comprising the GP (glycoprotein), and Z (matrix protein). While not wanting to be bound by any particular theory, it is believed that the GP is provided to elicit a protective immune response and the Z (matrix protein) is provided to enable assembly of VLPs and as a target for T cell immune responses, thereby enhancing the protective immune response and providing cross-protection.

For references, see Stahelin, *Front in Microbiol* 5:300 (2014); Marzi et al., *J Infect Dis* 204 Suppl 3:S1066 (2011); Warfield and Aman, *J Infect Dis* 204 Suppl 3:S1053 (2011); and Mire et al., *PLoS Negl Trop Dis* 7:e2600 (2013).

One or more genes may be optimized for use in an MVA vector. Optimization includes codon optimization, which employs silent mutations to change selected codons from the native sequences into synonymous codons that are optimally expressed by the host-vector system. Other types of optimization include the use of silent mutations to interrupt homopolymer stretches or transcription terminator motifs. Each of these optimization strategies can improve the stability of the gene, improve the stability of the transcript, or improve the level of protein expression from the gene. In exemplary embodiments, the number of homopolymer stretches in the GP or VP40 sequence will be reduced to stabilize the construct. A silent mutation may be provided for anything similar to a vaccinia termination signal. An extra nucleotide may be added in order to express the transmembrane, rather than the secreted, form of ebolavirus GP.

In exemplary embodiments, the GP and VP40 sequences are codon optimized for expression in MVA using a computer algorithm; GP and VP40 sequences with runs of ≥5 deoxyguanosines, ≥5 deoxycytidines, ≥5 deoxyadenosines, and ≥5 deoxythymidines are interrupted by silent mutation to minimize loss of expression due to frame shift mutations; and the GP sequence is modified through addition of an extra nucleotide to express the transmembrane, rather than the secreted, form of ebolavirus GP.

In one embodiment, the present invention provides a vaccine vector composition that is monovalent. As used herein the term monovalent refers to a vaccine vector composition that contains GP and matrix sequences from one species of *ebolavirus, Marbugvirus*, or *Arenavirus*.

In another embodiment, the present invention provides a vaccine that is bivalent. As used herein the term monovalent refers to a vaccine vector composition that contains two vectors having GP and matrix sequences from different species of *ebolavirus, Marbugvirus*, or *Arenavirus*.

In another embodiment, the present invention provides a vaccine that is trivalent. As used herein the term trivalent refers to a vaccine vector composition that contains three vectors having GP and matrix sequences from different species of *ebolavirus, Marbugvirus*, or *Arenavirus*.

In another embodiment, the present invention provides a vaccine that is quadrivalent. As used herein the term quadrivalent refers to a vaccine vector composition that contains four vectors having GP and matrix sequences from different species of *ebolavirus, Marbugvirus*, or *Arenavirus*. As used herein, the terms tetravalent and quadrivalent are synonymous.

In one embodiment, the recombinant viral vector (e.g., an MVA vector) comprises two heterologous gene inserts from an *Ebolavirus* species, a *Marbugvirus* species, or an *Arenavirus* species, wherein the first heterologous gene insert and the second heterologous gene insert are from the same species of *Ebolavirus, Marbugvirus*, or *Arenavirus* species.

In another embodiment, the recombinant viral vector (e.g., an MVA vector) comprises two heterologous gene inserts from an *Ebolavirus* species, a *Marbugvirus* species, or an *Arenavirus* species, wherein the first heterologous gene insert is from an *Ebolavirus, Marbugvirus*, or *Arenavirus* species different than the second heterologous gene insert. In one embodiment, the first heterologous gene insert is from the EBOV virus and the second heterologous gene insert is from an ebolavirus or a marburgvirus selected from SUDV, TAFV, BDBV, RESTV, MARV, or LASV.

In exemplary embodiments, the recombinant viral vector (e.g., an MVA vector) comprises three heterologous gene inserts from an *Ebolavirus* species, or a *Marbugvirus* species, or an *Arenavirus* species, wherein the first heterologous gene insert is from an *Ebolavirus* species, a *Marbugvirus* species, or an *Arenavirus* species different at least from one of the second or third heterologous gene inserts. In one embodiment, the first heterologous gene insert is from the EBOV virus and the second and third heterologous gene inserts are selected from an ebolavirus or a marburgvirus selected from SUDV, TAFV, BDBV, RESTV, MARV, or LASV. The second and third heterologous gene inserts may be the same or different.

The recombinant viral vectors of the present invention may be used alone, or in combination. In one embodiment, two different recombinant viral vectors are used in combination, where the difference may refer to the one or more heterologous gene inserts or the other components of the recombinant viral vector or both. In exemplary embodiments, two or more recombinant viral vectors are used in combination in order to protect against infection by all versions of ebolavirus, marburgvirus, and Lassa virus known to be lethal in humans.

The present invention also extends to host cells comprising the recombinant viral vector described above, as well as isolated virions prepared from host cells infected with the recombinant viral vector.

IV. Pharmaceutical Composition

The recombinant viral vectors of the present invention are readily formulated as pharmaceutical compositions for veterinary or human use, either alone or in combination. The pharmaceutical composition may comprise a pharmaceutically acceptable diluent, excipient, carrier, or adjuvant.

In one embodiment, the present invention is a vaccine effective to protect and/or treat a hemorrhagic fever virus (e.g., an ebolavirus) comprising a recombinant MVA vector that expresses at least one hemorrhagic fever virus polypeptide (e.g., a GP) or an immunogenic fragment thereof. The vaccine composition may comprise one or more additional therapeutic agents.

The pharmaceutical composition may comprise 1, 2, 3, 4 or more than 4 different recombinant MVA vectors.

In one embodiment, the present invention provides a vaccine vector composition that is monovalent. As used herein the term monovalent refers to a vaccine vector composition that contains GP and matrix sequences from one species of ebolavirus, Marbugvirus, or Arenavirus.

In another embodiment, the present invention provides a vaccine that is bivalent. As used herein the term monovalent refers to a vaccine vector composition that contains two vectors having GP and matrix sequences from different species of ebolavirus, Marbugvirus, or Arenavirus.

In another embodiment, the present invention provides a vaccine that is trivalent. As used herein the term trivalent refers to a vaccine vector composition that contains three vectors having GP and matrix sequences from different species of ebolavirus, Marbugvirus, or Arenavirus.

In another embodiment, the present invention provides a vaccine that is quadrivalent. As used herein the term monovalent refers to a vaccine vector composition that contains four vectors having GP and matrix sequences from different species of ebolavirus, Marbugvirus, or Arenavirus. As used herein, the terms tetravalent and quadrivalent are synonymous.

As used herein, the phrase "pharmaceutically acceptable carrier" encompasses any of the standard pharmaceutical carriers, such as those suitable for parenteral administration, such as, for example, by intramuscular, intraarticular (in the joints), intravenous, intradermal, intraperitoneal, and subcutaneous routes. Examples of such formulations include aqueous and non-aqueous, isotonic sterile injection solutions, which contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. One exemplary pharmaceutically acceptable carrier is physiological saline.

Other physiologically acceptable diluents, excipients, carriers, or adjuvants and their formulations are known to those skilled in the art.

The compositions utilized in the methods described herein can be administered by a route selected from, e.g., parenteral, intramuscular, intraarterial, intravascular, intravenous, intraperitoneal, subcutaneous, dermal, transdermal, ocular, inhalation, buccal, sublingual, perilingual, nasal, topical administration, and oral administration. The preferred method of administration can vary depending on various factors (e.g., the components of the composition being administered and the severity of the condition being treated). Formulations suitable for oral administration may consist of liquid solutions, such as an effective amount of the composition dissolved in a diluent (e.g., water, saline, or PEG-400), capsules, sachets or tablets, each containing a predetermined amount of the vaccine. The pharmaceutical composition may also be an aerosol formulation for inhalation, e.g., to the bronchial passageways. Aerosol formulations may be mixed with pressurized, pharmaceutically acceptable propellants (e.g., dichlorodifluoromethane, propane, or nitrogen).

For the purposes of this invention, pharmaceutical compositions suitable for delivering a therapeutic or biologically active agent can include, e.g., tablets, gelcaps, capsules, pills, powders, granulates, suspensions, emulsions, solutions, gels, hydrogels, oral gels, pastes, eye drops, ointments, creams, plasters, drenches, delivery devices, suppositories, enemas, injectables, implants, sprays, or aerosols. Any of these formulations can be prepared by well-known and accepted methods of art. See, for example, Remington: The Science and Practice of Pharmacy (21.sup.st ed.), ed. A. R. Gennaro, Lippincott Williams & Wilkins, 2005, and Encyclopedia of Pharmaceutical Technology, ed. J. Swarbrick, Informa Healthcare, 2006, each of which is hereby incorporated by reference.

The immunogenicity of the composition (e.g., vaccine) may be significantly improved if the composition of the present invention is co-administered with an immunostimulatory agent or adjuvant. Suitable adjuvants well-known to those skilled in the art include, e.g., aluminum phosphate, aluminum hydroxide, QS21, Quil A (and derivatives and components thereof), calcium phosphate, calcium hydroxide, zinc hydroxide, glycolipid analogs, octodecyl esters of an amino acid, muramyl dipeptides, polyphosphazene, lipoproteins, ISCOM-Matrix, DC-Chol, DDA, cytokines, and other adjuvants and derivatives thereof.

Pharmaceutical compositions according to the invention described herein may be formulated to release the composition immediately upon administration (e.g., targeted delivery) or at any predetermined time period after administration using controlled or extended release formulations. Administration of the pharmaceutical composition in controlled or extended release formulations is useful where the composition, either alone or in combination, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window in the gastrointestinal tract; or (iii) a short biological half-life, so that frequent dosing during a day is required in order to sustain a therapeutic level.

Many strategies can be pursued to obtain controlled or extended release in which the rate of release outweighs the rate of metabolism of the pharmaceutical composition. For example, controlled release can be obtained by the appropriate selection of formulation parameters and ingredients, including, e.g., appropriate controlled release compositions and coatings. Suitable formulations are known to those of skill in the art. Examples include single or multiple unit tablet or capsule compositions, oil solutions, suspensions, emulsions, microcapsules, microspheres, nanoparticles, patches, and liposomes.

Formulations suitable for oral administration can consist of (a) liquid solutions, such as an effective amount of the vaccine dissolved in diluents, such as water, saline or PEG 400; (b) capsules, sachets or tablets, each containing a predetermined amount of the vaccine, as liquids, solids, granules or gelatin; (c) suspensions in an appropriate liquid; (d) suitable emulsions; and (e) polysaccharide polymers such as chitins. The vaccine, alone or in combination with other suitable components, may also be made into aerosol formulations to be administered via inhalation, e.g., to the bronchial passageways. Aerosol formulations can be placed into pressurized acceptable propellants, such as dichlorodifluoromethane, propane, nitrogen, and the like.

Suitable formulations for rectal administration include, for example, suppositories, which consist of the vaccine with a suppository base. Suitable suppository bases include natural or synthetic triglycerides or paraffin hydrocarbons. In addition, it is also possible to use gelatin rectal capsules which consist of a combination of the vaccine with a base, including, for example, liquid triglycerides, polyethylene glycols, and paraffin hydrocarbons.

Pharmaceutical compositions comprising any of the nucleic acid molecules encoding Ebola viral proteins of the present invention are useful to immunize a subject against disease caused by ebolavirus infection. Thus, this invention further provides methods of immunizing a subject against disease caused by ebolavirus infection, e.g., hemorrhagic fever, comprising administering to the subject an immunoeffective amount of a pharmaceutical composition of the invention. This subject may be an animal, for example a mammal, such as a primate or preferably a human.

The vaccines of the present invention are also suitable for veterinary immunization. The vaccines of the present invention comprising nucleic acid molecules encoding ebolavirus structural gene products from the *Reston ebolavirus* species, which is known to infect animals, are particularly useful in such veterinary immunization methods.

The vaccines of the present invention may also be co-administered with cytokines to further enhance immunogenicity. The cytokines may be administered by methods known to those skilled in the art, e.g., as a nucleic acid molecule in plasmid form or as a protein or fusion protein.

Kits

This invention also provides kits comprising the vaccines of the present invention. For example, kits comprising a vaccine and instructions for use are within the scope of this invention.

V. Method of Use

The compositions of the invention can be used as vaccines for inducing an immune response to a filovirus or an arenavirus, such as a member of the genus *Ebolavirus*, the genus *Marburgvirus*, or the genus *Arenavirus*, including any species thereof.

In exemplary embodiments, the present invention provides a method of preventing a filovirus or arenavirus (e.g., ebolavirus) infection to a subject in need thereof (e.g., an unexposed) subject, said method comprising administering the composition of the present invention to the subject in a prophylactically effective amount. The result of the method is that the subject is partially or completely immunized against the virus.

In exemplary embodiments, the present invention provides a method of treating a filovirus or arenavirus (e.g., ebolavirus) infection in a subject in need thereof (e.g., an exposed subject, such as a subject who has been recently exposed but is not yet symptomatic, or a subject who has been recently exposed and is only mildly symptomatic), said method comprising administering the composition of the present invention to the subject in a therapeutically effective amount. The result of treatment is a subject that has an improved therapeutic profile.

In certain embodiments, the compositions of the invention can be used as vaccines for treating a subject infected with more than one filovirus or more than one areavirus, e.g., multiple species of *Ebolavirus* or *Arenavirus*. The recombinant viral vector comprises genes or sequences encoding viral proteins of multiple species of *Ebolavirus* or *Arenavirus* and/or the pharmaceutical composition comprises more than one type of recombinant viral vector, in terms of the heterologous gene inserts or sequences contained.

Typically the vaccines will be in an admixture and administered simultaneously, but may also be administered separately.

A subject to be treated according to the methods described herein (e.g., a subject infected with, an ebolavirus) may be one who has been diagnosed by a medical practitioner as having such a condition. Diagnosis may be performed by any suitable means. A subject in whom the development of an infection is being prevented may or may not have received such a diagnosis. One skilled in the art will understand that a subject to be treated according to the present invention may have been identified using standard tests or may have been identified, without examination, as one at high risk due to the presence of one or more risk factors (e.g., exposure to ebolavirus, etc.).

Prophylactic treatment may be administered, for example, to a subject not yet exposed to or infected by a hemorrhagic fever virus but who is susceptible to, or otherwise at risk of exposure or infection with an a hemorrhagic fever virus.

Therapeutic treatment may be administered, for example, to a subject already exposed to or infected by a hemorrhagic fever virus who is not yet ill, or showing symptoms or infection, suffering from a disorder in order to improve or stabilize the subject's condition (e.g., a patient already infected with an a hemorrhagic fever virus). The result is an improved therapeutic profile. In some instances, as compared with an equivalent untreated control, treatment may ameliorate a disorder or a symptom thereof by, e.g., 5%, 10%, 20%, 30%, 40%, 50%, 60%, 70%, 80%, 90%, 95%, or 100% as measured by any standard technique. In some instances, treating can result in the inhibition of viral replication, a decrease in viral titers or viral load, eradication or clearing of the virus.

In other embodiments, treatment may result in amelioration of one or more symptoms of the infection, including any symptom identified above. According to this embodiment, confirmation of treatment can be assessed by detecting an improvement in or the absence of symptoms.

In other embodiments, treatment may result in reduction or elimination of the ability of the subject to transmit the infection to another, uninfected subject. Confirmation of treatment according to this embodiment is generally assessed using the same methods used to determine amelioration of the disorder, but the reduction in viral titer or viral load necessary to prevent transmission may differ from the reduction in viral titer or viral load necessary to ameliorate the disorder.

In one embodiment, the present invention is a method of inducing an immune response in a subject (e.g., a human) by administering to the subject a recombinant viral vector that encodes at least one gene from a hemorrhagic fever virus, such as a member of genus *Ebolavirus* a member of genus *Marburgvirus*, or a member of genus *Arenavirus*. The immune response may be a cellular immune response or a humoral immune response, or a combination thereof.

In a particular embodiment, the present invention is a method of inducing an immune response in a subject (e.g., a human) by administering to the subject a recombinant viral vector that encodes at least one gene from a member of genus *Ebolavirus*, more particularly, EBOV. In certain embodiments, the recombinant viral vector encodes at least two genes from an ebolavirus, more particularly, EBOV. The immune response may be a cellular immune response or a humoral immune response, or a combination thereof.

In another particular embodiment, the present invention is a method of inducing an immune response in a subject (e.g., a human) by administering to the subject a recombinant viral vector that encodes at that encodes at least one gene from a member of genus *Marburgvirus*, more particularly, MARV. In certain embodiments, the recombinant viral vector encodes at least two genes from a marburgvirus, more particularly, MARV. The immune response may be a cellular immune response or a humoral immune response, or a combination thereof.

In a particular embodiment, the present invention is a method of inducing an immune response in a subject (e.g., a human) by administering to the subject a recombinant viral vector that encodes at least one gene from a member of genus *Ebolavirus*, more particularly, SUDV. In certain embodiments, the recombinant viral vector encodes at least two genes from an ebolavirus, more particularly, SUDV. The immune response may be a cellular immune response or a humoral immune response, or a combination thereof.

In a particular embodiment, the present invention is a method of inducing an immune response in a subject (e.g., a human) by administering to the subject a recombinant viral vector that encodes at least one gene from a member of genus *Ebolavirus*, more particularly, BDBV. In certain embodiments, the recombinant viral vector encodes at least two genes from an ebolavirus, more particularly, BDBV. The immune response may be a cellular immune response or a humoral immune response, or a combination thereof.

In a particular embodiment, the present invention is a method of inducing an immune response in a subject (e.g., a human) by administering to the subject a recombinant viral vector that encodes at least one gene from a member of genus *Arenavirus*, more particularly, LASV. In certain embodiments, the recombinant viral vector encodes at least two genes from an arenavirus, more particularly, LASV. The immune response may be a cellular immune response or a humoral immune response, or a combination thereof.

In another embodiment, the invention features a method of treating a filovirus infection (e.g., an ebolavirus infection) in a subject (e.g., a human) in need thereof by administering to the subject a recombinant viral vector that encodes at least one gene from the *Zaire ebolavirus* species of ebolavirus (e.g., the EBOV glycoprotein). The subject being treated may not have, but is at risk of developing, an infection by a filovirus, for example, an infection caused by a filovirus selected from TAFV, EBOV, SUDV, BDBV, MARV or a combination thereof.

In another embodiment, the invention features a method of treating a filovirus infection (e.g., an ebolavirus infection) in a subject (e.g., a human) by administering to the subject a recombinant viral vector that encodes at least one gene from the *Sudan ebolavirus* species of ebolavirus (e.g., the SUDV glycoprotein). The subject being treated may not have, but is at risk of developing, an infection by a filovirus, for example, an infection caused by a filovirus selected from TAFV, EBOV, SUDV, BDBV, MARV or a combination thereof.

In another embodiment, the invention features a method of treating a filovirus infection (e.g., an ebolavirus infection) in a subject (e.g., a human) by administering to the subject a recombinant viral vector that encodes at least one gene from the *Bundibugyo ebolavirus* species of ebolavirus (e.g., the BDBV glycoprotein). The subject being treated may not have, but is at risk of developing, an infection by a filovirus, for example, an infection caused by a filovirus selected from TAFV, EBOV, SUDV, BDBV, MARV or a combination thereof.

In another embodiment, the invention features a method of treating a filovirus infection (e.g., a marburgvirus infection) in a subject (e.g., a human) by administering to the subject a recombinant viral vector that encodes at least one gene from the *Marburg marburgvirus* species of marburgvirus (e.g., the MARV glycoprotein). The subject being treated may not have, but is at risk of developing, an infection by a filovirus, for example, an infection caused by a filovirus selected from TAFV, EBOV, SUDV, BDBV, MARV or a combination thereof.

In another embodiment, the invention features a method of treating an arenavirus infection (e.g., a Lassa virus infection) in a subject (e.g., a human) by administering to the subject a recombinant viral vector that encodes at least one gene from the *Lassa virus* species of arenavirus (e.g., the LASV glycoprotein). The subject being treated may not have, but is at risk of developing, an infection by an arenavirus, for example, an infection caused by LASV.

In another embodiment, the subject may already be infected with at least one filovirus or arenavirus (e.g., an ebolavirus or a Lassa virus). The infection may be caused by a hemorrhagic fever virus selected from the group consisting of TAFV, EBOV, SUDV, BDBV, MARV, LASV, or a combination thereof.

The composition may be administered, e.g., by injection (e.g., intramuscular, intraarterial, intravascular, intravenous, intraperitoneal, or subcutaneous).

It will be appreciated that more than one route of administering the vaccines of the present invention may be employed either simultaneously or sequentially (e.g., boosting). In addition, the vaccines of the present invention may be employed in combination with traditional immunization approaches such as employing protein antigens, vaccinia virus and inactivated virus, as vaccines. Thus, in one embodiment, the vaccines of the present invention are administered to a subject (the subject is "primed" with a vaccine of the present invention) and then a traditional vaccine is administered (the subject is "boosted" with a traditional vaccine). In another embodiment, a traditional vaccine is first administered to the subject followed by administration of a vaccine of the present invention. In yet another embodiment, a traditional vaccine and a vaccine of the present invention are co-administered.

While not to be bound by any specific mechanism, it is believed that upon inoculation with a pharmaceutical composition as described herein, the immune system of the host responds to the vaccine by producing antibodies, both secretory and serum, specific for ebolavirus, marburgvirus, or Lassa virus proteins; and by producing a cell-mediated immune response specific for ebolavirus, marburgvirus, or Lassa virus. As a result of the vaccination, the host becomes at least partially or completely immune to ebolavirus, marburgvirus, or Lassa virus infection, or resistant to developing moderate or severe disease caused by ebolavirus, marburgvirus, or Lassa virus infection.

In one aspect, methods are provided to alleviate, reduce the severity of, or reduce the occurrence of, one or more of the symptoms (e.g., fever, hemorrhagic fever, severe headache, muscle pain, malaise, extreme asthenia, conjunctivitis, popular rash, dysphagia, nausea, vomiting, bloody diarrhea followed by diffuse hemorrhages, delirium, shock, jaundice, thrombocytopenia, lymphocytopenia, neutrophilia, focal necrosis in various organs (e.g., kidneys and liver), and acute respiratory distress) associated with ebolavirus, marburgvirus, or Lassa virus infection comprising administering an effective amount of a pharmaceutical composition comprising a recombinant MVA viral vector that comprises GP and VP40 sequences from the *Zaire ebolavirus, Sudan ebolavirus, Taï Forest ebolavirus, Bundibugyo ebolavirus, Reston ebolavirus*, or *Marburg marburgvirus* species of filovirus; or comprising GP and Z sequences from the *Lassa virus* species of arenavirus; or comprising GP, Z, and NP sequences from the *Lassa virus* species of arenavirus.

In one embodiment, the MVA viral vector comprises GP and VP40 sequences from a *Zaire ebolavirus* species.

In one embodiment, the MVA viral vector comprises GP and VP40 sequences from a *Sudan ebolavirus* species.

In one embodiment, the MVA viral vector comprises GP and VP40 sequences from a *Bundibugyo ebolavirus* species.

In one embodiment, the MVA viral vector comprises GP and VP40 sequences from a *Marburg marburgvirus* species.

In one embodiment, the MVA viral vector comprises GP and Z sequences from a *Lassa virus* species.

In one embodiment, the MVA viral vector comprises GP, Z, and NP sequences from a *Lassa virus* species.

In another embodiment, a combination of at least two different recombinant MVA viral vectors are administered wherein the GP and VP40 sequences are from a *Zaire ebolavirus, Sudan ebolavirus, Taï Forest ebolavirus, Bundibugyo ebolavirus, Reston ebolavirus*, or *Marburg marburgvirus* species of filovirus. Also included in this embodiment are combinations of one recombinant MVA viral vector encoding GP and VP40 from a filovirus with another recombinant MVA viral vector encoding GP and Z or GP, Z, and NP from the *Lassa virus* species of arenavirus.

In one embodiment, the pharmaceutical composition comprises two recombinant MVA vaccines expressing GP and VP40 sequences from a *Zaire ebolavirus* and a *Bundibugyo ebolavirus* species of ebolavirus.

In one embodiment, the pharmaceutical composition comprises two recombinant MVA vaccines expressing GP and VP40 sequences from a *Zaire ebolavirus* and a *Sudan ebolavirus*.

In one embodiment, the pharmaceutical composition comprises two recombinant MVA vaccines expressing GP and VP40 sequences from a *Sudan ebolavirus* and a *Bundibugyo ebolavirus*.

In one embodiment, the pharmaceutical composition comprises two recombinant MVA vaccines expressing GP and VP40 sequences from a *Zaire ebolavirus* and a *Marburg marburgvirus*.

In one embodiment, the pharmaceutical composition comprises two recombinant MVA vaccines expressing GP and VP40 sequences from a *Bundibugyo ebolavirus* species and a *Marburg marburgvirus*

In one embodiment, the pharmaceutical composition comprises two recombinant MVA vaccines expressing GP and VP40 sequences from a *Sudan ebolavirus* and a *Marburg marburgvirus*.

In one embodiment, the pharmaceutical composition comprises two recombinant MVA vaccines, one expressing GP and VP40 sequences from a *Zaire ebolavirus* and the other expressing GP and Z sequences from a *Lassa virus*.

In one embodiment, the pharmaceutical composition comprises two recombinant MVA vaccines, one expressing GP and VP40 sequences from a *Sudan ebolavirus* and the other expressing GP and Z sequences from a *Lassa virus*.

In one embodiment, the pharmaceutical composition comprises two recombinant MVA vaccines, one expressing GP and VP40 sequences from a *Bundibugyo ebolavirus* and the other expressing GP and Z sequences from a *Lassa virus*.

In one embodiment, the pharmaceutical composition comprises two recombinant MVA vaccines, one expressing GP and VP40 sequences from a *Marburg marburgvirus* and the other expressing GP and Z sequences from a *Lassa virus*.

In one embodiment, the pharmaceutical composition comprises two recombinant MVA vaccines, one expressing GP and VP40 sequences from a *Zaire ebolavirus* and the other expressing GP, Z, and NP sequences from a *Lassa virus*.

In one embodiment, the pharmaceutical composition comprises two recombinant MVA vaccines, one expressing GP and VP40 sequences from a *Sudan ebolavirus* and the other expressing GP, Z, and NP sequences from a *Lassa virus*.

In one embodiment, the pharmaceutical composition comprises two recombinant MVA vaccines, one expressing GP and VP40 sequences from a *Bundibugyo ebolavirus* and the other expressing GP, Z, and NP sequences from a *Lassa virus*.

In one embodiment, the pharmaceutical composition comprises two recombinant MVA vaccines, one expressing GP and VP40 sequences from a *Marburg marburgvirus* and the other expressing GP, Z, and NP sequences from a *Lassa virus*.

In another embodiment, a combination of three or more different recombinant MVA viral vectors are administered wherein the GP and VP40 sequences are from a *Zaire ebolavirus*, a *Sudan ebolavirus*, a *Taï Forest ebolavirus*, a *Bundibugyo ebolavirus*, a *Reston ebolavirus*, or a *Marburg marburgvirus* species of filovirus. Also included in this embodiment are combinations of two or more recombinant MVA viral vectors encoding GP and VP40 from filoviruses with another recombinant MVA viral vector encoding GP and Z or GP, Z, and NP from the *Lassa virus* species of arenavirus.

In one embodiment, the pharmaceutical composition comprises three recombinant MVA vaccines expressing glycoprotein and matrix protein sequences from a *Zaire ebolavirus*, a *Bundibugyo ebolavirus*, and a *Sudan ebolavirus*.

In one embodiment, the pharmaceutical composition comprises three recombinant MVA vaccines expressing glycoprotein and matrix protein sequences from a *Zaire ebolavirus*, a *Bundibugyo ebolavirus*, and a *Marburg marburgvirus*.

In one embodiment, the pharmaceutical composition comprises three recombinant MVA vaccines expressing glycoprotein and matrix protein sequences from a *Zaire ebolavirus*, a *Sudan ebolavirus*, and a *Marburg marburgvirus*.

In one embodiment, the pharmaceutical composition comprises three recombinant MVA vaccines expressing glycoprotein and matrix protein sequences from a *Bundibugyo ebolavirus*, a *Sudan ebolavirus*, and a *Marburg marburgvirus*.

In one embodiment, the pharmaceutical composition comprises three recombinant MVA vaccines expressing glycoprotein and matrix protein sequences from a *Zaire ebolavirus*, a *Sudan ebolavirus*, and a *Lassa virus*.

In one embodiment, the pharmaceutical composition comprises three recombinant MVA vaccines expressing glycoprotein and matrix protein sequences from a *Zaire ebolavirus*, a *Bundibugyo ebolavirus*, and a *Lassa virus*.

In one embodiment, the pharmaceutical composition comprises three recombinant MVA vaccines expressing glycoprotein and matrix protein sequences from a *Zaire ebolavirus*, a *Marburg marburgvirus*, and a *Lassa virus*.

In one embodiment, the pharmaceutical composition comprises three recombinant MVA vaccines expressing glycoprotein and matrix protein sequences from a *Sudan ebolavirus*, a *Bundibugyo ebolavirus*, and a *Lassa virus*.

In one embodiment, the pharmaceutical composition comprises three recombinant MVA vaccines expressing glycoprotein and matrix protein sequences from a *Sudan ebolavirus*, a *Marburg marburgvirus*, and a *Lassa virus*.

In one embodiment, the pharmaceutical composition comprises three recombinant MVA vaccines expressing glycoprotein and matrix protein sequences from a *Bundibugyo ebolavirus*, a *Marburg marburgvirus*, and a *Lassa virus*.

In one embodiment, the pharmaceutical composition comprises three recombinant MVA vaccines expressing glycoprotein and matrix protein sequences from a *Zaire ebolavirus*, a *Sudan ebolavirus*, and a *Lassa virus*, and the recombinant MVA comprising *Lassa virus* sequences also expresses the nucleoprotein of a *Lassa virus*.

In one embodiment, the pharmaceutical composition comprises three recombinant MVA vaccines expressing glycoprotein and matrix protein sequences from a *Zaire ebolavirus*, a *Bundibugyo ebolavirus*, and a *Lassa virus*, and the recombinant MVA comprising *Lassa virus* sequences also expresses the nucleoprotein of a *Lassa virus*.

In one embodiment, the pharmaceutical composition comprises three recombinant MVA vaccines expressing glycoprotein and matrix protein sequences from a *Zaire ebolavirus*, a *Marburg marburgvirus*, and a *Lassa virus*, and the recombinant MVA comprising *Lassa virus* sequences also expresses the nucleoprotein of a *Lassa virus*.

In one embodiment, the pharmaceutical composition comprises three recombinant MVA vaccines expressing glycoprotein and matrix protein sequences from a *Sudan ebolavirus*, a *Bundibugyo ebolavirus*, and a *Lassa virus*, and the recombinant MVA comprising *Lassa virus* sequences also expresses the nucleoprotein of a *Lassa virus*.

In one embodiment, the pharmaceutical composition comprises three recombinant MVA vaccines expressing glycoprotein and matrix protein sequences from a *Sudan ebolavirus*, a *Marburg marburgvirus*, and a *Lassa virus*, and the recombinant MVA comprising *Lassa virus* sequences also expresses the nucleoprotein of a *Lassa virus*.

In one embodiment, the pharmaceutical composition comprises three recombinant MVA vaccines expressing glycoprotein and matrix protein sequences from a *Bundibugyo ebolavirus*, a *Marburg marburgvirus*, and a *Lassa virus*, and the recombinant MVA comprising *Lassa virus* sequences also expresses the nucleoprotein of a *Lassa virus*.

In one embodiment, the pharmaceutical composition comprises four recombinant MVA vaccines expressing glycoprotein and matrix protein sequences from a *Zaire ebolavirus*, a *Bundibugyo ebolavirus*, a *Sudan ebolavirus*, and a *Marburg marburgvirus*.

In one embodiment, the pharmaceutical composition comprises four recombinant MVA vaccines expressing glycoprotein and matrix protein sequences from a *Zaire ebolavirus*, a *Bundibugyo ebolavirus*, a *Sudan ebolavirus*, and a *Lassa virus*.

In one embodiment, the pharmaceutical composition comprises four recombinant MVA vaccines expressing glycoprotein and matrix protein sequences from a *Sudan ebolavirus*, a *Bundibugyo ebolavirus*, a *Marburg marburgvirus*, and a *Lassa virus*.

In one embodiment, the pharmaceutical composition comprises four recombinant MVA vaccines expressing glycoprotein and matrix protein sequences from a *Zaire ebolavirus*, a *Bundibugyo ebolavirus*, a *Marburg marburgvirus*, and a *Lassa virus*.

In one embodiment, the pharmaceutical composition comprises four recombinant MVA vaccines expressing glycoprotein and matrix protein sequences from a *Zaire ebolavirus*, a *Bundibugyo ebolavirus*, a *Sudan ebolavirus*, and a *Lassa virus*, and the recombinant MVA comprising *Lassa virus* sequences also expresses the nucleoprotein of a *Lassa virus*.

In one embodiment, the pharmaceutical composition comprises four recombinant MVA vaccines expressing glycoprotein and matrix protein sequences from a *Sudan ebolavirus*, a *Bundibugyo ebolavirus*, a *Marburg marburgvirus*, and a *Lassa virus*, and the recombinant MVA comprising *Lassa virus* sequences also expresses the nucleoprotein of a *Lassa virus*.

In one embodiment, the pharmaceutical composition comprises four recombinant MVA vaccines expressing glycoprotein and matrix protein sequences from a *Zaire ebolavirus*, a *Bundibugyo ebolavirus*, a *Marburg marburgvirus*, and a *Lassa virus*, and the recombinant MVA comprising *Lassa virus* sequences also expresses the nucleoprotein of a *Lassa virus*.

In another aspect, the invention provides methods of inducing an immune response to ebolavirus, marburgvirus, or *Lassa virus* comprising administering an effective amount of a pharmaceutical composition comprising a recombinant MVA vaccine expressing glycoprotein and matrix protein from at least one species of ebolavirus, marburgvirus, or *Lassa virus*. The Lassa vaccine of this aspect may also express the *Lassa virus* nucleoprotein.

In another aspect, the invention provides methods of providing anti-ebolavirus, anti-marburgvirus, or anti-Lassa virus immunity comprising administering an effective amount of a pharmaceutical composition comprising a recombinant MVA vaccine expressing glycoprotein and matrix protein from at least one species of ebolavirus, marburgvirus, or Lassa virus. The Lassa vaccine of this aspect may also express the *Lassa virus* nucleoprotein.

In another aspect, the invention provides methods of reducing the spread of ebolavirus, marburgvirus, or Lassa virus infection within a subject or from an infected subject to an uninfected subject, comprising administering an effective amount of a pharmaceutical composition comprising a recombinant MVA vaccine expressing glycoprotein and matrix protein from at least one species of ebolavirus, marburgvirus, or Lassa virus. The Lassa vaccine of this aspect may also express the Lassa virus nucleoprotein. In another aspect, the invention provides methods of reducing symptoms of ebolavirus, marburgvirus, or Lassa virus infection comprising administering an effective amount of a pharmaceutical composition comprising a recombinant MVA vaccine expressing glycoprotein and matrix protein from at least one species of ebolavirus, marburgvirus, or Lassa virus. The Lassa vaccine of this aspect may also express the *Lassa virus* nucleoprotein. In another aspect, the invention provides methods of inducing an immune response which is considered a surrogate marker for protection against ebolavirus, marburgvirus, or Lassa virus infection. Data for determination of whether a response constitutes a surrogate marker for protection are obtained using immune response data obtained using the measurements outlined above.

It will also be appreciated that single or multiple administrations of the vaccine compositions of the present invention may be carried out. For example, subjects who are particularly susceptible to ebolavirus, marburgvirus, or Lassa virus infection may require multiple immunizations to establish and/or maintain protective immune responses.

Levels of induced immunity can be monitored by measuring amounts of binding and neutralizing secretory and serum antibodies as well as levels of T cells, and dosages adjusted or vaccinations repeated as necessary to maintain desired levels of protection.

In one embodiment, administration is repeated at least twice, at least 3 times, at least 4 times, at least 5 times, at least 6 times, at least 7 times, at least 8 times, or more than 8 times.

In one embodiment, administration is repeated twice.

In one embodiment, about 2-8, about 4-8, or about 6-8 administrations are provided.

In one embodiment, about 1-4-week, 2-4 week, 3-4 week, 1 week, 2 week, 3 week, 4 week or more than 4 week intervals are provided between administrations.

In one specific embodiment, a 4-week interval is used between 2 administrations.

Dosage

The vaccines are administered in a manner compatible with the dosage formulation, and in such amount as will be therapeutically effective, immunogenic and protective. The quantity to be administered depends on the subject to be treated, including, for example, the capacity of the immune system of the individual to synthesize antibodies, and, if needed, to produce a cell-mediated immune response. Precise amounts of active ingredient required to be administered depend on the judgment of the practitioner and may be monitored on a patient-by-patient basis. However, suitable dosage ranges are readily determinable by one skilled in the art and generally range from about $5.0 \times 10^6$ $TCID_{50}$ to about $5.0 \times 10^9$ $TCID_{50}$. The dosage may also depend, without limitation, on the route of administration, the patient's state of health and weight, and the nature of the formulation.

The pharmaceutical compositions of the invention are administered in such an amount as will be therapeutically effective, immunogenic, and/or protective against a pathogenic species of ebolavirus. The dosage administered depends on the subject to be treated (e.g., the manner of administration and the age, body weight, capacity of the immune system, and general health of the subject being treated). The composition is administered in an amount to provide a sufficient level of expression that elicits an immune response without undue adverse physiological effects. Preferably, the composition of the invention is a heterologous viral vector that includes one or more polypeptides of the ebolavirus, marburgvirus, or Lassa virus (e.g., the ebolavirus, marburgvirus, or Lassa virus glycoprotein and large matrix protein; the Lassa vaccine of this invention may also express the Lassa virus nucleoprotein), or a nucleic acid molecule encoding one or more genes of the ebolavirus, marburgvirus, or Lassa virus, and is administered at a dosage of, e.g., between $1.0 \times 10^4$ and $9.9 \times 10^{12}$ $TCID_{50}$ of the viral vector, preferably between $1.0 \times 10^5$ $TCID_{50}$ and $1.0 \times 10^{11}$ $TCID_{50}$ pfu, more preferably between $1.0 \times 10^6$ and $1.0 \times 10^{10}$ $TCID_{50}$ pfu, or most preferably between $5.0 \times 10^6$ and $5.0 \times 10^9$ $TCID_{50}$. The composition may include, e.g., at least $5.0 \times 10^6$ $TCID_{50}$ of the viral vector (e.g., $1.0 \times 10^8$ $TCID_{50}$ of the viral vector). A physician or researcher can decide the appropriate amount and dosage regimen.

The composition of the method may include, e.g., between $1.0 \times 10^4$ and $9.9 \times 10^{12}$ $TCID_{50}$ of the viral vector, preferably between $1.0 \times 10^5$ $TCID_{50}$ and $1.0 \times 10^{11}$ $TCID_{50}$ pfu, more preferably between $1.0 \times 10^6$ and $1.0 \times 10^{10}$ $TCID_{50}$ pfu, or most preferably between $5.0 \times 10^6$ and $5.0 \times 10^9$ $TCID_{50}$. The composition may include, e.g., at least $5.0 \times 10^6$ $TCID_{50}$ of the viral vector (e.g., $1.0 \times 10^8$ $TCID_{50}$ of the viral vector). The method may include, e.g., administering the composition to the subject two or more times.

The invention also features a method of inducing an immune response to ebolavirus, marburgvirus, or Lassa virus in a subject (e.g., a human) that includes administering to the subject an effective amount of a recombinant viral vector that encodes at least one gene from the ebolavirus (e.g., the ebolavirus, marburgvirus, or Lassa virus glycoprotein and large matrix protein; the Lassa vaccine of this invention may also express the Lassa virus nucleoprotein). The infection may be caused by the *Zaire ebolavirus, Sudan ebolavirus, Taï Forest ebolavirus, Bundibugyo ebolavirus*, or *Reston ebolavirus* species of ebolavirus; by the *Marburg marburgvirus* species of marburgvirus; or by the *Lassa virus* species of arenavirus. The subject being treated may not have, but is at risk of developing, an infection by an ebolavirus, a marburgvirus, or an arenavirus. Alternatively, the subject may already be infected with an ebolavirus, a marburgvirus, or an arenavirus. The composition may be administered, e.g., by injection (e.g., intramuscular, intraarterial, intravascular, intravenous, intraperitoneal, or subcutaneous).

The term "effective amount" is meant the amount of a composition administered to improve, inhibit, or ameliorate a condition of a subject, or a symptom of a disorder, in a clinically relevant manner (e.g., improve, inhibit, or ameliorate infection by ebolavirus, marburgvirus, or arenavirus or provide an effective immune response to infection by ebolavirus, marburgvirus, or arenavirus). Any improvement in the subject is considered sufficient to achieve treatment. Preferably, an amount sufficient to treat is an amount that prevents the occurrence or one or more symptoms of ebolavirus, marburgvirus, or arenavirus infection or is an amount that reduces the severity of, or the length of time during which a subject suffers from, one or more symptoms of ebolavirus, marburgvirus, or arenavirus infection (e.g., by at least 10%, 20%, or 30%, more preferably by at least 50%, 60%, or 70%, and most preferably by at least 80%, 90%, 95%, 99%, or more, relative to a control subject that is not treated with a composition of the invention). A sufficient amount of the pharmaceutical composition used to practice the methods described herein (e.g., the treatment of ebolavirus infection) varies depending upon the manner of administration and the age, body weight, and general health of the subject being treated. Ultimately, the prescribers or researchers will decide the appropriate amount and dosage.

It is important to note that the value of the present invention may never be demonstrated in terms of actual clinical benefit. Instead, it is likely that the value of the invention will be demonstrated in terms of success against a surrogate marker for protection. For an indication such as ebolavirus, marburgvirus, or Lassa virus infection, in which it is impractical or unethical to attempt to measure clinical benefit of an intervention, the FDA's Accelerated Approval process allows approval of a new vaccine based on efficacy against a surrogate endpoint. Therefore, the value of the invention may lie in its ability to induce an immune response that constitutes a surrogate marker for protection.

Similarly, FDA may allow approval of vaccines against ebolaviruses, marburgviruses, or arenaviruses based on its Animal Rule. In this case, approval is achieved based on efficacy in animals. The value of the invention may lie in its ability to protect relevant animal species against infection with ebolaviruses, marburgviruses, or arenaviruses, thus providing adequate evidence to justify its approval.

The composition of the method may include, e.g., between $1.0 \times 10^4$ and $9.9 \times 10^{12}$ $TCID_{50}$ of the viral vector, preferably between $1.0 \times 10^5$ TCID$_{50}$ and $1.0 \times 10^{11}$ TCID$_{50}$ pfu, more preferably between $1.0 \times 10^6$ and $1.0 \times 10^{10}$ TCID$_{50}$ pfu, or most preferably between $5.0 \times 10^6$ and $5.0 \times 10^9$ TCID$_{50}$. The composition may include, e.g., at least $5.0 \times 10^6$ TCID$_{50}$ of the viral vector (e.g., $1.0 \times 10^8$ TCID$_{50}$ of the viral vector). The method may include, e.g., administering the composition two or more times.

In some instances it may be desirable to combine the ebolavirus, marburgvirus, or arenavirus vaccines of the present invention with vaccines which induce protective responses to other agents, particularly other viruses. For example, the vaccine compositions of the present invention can be administered simultaneously, separately or sequentially with other genetic immunization vaccines such as those for influenza (Ulmer, J. B. et al., Science 259:1745-1749 (1993); Raz, E. et al., PNAS (USA) 91:9519-9523 (1994)), malaria (Doolan, D. L. et al., J. Exp. Med. 183: 1739-1746 (1996); Sedegah, M. et al., PNAS (USA) 91:9866-9870 (1994)), and tuberculosis (Tascon, R. C. et al., Nat. Med. 2:888-892 (1996)).

Administration

As used herein, the term "administering" refers to a method of giving a dosage of a pharmaceutical composition of the invention to a subject. The compositions utilized in the methods described herein can be administered by a route selected from, e.g., parenteral, dermal, transdermal, ocular, inhalation, buccal, sublingual, perilingual, nasal, rectal, topical administration, and oral administration. Parenteral administration includes intravenous, intraperitoneal, subcutaneous, intraarterial, intravascular, and intramuscular administration. The preferred method of administration can vary depending on various factors (e.g., the components of the composition being administered and the severity of the condition being treated).

Administration of the pharmaceutical compositions (e.g., vaccines) of the present invention can be by any of the routes known to one of skill in the art. Administration may be by, e.g., intramuscular injection. The compositions utilized in the methods described herein can also be administered by a route selected from, e.g., parenteral, dermal, transdermal, ocular, inhalation, buccal, sublingual, perilingual, nasal, rectal, topical administration, and oral administration. Parenteral administration includes intravenous, intraperitoneal, subcutaneous, and intramuscular administration. The preferred method of administration can vary depending on various factors, e.g., the components of the composition being administered and the severity of the condition being treated.

In addition, single or multiple administrations of the compositions of the present invention may be given to a subject. For example, subjects who are particularly susceptible to ebolavirus infection may require multiple treatments to establish and/or maintain protection against the virus. Levels of induced immunity provided by the pharmaceutical compositions described herein can be monitored by, e.g., measuring amounts of neutralizing secretory and serum antibodies. The dosages may then be adjusted or repeated as necessary to maintain desired levels of protection against viral infection.

The claimed invention is further describe by way of the following non-limiting examples. Further aspects and embodiments of the present invention will be apparent to those of ordinary skill in the art, in view of the above disclosure and following experimental exemplification, included by way of illustration and not limitation, and with reference to the attached figures.

EXAMPLES

Example 1. MVA Vaccine Vectors

This Example provides information on exemplary MVA vaccine vectors.

Table 1 lists seven MVA vaccine vectors.

TABLE 1

MVA vaccine vectors

| Vaccine designation | GP sequence | Matrix protein sequence | Nucleoprotein sequence |
|---|---|---|---|
| GEO-EM01 | Optimized GP sequence for EBOV 2014 (current epidemic) | Optimized VP40 sequence for EBOV 2014 (current epidemic) | Not applicable |
| GEO-EM02 | Optimized GP sequence for EBOV, central EBOV sequence | Optimized VP40 sequence for EBOV, central EBOV sequence | Not applicable |
| GEO-EM03 | Optimized GP sequence for SUDV, central SUDV sequence | Optimized VP40 sequence for SUDV, central SUDV sequence | Not applicable |
| GEO-EM04 | Optimized GP sequence for BDBV, central BDBV sequence | Optimized VP40 sequence for BDBV, central BDBV sequence | Not applicable |
| GEO-EM05 | Optimized GP sequence for MARV, 1980 Mt. Elgon-Musoke strain | Optimized VP40 sequence for MARV, 1980 Mt. Elgon-Musoke strain | Not applicable |
| GEO-EM06 | Optimized GP sequence for LASV, Josiah strain | Optimized Z sequence for LASV, Josiah strain | Not applicable |
| GEO-EM07 | Optimized GP sequence for LASV, Josiah strain | Optimized Z sequence for LASV, Josiah strain | Optimized NP sequence for LASV, Josiah strain |

Table 2 lists the accession numbers for the GenBank sequences used for design of the five MVA vaccine vectors of this invention

TABLE 2

MVA vaccine vectors of this invention, source of sequences

| Vaccine designation | GenBank accession number for source sequence |
|---|---|
| GEO-EM01 | KM233103.1 |
| GEO-EM02 | KC242798.1 |
| GEO-EM03 | KC545390.1 |
| GEO-EM04 | KC545396.1 |
| GEO-EM05 | NC_001608 |

TABLE 2-continued

MVA vaccine vectors of this invention, source of sequences

| Vaccine designation | GenBank accession number for source sequence |
| --- | --- |
| GEO-EM06 | JN650517.1, JN650518.1 |
| GEO-EM07 | JN650517.1, JN650518.1 |

Example 2. Sequence Optimization

Example 2 illustrates the process for optimization of GP and VP40 sequences for use in an MVA vaccine vector. This Example shows the optimization of one GP and one VP40 sequence, both of which are included in GEO-EM01 (the vaccine for the 2014 EBOV strain). The process followed for vaccines against other strains is highly similar, involving the same set of operations.

The native nucleotide sequence for 2014 EBOV GP (which would lead to expression of sGP) was obtained from GenBank (accession number KM233103.1)

```
SEQ ID 01:
Native nucleotide sequence for 2014
EBOV GP, from GenBank:
ATGGGTGTTACAGGAATATTGCAGTTACCTCGTGA

TCGATTCAAGAGGACATCATTCTTTCTTTGGGTAA

TTATCCTTTTCCAAAGAACATTTTCCATCCCGCTT

GGAGTTATCCACAATAGTACATTACAGGTTAGTGA

TGTCGACAAACTAGTTTGTCGTGACAAACTGTCAT

CCACAAATCAATTGAGATCAGTTGGACTGAATCTC

GAGGGGAATGGAGTGGCAACTGACGTGCCATCTGT

GACTAAAAGATGGGGCTTCAGGTCCGGTGTCCCAC

CAAAGGTGGTCAATTATGAAGCTGGTGAATGGGCT

GAAAACTGCTACAATCTTGAAATCAAAAAACCTGA

CGGGAGTGAGTGTCTACCAGCAGCGCCAGACGGGA

TTCGGGGCTTCCCCCGGTGCCGGTATGTGCACAAA

GTATCAGGAACGGGACCATGTGCCGGAGACTTTGC

CTTCCACAAAGAGGGTGCTTTCTTCCTGTATGATC

GACTTGCTTCCACAGTTATCTACCGAGGAACGACT

TTCGCTGAAGGTGTCGTTGCATTTCTGATACTGCC

CCAAGCTAAGAAGGACTTCTTCAGCTCACACCCCT

TGAGAGAGCCGGTCAATGCAACGGAGGACCCGTCG

AGTGGCTATTATTCTACCACAATTAGATATCAGGC

TACCGGTTTTGGAACTAATGAGACAGAGTACTTGT

TCGAGGTTGACAATTTGACCTACGTCCAACTTGAA

TCAAGATTCACACCACAGTTTCTGCTCCAGCTGAA

TGAGACAATATATGCAAGTGGGAAGAGGAGCAACA

CCACGGGAAAACTAATTTGGAAGGTCAACCCCGAA

ATTGATACAACAATCGGGGAGTGGGCCTTCTGGGA

AACTAAAAAAACCTCACTAGAAAAATTCGCAGTGA

AGAGTTGTCTTTCACAGCTGTATCAAACGGACCCA

AAAACATCAGTGGTCAGAGTCCGGCGCGAACTTCT

TCCGACCCAGAGACCAACACAACAAATGAAGACCA

CAAAATCATGGCTTCAGAAAATTCCTCTGCAATGG

TTCAAGTGCACAGTCAAGGAAGGAAAGCTGCAGTG

TCGCATCTGACAACCCTTGCCACAATCTCCACGAG

TCCTCAACCTCCCACAACCAAAACAGGTCCGGACA

ACAGCACCCATAATACACCCGTGTATAAACTTGAC

ATCTCTGAGGCAACTCAAGTTGGACAACATCACCG

TAGAGCAGACAACGACAGCACAGCCTCCGACACTC

CCCCCGCCACGACCGCAGCCGGACCCTTAAAAGCA

GAGAACACCAACACGAGTAAGAGCGCTGACTCCCT

GGACCTCGCCACCACGACAAGCCCCCAAAACTACA

GCGAGACTGCTGGCAACAACAACACTCATCACCAA

GATACCGGAGAAGAGAGTGCCAGCAGCGGGAAGCT

AGGCTTAATTACCAATACTATTGCTGGAGTAGCAG

GACTGATCACAGGCGGGAGAAGGACTCGAAGAGAA

GTAATTGTCAATGCTCAACCCAAATGCAACCCCAA

TTTACATTACTGGACTACTCAGGATGAAGGTGCTG

CAATCGGATTGGCCTGGATACCATATTTCGGGCCA

GCAGCCGAAGGAATTTACACAGAGGGGCTAATGCA

CAACCAAGATGGTTTAATCTGTGGGTTGAGGCAGC

TGGCCAACGAAACGACTCAAGCTCTCCAACTGTTC

CTGAGAGCCACAACTGAGCTGCGAACCTTTTCAAT

CCTCAACCGTAAGGCAATTGACTTCCTGCTGCAGC

GATGGGGTGGCACATGCCACATTTTGGGACCGGAC

TGCTGTATCGAACCACATGATTGGACCAAGAACAT

AACAGACAAAATTGATCAGATTATTCATGATTTTG

TTGATAAAACCCTTCCGGACCAGGGGGACAATGAC

AATTGGTGGACAGGATGGAGACAATGGATACCGGC

AGGTATTGGAGTTACAGGTGTTATAATTGCAGTTA

TCGCTTTATTCTGTATATGCAAATTTGTCTTTTAG
```

A single A nucleotide (indicated below by a bold underlined letter) was added to the native 2014 EBOV GP sequence (SEQ ID 01) to create the full-length GP sequence (SEQ ID 02). The purpose of this addition was to eliminate expression of the secreted form of the Ebola glycoprotein (sGP) and to ensure that full-length GP will be expressed. (Volchkov et al., 1995), Virology 214, 421-430). The GP sequence was translated in the EditSeq program (DNAStar) to verify that the sequence will express the full-length GP protein. SEQ ID: 03 is the product of the in silico translation.

SEQ ID 02:
Full-length 2014 EBOV GP
nucleotide sequence:
ATGGGTGTTACAGGAATATTGCAGTTACCTCGTGA

TCGATTCAAGAGGACATCATTCTTTCTTTGGGTAA

TTATCCTTTTCCAAAGAACATTTTCCATCCCGCTT

GGAGTTATCCACAATAGTACATTACAGGTTAGTGA

TGTCGACAAACTAGTTTGTCGTGACAAACTGTCAT

CCACAAATCAATTGAGATCAGTTGGACTGAATCTC

GAGGGGAATGGAGTGGCAACTGACGTGCCATCTGT

GACTAAAAGATGGGGCTTCAGGTCCGGTGTCCCAC

CAAAGGTGGTCAATTATGAAGCTGGTGAATGGGCT

GAAAACTGCTACAATCTTGAAATCAAAAAACCTGA

CGGGAGTGAGTGTCTACCAGCAGCGCCAGACGGGA

TTCGGGGCTTCCCCCGGTGCCGGTATGTGCACAAA

GTATCAGGAACGGGACCATGTGCCGGAGACTTTGC

CTTCCACAAAGAGGGTGCTTTCTTCCTGTATGATC

GACTTGCTTCCACAGTTATCTACCGAGGAACGACT

TTCGCTGAAGGTGTCGTTGCATTTCTGATACTGCC

CCAAGCTAAGAAGGACTTCTTCAGCTCACACCCCT

TGAGAGAGCCGGTCAATGCAACGGAGGACCCGTCG

AGTGGCTATTATTCTACCACAATTAGATATCAGGC

TACCGGTTTTGGAACTAATGAGACAGAGTACTTGT

TCGAGGTTGACAATTTGACCTACGTCCAACTTGAA

TCAAGATTCACACCACAGTTTCTGCTCCAGCTGAA

TGAGACAATATATGCAAGTGGGAAGAGGAGCAACA

CCACGGGAAAACTAATTTGGAAGGTCAACCCCGAA

ATTGATACAACAATCGGGGAGTGGGCCTTCTGGAA

AACTA<u>A</u>AAAAAACCTCACTAGAAAAATTCGCAGTG

AAGAGTTGTCTTTCACAGCTGTATCAAACGGACCC

AAAAACATCAGTGGTCAGAGTCCGGCGCGAACTTC

TTCCGACCCAGAGACCAACACAACAAATGAAGACC

ACAAAATCATGGCTTCAGAAAATTCCTCTGCAATG

GTTCAAGTGCACAGTCAAGGAAGGAAAGCTGCAGT

GTCGCATCTGACAACCCTTGCCACAATCTCCACGA

GTCCTCAACCTCCCACAACCAAAACAGGTCCGGAC

AACAGCACCCATAATACACCCGTGTATAAACTTGA

CATCTCTGAGGCAACTCAAGTTGGACAACATCACC

GTAGAGCAGACAACGACAGCACAGCCTCCGACACT

CCCCCCGCCACGACCGCAGCCGGACCCTTAAAAGC

AGAGAACACCAACACGAGTAAGAGCGCTGACTCCC

TGGACCTCGCCACCACGACAAGCCCCCAAAACTAC

AGCGAGACTGCTGGCAACAACAACACTCATCACCA

AGATACCGGAGAAGAGAGTGCCAGCAGCGGGAAGC

TAGGCTTAATTACCAATACTATTGCTGGAGTAGCA

GGACTGATCACAGGCGGGAGAAGGACTCGAAGAGA

AGTAATTGTCAATGCTCAACCCAAATGCAACCCCA

ATTTACATTACTGGACTACTCAGGATGAAGGTGCT

GCAATCGGATTGGCCTGGATACCATATTTCGGGCC

AGCAGCCGAAGGAATTTACACAGAGGGGCTAATGC

ACAACCAAGATGGTTTAATCTGTGGGTTGAGGCAG

CTGGCCAACGAAACGACTCAAGCTCTCCAACTGTT

CCTGAGAGCCACAACTGAGCTGCGAACCTTTTCAA

TCCTCAACCGTAAGGCAATTGACTTCCTGCTGCAG

CGATGGGGTGGCACATGCCACATTTTGGGACCGGA

CTGCTGTATCGAACCACATGATTGGACCAAGAACA

TAACAGACAAAATTGATCAGATTATTCATGATTTT

GTTGATAAAACCCTTCCGGACCAGGGGGACAATGA

CAATTGGTGGACAGGATGGAGACAATGGATACCGG

CAGGTATTGGAGTTACAGGTGTTATAATTGCAGTT

ATCGCTTTATTCTGTATATGCAAATTTGTCTTTTA

G

SEQ ID 03:
Full-length 2014 EBOV GP
protein sequence, generated
in EditSeq software from
SEQ ID 02:
MGVTGILQLPRDRFKRTSFFLWVIILFQRTFSIPL

GVIHNSTLQVSDVDKLVCRDKLSSTNQLRSVGLNL

EGNGVATDVPSVTKRWGFRSGVPPKVVNYEAGEWA

ENCYNLEIKKPDGSECLPAAPDGIRGFPRCRYVHK

VSGTGPCAGDFAFHKEGAFFLYDRLASTVIYRGTT

FAEGVVAFLILPQAKKDFFSSHPLREPVNATEDPS

SGYYSTTIRYQATGFGTNETEYLFEVDNLTYVQLE

SRFTPQFLLQLNETIYASGKRSNTTGKLIWKVNPE

IDTTIGEWAFWETKKNLTRKIRSEELSFTAVSNGP

KNISGQSPARTSSDPETNTTNEDHKIMASENSSAM

VQVHSQGRKAAVSHLTTLATISTSPQPPTTKTGPD

NSTHNTPVYKLDISEATQVGQHHRRADNDSTASDT

PPATTAAGPLKAENTNTSKSADSLDLATTTSPQNY

SETAGNNNTHHQDTGEESASSGKLGLITNTIAGVA

GLITGGRRTRREVIVNAQPKCNPNLHYWTTQDEGA

AIGLAWIPYFGPAAEGIYTEGLMFINQDGLICGLR

QLANETTQALQLFLRATTELRTFSILNRKAIDFLL

QRWGGTCHILGPDCCIEPHDWTKNITDKIDQIIHD

FVDKTLPDQGDNDNWWTGWRQWIPAGIGVTGVIIA

VIALFCICKFVF

The full-length 2014 EBOV GP sequence (SEQ ID 02) was optimized for vaccinia virus expression using the online Gene Optimizer algorithm to generate SEQ ID 04.

SEQ ID 04:
Codon-optimized full-length
2014 EBOV GP sequence:
ATGGGAGTAACTGGAATTCTACAACTACCAAGAGA

TAGATTCAAAAGAACATCTTTTTTTCTATGGGTTA

TAATTCTATTTCAAAGAACATTTTCTATTCCATTG

GGAGTAATTCATAATTCTACATTGCAAGTATCTGA

TGTAGATAAACTAGTATGTAGAGATAAATTGTCTA

GTACAAATCAACTAAGATCTGTAGGATTGAATCTA

GAAGGAAATGGTGTAGCGACAGATGTTCCATCTGT

AACAAAAAGATGGGGTTTTAGATCTGGTGTACCAC

CAAAAGTAGTAAATTATGAAGCGGGAGAATGGGCG

GAAAATTGTTATAATCTAGAAATTAAAAAACCAGA

TGGATCTGAATGTCTACCAGCGGCGCCAGATGGAA

TTAGAGGATTTCCAAGATGTAGATATGTTCATAAA

GTATCTGGAACAGGACCATGTGCGGGAGATTTTGC

GTTTCATAAAGAAGGAGCATTTTTTCTATATGATA

GACTAGCGTCTACAGTAATATATAGAGGAACAACA

TTTGCGGAAGGTGTAGTAGCTTTTCTAATTCTACC

ACAAGCGAAAAAGATTTTTTAGTTCTCATCCAC

TAAGAGAACCAGTAAATGCGACAGAAGATCCTTCT

TCTGGATATTATTCTACTACAATTAGATATCAAGC

GACAGGATTTGGAACAAATGAAACAGAATATCTAT

TTGAAGTTGATAATCTAACATATGTACAACTAGAA

AGTAGATTCACACCACAATTTCTATTGCAATTGAA

TGAAACAATATATGCGTCTGGAAAAAGATCTAATA

CAACTGGAAAACTAATTTGGAAAGTAAATCCAGAA

ATTGATACAACAATTGGAGAATGGGCTTTTTGGGA

AACAAAAAAATTTGACAAGAAAAATTAGATCTG

AAGAATTGTCTTTTACAGCGGTATCTAATGGACCA

AAAAATATTTCTGGACAATCTCCAGCGAGAACTTC

TTCTGATCCAGAAACAAATACTACAAATGAAGATC

ACAAAATTATGGCGTCTGAAAATTCTTCTGCTATG

GTACAAGTACATTCTCAAGGAAGAAAAGCGGCGGT

ATCTCATCTAACAACACTAGCGACTATTTCTACAT

CTCCACAACCACCAACAACAAAAACTGGACCAGAT

AATAGTACACATAATACTCCAGTTTATAAACTAGA

TATTTCTGAAGCGACACAAGTTGGACAACATCATA

GAAGAGCGGATAATGATTCTACAGCGTCTGATACA

CCACCAGCTACAACAGCTGCTGGACCATTGAAAGC

GGAAAATACAAATACTTCTAAATCTGCGGATTCTC

TAGATTTGGCGACAACAACTTCTCCTCAAAATTAT

TCTGAAACAGCGGGAAATAATAATACTCATCATCA

AGATACTGGAGAAGAATCTGCGTCTAGTGGAAAAT

TGGGACTAATTACAAATACAATTGCGGGTGTAGCG

GGATTGATTACTGGTGGAAGAAGAACTAGAAGAGA

AGTAATAGTTAATGCGCAACCTAAATGTAATCCAA

ATCTACATTATTGGACAACTCAAGATGAAGGTGCT

GCGATTGGACTAGCTTGGATTCCATATTTTGGACC

TGCGGCGAAGGAATATATACTGAAGGACTAATGC

ATAATCAAGATGGACTAATTTGTGGACTAAGACAA

CTAGCGAATGAAACTACACAAGCGCTACAACTATT

TTTGAGAGCGACAACAGAACTAAGAACTTTTAGTA

TTCTAAATAGAAAAGCGATTGATTTTTTGCTACAA

AGATGGGAGGAACATGTCATATTCTAGGACCAGA

TTGTTGTATTGAACCACATGATTGGACAAAAAATA

TTACAGACAAAATTGATCAAATTATTCATGATTTT

GTTGATAAAACACTACCAGATCAAGGAGATAATGA

TAATTGGTGGACAGGATGGAGACAATGGATTCCAG

CGGGAATTGGAGTAACAGGTGTAATTATTGCGGTT

ATTGCGCTATTTGTATATGTAAATTTGTTTTTTA

A

The codon-optimized full-length 2014 EBOV GP sequence (SEQ ID 04) was searched for homopolymer stretches consisting of ≥5 G bases or ≥C bases. None were found.

The codon-optimized full-length 2014 EBOV GP sequence (SEQ ID 04) was searched for homopolymer stretches consisting of ≥5 T bases or ≥A bases. Fifteen such stretches were found and were eliminated through silent mutations as listed in Table 3, to generate SEQ ID 05.

TABLE 3

Elimination of homopolymer stretches in optimized 2014 EBOV GP sequence

| No. | Homopolymer | Changes (Silent mutation) | Mutation position (base number) in sequence | Codon change (silent mutation) |
|---|---|---|---|---|
| 1 | 7T | T to C | 57 | TTT to TTC |
| 2 | 5A | A to G | 252 | AAA to AAG |
| 3 | 6A | A to G | 342 | AAA to AAG |
| 4 | 6T | T to C | 477 | TTT to TTC |
| 5 | 6A | A to G | 570 | AAA to AAG |
| 6 | 7T | T to C | 579 | TTT to TTC |
| 7 | 6A | A to G | 795 | AAA to AAG |
| 8 | 5T | T to C | 870 | TTT to TTC |
| 9 | 9A | A to G | 882 885 | AAA to AAG |

TABLE 3-continued

Elimination of homopolymer stretches in optimized 2014 EBOV GP sequence

| No. | Homopolymer | Changes (Silent mutation) | Mutation position (base number) in sequence | Codon change (silent mutation) |
|---|---|---|---|---|
| 10 | 5A | A to G | 900 | AAA to AAG |
| 11 | 6A | A to G | 948 | AAA to AAG |
| 12 | 5A | A to G | 1143 | AAA to AAG |
| 13 | 5T | T to C | 1716 | TTT to TTC |
| 14 | 6T | T to C | 1776 | TTT to TTC |
| 15 | 6A | A to G | 1851 | AAA to AAG |

*Shown as lower case in SEQ ID NO: 5

```
SEQ ID 05:
Homopolymer-free, codon-optimized,
full-length 2014 EBOV GP sequence:
ATGGGAGTAACTGGAATTCTACAACTACCAAGAGA TAGATTCAAAAGAACATCTTTcTTTCTATGGGTTA

TAATTCTATTTCAAAGAACATTTTCTATTCCATTG

GGAGTAATTCATAATTCTACATTGCAAGTATCTGA

TGTAGATAAACTAGTATGTAGAGATAAATTGTCTA

GTACAAATCAACTAAGATCTGTAGGATTGAATCTA

GAAGGAAATGGTGTAGCGACAGATGTTCCATCTGT

AACAAAgAGATGGGGTTTTAGATCTGGTGTACCAC

CAAAAGTAGTAAATTATGAAGCGGGAGAATGGGCG

GAAAATTGTTATAATCTAGAAATTAAgAAACCAGA

TGGATCTGAATGTCTACCAGCGGCGCCAGATGGAA

TTAGAGGATTTCCAAGATGTAGATATGTTCATAAA

GTATCTGGAACAGGACCATGTGCGGGAGATTTTGC

GTTTCATAAAGAAGGAGCATTcTTTCTATATGATA

GACTAGCGTCTACAGTAATATATAGAGGAACAACA

TTTGCGGAAGGTGTAGTAGCTTTTCTAATTCTACC

ACAAGCGAAgAAAGATTTcTTTAGTTCTCATCCAC

TAAGAGAACCAGTAAATGCGACAGAAGATCCTTCT

TCTGGATATTATTCTACTACAATTAGATATCAAGC

GACAGGATTTGGAACAAATGAAACAGAATATCTAT

TTGAAGTTGATAATCTAACATATGTACAACTAGAA

AGTAGATTCACACCACAATTTCTATTGCAATTGAA

TGAAACAATATATGCGTCTGGAAAgAGATCTAATA

CAACTGGAAAACTAATTTGGAAAGTAAATCCAGAA

ATTGATACAACAATTGGAGAATGGGCTTTcTGGGA

AACAAAgAAgAATTTGACAAGAAAgATTAGATCTG

AAGAATTGTCTTTTACAGCGGTATCTAATGGACCA

AAgAATATTTCTGGACAATCTCCAGCGAGAACTTC

TTCTGATCCAGAAACAAATACTACAAATGAAGATC

ACAAAATTATGGCGTCTGAAAATTCTTCTGCTATG

GTACAAGTACATTCTCAAGGAAGAAAAGCGGCGGT

ATCTCATCTAACAACACTAGCGACTATTTCTACAT

CTCCACAACCACCAACAACAAAgACTGGACCAGAT

AATAGTACACATAATACTCCAGTTTATAAACTAGA

TATTTCTGAAGCGACACAAGTTGGACAACATCATA

GAAGAGCGGATAATGATTCTACAGCGTCTGATACA

CCACCAGCTACAACAGCTGCTGGACCATTGAAAGC

GGAAAATACAAATACTTCTAAATCTGCGGATTCTC

TAGATTTGGCGACAACAACTTCTCCTCAAAATTAT

TCTGAAACAGCGGGAAATAATAATACTCATCATCA

AGATACTGGAGAAGAATCTGCGTCTAGTGGAAAAT

TGGGACTAATTACAAATACAATTGCGGGTGTAGCG

GGATTGATTACTGGTGGAAGAAGAACTAGAAGAGA

AGTAATAGTTAATGCGCAACCTAAATGTAATCCAA

ATCTACATTATTGGACAACTCAAGATGAAGGTGCT

GCGATTGGACTAGCTTGGATTCCATATTTTGGACC

TGCGGCGGAAGGAATATATACTGAAGGACTAATGC

ATAATCAAGATGGACTAATTTGTGGACTAAGACAA

CTAGCGAATGAAACTACACAAGCGCTACAACTATT cTTGAGAGCGACAACAGAACTAAGAACTTTTAGTA

TTCTAAATAGAAAAGCGATTGATTTcTTGCTACAA

AGATGGGGAGGAACATGTCATATTCTAGGACCAGA

TTGTTGTATTGAACCACATGATTGGACAAAgAATA

TTACAGACAAAATTGATCAAATTATTCATGATTTT

GTTGATAAAACACTACCAGATCAAGGAGATAATGA

TAATTGGTGGACAGGATGGAGACAATGGATTCCAG

CGGGAATTGGAGTAACAGGTGTAATTATTGCGGTT

ATTGCGCTATTTGTATATGTAAATTTGTTTTTTA

A
```

The homopolymer-free, codon-optimized, full-length 2014 EBOV GP sequence (SEQ ID 05) was searched for vaccinia transcription terminator motifs. None were found.

A second stop codon and a vaccinia transcription terminator sequence were added at the end of the homopolymer-free, codon-optimized, full-length 2014 EBOV GP sequence (SEQ ID 05) to generate SEQ ID 06.

```
SEQ ID 06:
Homopolymer-free, codon-optimized,
full-length 2014 EBOV GP sequence
with stop codon and transcription
terminator added:
ATGGGAGTAACTGGAATTCTACAACTACCAAGAGA TAGATTCAAAAGAACATCTTTcTTTCTATGGGTTA

TAATTCTATTTCAAAGAACATTTTCTATTCCATTG
```

-continued
```
GGAGTAATTCATAATTCTACATTGCAAGTATCTGA
TGTAGATAAACTAGTATGTAGAGATAAATTGTCTA
GTACAAATCAACTAAGATCTGTAGGATTGAATCTA
GAAGGAAATGGTGTAGCGACAGATGTTCCATCTGT
AACAAAgAGATGGGGTTTTAGATCTGGTGTACCAC
CAAAAGTAGTAAATTATGAAGCGGGAGAATGGGCG
GAAAATTGTTATAATCTAGAAATTAAgAAACCAGA
TGGATCTGAATGTCTACCAGCGGCGCCAGATGGAA
TTAGAGGATTTCCAAGATGTAGATATGTTCATAAA
GTATCTGGAACAGGACCATGTGCGGGAGATTTTGC
GTTTCATAAAGAAGGAGCATTcTTTCTATATGATA
GACTAGCGTCTACAGTAATATATAGAGGAACAACA
TTTGCGGAAGGTGTAGTAGCTTTTCTAATTCTACC
ACAAGCGAAgAAAGATTTcTTTAGTTCTCATCCAC
TAAGAGAACCAGTAAATGCGACAGAAGATCCTTCT
TCTGGATATTATTCTACTACAATTAGATATCAAGC
GACAGGATTTGGAACAAATGAAACAGAATATCTAT
TTGAAGTTGATAATCTAACATATGTACAACTAGAA
AGTAGATTCACACCACAATTTCTATTGCAATTGAA
TGAAACAATATATGCGTCTGGAAgAGATCTAATA
CAACTGGAAAACTAATTTGGAAAGTAAATCCAGAA
ATTGATACAACAATTGGAGAATGGGCTTTcTGGGA
AACAAAgAAgAATTTGACAAGAAAgATTAGATCTG
AAGAATTGTCTTTTACAGCGGTATCTAATGGACCA
AAgAATATTTCTGGACAATCTCCAGCGAGAACTTC
TTCTGATCCAGAAACAAATACTACAAATGAAGATC
ACAAAATTATGGCGTCTGAAAATTCTTCTGCTATG
GTACAAGTACATTCTCAAGGAAGAAAAGCGGCGGT
ATCTCATCTAACAACACTAGCGACTATTTCTACAT
CTCCACAACCACCAACAACAAAgACTGGACCAGAT
AATAGTACACATAATACTCCAGTTTATAAACTAGA
TATTTCTGAAGCGACACAAGTTGGACAACATCATA
GAAGAGCGGATAATGATTCTACAGCGTCTGATACA
CCACCAGCTACAACAGCTGCTGGACCATTGAAAGC
GGAAAATACAAATACTTCTAAATCTGCGGATTCTC
TAGATTTGGCGACAACAACTTCTCCTCAAAATTAT
TCTGAAACAGCGGGAAATAATAATACTCATCATCA
AGATACTGGAGAAGAATCTGCGTCTAGTGGAAAAT
TGGGACTAATTACAAATACAATTGCGGGTGTAGCG
GGATTGATTACTGGTGGAAGAAGAACTAGAAGAGA
AGTAATAGTTAATGCGCAACCTAAATGTAATCCAA
ATCTACATTATTGGACAACTCAAGATGAAGGTGCT
GCGATTGGACTAGCTTGGATTCCATATTTTGGACC
TGCGGCGGAAGGAATATATACTGAAGGACTAATGC
ATAATCAAGATGGACTAATTTGTGGACTAAGACAA
CTAGCGAATGAAACTACACAAGCGCTACAACTATT
cTTGAGAGCGACAACAGAACTAAGAACTTTTAGTA
TTCTAAATAGAAAAGCGATTGATTTcTTGCTACAA
AGATGGGGAGGAACATGTCATATTCTAGGACCAGA
TTGTTGTATTGAACCACATGATTGGACAAAgAATA
TTACAGACAAAATTGATCAAATTATTCATGATTTT
GTTGATAAAACACTACCAGATCAAGGAGATAATGA
TAATTGGTGGACAGGATGGAGACAATGGATTCCAG
CGGGAATTGGAGTAACAGGTGTAATTATTGCGGTT
ATTGCGCTATTTTGTATATGTAAATTTGTTTTTTA
ATAATTTTTAT
```

The native nucleotide sequence for 2014 EBOV VP40 was obtained from GenBank (accession number KM233103.1)

```
SEQ ID 07:
Native nucleotide sequence
for 2014 EBOV VP40, from
GenBank:
ATGAGGCGGGTTATATTGCCTACTGCTCCTCCTGA
ATATATGGAGGCCATATACCCTGCCAGGTCAAATT
CAACAATTGCTAGGGGTGGCAACAGCAATACAGGC
TTCCTGACACCGGAGTCAGTCAATGGAGACACTCC
ATCGAATCCACTCAGGCCAATTGCTGATGACACCA
TCGACCATGCCAGCCACACACCAGGCAGTGTGTCA
TCAGCATTCATCCTCGAAGCTATGGTGAATGTCAT
ATCGGGCCCCAAAGTGCTAATGAAGCAAATTCCAA
TTTGGCTTCCTCTAGGTGTCGCTGATCAAAAGACC
TACAGCTTTGACTCAACTACGGCCGCCATCATGCT
TGCTTCATATACTATCACCCATTTCGGCAAGGCAA
CCAATCCGCTTGTCAGAGTCAATCGGCTGGGTCCT
GGAATCCCGGATCACCCCCTCAGGCTCCTGCGAAT
TGGAAACCAGGCTTTCCTCCAGGAGTTCGTTCTTC
CACCAGTCCAACTACCCCAGTATTTCACCTTTGAT
TTGACAGCACTCAAACTGATCACTCAACCACTGCC
TGCTGCAACATGGACCGATGACACTCCAACTGGAT
CAAATGGAGCGTTGCGTCCAGGAATTTCATTTCAT
CCAAAACTTCGCCCCATTCTTTTACCCAACAAAAG
TGGGAAGAAGGGGAACAGTGCCGATCTAACATCTC
CGGAGAAAATCCAAGCAATAATGACTTCACTCCAG
```

-continued
GACTTTAAGATCGTTCCAATTGATCCAACCAAAAA

TATCATGGGTATCGAAGTGCCAGAAACTCTGGTCC

ACAAGCTGACCGGTAAGAAGGTGACTTCCAAAAAT

GGACAACCAATCATCCCTGTTCTTTTGCCAAAGTA

CATTGGGTTGGACCCGGTGGCTCCAGGAGACCTCA

CCATGGTAATCACACAGGATTGTGACACGTGTCAT

TCTCCTGCAAGTCTTCCAGCTGTGGTTGAGAAGTA

A

The native nucleotide sequence for 2014 EBOV VP40 (SEQ ID 07) was optimized for vaccinia virus expression using the online Gene Optimizer algorithm.

The codon-optimized 2014 EBOV VP40 sequence was searched for homopolymer stretches consisting of ≥5 G bases or ≥C bases. None were found.

The codon-optimized 2014 EBOV VP40 sequence was searched for homopolymer stretches consisting of ≥5 T bases or ≥5 A bases. Five such stretches were found and were eliminated through silent mutations as listed in Table 4, to generate SEQ ID 08.

TABLE 4

Elimination of homopolymer stretches in optimized 2014 EBOV VP40 sequence

| No. | Homopolymer | Changes (Silent mutation) | Mutation position (base number) in sequence | Codon change (silent mutation) |
|---|---|---|---|---|
| 1 | 6A | A to G | 312 | AAA to AAG |
| 2 | 7A | A to G | 672 | AAA to AAG |
| 3 | 6A | A to G | 708 | AAA to AAG |
| 4 | 6A | A to G | 768 | AAA to AAG |
| 5 | 7A | A to G | 822 | AAA to AAG |

*Shown as lower case in SEQ ID NO: 8 and SEQ ID NO: 9

SEQ ID 08:
Homopolymer-free, codon-optimized
2014 EBOV VP40 sequence:
ATGAGAAGAGTAATTCTACCAACAGCGCCACCAGA

ATATATGGAAGCGATATATCCAGCGAGATCTAATT

CTACAATTGCGAGAGGTGGAAATTCTAATACTGGA

TTTCTAACACCAGAATCTGTAAATGGAGATACACC

ATCTAATCCACTAAGACCAATTGCGGATGATACAA

TAGATCATGCGAGTCATACTCCAGGATCTGTATCT

TCTGCTTTTATTCTAGAAGCTATGGTTAATGTAAT

TTCTGGACCAAAAGTACTAATGAAACAAATTCCAA

TTTGGCTACCATTGGGAGTAGCGGATCAAAAgACA

TATTCTTTTGATTCTACTACAGCGGCGATTATGCT

AGCGTCTTATACAATTACACATTTTGGAAAAGCGA

CAAATCCACTAGTTAGAGTAAATAGACTAGGACCT

GGAATACCAGATCATCCATTGAGACTACTAAGAAT

TGGAAATCAAGCTTTTCTACAAGAATTTGTTCTAC

-continued
CACCAGTACAACTACCACAATACTTTACATTTGAT

CTAACAGCGCTAAAACTAATTACACAACCATTGCC

AGCGGCGACATGGACAGATGATACACCAACAGGAT

CTAATGGTGCTCTAAGACCTGGTATTTCTTTTCAT

CCAAAACTAAGACCTATTCTATTGCCAAATAAATC

TGGAAAgAAAGGAAATTCTGCGGATCTAACATCTC

CAGAAAAgATTCAAGCGATTATGACATCTCTACAA

GACTTCAAAATTGTACCAATTGATCCAACAAAgAA

TATTATGGGAATTGAAGTACCAGAAACACTAGTTC

ATAAACTAACTGGAAAgAAAGTAACATCTAAAAAT

GGACAACCTATTATTCCAGTATTGCTACCTAAATA

TATTGGACTAGATCCAGTAGCGCCTGGAGATCTAA

CAATGGTTATTACACAAGATTGTGATACTTGTCAT

TCTCCAGCGAGTTTGCCTGCGGTAGTAGAAAAATA

A

The homopolymer-free, codon-optimized, full-length 2014 EBOV GP sequence (SEQ ID 08) was searched for vaccinia transcription terminator motifs. None were found.

A second stop codon and a vaccinia transcription terminator sequence were added at the end of the homopolymer-free, codon-optimized 2014 EBOV VP40 sequence (SEQ ID 08) to generate SEQ ID 09.

SEQ ID 09:
Homopolymer-free, codon-optimized
2014 EBOV VP40 sequence with stop
codon and transcription terminator
added:
ATGAGAAGAGTAATTCTACCAACAGCGCCACCAGA

ATATATGGAAGCGATATATCCAGCGAGATCTAATT

CTACAATTGCGAGAGGTGGAAATTCTAATACTGGA

TTTCTAACACCAGAATCTGTAAATGGAGATACACC

ATCTAATCCACTAAGACCAATTGCGGATGATACAA

TAGATCATGCGAGTCATACTCCAGGATCTGTATCT

TCTGCTTTTATTCTAGAAGCTATGGTTAATGTAAT

TTCTGGACCAAAAGTACTAATGAAACAAATTCCAA

TTTGGCTACCATTGGGAGTAGCGGATCAAAAgACA

TATTCTTTTGATTCTACTACAGCGGCGATTATGCT

AGCGTCTTATACAATTACACATTTTGGAAAAGCGA

CAAATCCACTAGTTAGAGTAAATAGACTAGGACCT

GGAATACCAGATCATCCATTGAGACTACTAAGAAT

TGGAAATCAAGCTTTTCTACAAGAATTTGTTCTAC

CACCAGTACAACTACCACAATACTTTACATTTGAT

CTAACAGCGCTAAAACTAATTACACAACCATTGCC

AGCGGCGACATGGACAGATGATACACCAACAGGAT

CTAATGGTGCTCTAAGACCTGGTATTTCTTTTCAT

```
CCAAAACTAAGACCTATTCTATTGCCAAATAAATC

TGGAAAgAAAGGAAATTCTGCGGATCTAACATCTC

CAGAAAAgATTCAAGCGATTATGACATCTCTACAA

GACTTCAAAATTGTACCAATTGATCCAACAAAgAA

TATTATGGGAATTGAAGTACCAGAAACACTAGTTC

ATAAACTAACTGGAAAgAAAGTAACATCTAAAAAT

GGACAACCTATTATTCCAGTATTGCTACCTAAATA

TATTGGACTAGATCCAGTAGCGCCTGGAGATCTAA

CAATGGTTATTACACAAGATTGTGATACTTGTCAT

TCTCCAGCGAGTTTGCCTGCGGTAGTAGAAAAATA

ATAATTTTTAT
```

Example 3: Additional Antigen Sequences for Filovirus MVA Vaccine

In another exemplary embodiment, sequences from Zaire Ebola (ZEBOV) and Sudan Ebola Virus (SUDV) are prepared in shuttle plasmids and optimized. Viral sequences are then inserted into MVA vector vaccines described herein. These sequences are modified from native sequences using the methods described herein.

TABLE 5

Zaire Ebola VP40 mutation table

| Changes (Silent mutation) | Mutation position on VP40 |
|---|---|
| A to G | 312 |
| A to G | 672 |
| A to G | 708 |
| A to G | 768 |
| A to G | 822 |

*Shown as lower case in SEQ ID NO: 10

```
SEQ ID 10:
pGEO-ZEBOV2014 VP40 sequence optimized
for insertion into MVA vector:
(FIG. 3)
GAATTCGGAGTATACGAACCGGGAAAGAGAAGATG

GTTAAAAATAAAGCGAGACTATTTGAACGAGGGTT

CCATGGCAGATTCTGCCGATTTAGTAGTACTAGGT

GCTTACTATGGTAAAGGAGCAAAGGGTGGTATCAT

GGCAGTCTTTCTAATGGGTTGTTACGACGATGAAT

CCGGTAAATGGAAGACGGTTACCAAGTGTTCAGGA

CACGATGATAATACGTTAAGGGAGTTGCAAGACCA

ATTAAAGATGATTAAAATTAACAAGGATCCCAAAA

AAATTCCAGAGTGGTTAGTAGTTAATAAAATCTAT

ATTCCCGATTTTGTAGTAGAGGATCCAAAACAATC

TCAGATATGGGAAATTTCAGGAGCAGAGTTTACAT

CTTCCAAGTCCCATACCGCAAATGGAATATCCATT

AGATTTCCTAGATTTACTAGGATAAGAGAGGATAA

AACGTGGAAAGAATCTACTCATCTAAACGATTTAG

TAAACTTGACTAAATCTTAATTTTTATGGCGCGCC

TTTCATTTTGTTTTTTTCTATGCTATAAATGGTGA

GCAAGGGCGAGGAGCTGTTCACCGGGGTGGTGCCC

ATCCTGGTCGAGCTGGACGGCGACGTAAACGCCA

CAAGTTCAGCGTGTCCGGCGAGGGCGAGGGCGATG

CCACCTACGGCAAGCTGACCCTGAAGTTCATCTGC

ACCACCGGCAAGCTGCCCGTGCCCTGGCCCACCCT

CGTGACCACCCTGACCTACGGCGTGCAGTGCTTCA

GCCGCTACCCCGACCACATGAAGCAGCACGACTTC

TTCAAGTCCGCCATGCCCGAAGGCTACGTCCAGGA

GCGCACCATCTTCTTCAAGGACGACGGCAACTACA

AGACCCGCGCCGAGGTGAAGTTCGAGGGCGACACC

CTGGTGAACCGCATCGAGCTGAAGGGCATCGACTT

CAAGGAGGACGGCAACATCCTGGGGCACAAGCTGG

AGTACAACTACAACAGCCACAACGTCTATATCATG

GCCGACAAGCAGAAGAACGGCATCAAGGTGAACTT

CAAGATCCGCCACAACATCGAGGACGGCAGCGTGC

AGCTCGCCGACCACTACCAGCAGAACACCCCCATC

GGCGACGGCCCCGTGCTGCTGCCCGACAACCACTA

CCTGAGCACCCAGTCCGCCCTGAGCAAAGACCCCA

ACGAGAAGCGCGATCACATGGTCCTGCTGGAGTTC

GTGACCGCCGCCGGGATCACTCTCGGCATGCACGA

GCTGTACAAGTAAGAGCTCCCCGATTTTGTAGTAG

AGGATCCAAAACAATCTCAGATATGGGAAATTTCA

GGAGCAGAGTTTACATCTTCCAAGTCCCATACCGC

AAATGGAATATCCATTAGATTTCCTAGATTTACTA

GGATAAGAGAGGATAAAACGTGGAAAGAATCTACT

CATCTAAACGATTTAGTAAACTTGACTAAATCTTA

ATTTTTATCTCGAGGCCGCTGGTACCCAACCTAAA

AATTGAAAATAAATACAAAGGTTCTTGAGGGTTGT

GTTAAATTGAAAGCGAGAAATAATCATAAATAAGC

CCgggATGAGAAGAGTAATTCTACCAACAGCGCCA

CCAGAATATATGGAAGCGATATATCCAGCGAGATC

TAATTCTACAATTGCGAGAGGTGGAAATTCTAATA

CTGGATTTCTAACACCAGAATCTGTAAATGGAGAT

ACACCATCTAATCCACTAAGACCAATTGCGGATGA

TACAATAGATCATGCGAGTCATACTCCAGGATCTG

TATCTTCTGCTTTTATTCTAGAAGCTATGGTTAAT

GTAATTTCTGGACCAAAAGTACTAATGAAACAAAT
```

-continued

TCCAATTTGGCTACCATTGGGAGTAGCGGATCAAA
AgACATATTCTTTTGATTCTACTACAGCGGCGATT
ATGCTAGCGTCTTATACAATTACACATTTTGGAAA
AGCGACAAATCCACTAGTTAGAGTAAATAGACTAG
GACCTGGAATACCAGATCATCCATTGAGACTACTA
AGAATTGGAAATCAAGCTTTTCTACAAGAATTTGT
TCTACCACCAGTACAACTACCACAATACTTTACAT
TTGATCTAACAGCGCTAAAACTAATTACACAACCA
TTGCCAGCGGCGACATGGACAGATGATACACCAAC
AGGATCTAATGGTGCTCTAAGACCTGGTATTTCTT
TTCATCCAAAACTAAGACCTATTCTATTGCCAAAT
AAATCTGGAAAgAAAGGAAATTCTGCGGATCTAAC
ATCTCCAGAAAAgATTCAAGCGATTATGACATCTC
TACAAGACTTCAAAATTGTACCAATTGATCCAACA
AAgAATATTATGGGAATTGAAGTACCAGAAACACT
AGTTCATAAACTAACTGGAAAgAAAGTAACATCTA
AAAATGGACAACCTATTATTCCAGTATTGCTACCT
AAATATATTGGACTAGATCCAGTAGCGCCTGGAGA
TCTAACAATGGTTATTACACAAGATTGTGATACTT
GTCATTCTCCAGCGAGTTTGCCTGCGGTAGTAGAA
AAATAATAATTTTTATgTCGACCTGCAGCTAATGT
ATTAGTTAAATATTAAAACTTACCACGTAAAACTT
AAAATTTAAAATGATATTTCATTGACAGATAGATC
ACACATTATGAACTTTCAAGGACTTGTGTTAACTG
ACAATTGCAAAAATCAATGGGTCGTTGGACCATTA
ATAGGAAAAGGTGGATTTGGTAGTATTTATACTAC
TAATGACAATAATTATGTAGTAAAAATAGAGCCCA
AAGCTAACGGATCATTATTTACCGAACAGGCATTT
TATACTAGAGTACTTAAACCATCCGTTATCGAAGA
ATGGAAAAAATCTCACAATATAAAGCACGTAGGTC
TTATCACGTGCAAGGCATTTGGTCTATACAAATCC
ATTAATGTGGAATATCGATTCTTGGTAATTAATAG
ATTAGGTGCAGATCTAGATGCGGTGATCAGAGCCA
ATAATAATAGATTACCAAAAAGGTCGGTGATGTTG
ATCGGAATCGAAATCTTAAATACCATACAATTTAT
GCACGAGCAAGGATATTCTCACGGAGATATTAAAG
CGAGTAATATAGTCTTGGATCAAATAGATAAGAAT
AAATTATATCTAGTGGATTACGGATTGGTTTCTAA
ATTCATGTCAAGCTTGTCTCCCTATAGTGAGTCGT
ATTAGAGCTTGGCGTAATCATGGTCATAGCTGTTT
CCTGTGTGAAATTGTTATCCGCTCACAATTCCACA

-continued

CAACATACGAGCCGGAAGCATAAAGTGTAAAGCCT
GGGGTGCCTAATGAGTGAGCTAACTCACATTAATT
GCGTTGCGCTCACTGCCCGCTTTCGAGTCGGGAAA
CCTGTCGTGCCAGCTGCATTAATGAATCGGCCAAC
GCGCGGGGAGAGGCGGTTTGCGTATTGGGCGCTCT
TCCGCTTCCTCGCTCACTGACTCGCTGCGCTCGGT
CGTTCGGCTGCGGCGAGCGGTATCAGCTCACTCAA
AGGCGGTAATACGGTTATCCACAGAATCAGGGGAT
AACGCAGGAAAGAACATGTGAGCAAAAGGCCAGCA
AAAGGCCAGGAACCGTAAAAAGGCCGCGTTGCTGG
CGTTTTTCGATAGGCTCCGCCCCCCTGACGAGCAT
CACAAAAATCGACGCTCAAGTCAGAGGTGGCGAAA
CCCGACAGGACTATAAAGATACCAGGCGTTTCCCC
CTGGAAGCTCCCTCGTGCGCTCTCCTGTTCCGACC
CTGCCGCTTACCGGATACCTGTCCGCCTTTCTCCC
TTCGGGAAGCGTGGCGCTTTCTCATAGCTCACGCT
GTAGGTATCTCAGTTCGGTGTAGGTCGTTCGCTCC
AAGCTGGGCTGTGTGCACGAACCCCCCGTTCAGCC
CGACCGCTGCGCCTTATCCGGTAACTATCGTCTTG
AGTCCAACCCGGTAAGACACGACTTATCGCCACTG
GCAGCAGCCACTGGTAACAGGATTAGCAGAGCGAG
GTATGTAGGCGGTGCTACAGAGTTCTTGAAGTGGT
GGCCTAACTACGGCTACACTAGAAGGACAGTATTT
GGTATCTGCGCTCTGCTGAAGCCAGTTACCTTCGG
AAAAAGAGTTGGTAGCTCTTGATCCGGCAAACAAA
CCACCGCTGGTAGCGGTGGTTTTTTTGTTTGCAAG
CAGCAGATTACGCGCAGAAAAAAAGGATCTCAAGA
AGATCCTTTGATCTTTTCTACGGGGTCTGACGCTC
AGTGGAACGAAAACTCACGTTAAGGGATTTTGGTC
ATGAGATTATCAAAAAGGATCTTCACCTAGATCCT
TTTAAATTAAAAATGAAGTTTTAAATCAATCTAAA
GTATATATGAGTAAACTTGGTCTGACAGTTACCAA
TGCTTAATCAGTGAGGCACCTATCTCAGCGATCTG
TCTATTTCGTTCATCCATAGTTGCCTGACTCCCCG
TCGTGTAGATAACTACGATACGGGAGGGCTTACCA
TCTGGCCCCAGTGCTGCAATGATACCGCGAGACCC
ACGCTCACCGGCTCCAGATTTATCAGCAATAAACC
AGCCAGCCGGAAGGGCCGAGCGCAGAAGTGGTCCT
GCAACTTTATCCGCCTCCATCCAGTCTATTAATTG
TTGCCGGGAAGCTAGAGTAAGTAGTTCGCCAGTTA
ATAGTTTGCGCAACGTTGTTGGCATTGCTACAGGC

-continued

ATCGTGGTGTCACGCTCGTCGTTTGGTATGGCTTC

ATTCAGCTCCGGTTCCCAACGATCAAGGCGAGTTA

CATGATCCCCATGTTGTGCAAAAAAGCGGTTAGC

TCCTTCGGTCCTCCGATCGTTGTCAGAAGTAAGTT

GGCCGCAGTGTTATCACTCATGGTTATGGCAGCAC

TGCATAATTCTCTTACTGTCATGCCATCCGTAAGA

TGCTTTTCTGTGACTGGTGAGTACTCAACCAAGTC

ATTCTGAGAATAGTGTATGCGGCGACCGAGTTGCT

CTTGCCCGGCGTCAATACGGGATAATACCGCGCCA

CATAGCAGAACTTTAAAAGTGCTCATCATTGGAAA

ACGTTCTTCGGGGCGAAAACTCTCAAGGATCTTAC

CGCTGTTGAGATCCAGTTCGATGTAACCCACTCGT

GCACCCAACTGATCTTCAGCATCTTTTACTTTCAC

CAGCGTTTCTGGGTGAGCAAAAACAGGAAGGCAAA

ATGCCGCAAAAAGGGAATAAGGGCGACACGGAAA

TGTTGAATACTCATACTCTTCCTTTTTCAATATTA

TTGAAGCATTTATCAGGGTTATTGTCTCATGAGCG

GATACATATTTGAATGTATTTAGAAAAATAAACAA

ATAGGGGTTCCGCGCACATTTCCCCGAAAGTGCC

ACCTGACGTCTAAGAAACCATTATTATCATGACAT

TAACCTATAAAAATAGGCGTATCACGAGGCCCTTT

CGTCTCGCGCGTTTCGGTGATGACGGTGAAAACCT

CTGACACATGCAGCTCCCGGAGACGGTCACAGCTT

GTCTGTAAGCGGATGCCGGGAGCAGACAAGCCCGT

CAGGGCGCGTCAGCGGGTGTTGGCGGGTGTCGGG

CTGGCTTAACTATGCGGCATCAGAGCAGATTGTAC

TGAGAGTGCACCATATGCGGTGTGAAATACCGCAC

AGATGCGTAAGGAGAAAATACCGCATCAGGCGCCA

TTCGCCATTCAGGCTGCGCAACTGTTGGGAAGGGC

GATCGGTGCGGGCCTCTTCGCTATTACGCCAGCTG

GCGAAAGGGGATGTGCTGCAAGGCGATTAAGTTG

GGTAACGCCAGGGTTTTCCCAGTCACGACGTTGTA

AAACGACGGCCAGTGAATTGGATTTAGGTGACACT

ATA

TABLE 6

| Zaire Ebola Glycoprotein mutation table | |
|---|---|
| Changes (Silent mutation) | Mutation position on GP |
| T to C | 57 |
| A to G | 252 |
| A to G | 342 |
| T to C | 477 |

TABLE 6-continued

| Zaire Ebola Glycoprotein mutation table | |
|---|---|
| Changes (Silent mutation) | Mutation position on GP |
| A to G | 570 |
| T to C | 579 |
| A to G | 795 |
| T to C | 870 |
| A to G | 882 |
| | 885 |
| A to G | 900 |
| A to G | 948 |
| A to G | 1143 |
| T to C | 1716 |
| T to C | 1776 |
| A to G | 1851 |

*Shown as lower case in SEQ ID NO: 11

SEQ ID 11:
pGEO-ZEBOV2014 GP sequence optimized
for insertion into MVA vector:
(FIG. 2)
GAATTCCCTGGGACATACGTATATTTCTATGATCT

GTCTTATATGAAGTCTATACAGCGAATAGATTCAG

AATTTCTACATAATTATATATTGTACGCTAATAAG

TTTAATCTAACACTCCCCGAAGATTTGTTTATAAT

CCCTACAAATTTGGATATTCTATGGCGTACAAAGG

AATATATAGACTCGTTCGATATTAGTACAGAAACA

TGGAATAAATTATTATCCAATTATTATATGAAGAT

GATAGAGTATGCTAAACTTTATGTACTAAGTCCTA

TTCTCGCTGAGGAGTTGGATAATTTTGAGAGGACG

GGAGAATTAACTAGTATTGTACAAGAAGCCATTTT

ATCTCTAAATTTACGAATTAAGATTTTAAATTTTA

AACATAAAGATGATGATACGTATATACACTTTTGT

AAAATATTATTCGGTGTCTATAACGGAACAAACGC

TACTATATATTATCATAGACCTCTAACGGGATATA

TGAATATGATTTCAGATACTATATTTGTTCCTGTA

GATAATAACTAAGGCGCGCCTTTCATTTTGTTTTT

TTCTATGCTATAAATGGTGAGCAAGGGCGAGGAGC

TGTTCACCGGGGTGGTGCCCATCCTGGTCGAGCTG

GACGGCGACGTAAACGGCCACAAGTTCAGCGTGTC

CGGCGAGGGCGAGGGCGATGCCACCTACGGCAAGC

TGACCCTGAAGTTCATCTGCACCACCGGCAAGCTG

CCCGTGCCCTGGCCCACCCTCGTGACCACCCTGAC

CTACGGCGTGCAGTGCTTCAGCCGCTACCCCGACC

ACATGAAGCAGCACGACTTCTTCAAGTCCGCCATG

CCCGAAGGCTACGTCCAGGAGCGCACCATCTTCTT

CAAGGACGACGGCAACTACAAGACCCGCGCCGAGG

TGAAGTTCGAGGGCGACACCCTGGTGAACCGCATC

-continued

GAGCTGAAGGGCATCGACTTCAAGGAGGACGGCAA

CATCCTGGGGCACAAGCTGGAGTACAACTACAACA

GCCACAACGTCTATATCATGGCCGACAAGCAGAAG

AACGGCATCAAGGTGAACTTCAAGATCCGCCACAA

CATCGAGGACGGCAGCGTGCAGCTCGCCGACCACT

ACCAGCAGAACACCCCCATCGGCGACGGCCCCGTG

CTGCTGCCCGACAACCACTACCTGAGCACCCAGTC

CGCCCTGAGCAAAGACCCCAACGAGAAGCGCGATC

ACATGGTCCTGCTGGAGTTCGTGACCGCCGCCGGG

ATCACTCTCGGCATGCACGAGCTGTACAAGTAAGA

GCTCGAGGACGGGAGAATTAACTAGTATTGTACAA

GAAGCCATTTTATCTCTAAATTTACGAATTAAGAT

TTTAAATTTTAAACATAAAGATGATGATACGTATA

TACACTTTTGTAAAATATTATTCGGTGTCTATAAC

GGAACAAACGCTACTATATATTATCATAGACCTCT

AACGGGATATATGAATATGATTTCAGATACTATAT

TTGTTCCTGTAGATAATAACTAACTCGAGGCCGCT

GGTACCCAACCTAAAAATTGAAAATAAATACAAAG

GTTCTTGAGGGTTGTGTTAAATTGAAAGCGAGAAA

TAATCATAAATAAGCCCgggATGGGAGTAACTGGA

ATTCTACAACTACCAAGAGATAGATTCAAAAGAAC

ATCTTTcTTTCTATGGGTTATAATTCTATTTCAAA

GAACATTTTCTATTCCATTGGGAGTAATTCATAAT

TCTACATTGCAAGTATCTGATGTAGATAAACTAGT

ATGTAGAGATAAATTGTCTAGTACAAATCAACTAA

GATCTGTAGGATTGAATCTAGAAGGAAATGGTGTA

GCGACAGATGTTCCATCTGTAACAAAgAGATGGGG

TTTTAGATCTGGTGTACCACCAAAAGTAGTAAATT

ATGAAGCGGGAGAATGGGCGGAAAATTGTTATAAT

CTAGAAATTAAgAAACCAGATGGATCTGAATGTCT

ACCAGCGGCGCCAGATGGAATTAGAGGATTTCCAA

GATGTAGATATGTTCATAAAGTATCTGGAACAGGA

CCATGTGCGGGAGATTTTGCGTTTCATAAAGAAGG

AGCATTcTTTCTATATGATAGACTAGCGTCTACAG

TAATATATAGAGGAACAACATTTGCGGAAGGTGTA

GTAGCTTTTCTAATTCTACCACAAGCGAAgAAAGA

TTTcTTTAGTTCTCATCCACTAAGAGAACCAGTAA

ATGCGACAGAAGATCCTTCTTCTGGATATTATTCT

ACTACAATTAGATATCAAGCGACAGGATTTGGAAC

AAATGAAACAGAATATCTATTTGAAGTTGATAATC

TAACATATGTACAACTAGAAAGTAGATTCACACCA

-continued

CAATTTCTATTGCAATTGAATGAAACAATATATGC

GTCTGGAAAgAGATCTAATACAACTGGAAAACTAA

TTTGGAAAGTAAATCCAGAAATTGATACAACAATT

GGAGAATGGGCTTTcTGGGAAACAAAgAAgAATTT

GACAAGAAAgATTAGATCTGAAGAATTGTCTTTTA

CAGCGGTATCTAATGGACCAAAgAATATTTCTGGA

CAATCTCCAGCGAGAACTTCTTCTGATCCAGAAAC

AAATACTACAAATGAAGATCACAAAATTATGGCGT

CTGAAAATTCTTCTGCTATGGTACAAGTACATTCT

CAAGGAAGAAAAGCGGCGGTATCTCATCTAACAAC

ACTAGCGACTATTTCTACATCTCCACAACCACCAA

CAACAAAgACTGGACCAGATAATAGTACACATAAT

ACTCCAGTTTATAAACTAGATATTTCTGAAGCGAC

ACAAGTTGGACAACATCATAGAAGAGCGGATAATG

ATTCTACAGCGTCTGATACACCACCAGCTACAACA

GCTGCTGGACCATTGAAAGCGGAAAATACAAATAC

TTCTAAATCTGCGGATTCTCTAGATTTGGCGACAA

CAACTTCTCCTCAAAATTATTCTGAAACAGCGGGA

AATAATAATACTCATCATCAAGATACTGGAGAAGA

ATCTGCGTCTAGTGGAAAATTGGGACTAATTACAA

ATACAATTGCGGGTGTAGCGGGATTGATTACTGGT

GGAAGAAGAACTAGAAGAGAAGTAATAGTTAATGC

GCAACCTAAATGTAATCCAAATCTACATTATTGGA

CAACTCAAGATGAAGGTGCTGCGATTGGACTAGCT

TGGATTCCATATTTTGGACCTGCGGCGGAAGGAAT

ATATACTGAAGGACTAATGCATAATCAAGATGGAC

TAATTTGTGGACTAAGCAACTAGCGAATGAAACT

ACACAAGCGCTACAACTATTcTTGAGAGCGACAAC

AGAACTAAGAACTTTTAGTATTCTAAATAGAAAAG

CGATTGATTTcTTGCTACAAAGATGGGGAGGAACA

TGTCATATTCTAGGACCAGATTGTTGTATTGAACC

ACATGATTGGACAAAgAATATTACAGACAAAATTG

ATCAAATTATTCATGATTTTGTTGATAAAACACTA

CCAGATCAAGGAGATAATGATAATTGGTGGACAGG

ATGGAGACAATGGATTCCAGCGGGAATTGGAGTAA

CAGGTGTAATTATTGCGGTTATTGCGCTATTTTGT

ATATGTAAATTTGTTTTTTAATAATTTTTATgTCG

ACCTGCAGTCAAACTCTAATGACCACATCTTTTTT

TAGAGATGAAAAATTTTCCACATCTCCTTTTGTAG

ACACGACTAAACATTTTGCAGAAAAAAGTTTATTA

GTGTTTAGATAATCGTATACTTCATCAGTGTAGAT

-continued

AGTAAATGTGAACAGATAAAAGGTATTCTTGCTCA
ATAGATTGGTAAATTCCATAGAATATATTAATCCT
TTCTTCTTGAGATCCCACATCATTTCAACCAGAGA
CGTTTTATCCAATGATTTACCTCGTACTATACCAC
ATACAAAACTAGATTTTGCAGTGACGTCGTATCTG
GTATTCCTACCAAACAAAATTTTACTTTTAGTTCT
TTTAGAAAATTCTAAGGTAGAATCTCTATTTGCCA
ATATGTCATCTATGGAATTACCACTAGCAAAAAAT
GATAGAAATATATATTGATACATCGCAGCTGGTTT
TGATCTACTATACTTTAAAAACGAATCAGATTCCA
TAATTGCCTGTATATCATCAGCTGAAAAACTATGT
TTTACACGTATTCCTTCGGCATTTCTTTTTAATGA
TATATCTTGTTTAGACAATGATAAAGTTATCATGT
CCATGAGAGACGCGTCTCCGTATCGTATAAATATT
TCATTAGATGTTAGACGCTTCATTAGGGGTATACT
TCTATAAGGTTTCTTAATCAGTCCATCATTGGTTG
CGTCAAGAACAAGCTTGTCTCCCTATAGTGAGTCG
TATTAGAGCTTGGCGTAATCATGGTCATAGCTGTT
TCCTGTGTGAAATTGTTATCCGCTCACAATTCCAC
ACAACATACGAGCCGGAAGCATAAAGTGTAAAGCC
TGGGGTGCCTAATGAGTGAGCTAACTCACATTAAT
TGCGTTGCGCTCACTGCCCGCTTTCGAGTCGGGAA
ACCTGTCGTGCCAGCTGCATTAATGAATCGGCCAA
CGCGCGGGGAGAGGCGGTTTGCGTATTGGGCGCTC
TTCCGCTTCCTCGCTCACTGACTCGCTGCGCTCGG
TCGTTCGGCTGCGGCGAGCGGTATCAGCTCACTCA
AAGGCGGTAATACGGTTATCCACAGAATCAGGGGA
TAACGCAGGAAAGAACATGTGAGCAAAAGGCCAGC
AAAAGGCCAGGAACCGTAAAAAGGCCGCGTTGCTG
GCGTTTTTCGATAGGCTCCGCCCCCCTGACGAGCA
TCACAAAAATCGACGCTCAAGTCAGAGGTGGCGAA
ACCCGACAGGACTATAAAGATACCAGGCGTTTCCC
CCTGGAAGCTCCCTCGTGCGCTCTCCTGTTCCGAC
CCTGCCGCTTACCGGATACCTGTCCGCCTTTCTCC
CTTCGGGAAGCGTGGCGCTTTCTCATAGCTCACGC
TGTAGGTATCTCAGTTCGGTGTAGGTCGTTCGCTC
CAAGCTGGGCTGTGTGCACGAACCCCCCGTTCAGC
CCGACCGCTGCGCCTTATCCGGTAACTATCGTCTT
GAGTCCAACCCGGTAAGACACGACTTATCGCCACT
GGCAGCAGCCACTGGTAACAGGATTAGCAGAGCGA
GGTATGTAGGCGGTGCTACAGAGTTCTTGAAGTGG

-continued

TGGCCTAACTACGGCTACACTAGAAGGACAGTATT
TGGTATCTGCGCTCTGCTGAAGCCAGTTACCTTCG
GAAAAAGAGTTGGTAGCTCTTGATCCGGCAAACAA
ACCACCGCTGGTAGCGGTGGTTTTTTTGTTTGCAA
GCAGCAGATTACGCGCAGAAAAAAAGGATCTCAAG
AAGATCCTTTGATCTTTTCTACGGGGTCTGACGCT
CAGTGGAACGAAAACTCACGTTAAGGGATTTTGGT
CATGAGATTATCAAAAGGATCTTCACCTAGATCC
TTTTAAATTAAAAATGAAGTTTTAAATCAATCTAA
AGTATATATGAGTAAACTTGGTCTGACAGTTACCA
ATGCTTAATCAGTGAGGCACCTATCTCAGCGATCT
GTCTATTTCGTTCATCCATAGTTGCCTGACTCCCC
GTCGTGTAGATAACTACGATACGGGAGGGCTTACC
ATCTGGCCCCAGTGCTGCAATGATACCGCGAGACC
CACGCTCACCGGCTCCAGATTTATCAGCAATAAAC
CAGCCAGCCGGAAGGGCCGAGCGCAGAAGTGGTCC
TGCAACTTTATCCGCCTCCATCCAGTCTATTAATT
GTTGCCGGGAAGCTAGAGTAAGTAGTTCGCCAGTT
AATAGTTTGCGCAACGTTGTTGGCATTGCTACAGG
CATCGTGGTGTCACGCTCGTCGTTTGGTATGGCTT
CATTCAGCTCCGGTTCCCAACGATCAAGGCGAGTT
ACATGATCCCCCATGTTGTGCAAAAAAGCGGTTAG
CTCCTTCGGTCCTCCGATCGTTGTCAGAAGTAAGT
TGGCCGCAGTGTTATCACTCATGGTTATGGCAGCA
CTGCATAATTCTCTTACTGTCATGCCATCCGTAAG
ATGCTTTTCTGTGACTGGTGAGTACTCAACCAAGT
CATTCTGAGAATAGTGTATGCGGCGACCGAGTTGC
TCTTGCCCGGCGTCAATACGGGATAATACCGCGCC
ACATAGCAGAACTTTAAAAGTGCTCATCATTGGAA
AACGTTCTTCGGGGCGAAAACTCTCAAGGATCTTA
CCGCTGTTGAGATCCAGTTCGATGTAACCCACTCG
TGCACCCAACTGATCTTCAGCATCTTTTACTTTCA
CCAGCGTTTCTGGGTGAGCAAAAACAGGAAGGCAA
AATGCCGCAAAAAAGGGAATAAGGGCGACACGGAA
ATGTTGAATACTCATACTCTTCCTTTTTCAATATT
ATTGAAGCATTTATCAGGGTTATTGTCTCATGAGC
GGATACATATTTGAATGTATTTAGAAAAATAAACA
AATAGGGGTTCCGCGCACATTTCCCCGAAAAGTGC
CACCTGACGTCTAAGAAACCATTATTATCATGACA
TTAACCTATAAAAATAGGCGTATCACGAGGCCCTT
TCGTCTCGCGCGTTTCGGTGATGACGGTGAAAACC

```
TCTGACACATGCAGCTCCCGGAGACGGTCACAGCT

TGTCTGTAAGCGGATGCCGGGAGCAGACAAGCCCG

TCAGGGCGCGTCAGCGGGTGTTGGCGGGTGTCGGG

GCTGGCTTAACTATGCGGCATCAGAGCAGATTGTA

CTGAGAGTGCACCATATGCGGTGTGAAATACCGCA

CAGATGCGTAAGGAGAAAATACCGCATCAGGCGCC

ATTCGCCATTCAGGCTGCGCAACTGTTGGGAAGGG

CGATCGGTGCGGGCCTCTTCGCTATTACGCCAGCT

GGCGAAAGGGGGATGTGCTGCAAGGCGATTAAGTT

GGGTAACGCCAGGGTTTTCCCAGTCACGACGTTGT
```

```
AAAACGACGGCCAGTGAATTGGATTTAGGTGACAC

TATA
```

TABLE 7

Sudan Ebola VP40 mutation table

| Changes (Silent mutation) | Mutation position on VP40 |
|---|---|
| A to G | 111 |
| A to G | 312 |
| A to G | 663 |
| A to G | 675 |
| A to G | 822 |
| A to G | 837 |
| A to G | 978 |

*Shown as lower case in SEQ ID NO: 12

```
SEQ ID 12:
pGEO-SUDV2014 VP40 sequence optimized for insertion into MVA vector: (FIG. 7)
GAATTCGGAGTATACGAACCGGGAAAGAGAAGATGGTTAAAAATAAAGCGAGACTATTTGAACGAGGGTTCCATGGC

AGATTCTGCCGATTTAGTAGTACTAGGTGCTTACTATGGTAAAGGAGCAAAGGGTGGTATCATGGCAGTCTTTCTAA

TGGGTTGTTACGACGATGAATCCGGTAAATGGAAGACGGTTACCAAGTGTTCAGGACACGATGATAATACGTTAAGG

GAGTTGCAAGACCAATTAAAGATGATTAAAATTAACAAGGATCCCAAAAAAATTCCAGAGTGGTTAGTAGTTAATAA

AATCTATATTCCCGATTTTGTAGTAGAGGATCCAAAACAATCTCAGATATGGGAAATTTCAGGAGCAGAGTTTACAT

CTTCCAAGTCCCATACCGCAAATGGAATATCCATTAGATTTCCTAGATTTACTAGGATAAGAGAGGATAAAACGTGG

AAAGAATCTACTCATCTAAACGATTTAGTAAACTTGACTAAATCTTAATTTTTATGGCGCGCCTTTCATTTTGTTTT

TTTCTATGCTATAAATGGTGAGCAAGGGCGAGGAGCTGTTCACCGGGGTGGTGCCCATCCTGGTCGAGCTGGACGGC

GACGTAAACGGCCACAAGTTCAGCGTGTCCGGCGAGGGCGAGGGCGATGCCACCTACGGCAAGCTGACCCTGAAGTT

CATCTGCACCACCGGCAAGCTGCCCGTGCCCTGGCCCACCCTCGTGACCACCCTGACCTACGGCGTGCAGTGCTTCA

GCCGCTACCCCGACCACATGAAGCAGCACGACTTCTTCAAGTCCGCCATGCCCGAAGGCTACGTCCAGGAGCGCACC

ATCTTCTTCAAGGACGACGGCAACTACAAGACCCGCGCCGAGGTGAAGTTCGAGGGCGACACCCTGGTGAACCGCAT

CGAGCTGAAGGGCATCGACTTCAAGGAGGACGGCAACATCCTGGGGCACAAGCTGGAGTACAACTACAACAGCCACA

ACGTCTATATCATGGCCGACAAGCAGAAGAACGGCATCAAGGTGAACTTCAAGATCCGCCACAACATCGAGGACGGC

AGCGTGCAGCTCGCCGACCACTACCAGCAGAACACCCCCATCGGCGACGGCCCCGTGCTGCTGCCCGACAACCACTA

CCTGAGCACCCAGTCCGCCCTGAGCAAAGACCCCAACGAGAAGCGCGATCACATGGTCCTGCTGGAGTTCGTGACCG

CCGCCGGGATCACTCTCGGCATGCACGAGCTGTACAAGTAAGAGCTCCCCGATTTTGTAGTAGAGGATCCAAAACAA

TCTCAGATATGGGAAATTTCAGGAGCAGAGTTTACATCTTCCAAGTCCCATACCGCAAATGGAATATCCATTAGATT

TCCTAGATTTACTAGGATAAGAGAGGATAAAACGTGGAAAGAATCTACTCATCTAAACGATTTAGTAAACTTGACTA

AATCTTAATTTTTATCTCGAGGCCGCTGGTACCCAACCTAAAAATTGAAAATAAATACAAAGGTTCTTGAGGGTTGT

GTTAAATTGAAAGCGAGAAATAATCATAAATAAGCCCgggATGAAAAGAGTAACAGTACCAACAGCGCCACCAGCGT

ATGCGGATATAGGATATCCAATGTCTATGCTACCTATTAAATCTTCTAGAGCGGTATCTGGAATTCAACAAAgCAA

GAAGTACTACCTGGAATGGATACACCATCTAATTCTATGAGACCAGTAGCGGATGATAATATTGATCATACTTCTCA

TACTCCAAATGGTGTAGCGTCTGCTTTTATTCTAGAAGCGACAGTAAATGTAATTTCTGGACCAAAAGTACTAATGA

AACAAATTCCAATTTGGCTACCACTAGGAATTGCGGATCAAAAgACATATTCTTTTGATTCTACAACAGCGGCGATT

ATGCTAGCGTCTTATACAATTACACATTTTGGAAAAGCGAATAATCCACTAGTTAGAGTAAATAGACTAGGACAAGG

AATACCAGATCATCCACTAAGACTACTAAGAATGGGAAATCAAGCTTTTCTACAAGAATTTGTTCTACCACCAGTAC
```

-continued

```
AACTACCACAATACTTTACATTTGATCTAACAGCGCTAAAACTAGTAACACAACCACTACCAGCGGCGACATGGACA
GATGAAACTCCATCTAATCTAAGTGGTGCTCTAAGACCAGGACTATCTTTTCATCCAAAACTAAGACCTGTACTACT
ACCAGGAAAgACTGGAAAgAAAGGACATGTATCTGATTTGACAGCGCCAGACAAAATTCAAACAATAGTAAATCTAA
TGCAAGACTTCAAAATTGTACCAATTGATCCAGCGAAATCTATTATTGGAATTGAAGTACCAGAACTACTAGTTCAT
AAATTGACTGGAAAgAAAATGTCTCAAAAgAATGGACAACCTATTATTCCAGTACTATTGCCTAAATATATTGGTCT
AGATCCTATTTCTCCTGGAGATCTAACAATGGTTATTACACCAGATTATGATGATTGTCATTCTCCAGCGTCTTGTT
CTTATCTATCTGAAAAgTAAtaagTCGACCTGCAGCTAATGTATTAGTTAAATATTAAAACTTACCACGTAAAACTT
AAAATTTAAAATGATATTTCATTGACAGATAGATCACACATTATGAACTTTCAAGGACTTGTGTTAACTGACAATTG
CAAAAATCAATGGGTCGTTGGACCATTAATAGGAAAAGGTGGATTTGGTAGTATTTATACTACTAATGACAATAATT
ATGTAGTAAAAATAGAGCCCAAAGCTAACGGATCATTATTTACCGAACAGGCATTTTATACTAGAGTACTTAAACCA
TCCGTTATCGAAGAATGGAAAAAATCTCACAATATAAAGCACGTAGGTCTTATCACGTGCAAGGCATTTGGTCTATA
CAAATCCATTAATGTGGAATATCGATTCTTGGTAATTAATAGATTAGGTGCAGATCTAGATGCGGTGATCAGAGCCA
ATAATAATAGATTACCAAAAAGGTCGGTGATGTTGATCGGAATCGAAATCTTAAATACCATACAATTTATGCACGAG
CAAGGATATTCTCACGGAGATATTAAAGCGAGTAATATAGTCTTGGATCAAATAGATAAGAATAAATTATATCTAGT
GGATTACGGATTGGTTTCTAAATTCATGTCAAGCTTGTCTCCCTATAGTGAGTCGTATTAGAGCTTGGCGTAATCAT
GGTCATAGCTGTTTCCTGTGTGAAATTGTTATCCGCTCACAATTCCACACAACATACGAGCCGGAAGCATAAAGTGT
AAAGCCTGGGGTGCCTAATGAGTGAGCTAACTCACATTAATTGCGTTGCGCTCACTGCCCGCTTTCGAGTCGGGAAA
CCTGTCGTGCCAGCTGCATTAATGAATCGGCCAACGCGCGGGGAGAGGCGGTTTGCGTATTGGGCGCTCTTCCGCTT
CCTCGCTCACTGACTCGCTGCGCTCGGTCGTTCGGCTGCGGCGAGCGGTATCAGCTCACTCAAAGGCGGTAATACGG
TTATCCACAGAATCAGGGGATAACGCAGGAAAGAACATGTGAGCAAAAGGCCAGCAAAAGGCCAGGAACCGTAAAAA
GGCCGCGTTGCTGGCGTTTTTCGATAGGCTCCGCCCCCCTGACGAGCATCACAAAAATCGACGCTCAAGTCAGAGGT
GGCGAAACCCGACAGGACTATAAAGATACCAGGCGTTTCCCCCTGGAAGCTCCCTCGTGCGCTCTCCTGTTCCGACC
CTGCCGCTTACCGGATACCTGTCCGCCTTTCTCCCTTCGGGAAGCGTGGCGCTTTCTCATAGCTCACGCTGTAGGTA
TCTCAGTTCGGTGTAGGTCGTTCGCTCCAAGCTGGGCTGTGTGCACGAACCCCCCGTTCAGCCCGACCGCTGCGCCT
TATCCGGTAACTATCGTCTTGAGTCCAACCCGGTAAGACACGACTTATCGCCACTGGCAGCAGCCACTGGTAACAGG
ATTAGCAGAGCGAGGTATGTAGGCGGTGCTACAGAGTTCTTGAAGTGGTGGCCTAACTACGGCTACACTAGAAGGAC
AGTATTTGGTATCTGCGCTCTGCTGAAGCCAGTTACCTTCGGAAAAAGAGTTGGTAGCTCTTGATCCGGCAAACAAA
CCACCGCTGGTAGCGGTGGTTTTTTTGTTTGCAAGCAGCAGATTACGCGCAGAAAAAAAGGATCTCAAGAAGATCCT
TTGATCTTTTCTACGGGGTCTGACGCTCAGTGGAACGAAAACTCACGTTAAGGGATTTTGGTCATGAGATTATCAAA
AAGGATCTTCACCTAGATCCTTTTAAATTAAAAATGAAGTTTTAAATCAATCTAAAGTATATATGAGTAAACTTGGT
CTGACAGTTACCAATGCTTAATCAGTGAGGCACCTATCTCAGCGATCTGTCTATTTCGTTCATCCATAGTTGCCTGA
CTCCCCGTCGTGTAGATAACTACGATACGGGAGGGCTTACCATCTGGCCCCAGTGCTGCAATGATACCGCGAGACCC
ACGCTCACCGGCTCCAGATTTATCAGCAATAAACCAGCCAGCCGGAAGGGCCGAGCGCAGAAGTGGTCCTGCAACTT
TATCCGCCTCCATCCAGTCTATTAATTGTTGCCGGGAAGCTAGAGTAAGTAGTTCGCCAGTTAATAGTTTGCGCAAC
GTTGTTGGCATTGCTACAGGCATCGTGGTGTCACGCTCGTCGTTTGGTATGGCTTCATTCAGCTCCGGTTCCCAACG
ATCAAGGCGAGTTACATGATCCCCCATGTTGTGCAAAAAAGCGGTTAGCTCCTTCGGTCCTCCGATCGTTGTCAGAA
GTAAGTTGGCCGCAGTGTTATCACTCATGGTTATGGCAGCACTGCATAATTCTCTTACTGTCATGCCATCCGTAAGA
TGCTTTTCTGTGACTGGTGAGTACTCAACCAAGTCATTCTGAGAATAGTGTATGCGGCGACCGAGTTGCTCTTGCCC
GGCGTCAATACGGGATAATACCGCGCCACATAGCAGAACTTTAAAAGTGCTCATCATTGGAAAACGTTCTTCGGGGC
GAAAACTCTCAAGGATCTTACCGCTGTTGAGATCCAGTTCGATGTAACCCACTCGTGCACCCAACTGATCTTCAGCA
TCTTTTACTTTCACCAGCGTTTCTGGGTGAGCAAAAACAGGAAGGCAAAATGCCGCAAAAAAGGGAATAAGGGCGAC
```

-continued

```
ACGGAAATGTTGAATACTCATACTCTTCCTTTTTCAATATTATTGAAGCATTTATCAGGGTTATTGTCTCATGAGCG
GATACATATTTGAATGTATTTAGAAAAATAAACAAATAGGGGTTCCGCGCACATTTCCCCGAAAAGTGCCACCTGAC
GTCTAAGAAACCATTATTATCATGACATTAACCTATAAAAATAGGCGTATCACGAGGCCCTTTCGTCTCGCGCGTTT
CGGTGATGACGGTGAAAACCTCTGACACATGCAGCTCCCGGAGACGGTCACAGCTTGTCTGTAAGCGGATGCCGGGA
GCAGACAAGCCCGTCAGGGCGCGTCAGCGGGTGTTGGCGGGTGTCGGGGCTGGCTTAACTATGCGGCATCAGAGCAG
ATTGTACTGAGAGTGCACCATATGCGGTGTGAAATACCGCACAGATGCGTAAGGAGAAAATACCGCATCAGGCGCCA
TTCGCCATTCAGGCTGCGCAACTGTTGGGAAGGGCGATCGGTGCGGGCCTCTTCGCTATTACGCCAGCTGGCGAAAG
GGGGATGTGCTGCAAGGCGATTAAGTTGGGTAACGCCAGGGTTTTCCCAGTCACGACGTTGTAAAACGACGGCCAGT
GAATTGGATTTAGGTGACACTATA
```

TABLE 8

Sudan Ebola Glycoprotein mutation table

| Changes (Silent mutation) | Mutation position on GP |
|---|---|
| T to C | 57 |
| A to G | 87 |
| T to C | 93 |
| A to G | 252 |
| A to G | 342 |
| T to C | 477 |
| A to G | 882, 885 |
| A to G | 1035 |
| A to G | 1407 |
| A to G | 1491 |
| T to C | 1776 |
| A to G | 1851 |

*Shown as lower case in SEQ ID NO: 13

```
SEQ ID 13:
pGEO-SUDV2014 GP sequence optimized for insertion into MVA vector: (FIG. 8)
GAATTCCCTGGGACATACGTATATTTCTATGATCTGTCTTATATGAAGTCTATACAGCGAATAGATTCAGAATTT
CTACATAATTATATATTGTACGCTAATAAGTTTAATCTAACACTCCCCGAAGATTTGTTTATAATCCCTACAAAT
TTGGATATTCTATGGCGTACAAAGGAATATATAGACTCGTTCGATATTAGTACAGAAACATGGAATAAATTATTA
TCCAATTATTATATGAAGATGATAGAGTATGCTAAACTTTATGTACTAAGTCCTATTCTCGCTGAGGAGTTGGAT
AATTTTGAGAGGACGGGAGAATTAACTAGTATTGTACAAGAAGCCATTTTATCTCTAAATTTACGAATTAAGATT
TTAAATTTTAAACATAAAGATGATGATACGTATATACACTTTTGTAAAATATTATTCGGTGTCTATAACGGAACA
AACGCTACTATATATTATCATAGACCTCTAACGGGATATATGAATATGATTTCAGATACTATATTTGTTCCTGTA
GATAATAACTAAGGCGCGCCTTTCATTTTGTTTTTTTCTATGCTATAAATGGTGAGCAAGGGCGAGGAGCTGTTC
ACCGGGGTGGTGCCCATCCTGGTCGAGCTGGACGGCGACGTAAACGGCCACAAGTTCAGCGTGTCCGGCGAGGGC
GAGGGCGATGCCACCTACGGCAAGCTGACCCTGAAGTTCATCTGCACCACCGGCAAGCTGCCCGTGCCCTGGCCC
ACCCTCGTGACCACCCTGACCTACGGCGTGCAGTGCTTCAGCCGCTACCCCGACCACATGAAGCAGCACGACTTC
TTCAAGTCCGCCATGCCCGAAGGCTACGTCCAGGAGCGCACCATCTTCTTCAAGGACGACGGCAACTACAAGACC
CGCGCCGAGGTGAAGTTCGAGGGCGACACCCTGGTGAACCGCATCGAGCTGAAGGGCATCGACTTCAAGGAGGAC
GGCAACATCCTGGGGCACAAGCTGGAGTACAACTACAACAGCCACAACGTCTATATCATGGCCGACAAGCAGAAG
AACGGCATCAAGGTGAACTTCAAGATCCGCCACAACATCGAGGACGGCAGCGTGCAGCTCGCCGACCACTACCAG
CAGAACACCCCCATCGGCGACGGCCCCGTGCTGCTGCCCGACAACCACTACCTGAGCACCCAGTCCGCCCTGAGC
AAAGACCCCAACGAGAAGCGCGATCACATGGTCCTGCTGGAGTTCGTGACCGCCGCGGGATCACTCTCGGCATG
CACGAGCTGTACAAGTAAGAGCTCGAGGACGGGAGAATTAACTAGTATTGTACAAGAAGCCATTTTATCTCTAAA
TTTACGAATTAAGATTTTAAATTTTAAACATAAAGATGATGATACGTATATACACTTTTGTAAAATATTATTCGG
TGTCTATAACGGAACAAACGCTACTATATATTATCATAGACCTCTAACGGGATATATGAATATGATTTCAGATAC
TATATTTGTTCCTGTAGATAATAACTAACTCGAGGCCGCTGGTACCCAACCTAAAAATTGAAAATAAATACAAAG
```

-continued

```
GTTCTTGAGGGTTGTGTTAAATTGAAAGCGAGAAATAATCATAAATAAGCCCgggATGGGAGGACTATCTCTACT
ACAACTACCAAGAGATAAGTTTAGAAAATCTTCTTTcTTTGTTTGGGTTATAATTCTATTTCAAAAgGCGTTcTC
TATGCCATTGGGAGTAGTAACAAATTCTACACTAGAAGTAACAGAAATTGATCAACTAGTATGTAAAGATCATCT
AGCGTCTACAGATCAATTGAAATCTGTTGGATTGAATCTAGAAGGATCTGGTGTATCTACAGATATTCCATCTGC
GACAAAgAGATGGGGTTTTAGAAGTGGTGTACCACCAAAAGTAGTATCTTATGAAGCGGGAGAATGGGCGGAAAA
TTGTTATAATCTAGAAATTAAgAAACCAGATGGATCTGAATGTTTGCCACCACCACCAGATGGTGTTAGAGGATT
TCCAAGATGTAGATATGTTCATAAAGCGCAAGGAACAGGACCATGTCCTGGAGATTATGCGTTTCATAAAGATGG
TGCATTcTTTCTATATGATAGATTGGCGTCTACTGTAATATATAGAGGTGTAAATTTTGCGGAAGGTGTAATTGC
TTTTCTAATTCTAGCGAAACCTAAAGAAACATTTCTACAATCTCCACCAATTAGAGAAGCGGTTAATTATACAGA
AAATACTTCATCTTATTATGCGACATCTTATCTAGAATATGAAATTGAAAATTTTGGAGCGCAACATTCTACAAC
TTTGTTCAAAATTGATAATAATACTTTTGTTAGACTAGATAGACCACATACACCACAATTTTTGTTTCAATTGAA
TGATACAATTCATCTACATCAACAACTATCTAATACAACTGGAAGATTGATTTGGACACTAGATGCGAATATTAA
TGCGGATATTGGAGAATGGGCTTTcTGGGAAAATAAgAAgAATCTATCTGAACAACTAAGAGGAGAAGAATTGTC
TTTTGAAGCGCTATCTCTAAATGAAACTGAAGATGATGATGCGGCGTCTAGTAGAATTACAAAAGGAAGAATTTC
TGATAGAGCGACAAGACAATATTCTGATCTAGTACCAAAgAATCCACCTGGAATGGTTCCATTGCATATTCCAGA
AGGAGAAACAACACTACCATCTCAAAATTCTACTGAAGGAAGAAGAGTATCTGTAAATACTCAAGAAACAATTAC
AGAAACAGCGGCGACAATTATTGGAACAAATGGAAATCATATGCAAATTTCTACTATTGGAATTAGACCATCTTC
TTCTCAAATTCCATCTTCTAGTCCAACAACAGCGCCATCTCCAGAAGCGCAAACACCAACAACACATACAAGTGG
ACCATCTGTAATGGCGACAGAAGAACCTACAACACCACCAGGATCTTCTCCAGGTCCAACTACAGAAGCGCCAAC
TCTAACTACACCAGAAAATATTACAACAGCTGTAAAgACAGTACTACCACAAGAATCTACTTCTAATGGACTAAT
TACATCTACAGTAACTGGAATTCTAGGATCTCTAGGACTAAGAAAgAGATCTAGAAGACAAACAAATACAAAAGC
GACTGGAAAATGTAATCCAAATCTACATTATTGGACAGCGCAAGAACAACATAATGCGGCGGGAATTGCTTGGAT
TCCATATTTTGGACCAGGTGCTGAAGGAATATATACTGAAGGTCTAATGCATAATCAAAATGCGCTAGTATGTGG
ACTAAGACAACTAGCGAATGAAACAACTCAAGCGCTACAACTATTTCTAAGAGCGACTACAGAACTAAGAACATA
TACAATTCTAAATAGAAAAGCTATTGATTTcTTGTTGAGAAGATGGGGAGGAACATGTAGAATATTGGGACCAGA
TTGTTGTATTGAACCACATGATTGGACAAAgAATATTACTGACAAAATTAATCAAATTATTCATGACTTTATTGA
TAATCCACTACCAAATCAAGATAATGATGATAATTGGTGGACAGGATGGAGACAATGGATTCCAGCGGGAATAGG
AATTACTGGAATTATTATTGCGATTATAGCGCTACTATGTGTATGTAAACTACTATGTTAATAAgTCGACCTGCA
GTCAAACTCTAATGACCACATCTTTTTTTAGAGATGAAAAATTTTCCACATCTCCTTTTGTAGACACGACTAAAC
ATTTTGCAGAAAAAAGTTTATTAGTGTTTAGATAATCGTATACTTCATCAGTGTAGATAGTAAATGTGAACAGAT
AAAAGGTATTCTTGCTCAATAGATTGGTAAATTCCATAGAATATATTAATCCTTTCTTCTTGAGATCCCACATCA
TTTCAACCAGAGACGTTTTATCCAATGATTTACCTCGTACTATACCACATACAAAACTAGATTTTGCAGTGACGT
CGTATCTGGTATTCCTACCAAACAAAATTTTACTTTTAGTTCTTTTAGAAAATTCTAAGGTAGAATCTCTATTTG
CCAATATGTCATCTATGGAATTACCACTAGCAAAAAATGATAGAAATATATATTGATACATCGCAGCTGGTTTTG
ATCTACTATACTTTAAAAACGAATCAGATTCCATAATTGCCTGTATATCATCAGCTGAAAAACTATGTTTTACAC
GTATTCCTTCGGCATTTCTTTTTAATGATATATCTTGTTTAGACAATGATAAAGTTATCATGTCCATGAGAGACG
CGTCTCCGTATCGTATAAATATTTCATTAGATGTTAGACGCTTCATTAGGGGTATACTTCTATAAGGTTTCTTAA
TCAGTCCATCATTGGTTGCGTCAAGAACAAGCTTGTCTCCCTATAGTGAGTCGTATTAGAGCTTGGCGTAATCAT
GGTCATAGCTGTTTCCTGTGTGAAATTGTTATCCGCTCACAATTCCACACAACATACGAGCCGGAAGCATAAAGT
GTAAAGCCTGGGGTGCCTAATGAGTGAGCTAACTCACATTAATTGCGTTGCGCTCACTGCCCGCTTTCGAGTCGG
GAAACCTGTCGTGCCAGCTGCATTAATGAATCGGCCAACGCGCGGGGAGAGGCGGTTTGCGTATTGGGCGCTCTT
```

-continued

```
CCGCTTCCTCGCTCACTGACTCGCTGCGCTCGGTCGTTCGGCTGCGGCGAGCGGTATCAGCTCACTCAAGGCGG
TAATACGGTTATCCACAGAATCAGGGGATAACGCAGGAAAGAACATGTGAGCAAAAGGCCAGCAAAAGGCCAGGA
ACCGTAAAAAGGCCGCGTTGCTGGCGTTTTTCGATAGGCTCCGCCCCCCTGACGAGCATCACAAAAATCGACGCT
CAAGTCAGAGGTGGCGAAACCCGACAGGACTATAAAGATACCAGGCGTTTCCCCCTGGAAGCTCCCTCGTGCGCT
CTCCTGTTCCGACCCTGCCGCTTACCGGATACCTGTCCGCCTTTCTCCCTTCGGGAAGCGTGGCGCTTTCTCATA
GCTCACGCTGTAGGTATCTCAGTTCGGTGTAGGTCGTTCGCTCCAAGCTGGGCTGTGTGCACGAACCCCCCGTTC
AGCCCGACCGCTGCGCCTTATCCGGTAACTATCGTCTTGAGTCCAACCCGGTAAGACACGACTTATCGCCACTGG
CAGCAGCCACTGGTAACAGGATTAGCAGAGCGAGGTATGTAGGCGGTGCTACAGAGTTCTTGAAGTGGTGGCCTA
ACTACGGCTACACTAGAAGGACAGTATTTGGTATCTGCGCTCTGCTGAAGCCAGTTACCTTCGGAAAAAGAGTTG
GTAGCTCTTGATCCGGCAAACAAACCACCGCTGGTAGCGGTGGTTTTTTTGTTTGCAAGCAGCAGATTACGCGCA
GAAAAAAAGGATCTCAAGAAGATCCTTTGATCTTTTCTACGGGGTCTGACGCTCAGTGGAACGAAAACTCACGTT
AAGGGATTTTGGTCATGAGATTATCAAAAAGGATCTTCACCTAGATCCTTTTAAATTAAAAATGAAGTTTTAAAT
CAATCTAAAGTATATATGAGTAAACTTGGTCTGACAGTTACCAATGCTTAATCAGTGAGGCACCTATCTCAGCGA
TCTGTCTATTTCGTTCATCCATAGTTGCCTGACTCCCCGTCGTGTAGATAACTACGATACGGGAGGGCTTACCAT
CTGGCCCCAGTGCTGCAATGATACCGCGAGACCCACGCTCACCGGCTCCAGATTTATCAGCAATAAACCAGCCAG
CCGGAAGGGCCGAGCGCAGAAGTGGTCCTGCAACTTTATCCGCCTCCATCCAGTCTATTAATTGTTGCCGGGAAG
CTAGAGTAAGTAGTTCGCCAGTTAATAGTTTGCGCAACGTTGTTGGCATTGCTACAGGCATCGTGGTGTCACGCT
CGTCGTTTGGTATGGCTTCATTCAGCTCCGGTTCCCAACGATCAAGGCGAGTTACATGATCCCCATGTTGTGCA
AAAAAGCGGTTAGCTCCTTCGGTCCTCCGATCGTTGTCAGAAGTAAGTTGGCCGCAGTGTTATCACTCATGGTTA
TGGCAGCACTGCATAATTCTCTTACTGTCATGCCATCCGTAAGATGCTTTTCTGTGACTGGTGAGTACTCAACCA
AGTCATTCTGAGAATAGTGTATGCGGCGACCGAGTTGCTCTTGCCCGGCGTCAATACGGGATAATACCGCGCCAC
ATAGCAGAACTTTAAAAGTGCTCATCATTGGAAAACGTTCTTCGGGGCGAAAACTCTCAAGGATCTTACCGCTGT
TGAGATCCAGTTCGATGTAACCCACTCGTGCACCCAACTGATCTTCAGCATCTTTTACTTTCACCAGCGTTTCTG
GGTGAGCAAAAACAGGAAGGCAAAATGCCGCAAAAAAGGGAATAAGGGCGACACGGAAATGTTGAATACTCATAC
TCTTCCTTTTTCAATATTATTGAAGCATTTATCAGGGTTATTGTCTCATGAGCGGATACATATTTGAATGTATTT
AGAAAAATAAACAAATAGGGGTTCCGCGCACATTTCCCCGAAAAGTGCCACCTGACGTCTAAGAAACCATTATTA
TCATGACATTAACCTATAAAAATAGGCGTATCACGAGGCCCTTTCGTCTCGCGCGTTTCGGTGATGACGGTGAAA
ACCTCTGACACATGCAGCTCCCGGAGACGGTCACAGCTTGTCTGTAAGCGGATGCCGGGAGCAGACAAGCCCGTC
AGGGCGCGTCAGCGGGTGTTGGCGGGTGTCGGGGCTGGCTTAACTATGCGGCATCAGAGCAGATTGTACTGAGAG
TGCACCATATGCGGTGTGAAATACCGCACAGATGCGTAAGGAGAAAATACCGCATCAGGCGCCATTCGCCATTCA
GGCTGCGCAACTGTTGGGAAGGGCGATCGGTGCGGGCCTCTTCGCTATTACGCCAGCTGGCGAAAGGGGGATGTG
CTGCAAGGCGATTAAGTTGGGTAACGCCAGGGTTTTCCCAGTCACGACGTTGTAAAACGACGGCCAGTGAATTGG
ATTTAGGTGACACTATA
```

Example 4: MVA Vaccine Incorporating Marburg Virus Sequences

In an exemplary embodiment, sequences from Marburg virus (MARV) are prepared and optimized in shuttle plasmids and then the viral sequences are incorporated into an MVA vector. Such MVA vectors may be used individually as part of an administration protocol to elicit an immune response to Marburg virus or as part of a multivalent vaccine composition having one or more MVA vectors expressing EBOV and Marburg antigens to elicit an immune response.

TABLE 9

Marburg VP40 mutation table

| Changes (Silent mutation) | Mutation position on VP40 |
|---|---|
| A to G | 357 |
| T to C | 465 |
| A to G | 519 |
| A to G | 630 |

TABLE 9-continued

Marburg VP40 mutation table

| Changes (Silent mutation) | Mutation position on VP40 |
|---|---|
| A to G | 654 |
| A to G | 717 |
| A to G | 729 |
| A to G | 792 |

*Shown as lower case in SEQ ID NO: 14

Exemplary Marburg VP40 and GP sequences are provided below.

```
SEQ ID 14:
pGEO-MARV2014 VP40 sequence optimized for insertion into MVA vector: (FIG. 9)
GAATTCGGAGTATACGAACCGGGAAAGAGAAGATGGTTAAAAATAAAGCGAGACTATTTGAACGAGGGTTCCATGGC

AGATTCTGCCGATTTAGTAGTACTAGGTGCTTACTATGGTAAAGGAGCAAAGGGTGGTATCATGGCAGTCTTTCTAA

TGGGTTGTTACGACGATGAATCCGGTAAATGGAAGACGGTTACCAAGTGTTCAGGACACGATGATAATACGTTAAGG

GAGTTGCAAGACCAATTAAAGATGATTAAAATTAACAAGGATCCCAAAAAAATTCCAGAGTGGTTAGTAGTTAATAA

AATCTATATTCCCGATTTTGTAGTAGAGGATCCAAAACAATCTCAGATATGGGAAATTTCAGGAGCAGAGTTTACAT

CTTCCAAGTCCCATACCGCAAATGGAATATCCATTAGATTTCCTAGATTTACTAGGATAAGAGAGGATAAAACGTGG

AAAGAATCTACTCATCTAAACGATTTAGTAAACTTGACTAAATCTTAATTTTTATGGCGCGCCTTTCATTTTGTTTT

TTTCTATGCTATAAATGGTGAGCAAGGGCGAGGAGCTGTTCACCGGGGTGGTGCCCATCCTGGTCGAGCTGGACGGC

GACGTAAACGGCCACAAGTTCAGCGTGTCCGGCGAGGGCGAGGGCGATGCCACCTACGGCAAGCTGACCCTGAAGTT

CATCTGCACCACCGGCAAGCTGCCCGTGCCCTGGCCCACCCTCGTGACCACCCTGACCTACGGCGTGCAGTGCTTCA

GCCGCTACCCCGACCACATGAAGCAGCACGACTTCTTCAAGTCCGCCATGCCCGAAGGCTACGTCCAGGAGCGCACC

ATCTTCTTCAAGGACGACGGCAACTACAAGACCCGCGCCGAGGTGAAGTTCGAGGGCGACACCCTGGTGAACCGCAT

CGAGCTGAAGGGCATCGACTTCAAGGAGGACGGCAACATCCTGGGGCACAAGCTGGAGTACAACTACAACAGCCACA

ACGTCTATATCATGGCCGACAAGCAGAAGAACGGCATCAAGGTGAACTTCAAGATCCGCCACAACATCGAGGACGGC

AGCGTGCAGCTCGCCGACCACTACCAGCAGAACACCCCCATCGGCGACGGCCCCGTGCTGCTGCCCGACAACCACTA

CCTGAGCACCCAGTCCGCCCTGAGCAAAGACCCCAACGAGAAGCGCGATCACATGGTCCTGCTGGAGTTCGTGACCG

CCGCCGGGATCACTCTCGGCATGCACGAGCTGTACAAGTAAGAGCTCCCCGATTTTGTAGTAGAGGATCCAAAACAA

TCTCAGATATGGGAAATTTCAGGAGCAGAGTTTACATCTTCCAAGTCCCATACCGCAAATGGAATATCCATTAGATT

TCCTAGATTTACTAGGATAAGAGAGGATAAAACGTGGAAAGAATCTACTCATCTAAACGATTTAGTAAACTTGACTA

AATCTTAATTTTTATCTCGAGGCCGCTGGTACCCAACCTAAAAATTGAAAATAAATACAAAGGTTCTTGAGGGTTGT

GTTAAATTGAAAGCGAGAAATAATCATAAATAAGCCCgggATGGCGTCTAGTTCTAATTATAATACTTATATGCAAT

ATCTAAATCCACCACCATATGCGGATCATGGTGCTAATCAACTAATTCCAGCGGATCAACTATCTAATCAACATGGA

ATTACACCAAATTATGTTGGAGATCTAAATCTAGATGATCAGTTTAAAGGAAATGTTTGTCATGCGTTTACACTAGA

AGCGATTATTGATATTCTGCGTATAATGAAAGAACAGTAAAAGGTGTACCAGCTTGGCTACCACTAGGAATTATGT

CTAATTTTGAATATCCACTAGCGCATACAGTAGCGGCGCTATTGACAGGATCTTATACAATTACACAGTTTACACAT

AATGGACAAAgTTTGTTAGAGTAAATAGACTAGGAACTGGAATACCAGCGCATCCACTAAGAATGCTAAGAGAAGG

AAATCAAGCTTTTATTCAAAATATGGTTATTCCAAGAAATTTcTCTACAAATCAGTTTACTTATAATCTAACTAATC

TAGTACTATCTGTACAAAAgCTACCAGATGATGCTTGGAGACCATCTAAAGATAAACTAATTGGAAATACAATGCAT

CCAGCGATTTCTATTCATCCAAATCTACCACCAATAGTACTACCAACTGTAAAgAAACAAGCGTATAGACAACATAA gAATCCAAATAATGGACCACTATTGGCGATTTCTGGAATTCTACATCAACTAAGAGTAGAAAAgGTACCAGAAAAgA

CATCTTTGTTTAGAATTTCTCTACCAGCGGATATGTTTTCTGTAAAAGAAGGAATGATGAAgAAAAGAGGAGAATCT

TCTCCAGTAGTATATTTTCAAGCGCCAGAAAATTTTCCATTGAATGGTTTTAATAATAGACAAGTAGTACTAGCGTA
```

-continued

```
TGCGAATCCAACACTATCTGCGATATAAtaagTCGACCTGCAGCTAATGTATTAGTTAAATATTAAAACTTACCACG
TAAAACTTAAAATTTAAAATGATATTTCATTGACAGATAGATCACACATTATGAACTTTCAAGGACTTGTGTTAACT
GACAATTGCAAAAATCAATGGGTCGTTGGACCATTAATAGGAAAAGGTGGATTTGGTAGTATTTATACTACTAATGA
CAATAATTATGTAGTAAAAATAGAGCCCAAAGCTAACGGATCATTATTTACCGAACAGGCATTTTATACTAGAGTAC
TTAAACCATCCGTTATCGAAGAATGGAAAAAATCTCACAATATAAAGCACGTAGGTCTTATCACGTGCAAGGCATTT
GGTCTATACAAATCCATTAATGTGGAATATCGATTCTTGGTAATTAATAGATTAGGTGCAGATCTAGATGCGGTGAT
CAGAGCCAATAATAATAGATTACCAAAAAGGTCGGTGATGTTGATCGGAATCGAAATCTTAAATACCATACAATTTA
TGCACGAGCAAGGATATTCTCACGGAGATATTAAAGCGAGTAATATAGTCTTGGATCAAATAGATAAGAATAAATTA
TATCTAGTGGATTACGGATTGGTTTCTAAATTCATGTCAAGCTTGTCTCCCTATAGTGAGTCGTATTAGAGCTTGGC
GTAATCATGGTCATAGCTGTTTCCTGTGTGAAATTGTTATCCGCTCACAATTCCACACAACATACGAGCCGGAAGCA
TAAAGTGTAAAGCCTGGGGTGCCTAATGAGTGAGCTAACTCACATTAATTGCGTTGCGCTCACTGCCCGCTTTCGAG
TCGGGAAACCTGTCGTGCCAGCTGCATTAATGAATCGGCCAACGCGCGGGGAGAGGCGGTTTGCGTATTGGGCGCTC
TTCCGCTTCCTCGCTCACTGACTCGCTGCGCTCGGTCGTTCGGCTGCGGCGAGCGGTATCAGCTCACTCAAAGGCGG
TAATACGGTTATCCACAGAATCAGGGGATAACGCAGGAAAGAACATGTGAGCAAAAGGCCAGCAAAAGGCCAGGAAC
CGTAAAAAGGCCGCGTTGCTGGCGTTTTTCGATAGGCTCCGCCCCCCTGACGAGCATCACAAAAATCGACGCTCAAG
TCAGAGGTGGCGAAACCCGACAGGACTATAAAGATACCAGGCGTTTCCCCCTGGAAGCTCCCTCGTGCGCTCTCCTG
TTCCGACCCTGCCGCTTACCGGATACCTGTCCGCCTTTCTCCCTTCGGGAAGCGTGGCGCTTTCTCATAGCTCACGC
TGTAGGTATCTCAGTTCGGTGTAGGTCGTTCGCTCCAAGCTGGGCTGTGTGCACGAACCCCCCGTTCAGCCCGACCG
CTGCGCCTTATCCGGTAACTATCGTCTTGAGTCCAACCCGGTAAGACACGACTTATCGCCACTGGCAGCAGCCACTG
GTAACAGGATTAGCAGAGCGAGGTATGTAGGCGGTGCTACAGAGTTCTTGAAGTGGTGGCCTAACTACGGCTACACT
AGAAGGACAGTATTTGGTATCTGCGCTCTGCTGAAGCCAGTTACCTTCGGAAAAAGAGTTGGTAGCTCTTGATCCGG
CAAACAAACCACCGCTGGTAGCGGTGGTTTTTTTGTTTGCAAGCAGCAGATTACGCGCAGAAAAAAAGGATCTCAAG
AAGATCCTTTGATCTTTTCTACGGGGTCTGACGCTCAGTGGAACGAAAACTCACGTTAAGGGATTTTGGTCATGAGA
TTATCAAAAAGGATCTTCACCTAGATCCTTTTAAATTAAAAATGAAGTTTTAAATCAATCTAAAGTATATATGAGTA
AACTTGGTCTGACAGTTACCAATGCTTAATCAGTGAGGCACCTATCTCAGCGATCTGTCTATTTCGTTCATCCATAG
TTGCCTGACTCCCCGTCGTGTAGATAACTACGATACGGGAGGGCTTACCATCTGGCCCCAGTGCTGCAATGATACCG
CGAGACCCACGCTCACCGGCTCCAGATTTATCAGCAATAAACCAGCCAGCCGGAAGGGCCGAGCGCAGAAGTGGTCC
TGCAACTTTATCCGCCTCCATCCAGTCTATTAATTGTTGCCGGGAAGCTAGAGTAAGTAGTTCGCCAGTTAATAGTT
TGCGCAACGTTGTTGGCATTGCTACAGGCATCGTGGTGTCACGCTCGTCGTTTGGTATGGCTTCATTCAGCTCCGGT
TCCCAACGATCAAGGCGAGTTACATGATCCCCCATGTTGTGCAAAAAAGCGGTTAGCTCCTTCGGTCCTCCGATCGT
TGTCAGAAGTAAGTTGGCCGCAGTGTTATCACTCATGGTTATGGCAGCACTGCATAATTCTCTTACTGTCATGCCAT
CCGTAAGATGCTTTTCTGTGACTGGTGAGTACTCAACCAAGTCATTCTGAGAATAGTGTATGCGGCGACCGAGTTGC
TCTTGCCCGGCGTCAATACGGGATAATACCGCGCCACATAGCAGAACTTTAAAAGTGCTCATCATTGGAAAACGTTC
TTCGGGGCGAAAACTCTCAAGGATCTTACCGCTGTTGAGATCCAGTTCGATGTAACCCACTCGTGCACCCAACTGAT
CTTCAGCATCTTTTACTTTCACCAGCGTTTCTGGGTGAGCAAAAACAGGAAGGCAAAATGCCGCAAAAAAGGGAATA
AGGGCGACACGGAAATGTTGAATACTCATACTCTTCCTTTTTCAATATTATTGAAGCATTTATCAGGGTTATTGTCT
CATGAGCGGATACATATTTGAATGTATTTAGAAAAATAAACAAATAGGGGTTCCGCGCACATTTCCCCGAAAAGTGC
CACCTGACGTCTAAGAAACCATTATTATCATGACATTAACCTATAAAAATAGGCGTATCACGAGGCCCTTTCGTCTC
GCGCGTTTCGGTGATGACGGTGAAAACCTCTGACACATGCAGCTCCCGGAGACGGTCACAGCTTGTCTGTAAGCGGA
TGCCGGGAGCAGACAAGCCCGTCAGGGCGCGTCAGCGGGTGTTGGCGGGTGTCGGGGCTGGCTTAACTATGCGGCAT
CAGAGCAGATTGTACTGAGAGTGCACCATATGCGGTGTGAAATACCGCACAGATGCGTAAGGAGAAAATACCGCATC
```

-continued

```
AGGCGCCATTCGCCATTCAGGCTGCGCAACTGTTGGGAAGGGCGATCGGTGCGGCCTCTTCGCTATTACGCCAGCT

GGCGAAAGGGGATGTGCTGCAAGGCGATTAAGTTGGGTAACGCCAGGGTTTTCCCAGTCACGACGTTGTAAAACGA

CGGCCAGTGAATTGGATTTAGGTGACACTATA
```

TABLE 10

Marburg Glycoprotein mutation table

| Changes (Silent mutation) | Mutation position on GP |
|---|---|
| T to C | 18 |
| T to C | 21 |
| A to G | 129 |
| A to G | 174 |
| A to G | 237 |
| T to C | 429 |
| T to C | 480 |
| A to G | 516 |
| A to G | 666 |
| A to G | 861 |
| A to G | 1125 |
| A to G | 1143 |
| A to G | 1182 |
| A to G | 666 |
| A to G | 861 |
| A to G | 1125 |
| A to G | 1143 |

TABLE 10-continued

Marburg Glycoprotein mutation table

| Changes (Silent mutation) | Mutation position on GP |
|---|---|
| A to G | 1182 |
| A to G | 1302 |
| A to G | 1395 |
| T to C | 1404 |
| A to G | 1527 |
| T to C | 1605 |
| T to C | 1608 |
| A to G | 1650 |
| A to G | 1656 |
| T to C | 1749 |
| A to G | 1884 |
| A to G | 1899 |
| T to C | 2028 |
| A to G | 2034 |

*Shown as lower case in SEQ ID NO: 15

```
SEQ ID 15:
pGEO-MARV2014 GP sequence optimized for insertion into MVA vector: (FIG. 10)
GAATTCCCTGGGACATACGTATATTTCTATGATCTGTCTTATATGAAGTCTATACAGCGAATAGATTCAGAATTTC

TACATAATTATATATTGTACGCTAATAAGTTTAATCTAACACTCCCCGAAGATTTGTTTATAATCCCTACAAATTT

GGATATTCTATGGCGTACAAAGGAATATATAGACTCGTTCGATATTAGTACAGAAACATGGAATAAATTATTATCC

AATTATTATATGAAGATGATAGAGTATGCTAAACTTTATGTACTAAGTCCTATTCTCGCTGAGGAGTTGGATAATT

TTGAGAGGACGGGAGAATTAACTAGTATTGTACAAGAAGCCATTTTATCTCTAAATTTACGAATTAAGATTTTAAA

TTTTAAACATAAAGATGATGATACGTATATACACTTTTGTAAAATATTATTCGGTGTCTATAACGGAACAAACGCT

ACTATATATTATCATAGACCTCTAACGGGATATATGAATATGATTTCAGATACTATATTTGTTCCTGTAGATAATA

ACTAAGGCGCGCCTTTCATTTTGTTTTTTTCTATGCTATAAATGGTGAGCAAGGGCGAGGAGCTGTTCACCGGGGT

GGTGCCCATCCTGGTCGAGCTGGACGGCGACGTAAACGGCCACAAGTTCAGCGTGTCCGGCGAGGGCGAGGGCGAT

GCCACCTACGGCAAGCTGACCCTGAAGTTCATCTGCACCACCGGCAAGCTGCCCGTGCCCTGGCCCACCCTCGTGA

CCACCCTGACCTACGGCGTGCAGTGCTTCAGCCGCTACCCCGACCACATGAAGCAGCACGACTTCTTCAAGTCCGC

CATGCCCGAAGGCTACGTCCAGGAGCGCACCATCTTCTTCAAGGACGACGGCAACTACAAGACCCGCGCCGAGGTG

AAGTTCGAGGGCGACACCCTGGTGAACCGCATCGAGCTGAAGGGCATCGACTTCAAGGAGGACGGCAACATCCTGG

GGCACAAGCTGGAGTACAACTACAACAGCCACAACGTCTATATCATGGCCGACAAGCAGAAGAACGGCATCAAGGT

GAACTTCAAGATCCGCCACAACATCGAGGACGGCAGCGTGCAGCTCGCCGACCACTACCAGCAGAACACCCCCATC

GGCGACGGCCCCGTGCTGCTGCCCGACAACCACTACCTGAGCACCCAGTCCGCCCTGAGCAAAGACCCCAACGAGA

AGCGCGATCACATGGTCCTGCTGGAGTTCGTGACCGCCGCCGGGATCACTCTCGGCATGCACGAGCTGTACAAGTA

AGAGCTCGAGGACGGGAGAATTAACTAGTATTGTACAAGAAGCCATTTTATCTCTAAATTTACGAATTAAGATTTT

AAATTTTAAACATAAAGATGATGATACGTATATACACTTTTGTAAAATATTATTCGGTGTCTATAACGGAACAAAC

GCTACTATATATTATCATAGACCTCTAACGGGATATATGAATATGATTTCAGATACTATATTTGTTCCTGTAGATA

ATAACTAACTCGAGGCCGCTGGTACCCAACCTAAAAATTGAAAATAAATACAAAGGTTCTTGAGGGTTGTGTTAAA

TTGAAAGCGAGAAATAATCATAAATAAGCCCgggATGTGGACAACATGTTTcTTcATTTCTCTAATTCTAATTCAA
```

-continued

```
GGAATTAAAACACTACCAATTCTAGAAATTGCGTCTAATGATCAACCACAAAATGTAGATTCTGTATGTTCTGGAA
CACTACAAAAgACTGAAGATGTACATTTGATGGGTTTTACACTATCTGGACAAAAgGTAGCGGATTCTCCACTAGA
AGCGTCTAAAAGATGGGCGTTTAGAACAGGTGTACCACCAAAgAATGTTGAATATACAGAAGGAGAAGAAGCGAAA
ACTTGTTATAATATTTCTGTAACAGATCCATCTGGAAAATCTCTACTACTAGATCCACCAACTAATGTTAGAGATT
ATCCAAAATGTAAAACAATTCATCATATTCAAGGACAAAATCCACATGCGCAAGGAATTGCGCTACATCTATGGGG
AGCATTcTTTCTATATGATAGAATAGCGTCTACAACAATGTATAGAGGAAAAGTTTTcACTGAAGGAAATATTGCG
GCTATGATAGTAAATAAgACAGTTCACAAAATGATATTTTCTAGACAAGGACAAGGATATAGACATATGAATCTAA
CATCTACAAATAAATATTGGACATCTTCTAATGGAACACAAACAAATGATACAGGATGTTTTGGAACATTGCAAGA
ATATAATAGTACAAAgAATCAAACATGTGCGCCATCTAAAACTCCACCACCACCTCCAACAGCGCATCCAGAAATT
AAACCTACATCTACACCAACAGATGCGACAAGATTGAATACAACAAATCCAAATTCTGATGATGAAGATCTAACAA
CATCTGGATCTGGAAGTGGAGAACAAGAACCATATACAACAAGTGATGCGGTTACAAAgCAAGGACTATCTTCTAC
AATGCCACCAACACTATCTCCACAACCTGGAACTCCACAACAAGGTGGAAATAATACAAATCATTCTCAAGATGCG
GCGACAGAACTAGATAATACTAATACAACTGCGCAACCACCAATGCCATCTCATAATACTACAACTATTTCTACTA
ATAATACTTCTAAACATAATCTATCTACATTGTCTGAACCACCTCAAAATACTACTAATCCTAATACTCAATCTAT
GGCGACTGAAAATGAAAAgACTTCTGCGCCTCCAAAgACAACTCTACCACCAACTGAATCTCCAACAACAGAAAAg
AGTACAAATAATACAAAATCTCCAACTACAATGGAACCTAATACAACTAATGGACACTTTACATCTCCATCTTCTA
CTCCTAATTCTACAACACAACATTTGATATACTTTAGAAGAAAgAGATCTATTTTGTGGAGAGAAGGAGATATGTT
TCCATTTCTAGATGGATTGATTAATGCGCCAATTGATTTTGATCCAGTACCAAATACAAAgACAATTTTcGATGAA
TCTTCTTCTTCTGGTGCTTCTGCGGAAGAAGATCAACATGCGTCTAGTAATATTAGTCTAACATTGTCTTATCTAC
CTCATACTTCTGAAAATACTGCGTATAGTGGAGAAAATGAgAATGATTGTGATGCGGAACTAAGAATTTGGAGTGT
ACAAGAAGATGATCTAGCGGCGGGATTGTCTTGGATTCCTTTcTTcGGACCTGGAATTGAAGGACTATATACAGCG
GGATTGATTAAgAATCAgAATAATCTAGTATGTAGACTAAGAAGATTGGCGAATCAAACAGCGAAATCTCTAGAAC
TACTACTAAGAGTAACAACTGAAGAAAGAACATTcTCTTTGATTAATAGACATGCGATTGATTTTCTATTGACAAG
ATGGGGAGGAACATGTAAAGTACTAGGACCAGATTGTTGTATTGGAATAGAAGATCTATCTAGAAATATTTCAGAA
CAAATTGATCAAATTAAgAAAGATGAACAAAAgGAAGGAACTGGATGGGGACTAGGTGGAAAATGGTGGACATCTG
ATTGGGGAGTACTAACAAATCTAGGAATTCTACTATTGCTATCTATTGCGGTACTAATTGCGTTGTCTTGTATATG
TAGAATTTTcACAAAgTATATTGGATAATAAgTCGACCTGCAGTCAAACTCTAATGACCACATCTTTTTTTAGAGA
TGAAAAATTTTCCACATCTCCTTTTGTAGACACGACTAAACATTTTGCAGAAAAAAGTTTATTAGTGTTTAGATAA
TCGTATACTTCATCAGTGTAGATAGTAAATGTGAACAGATAAAAGGTATTCTTGCTAATAGATTGGTAAATTCCA
TAGAATATATTAATCCTTTCTTCTTGAGATCCCACATCATTTCAACCAGAGACGTTTTATCCAATGATTTACCTCG
TACTATACCACATACAAAACTAGATTTTGCAGTGACGTCGTATCTGGTATTCCTACCAAACAAAATTTTACTTTTA
GTTCTTTTAGAAAATTCTAAGGTAGAATCTCTATTTGCCAATATGTCATCTATGGAATTACCACTAGCAAAAAATG
ATAGAAATATATATTGATACATCGCAGCTGGTTTTGATCTACTATACTTTAAAAACGAATCAGATTCCATAATTGC
CTGTATATCATCAGCTGAAAAACTATGTTTTACACGTATTCCTTCGGCATTTCTTTTTAATGATATATCTTGTTTA
GACAATGATAAAGTTATCATGTCCATGAGAGACGCGTCTCCGTATCGTATAAATATTTCATTAGATGTTAGACGCT
TCATTAGGGGTATACTTCTATAAGGTTTCTTAATCAGTCCATCATTGGTTGCGTCAAGAACAAGCTTGTCTCCCTA
TAGTGAGTCGTATTAGAGCTTGGCGTAATCATGGTCATAGCTGTTTCCTGTGTGAAATTGTTATCCGCTCACAATT
CCACACAACATACGAGCCGGAAGCATAAAGTGTAAAGCCTGGGGTGCCTAATGAGTGAGCTAACTCACATTAATTG
CGTTGCGCTCACTGCCCGCTTTCGAGTCGGGAAACCTGTCGTGCCAGCTGCATTAATGAATCGGCCAACGCGCGGG
GAGAGGCGGTTTGCGTATTGGGCGCTCTTCCGCTTCCTCGCTCACTGACTCGCTGCGCTCGGTCGTTCGGCTGCGG
CGAGCGGTATCAGCTCACTCAAAGGCGGTAATACGGTTATCCACAGAATCAGGGGATAACGCAGGAAAGAACATGT
```

-continued

```
GAGCAAAAGGCCAGCAAAAGGCCAGGAACCGTAAAAAGGCCGCGTTGCTGGCGTTTTTCGATAGGCTCCGCCCCC

TGACGAGCATCACAAAAATCGACGCTCAAGTCAGAGGTGGCGAAACCCGACAGGACTATAAAGATACCAGGCGTTT

CCCCCTGGAAGCTCCCTCGTGCGCTCTCCTGTTCCGACCCTGCCGCTTACCGGATACCTGTCCGCCTTTCTCCCTT

CGGGAAGCGTGGCGCTTTCTCATAGCTCACGCGTGTAGGTATCTCAGTTCGGTGTAGGTCGTTCGCTCCAAGCTGGG

CTGTGTGCACGAACCCCCCGTTCAGCCCGACCGCTGCGCCTTATCCGGTAACTATCGTCTTGAGTCCAACCCGGTA

AGACACGACTTATCGCCACTGGCAGCAGCCACTGGTAACAGGATTAGCAGAGCGAGGTATGTAGGCGGTGCTACAG

AGTTCTTGAAGTGGTGGCCTAACTACGGCTACACTAGAAGGACAGTATTTGGTATCTGCGCTCTGCTGAAGCCAGT

TACCTTCGGAAAAAGAGTTGGTAGCTCTTGATCCGGCAAACAAACCACCGCTGGTAGCGGTGGTTTTTTGTTTGC

AAGCAGCAGATTACGCGCAGAAAAAAAGGATCTCAAGAAGATCCTTTGATCTTTTCTACGGGGTCTGACGCTCAGT

GGAACGAAAACTCACGTTAAGGGATTTTGGTCATGAGATTATCAAAAAGGATCTTCACCTAGATCCTTTTAAATTA

AAAATGAAGTTTTAAATCAATCTAAAGTATATATGAGTAAACTTGGTCTGACAGTTACCAATGCTTAATCAGTGAG

GCACCTATCTCAGCGATCTGTCTATTTCGTTCATCCATAGTTGCCTGACTCCCCGTCGTGTAGATAACTACGATAC

GGGAGGGCTTACCATCTGGCCCCAGTGCTGCAATGATACCGCGAGACCCACGCTCACCGGCTCCAGATTTATCAGC

AATAAACCAGCCAGCCGGAAGGGCCGAGCGCAGAAGTGGTCCTGCAACTTTATCCGCCTCCATCCAGTCTATTAAT

TGTTGCCGGGAAGCTAGAGTAAGTAGTTCGCCAGTTAATAGTTTGCGCAACGTTGTTGGCATTGCTACAGGCATCG

TGGTGTCACGCTCGTCGTTTGGTATGGCTTCATTCAGCTCCGGTTCCCAACGATCAAGGCGAGTTACATGATCCCC

CATGTTGTGCAAAAAAGCGGTTAGCTCCTTCGGTCCTCCGATCGTTGTCAGAAGTAAGTTGGCCGCAGTGTTATCA

CTCATGGTTATGGCAGCACTGCATAATTCTCTTACTGTCATGCCATCCGTAAGATGCTTTTCTGTGACTGGTGAGT

ACTCAACCAAGTCATTCTGAGAATAGTGTATGCGGCGACCGAGTTGCTCTTGCCCGGCGTCAATACGGGATAATAC

CGCGCCACATAGCAGAACTTTAAAAGTGCTCATCATTGGAAAACGTTCTTCGGGGCGAAAACTCTCAAGGATCTTA

CCGCTGTTGAGATCCAGTTCGATGTAACCCACTCGTGCACCCAACTGATCTTCAGCATCTTTTACTTTCACCAGCG

TTTCTGGGTGAGCAAAAACAGGAAGGCAAAATGCCGCAAAAAAGGGAATAAGGGCGACACGGAAATGTTGAATACT

CATACTCTTCCTTTTTCAATATTATTGAAGCATTTATCAGGGTTATTGTCTCATGAGCGGATACATATTTGAATGT

ATTTAGAAAAATAAACAAATAGGGGTTCCGCGCACATTTCCCCGAAAAGTGCCACCTGACGTCTAAGAAACCATTA

TTATCATGACATTAACCTATAAAAATAGGCGTATCACGAGGCCCTTTCGTCTCGCGCGTTTCGGTGATGACGGTGA

AAACCTCTGACACATGCAGCTCCCGGAGACGGTCACAGCTTGTCTGTAAGCGGATGCCGGGAGCAGACAAGCCCGT

CAGGGCGCGTCAGCGGGTGTTGGCGGGTGTCGGGGCTGGCTTAACTATGCGGCATCAGAGCAGATTGTACTGAGAG

TGCACCATATGCGGTGTGAAATACCGCACAGATGCGTAAGGAGAAAATACCGCATCAGGCGCCATTCGCCATTCAG

GCTGCGCAACTGTTGGGAAGGGCGATCGGTGCGGGCCTCTTCGCTATTACGCCAGCTGGCGAAAGGGGGATGTGCT

GCAAGGCGATTAAGTTGGGTAACGCCAGGGTTTTCCCAGTCACGACGTTGTAAAACGACGGCCAGTGAATTGGATT

TAGGTGACACTATA
```

Example 5: MVA Vaccine Incorporating Lassa Virus Sequences

In an exemplary embodiment, sequences from Lassa Virus (LARV) are prepared and optimized in shuttle plasmids and then the viral sequences are incorporated into an MVA vector. Such MVA vectors may be used individually as part of an administration protocol to elicit an immune response to Lassa Virus or as part of a multivalent vaccine composition having one or more MVA vectors expressing EBOV and Lassa Virus antigens to elicit an immune response. Original Lassa GP and Z Sequences are obtained from Genbank (GenBank: JN650517.1 and JN650518.1) and optimized as described herein for insertion into MVA vectors.

TABLE 11

Lassa Glycoprotein mutation table

| Changes (Silent mutation) | Mutation position on GP |
|---|---|
| T to C | 21 |
| T to C | 24 |
| T to C | 114 |
| A to G | 264 |
| T to C | 351 |
| A to G | 375 |
| A to G | 378 |
| A to G | 483 |
| T to C | 573 |
| A to G | 669 |

TABLE 11-continued

Lassa Glycoprotein mutation table

| Changes (Silent mutation) | Mutation position on GP |
|---|---|
| T to C | 699 |
| T to C | 786 |
| A to G | 816 |
| A to G | 912 |
| A to G | 1056 |
| T to C | 1197 |
| A to G | 1251 |
| A to G | 1275 |
| T to C | 1308 |
| T to C | 1320 |
| A to G | 1353 |

*Shown as lower case in SEQ ID NO: 16

Exemplary Lassa Virus GP and Z sequences are provided below.

```
SEQ ID 16:
Optimized Lassa GP sequence (GVX-LAS.GP) for
insertion into MVA vector:
ATGGGACAAATAGTAACATTcTTcCAAGAAGTACCACATGTAATTGAAGA

AGTAATGAATATTGTACTAATTGCGCTATCTGTACTAGCGGTATTGAAAG

GATTGTATAATTTcGCGACATGTGGACTAGTAGGACTAGTTACATTTCTA

CTACTATGTGGAAGATCTTGTACAACTTCTTTGTATAAAGGAGTATATGA

ACTACAAACACTAGAATTGAATATGGAAACTCTAAATATGACAATGCCTC

TATCATGTACAAAgAATAATTCTCATCATTATATTATGGTTGGAAATGAA

ACAGGACTAGAACTAACACTAACAAATACTTCTATTATTAATCATAAATT cTGTAATCTATCTGATGCGCATAAgAAgAATCTATATGATCATGCGCTAA

TGTCTATTATTTCTACATTTCATCTATCTATTCCAAACTTTAATCAATAT

GAAGCTATGTCTTGTGACTTTAATGGTGGAAAgATTTCTGTACAATATAA

TCTAAGTCATTCTTATGCGGGAGATGCGGCGAATCATTGTGGAACAGTAG

CGAATGGTGTACTACAAACTTTcATGAGAATGGCGTGGGGAGGATCTTAT

ATTGCGCTAGATTCTGGAAGAGGAAATTGGGATTGTATTATGACATCTTA

TCAATATCTAATTATTCAgAATACAACATGGGAAGATCATTGTCAATTcT

CTAGACCATCTCCAATAGGATATCTAGGACTACTATCTCAAAGAACAAGA

GATATATATATTAGTAGAAGATTGCTAGGAACTTTcACATGGACACTATC

TGATTCTGAAGGAAAgGATACACCTGGAGGATATTGTCTAACAAGATGGA

TGCTAATTGAAGCGGAATTGAAATGTTTTGGAAATACTGCGGTAGCGAAA

TGTAATGAAAAgCATGATGAAGAATTTTGTGATATGCTAAGACTATTTGA

CTTTAATAAACAAGCGATTCAAAGATTGAAAGCGGAAGCGCAAATGAGTA

TTCAATTGATAAATAAAGCGGTTAATGCTTTGATTAATGATCAACTAATT

ATGAAgAATCATCTAAGAGATATTATGGGAATTCCATATTGTAATTATAG

TAAATATTGGTATCTAAATCATACAACAACTGGAAGAACATCTCTACCAA

AATGTTGGCTAGTATCTAATGGATCTTATCTAAATGAAACACATTTcTCT

GATGATATTGAACAACAAGCGGATAATATGATTACAGAAATGCTACAAAA
```

```
gGAATATATGGAAAGACAAGGAAAgACACCACTAGGATTGGTAGATCTAT

TTGTTTTcTCTACATCTTTcTATCTAATTAGTATATTTCTACATCTAGTA

AAgATTCCAACACATAGACATATAGTAGGAAAATCTTGTCCAAAACCACA

TAGATTGAATCATATGGGAATATGTTCTTGTGGATTGTATAAACAACCAG

GTGTACCAGTTAAATGGAAAAGATAAtaa
```

```
SEQ ID 17:
Optimized Z sequence (GVX-LAS.Z) for insertion
into MVA vector:
ATGGGAAATAAACAAGCGAAAGCGCCAGAATCTAAAGATTCTCCAAGAGC

GAGTCTAATTCCAGATGCGACACATCTAGGACCACAATTTTGTAAATCTT

GTTGGTTTGAAAATAAAGGACTAGTAGAATGTAATAATCATTATCTATGT

CTAAATTGTCTAACACTACTACTATCTGTATCTAATAGATGTCCAATATG

CAAAATGCCACTACCAACAAAACTAAGACCATCTGCTGCTCCAACAGCGC

CACCAACAGGTGCTGCTGATTCTATTAGACCACCACCATATTCTCCATAA taa
```

Example 6: Immunogenic and Protective Potential of the MVA/Z-VLP Vaccine

To test for the immunogenic and protective potential of the MVA/Z-VLP vaccine, two rodent models for Ebola virus (EBOV) infection and disease were tested for vaccine-elicited immune responses and protection against an EBOV challenge. The guinea pig and Syrian Golden Hamster (SGH) models were chosen because of the extensive experience with these models and the availability of suitable challenge stocks at the NIH Rocky Mountain Laboratories (RML) where challenges can be conducted under BSL4 containment.

Animal Study

Hamsters and guinea pigs were acquired by BIOQUAL, Inc., and randomized into two groups per species: a six-animal MVA/Z-VLP group and a two-animal MVA control (parental MVA, with no vaccine insert) group. Animals in the MVA/Z-VLP and MVA control groups were immunized intramuscularly at BIOQUAL. Two groups of naïve animals were also acquired and housed at BIOQUAL but were not vaccinated. All animals (MVA/Z-VLP, MVA control, and naïve control) were shipped to RML for challenge of the guinea pigs with guinea pig-adapted and the hamsters with mouse-adapted EBOV. Challenge was intraperitoneal with 10 plaque forming units of the respective adapted EBOV strains.

Table 12 summarizes the trial groups and procedures.

TABLE 12

Trial Groups and Procedures

| Group | Species and no. of animals[1] | Vaccine[2] | Immunization and bleed schedule (week in study) | | | Sampling schedule (days post challenge)[3] | | |
|---|---|---|---|---|---|---|---|---|
| | | | Imm. | Bleed for serum | Challenge | Weight | Bleed for serum |
| 1 | 6 guinea pigs[4] | MVA/Z-VLP | 0,4 | 0, 4, 6 | 11 | 1-14 | 42 |
| 2 | 2 guinea pigs | Parental MVA | 0,4 | 0, 4, 6 | 11 | 1-14 | 42 |
| 3 | 6 guinea pigs | none | N/A | 0, 4, 6 | 11 | 1-14 | 42 |
| 4 | 6 SGH | MVA/Z-VLP | 0,4 | 0, 4, 6 | 11 | 1-14 | 42 |
| 5 | 2 SGH | Parental MVA | 0,4 | 0, 4, 6 | 11 | 1-14 | 42 |
| 6 | 6 SGH | none | N/A | 0, 4, 6 | 11 | 1-14 | 42 |

[1]Young adult animals were used for vaccinations
[2]MVA/Z-VLP and parental MVA were used at a dose of $1 \times 10^8$ tissue culture infectious doses (TCID)50
[3]Animals were euthanized on day 42.
[4]One guinea pig died of unrelated causes before the $2^{nd}$ vaccination Immune Responses Vaccine induced binding Ab was determined by an ELISA using a secreted EBOV glycoprotein produced by a recombinant baculovirus in insect cells Plates were coated with the secreted EBOV glycoprotein or a control baculovirus supernatant that expressed no EBOV antigens. After blocking with 5% dry milk in 2% normal goat serum, serial serum dilutions were added to duplicate wells coated with both the EBOV glycoprotein and control supernatant. Antibody binding was detected by peroxidase-labeled anti-guinea pig IgG or peroxidase-labeled anti-hamster IgG and tetramethylbenzidine substrate. Reactions were stopped with 1N hydrochloric acid. Each plate included a standard curve generated using anti-guinea pig IgG and guinea pig IgG or anti-hamster IgG and hamster IgG. Standard curves were fitted, and sample concentrations were interpolated as micrograms of antibody per milliliter of serum using SoftMax Pro v.5.4.5. Background was calculated as antibody raised in wells coated with control baculovirus supernatant and was subtracted from EBOV glycoprotein antibody titers to obtain final results. These data are shown in FIGS. 11A and 11B.

The results of the binding Ab assays showed a single inoculation of MVA/Z-VLP eliciting similar titers of binding Ab as a single inoculation of a chimeric VSV expressing GP. It was, a chimeric VSV vector (rVSV-ZEBOV), which achieved protection against Ebola in Guinea (Agnandji, S. T., *N Engl J Med* (2015)).

Neutralizing Antibody

Neutralizing antibody titers were determined by focus reduction neutralization assay. Vero cells were seeded into 96-well plates at a density adequate to generate a confluent monolayer on the day of infection. Serum dilutions were prepared in PBS. For each dilution, 10 µL of diluted serum was mixed with 10 µL of medium containing 100 focus-forming units (PFU) of ZEBOV-GFP (total volume of 20 µL). After 30 min at 37° C., the media was removed from cells, the serum-virus mixture was added and the samples were incubated for 60 min at 37° C. Then the mixture was removed from the cells, 100 µL of 1.2% carboxymethylcellulose-MEM was added and the cells were incubated for 4 days at 37° C. The neutralizing antibody titer of the serum samples was considered positive at a dilution showing a >80% reduction in GFP-foci compared with the control without serum. These data are shown in FIGS. 12A and 12B.

The titers are comparable to those from other vaccines that have shown protective efficacy against EBOV in rodents and non-human primates. For example, neutralizing titers elicited by other EBOV vaccine candidates (including VSVAG/ZEBOVGP, Adeno, and VLP) in rodents or non-human primates vary from 1:20 to 1:160 (Ye, L., et al. *Virology* 351, 260-270 (2006); Marzi, A., et al. *J Infect Dis* 204 Suppl 3, S1066-1074 (2011); Feldmann, H., et al. *PLoS Pathog* 3(2007), Warfield, K. L., et al. *J Infect Dis* 15, 8 (2007)).

Challenge Results

The guinea pigs and hamsters were challenged intraperitoneally with 10 pfu of either guinea pig-adapted or mouse-adapted EBOV, respectively. The animals were weighed daily for 14 days. On day 42 post challenge, a terminal serum sample will be taken from all the survivors. These data are down in FIG. 13A-13D.

All of the control guinea pigs (the two vaccinated with parental MVA and the 6 unvaccinated) succumbed to the lethal challenge. One of the two hamsters receiving parental MVA succumbed and four of the unvaccinated SGHs succumbed. Minimal weight loss (1-2%) occurred on days 5-7 for the vaccinated guinea pigs and no weight loss, but a leveling in weight gain, occurred on days 4-6 for the vaccinated SGHs. In contrast, all of the unvaccinated animals underwent major losses in weight.

The complete protection elicited in rodents by MVA/Z-VLP is comparable to that seen from other vaccines that have shown protective efficacy. For example, it has been shown that a VSV-based vaccine candidate (VSVDG/ZEBOV) protects SGH and guinea pigs from lethal challenge with the Zaire strain of Ebola (Marzi, A., et al. *J Infect Dis* 204 Suppl 3, S1066-1074 (2011); Tsuda, Y., et al. *J Infect Dis* 204, 8, (2011)).

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

All references cited herein are incorporated by reference in their entirety.

The invention claimed is:

1. A recombinant modified vaccinia ankara (MVA) vector comprising:
   i) a first nucleic acid encoding a Marburg virus (MARV) glycoprotein, and
   ii) a second nucleic acid sequence encoding a Marburg virus (MARV) VP40 matrix protein;
   wherein both the first nucleic acid sequence and the second nucleic acid sequence are under the control of one or more promoters compatible with poxvirus expression systems;
   wherein the first nucleic acid is located between MVA genes I8R and G1L;
   wherein the second nucleic acid sequence is located between MVA genes A50R and B1R in a restructured and modified deletion site III; and
   wherein the MARV glycoprotein and the MARV VP40 matrix protein are capable of assembling into virus-like particles (VLPs) when expressed in a host cell.

2. The recombinant MVA vector of claim 1, wherein the first nucleic acid sequence and the second nucleic acid sequence is optimized by one or more method selected from the group consisting of i) changing selected codons to other synonymous codons that are optimal for protein expression by MVA, ii) interrupting homopolymer stretches using silent mutations, and iii) interrupting transcription terminator motifs using silent mutations.

3. The recombinant MVA vector of claim 1, wherein the MARV glycoprotein and MARV VP40 matrix protein are derived from the same MARV strain.

4. The recombinant MVA vector of claim 1, wherein the first nucleic acid sequence comprises nucleic acids 1631-3676 of SEQ ID NO:15, or a nucleic acid sequence at least 95% identical thereto.

5. The recombinant MVA vector of claim 1, wherein the first nucleic acid sequence comprises nucleic acids 1631-3676 of SEQ ID NO:15.

6. The recombinant MVA vector of claim 1, wherein the second nucleic acid sequence comprises nucleic acids 1581-2492 of SEQ ID NO:14, or a nucleic acid sequence at least 95% identical thereto.

7. The recombinant MVA vector of claim 1, wherein the second nucleic acid sequence comprises nucleic acids 1581-2492 of SEQ ID NO:14.

8. The recombinant MVA vector of claim 1, wherein the first nucleic acid sequence comprises nucleic acids 1631-3676 of SEQ ID NO:15, and the second nucleic acid sequence comprises nucleic acids 1581-2492 of SEQ ID NO:14.

9. A recombinant modified vaccinia ankara (MVA) vector comprising:
   i) a first nucleic acid sequence encoding a Marburg virus glycoprotein comprising nucleic acids 1631-3676 of SEQ ID NO:15, or a nucleic acid sequence at least 95% identical thereto, and
   ii) a second nucleic acid sequence encoding a Marburg virus VP40 matrix protein comprising nucleic acids 1581-2492 of SEQ ID NO:14, or a nucleic acid sequence at least 95% identical thereto;
   wherein both the first nucleic acid sequence and the second nucleic acid sequence are under the control of one or more promoters compatible with poxvirus expression systems;
   wherein the first nucleic acid is located between MVA genes I8R and G1L;
   wherein the second nucleic acid sequence is located between MVA genes A50R and B1R in a restructured and modified deletion site III; and
   wherein the Marburg virus glycoprotein and the Marburg virus VP40 matrix protein are capable of assembling into virus-like particles (VLPs) when expressed in a host cell.

10. A pharmaceutical composition comprising at least one recombinant MVA vector of claim 1 and a pharmaceutically acceptable carrier.

11. A pharmaceutical composition comprising at least one recombinant MVA vector of claim 9 and a pharmaceutically acceptable carrier.

* * * * *

SEQUENCE LISTING

<160> NUMBER OF SEQ ID NOS: 17

<210> SEQ ID NO 1
<211> LENGTH: 2030
<212> TYPE: DNA
<213> ORGANISM: Ebola virus

<400> SEQUENCE: 1

| | | | | | |
|---|---|---|---|---|---:|
| atgggtgtta | caggaatatt | gcagttacct | cgtgatcgat | tcaagaggac | atcattcttt | 60 |
| ctttgggtaa | ttatcctttt | ccaaagaaca | ttttccatcc | cgcttggagt | tatccacaat | 120 |
| agtacattac | aggttagtga | tgtcgacaaa | ctagtttgtc | gtgacaaact | gtcatccaca | 180 |
| aatcaattga | gatcagttgg | actgaatctc | gaggggaatg | gagtggcaac | tgacgtgcca | 240 |
| tctgtgacta | aaagatgggg | cttcaggtcc | ggtgtcccac | caaaggtggt | caattatgaa | 300 |
| gctggtgaat | gggctgaaaa | ctgctacaat | cttgaaatca | aaaaacctga | cgggagtgag | 360 |
| tgtctaccag | cagcgccaga | cgggattcgg | ggcttccccc | ggtgccggta | tgtgcacaaa | 420 |
| gtatcaggaa | cgggaccatg | tgccggagac | tttgccttcc | acaaagaggg | tgctttcttc | 480 |
| ctgtatgatc | gacttgcttc | cacagttatc | taccgaggaa | cgactttcgc | tgaaggtgtc | 540 |
| gttgcatttc | tgatactgcc | ccaagctaag | aaggacttct | tcagctcaca | ccccttgaga | 600 |
| gagccggtca | atgcaacgga | ggacccgtcg | agtggctatt | attctaccac | aattagatat | 660 |
| caggctaccg | gttttggaac | taatgagaca | gagtacttgt | tcgaggttga | caatttgacc | 720 |
| tacgtccaac | ttgaatcaag | attcacacca | cagtttctgc | tccagctgaa | tgagacaata | 780 |
| tatgcaagtg | gaagaggag | caacaccacg | ggaaaactaa | tttggaaggt | caaccccgaa | 840 |
| attgatacaa | caatcgggga | gtgggccttc | tgggaaacta | aaaaaacctc | actagaaaaa | 900 |
| ttcgcagtga | agagttgtct | ttcacagctg | tatcaaacgg | acccaaaaac | atcagtggtc | 960 |
| agagtccggc | gcgaacttct | tccgacccag | agaccaacac | aacaaatgaa | gaccacaaaa | 1020 |
| tcatggcttc | agaaaattcc | tctgcaatgg | ttcaagtgca | cagtcaagga | aggaaagctg | 1080 |
| cagtgtcgca | tctgacaacc | cttgccacaa | tctccacgag | tcctcaacct | cccacaacca | 1140 |
| aaacaggtcc | ggacaacagc | acccataata | cacccgtgta | taaacttgac | atctctgagg | 1200 |
| caactcaagt | tggacaacat | caccgtagag | cagacaacga | cagcacagcc | tccgacactc | 1260 |
| cccccgccac | gaccgcagcc | ggaccccttaa | aagcagagaa | caccaacacg | agtaagagcg | 1320 |
| ctgactccct | ggacctcgcc | accacgacaa | gcccccaaaa | ctacagcgag | actgctggca | 1380 |
| acaacaacac | tcatcaccaa | gataccggag | aagagagtgc | cagcagcggg | aagctaggct | 1440 |
| taattaccaa | tactattgct | ggagtagcag | gactgatcac | aggcgggaga | aggactcgaa | 1500 |
| gagaagtaat | tgtcaatgct | caacccaaat | gcaaccccaa | tttacattac | tggactactc | 1560 |
| aggatgaagg | tgctgcaatc | ggattggcct | ggataccata | tttcgggcca | gcagccgaag | 1620 |
| gaatttacac | agagggcta | atgcacaacc | aagatggttt | aatctgtggg | ttgaggcagc | 1680 |
| tggccaacga | aacgactcaa | gctctccaac | tgttcctgag | agccacaact | gagctgcgaa | 1740 |
| ccttttcaat | cctcaaccgt | aaggcaattg | acttcctgct | gcagcgatgg | ggtgcacat | 1800 |
| gccacatttt | gggaccggac | tgctgtatcg | aaccacatga | ttggaccaag | aacataacag | 1860 |
| acaaaattga | tcagattatt | catgattttg | ttgataaaac | ccttccggac | caggggggaca | 1920 |
| atgacaattg | gtgacagga | tggagacaat | ggataccggc | aggtattgga | gttacaggtg | 1980 |
| ttataattgc | agttatcgct | ttattctgta | tatgcaaatt | tgtcttttag | | 2030 |

```
<210> SEQ ID NO 2
<211> LENGTH: 2031
<212> TYPE: DNA
<213> ORGANISM: Ebola virus
<220> FEATURE:
<221> NAME/KEY: misc_feature
<222> LOCATION: (880)..(880)
<223> OTHER INFORMATION: Addition of A nucleotide

<400> SEQUENCE: 2
atgggtgtta caggaatatt gcagttacct cgtgatcgat tcaagaggac atcattcttt      60
ctttgggtaa ttatcctttt ccaaagaaca ttttccatcc cgcttggagt tatccacaat     120
agtacattac aggttagtga tgtcgacaaa ctagtttgtc gtgacaaact gtcatccaca     180
aatcaattga gatcagttgg actgaatctc gaggggaatg gagtggcaac tgacgtgcca     240
tctgtgacta aaagatgggg cttcaggtcc ggtgtcccac caaaggtggt caattatgaa     300
gctggtgaat gggctgaaaa ctgctacaat cttgaaatca aaaaacctga cgggagtgag     360
tgtctaccag cagcgccaga cgggattcgg ggcttccccc ggtgccggta tgtgcacaaa     420
gtatcaggaa cgggaccatg tgccggagac tttgccttcc acaaagaggg tgctttcttc     480
ctgtatgatc gacttgcttc cacagttatc taccgaggaa cgactttcgc tgaaggtgtc     540
gttgcatttc tgatactgcc ccaagctaag aaggacttct tcagctcaca ccccttgaga     600
gagccggtca tgcaacggaa ggacccgtcg agtggctatt attctaccac aattagatat     660
caggctaccg gttttggaac taatgagaca gagtacttgt tcgaggttga caatttgacc     720
tacgtccaac ttgaatcaag attcacacca cagtttctgc tccagctgaa tgagacaata     780
tatgcaagtg ggaagaggag caacaccacg ggaaaactaa tttggaaggt caaccccgaa     840
attgatacaa caatcgggga gtgggccttc tgggaaacta aaaaaaacct cactagaaaa     900
attcgcagtg aagagttgtc tttcacagct gtatcaaacg acccaaaaaa catcagtggt     960
cagagtccgg cgcgaacttc ttccgaccca gagaccaaca caacaaatga agaccacaaa    1020
atcatggctt cagaaaattc ctctgcaatg gttcaagtgc acagtcaagg aaggaaagct    1080
gcagtgtcgc atctgacaac ccttgccaca atctccacga gtcctcaacc tcccacaacc    1140
aaaacaggtc cggacaacag cacccataat acacccgtgt ataaacttga catctctgag    1200
gcaactcaag ttggacaaca tcaccgtaga gcagacaacg acagcacagc ctccgacact    1260
cccccgcca cgaccgcagc cggacccctta aaagcagaga acaccaacac gagtaagagc    1320
gctgactccc tggacctcgc caccacgaca agcccccaaa actacagcga gactgctggc    1380
aacaacaaca ctcatcacca agataccgga gaagagagtg ccagcagcgg gaagctaggc    1440
ttaattacca atactattgc tggagtagca ggactgatca caggcgggag aaggactcga    1500
agagaagtaa ttgtcaatgc tcaacccaaa tgcaacccca atttacatta ctggactact    1560
caggatgaag gtgctgcaat cggattggcc tggataccat atttcgggcc agcagccgaa    1620
ggaatttaca cagaggggct aatgcacaac caagatggtt taatctgtgg gttgaggcag    1680
ctggccaacg aaacgactca agctctccaa ctgttcctga gagccacaac tgagctgcga    1740
acctttcaa tcctcaaccg taaggcaatt gacttcctgc tgcagcgatg gggtggcaca    1800
tgccacattt gggaccggga ctgctgtatc gaaccacatg attggaccaa gaacataaca    1860
gacaaaattg atcagattat tcatgatttt gttgataaaa cccttccgga ccaggggac    1920
aatgacaatt ggtggacagg atggagacaa tggataccgg caggtattgg agttacaggt    1980
gttataattg cagttatcgc tttattctgt atatgcaaat ttgtcttta g              2031
```

```
<210> SEQ ID NO 3
<211> LENGTH: 676
<212> TYPE: PRT
<213> ORGANISM: Ebola virus

<400> SEQUENCE: 3

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Val Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Ala Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Asn Leu Thr Arg Lys Ile Arg Ser Glu
    290                 295                 300

Glu Leu Ser Phe Thr Ala Val Ser Asn Gly Pro Lys Asn Ile Ser Gly
305                 310                 315                 320

Gln Ser Pro Ala Arg Thr Ser Ser Asp Pro Glu Thr Asn Thr Thr Asn
                325                 330                 335

Glu Asp His Lys Ile Met Ala Ser Glu Asn Ser Ser Ala Met Val Gln
            340                 345                 350

Val His Ser Gln Gly Arg Lys Ala Ala Val Ser His Leu Thr Thr Leu
        355                 360                 365

Ala Thr Ile Ser Thr Ser Pro Gln Pro Pro Thr Thr Lys Thr Gly Pro
    370                 375                 380
```

-continued

Asp Asn Ser Thr His Asn Thr Pro Val Tyr Lys Leu Asp Ile Ser Glu
385                 390                 395                 400

Ala Thr Gln Val Gly Gln His Arg Arg Ala Asp Asn Asp Ser Thr
            405                 410                 415

Ala Ser Asp Thr Pro Pro Ala Thr Thr Ala Ala Gly Pro Leu Lys Ala
            420                 425                 430

Glu Asn Thr Asn Thr Ser Lys Ser Ala Asp Ser Leu Asp Leu Ala Thr
            435                 440                 445

Thr Thr Ser Pro Gln Asn Tyr Ser Glu Thr Ala Gly Asn Asn Asn Thr
        450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
            485                 490                 495

Arg Arg Thr Arg Arg Glu Val Ile Val Asn Ala Gln Pro Lys Cys Asn
            500                 505                 510

Pro Asn Leu His Tyr Trp Thr Thr Gln Asp Glu Gly Ala Ala Ile Gly
            515                 520                 525

Leu Ala Trp Ile Pro Tyr Phe Gly Pro Ala Ala Glu Gly Ile Tyr Thr
            530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
            565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
            595                 600                 605

Cys Ile Glu Pro His Asp Trp Thr Lys Asn Ile Thr Asp Lys Ile Asp
        610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
            645                 650                 655

Gly Val Thr Gly Val Ile Ile Ala Val Ile Ala Leu Phe Cys Ile Cys
            660                 665                 670

Lys Phe Val Phe
        675

<210> SEQ ID NO 4
<211> LENGTH: 2031
<212> TYPE: DNA
<213> ORGANISM: Ebola virus

<400> SEQUENCE: 4
atgggagtaa ctggaattct acaactacca agagatagat tcaaaagaac atctttttt         60 ctatgggtta taattctatt tcaaagaaca ttttctattc cattgggagt aattcataat        120
tctacattgc aagtatctga gtagataaa ctagtatgta gagataaatt gtctagtaca        180
aatcaactaa gatctgtagg attgaatcta gaaggaaatg gtgtagcgac agatgttcca        240
tctgtaacaa aaagatgggg ttttagatct ggtgtaccac caaaagtagt aaattatgaa        300
gcgggagaat gggcggaaaa ttgttataat ctagaaatta aaaaaccaga tggatctgaa        360
tgtctaccag cggcgccaga tggaattaga ggatttccaa gatgtagata tgttcataaa        420

| | |
|---|---|
| gtatctggaa caggaccatg tgcgggagat tttgcgtttc ataaagaagg agcatttttt | 480 |
| ctatatgata gactagcgtc tacagtaata tatagaggaa caacatttgc ggaaggtgta | 540 |
| gtagcttttc taattctacc acaagcgaaa aaagatttt ttagttctca tccactaaga | 600 |
| gaaccagtaa atgcgacaga agatccttct tctggatatt attctactac aattagatat | 660 |
| caagcgacag gatttggaac aaatgaaaca gaatatctat ttgaagttga taatctaaca | 720 |
| tatgtacaac tagaaagtag attcacacca caatttctat tgcaattgaa tgaaacaata | 780 |
| tatgcgtctg gaaaaagatc taatacaact ggaaaactaa tttggaaagt aaatccagaa | 840 |
| attgatacaa caattggaga atgggctttt tgggaaacaa aaaaaaattt gacaagaaaa | 900 |
| attagatctg aagaattgtc ttttacagcg gtatctaatg gaccaaaaaa tatttctgga | 960 |
| caatctccag cgagaacttc ttctgatcca gaaacaaata ctacaaatga agatcacaaa | 1020 |
| attatggcgt ctgaaaattc ttctgctatg gtacaagtac attctcaagg aagaaaagcg | 1080 |
| gcggtatctc atctaacaac actagcgact atttctacat ctccacaacc accaacaaca | 1140 |
| aaaactggac cagataatag tacacataat actccagttt ataaactaga tatttctgaa | 1200 |
| gcgacacaag ttggacaaca tcatagaaga gcggataatg attctacagc gtctgataca | 1260 |
| ccaccagcta acagctgc tggaccattg aaagcggaaa atacaaatac ttctaaatct | 1320 |
| gcggattctc tagatttggc gacaacaact tctcctcaaa attattctga acagcggga | 1380 |
| aataataata ctcatcatca agatactgga gaagaatctg cgtctagtgg aaaattggga | 1440 |
| ctaattacaa atacaattgc gggtgtagcg ggattgatta ctggtggaag aagaactaga | 1500 |
| agagaagtaa tagttaatgc gcaacctaaa tgtaatccaa atctacatta ttggacaact | 1560 |
| caagatgaag gtgctgcgat tggactagct tggattccat attttggacc tgcggcggaa | 1620 |
| ggaatatata ctgaaggact aatgcataat caagatggac taatttgtgg actaagacaa | 1680 |
| ctagcgaatg aaactacaca agcgctacaa ctattttga gagcgacaac agaactaaga | 1740 |
| acttttagta ttctaaatag aaaagcgatt gattttttgc tacaaagatg gggaggaaca | 1800 |
| tgtcatattc taggaccaga ttgttgtatt gaaccacatg attggacaaa aaatattaca | 1860 |
| gacaaaattg atcaaattat tcatgatttt gttgataaaa cactaccaga tcaaggagat | 1920 |
| aatgataatt ggtggacagg atggagacaa tggattccag cgggaattgg agtaacaggt | 1980 |
| gtaattattg cggttattgc gctattttgt atatgtaaat ttgttttta a | 2031 |

<210> SEQ ID NO 5
<211> LENGTH: 2031
<212> TYPE: DNA
<213> ORGANISM: Ebola virus

<400> SEQUENCE: 5

| | |
|---|---|
| atgggagtaa ctggaattct acaactacca agagatagat tcaaaagaac atctttcttt | 60 |
| ctatgggtta taattctatt tcaaagaaca ttttctattc cattgggagt aattcataat | 120 |
| tctacattgc aagtatctga tgtagataaa ctagtatgta gagataaatt gtctagtaca | 180 |
| aatcaactaa gatctgtagg attgaatcta gaaggaaatg gtgtagcgac agatgttcca | 240 |
| tctgtaacaa agagatgggg ttttagatct ggtgtaccac caaagtagt aaattatgaa | 300 |
| gcgggagaat gggcggaaaa ttgttataat ctagaaatta gaaaccaga tggatctgaa | 360 |
| tgtctaccag cggcgccaga tggaattaga ggatttccaa gatgtagata tgttcataaa | 420 |
| gtatctggaa caggaccatg tgcgggagat tttgcgtttc ataaagaagg agcattcttt | 480 |
| ctatatgata gactagcgtc tacagtaata tatagaggaa caacatttgc ggaaggtgta | 540 |

-continued

```
gtagcttttc taattctacc acaagcgaag aaagatttct ttagttctca tccactaaga    600
gaaccagtaa atgcgacaga agatccttct tctggatatt attctactac aattagatat    660
caagcgacag gatttggaac aaatgaaaca gaatatctat ttgaagttga taatctaaca    720
tatgtacaac tagaaagtag attcacacca caatttctat tgcaattgaa tgaaacaata    780
tatgcgtctg gaaagagatc taatacaact ggaaaactaa tttggaaagt aaatccagaa    840
attgatacaa caattggaga atgggctttc tgggaaacaa agaagaattt gacaagaaag    900
attagatctg aagaattgtc ttttacagcg gtatctaatg gaccaaagaa tatttctgga    960
caatctccag cgagaacttc ttctgatcca gaaacaaata ctacaaatga agatcacaaa   1020
attatggcgt ctgaaaattc ttctgctatg gtacaagtac attctcaagg aagaaaagcg   1080
gcggtatctc atctaacaac actagcgact atttctacat ctccacaacc accaacaaca   1140
aagactggac cagataatag tacacataat actccagttt ataaactaga tatttctgaa   1200
gcgacacaag ttggacaaca tcatagaaga gcggataatg attctacagc gtctgataca   1260
ccaccagcta caacagctgc tggaccattg aaagcggaaa atacaaatac ttctaaatct   1320
gcggattctc tagatttggc gacaacaact tctcctcaaa attattctga aacagcggga   1380
aataataata ctcatcatca agatactgga gaagaatctg cgtctagtgg aaaattggga   1440
ctaattacaa atacaattgc gggtgtagcg ggattgatta ctggtggaag aagaactaga   1500
agagaagtaa tagttaatgc gcaacctaaa tgtaatccaa atctacatta ttggacaact   1560
caagatgaag gtgctgcgat tggactagct tggattccat attttggacc tgcggcggaa   1620
ggaatatata ctgaaggact aatgcataat caagatggac taatttgtgg actaagacaa   1680
ctagcgaatg aaactacaca agcgctacaa ctattcttga gagcgacaac agaactaaga   1740
acttttagta ttctaaatag aaaagcgatt gatttcttgc tacaaagatg gggaggaaca   1800
tgtcatattc taggaccaga ttgttgtatt gaaccacatg attggacaaa gaatattaca   1860
gacaaaattg atcaaattat tcatgatttt gttgataaaa cactaccaga tcaaggagat   1920
aatgataatt ggtggacagg atggagacaa tggattccag cgggaattgg agtaacaggt   1980
gtaattattg cggttattgc gctattttgt atatgtaaat ttgtttttta a            2031
```

```
<210> SEQ ID NO 6
<211> LENGTH: 2041
<212> TYPE: DNA
<213> ORGANISM: Ebola virus

<400> SEQUENCE: 6
atgggagtaa ctggaattct acaactacca agagatagat tcaaaagaac atctttcttt     60
ctatgggtta taattctatt tcaaagaaca ttttctattc cattgggagt aattcataat    120
tctacattgc aagtatctga tgtagataaa ctagtatgta gagataaatt gtctagtaca    180
aatcaactaa gatctgtagg attgaatcta gaaggaaatg gtgtagcgac agatgttcca    240
tctgtaacaa agagatgggg ttttagatct ggtgtaccac caaaagtagt aaattatgaa    300
gcgggagaat gggcggaaaa ttgttataat ctagaaatta agaaaccaga tggatctgaa    360
tgtctaccag cggcgccaga tggaattaga ggatttccaa gatgtagata tgttcataaa    420
gtatctggaa caggaccatg tgcgggagat tttgcgtttc ataaagaagg agcattcttt    480
ctatatgata gactagcgtc tacagtaata tatagaggaa caacatttgc ggaaggtgta    540
gtagcttttc taattctacc acaagcgaag aaagatttct ttagttctca tccactaaga    600
gaaccagtaa atgcgacaga agatccttct tctggatatt attctactac aattagatat    660
```

```
caagcgacag gatttggaac aaatgaaaca gaatatctat ttgaagttga taatctaaca    720
tatgtacaac tagaaagtag attcacacca caatttctat tgcaattgaa tgaaacaata    780
tatgcgtctg gaagagatc taatacaact ggaaaactaa tttggaaagt aaatccagaa    840
attgatacaa caattggaga atgggctttc tgggaaacaa agaagaattt gacaagaaag    900
attagatctg aagaattgtc ttttacagcg gtatctaatg gaccaaagaa tatttctgga    960
caatctccag cgagaacttc ttctgatcca gaaacaaata ctacaaatga agatcacaaa    1020
attatggcgt ctgaaaattc ttctgctatg gtacaagtac attctcaagg aagaaaagcg    1080
gcggtatctc atctaacaac actagcgact atttctacat ctccacaacc accaacaaca    1140
aagactggac cagataatag tacacataat actccagttt ataaactaga tatttctgaa    1200
gcgacacaag ttggacaaca tcatagaaga gcggataatg attctacagc gtctgataca    1260
ccaccagcta caacagctgc tggaccattg aaagcggaaa atacaaatac ttctaaatct    1320
gcggattctc tagatttggc gacaacaact tctcctcaaa attattctga acagcggga    1380
aataataata ctcatcatca agatactgga gaagaatctg cgtctagtgg aaaattggga    1440
ctaattacaa atacaattgc gggtgtagcg ggattgatta ctggtggaag aagaactaga    1500
agagaagtaa tagttaatgc gcaacctaaa tgtaatccaa atctacatta ttggacaact    1560
caagatgaag gtgctgcgat tggactagct tggattccat attttggacc tgcggcggaa    1620
ggaatatata ctgaaggact aatgcataat caagatggac taatttgtgg actaagacaa    1680
ctagcgaatg aaactacaca agcgctacaa ctattcttga gagcgacaac agaactaaga    1740
actttttagta ttctaaatag aaaagcgatt gatttcttgc tacaaagatg gggaggaaca    1800
tgtcatattc taggaccaga ttgttgtatt gaaccacatg attggacaaa gaatattaca    1860
gacaaaattg atcaaattat tcatgatttt gttgataaaa cactaccaga tcaaggagat    1920
aatgataatt ggtggacagg atggagacaa tggattccag cgggaattgg agtaacaggt    1980
gtaattattg cggttattgc gctattttgt atatgtaaat ttgttttta ataattttta    2040
t                                                                  2041
```

<210> SEQ ID NO 7
<211> LENGTH: 981
<212> TYPE: DNA
<213> ORGANISM: Ebola virus

<400> SEQUENCE: 7

```
atgaggcggg ttatattgcc tactgctcct cctgaatata tggaggccat atacctgcc     60
aggtcaaatt caacaattgc tagggtggc aacagcaata caggcttcct gacaccggag    120
tcagtcaatg gagacactcc atcgaatcca ctcaggccaa ttgctgatga caccatcgac    180
catgccagcc acacaccagg cagtgtgtca tcagcattca tcctcgaagc tatggtgaat    240
gtcatatcgg cccccaaagt gctaatgaag caaattccaa tttggcttcc tctaggtgtc    300
gctgatcaaa agacctacag ctttgactca actacggccg ccatcatgct tgcttcatat    360
actatcaccc atttcggcaa ggcaaccaat ccgcttgtca gagtcaatcg gctgggtcct    420
ggaatcccgg atcacccct caggctcctg cgaattggaa accaggcttt cctccaggag    480
ttcgttcttc caccagtcca actaccccag tatttcacct ttgatttgac agcactcaaa    540
ctgatcactc aaccactgcc tgctgcaaca tggaccgatg acactccaac tggatcaaat    600
ggagcgttgc gtccaggaat ttcatttcat ccaaaacttc gccccattct tttacccaac    660
aaaagtggga agaaggggaa cagtgccgat ctaacatctc cggagaaaat ccaagcaata    720
```

| | |
|---|---|
| atgacttcac tccaggactt aagatcgtt ccaattgatc caaccaaaaa tatcatgggt | 780 |
| atcgaagtgc cagaaactct ggtccacaag ctgaccggta agaaggtgac ttccaaaaat | 840 |
| ggacaaccaa tcatccctgt tcttttgcca aagtacattg ggttggaccc ggtggctcca | 900 |
| ggagacctca ccatggtaat cacacaggat tgtgacacgt gtcattctcc tgcaagtctt | 960 |
| ccagctgtgg ttgagaagta a | 981 |

<210> SEQ ID NO 8
<211> LENGTH: 981
<212> TYPE: DNA
<213> ORGANISM: Ebola virus

<400> SEQUENCE: 8

| | |
|---|---|
| atgagaagag taattctacc aacagcgcca ccagaatata tggaagcgat atatccagcg | 60 |
| agatctaatt ctacaattgc gagaggtgga aattctaata ctggatttct aacaccagaa | 120 |
| tctgtaaatg gagatacacc atctaatcca ctaagaccaa ttgcggatga tacaatagat | 180 |
| catgcgagtc atactccagg atctgtatct tctgctttta ttctagaagc tatggttaat | 240 |
| gtaatttctg gaccaaaagt actaatgaaa caaattccaa tttggctacc attgggagta | 300 |
| gcggatcaaa agacatattc ttttgattct actacagcgg cgattatgct agcgtcttat | 360 |
| acaattacac attttggaaa agcgacaaat ccactagtta gagtaaatag actaggacct | 420 |
| ggaataccag atcatccatt gagactacta agaattggaa atcaagcttt tctacaagaa | 480 |
| tttgttctac caccagtaca actaccacaa tactttacat ttgatctaac agcgctaaaa | 540 |
| ctaattacac aaccattgcc agcggcgaca tggacagatg atacaccaac aggatctaat | 600 |
| ggtgctctaa gacctggtat ttcttttcat ccaaaactaa gacctattct attgccaaat | 660 |
| aaatctggaa agaaggaaa ttctgcggat ctaacatctc cagaaaagat tcaagcgatt | 720 |
| atgacatctc tacaagactt caaaattgta ccaattgatc aacaaagaa tattatggga | 780 |
| attgaagtac agaaacact agttcataaa ctaactggaa agaaagtaac atctaaaaat | 840 |
| ggacaaccta ttattccagt attgctacct aaatatattg gactagatcc agtagcgcct | 900 |
| ggagatctaa caatggttat tacacaagat tgtgatactt gtcattctcc agcgagtttg | 960 |
| cctgcggtag tagaaaaata a | 981 |

<210> SEQ ID NO 9
<211> LENGTH: 991
<212> TYPE: DNA
<213> ORGANISM: Ebola virus

<400> SEQUENCE: 9

| | |
|---|---|
| atgagaagag taattctacc aacagcgcca ccagaatata tggaagcgat atatccagcg | 60 |
| agatctaatt ctacaattgc gagaggtgga aattctaata ctggatttct aacaccagaa | 120 |
| tctgtaaatg gagatacacc atctaatcca ctaagaccaa ttgcggatga tacaatagat | 180 |
| catgcgagtc atactccagg atctgtatct tctgctttta ttctagaagc tatggttaat | 240 |
| gtaatttctg gaccaaaagt actaatgaaa caaattccaa tttggctacc attgggagta | 300 |
| gcggatcaaa agacatattc ttttgattct actacagcgg cgattatgct agcgtcttat | 360 |
| acaattacac attttggaaa agcgacaaat ccactagtta gagtaaatag actaggacct | 420 |
| ggaataccag atcatccatt gagactacta agaattggaa atcaagcttt tctacaagaa | 480 |
| tttgttctac caccagtaca actaccacaa tactttacat ttgatctaac agcgctaaaa | 540 |
| ctaattacac aaccattgcc agcggcgaca tggacagatg atacaccaac aggatctaat | 600 |

| | | |
|---|---|---|
| ggtgctctaa gacctggtat ttcttttcat ccaaaactaa gacctattct attgccaaat | 660 | |
| aaatctggaa agaaaggaaa ttctgcggat ctaacatctc cagaaaagat tcaagcgatt | 720 | |
| atgacatctc tacaagactt caaaattgta ccaattgatc aacaaagaa tattatggga | 780 | |
| attgaagtac cagaaacact agttcataaa ctaactggaa agaaagtaac atctaaaaat | 840 | |
| ggacaaccta ttattccagt attgctacct aaatatattg gactagatcc agtagcgcct | 900 | |
| ggagatctaa caatggttat tacacaagat tgtgatactt gtcattctcc agcgagtttg | 960 | |
| cctgcggtag tagaaaaata ataatttta t | 991 | |

<210> SEQ ID NO 10
<211> LENGTH: 5883
<212> TYPE: DNA
<213> ORGANISM: Ebola virus

<400> SEQUENCE: 10

| | | |
|---|---|---|
| gaattcggag tatacgaacc gggaaagaga agatggttaa aaataaagcg agactatttg | 60 | |
| aacgagggtt ccatggcaga ttctgccgat ttagtagtac taggtgctta ctatggtaaa | 120 | |
| ggagcaaagg gtggtatcat ggcagtcttt ctaatgggtt gttacgacga tgaatccggt | 180 | |
| aaatggaaga cggttaccaa gtgttcagga cacgatgata atacgttaag ggagttgcaa | 240 | |
| gaccaattaa agatgattaa aattaacaag gatcccaaaa aaattccaga gtggttagta | 300 | |
| gttaataaaa tctatattcc cgattttgta gtagaggatc caaaacaatc tcagatatgg | 360 | |
| gaaatttcag gagcagagtt tacatcttcc aagtcccata ccgcaaatgg aatatccatt | 420 | |
| agatttccta gatttactag gataagagag gataaaacgt ggaaagaatc tactcatcta | 480 | |
| aacgatttag taaacttgac taaatcttaa tttttatggc gcgcctttca ttttgttttt | 540 | |
| ttctatgcta taaatggtga gcaagggcga ggagctgttc accggggtgg tgcccatcct | 600 | |
| ggtcgagctg gacggcgacg taaacggcca caagttcagc gtgtccggcg agggcgaggg | 660 | |
| cgatgccacc tacggcaagc tgaccctgaa gttcatctgc accaccggca agctgcccgt | 720 | |
| gcccctggccc accctcgtga ccaccctgac ctacggcgtg cagtgcttca gccgctaccc | 780 | |
| cgaccacatg aagcagcacg acttcttcaa gtccgccatg cccgaaggct acgtccagga | 840 | |
| gcgcaccatc ttcttcaagg acgacggcaa ctacaagacc cgcgccgagg tgaagttcga | 900 | |
| gggcgacacc ctggtgaacc gcatcgagct gaagggcatc gacttcaagg aggacggcaa | 960 | |
| catcctgggg cacaagctgg agtacaacta caacagccac aacgtctata tcatggccga | 1020 | |
| caagcagaag aacggcatca aggtgaactt caagatccgc cacaacatcg aggacggcag | 1080 | |
| cgtgcagctc gccgaccact accagcagaa cacccccatc ggcgacggcc ccgtgctgct | 1140 | |
| gcccgacaac cactacctga gcacccagtc cgccctgagc aaagacccca acgagaagcg | 1200 | |
| cgatcacatg gtcctgctgg agttcgtgac cgccgccggg atcactctcg gcatgcacga | 1260 | |
| gctgtacaag taagagctcc ccgattttgt agtagaggat ccaaaacaat ctcagatatg | 1320 | |
| ggaaatttca ggagcagagt ttacatcttc caagtcccat accgcaaatg gaatatccat | 1380 | |
| tagatttcct agatttacta ggataagaga ggataaaacg tggaaagaat ctactcatct | 1440 | |
| aaacgattta gtaaacttga ctaaatctta atttttatct cgaggccgct ggtacccaac | 1500 | |
| ctaaaaattg aaaataaata caaaggttct tgagggttgt gttaaattga agcgagaaa | 1560 | |
| taatcataaa taagcccggg atgagaagag taattctacc aacagcgcca ccagaatata | 1620 | |
| tggaagcgat atatccagcg agatctaatt ctacaattgc gagaggtgga aattctaata | 1680 | |
| ctggatttct aacaccagaa tctgtaaatg gagatacacc atctaatcca ctaagaccaa | 1740 | |

```
ttgcggatga tacaatagat catgcgagtc atactccagg atctgtatct tctgctttta    1800
ttctagaagc tatggttaat gtaatttctg gaccaaaagt actaatgaaa caaattccaa    1860
tttggctacc attgggagta gcggatcaaa agacatattc ttttgattct actacagcgg    1920
cgattatgct agcgtcttat acaattacac attttggaaa agcgacaaat ccactagtta    1980
gagtaaatag actaggacct ggaataccag atcatccatt gagactacta agaattggaa    2040
atcaagcttt tctacaagaa tttgttctac caccagtaca actaccacaa tactttacat    2100
ttgatctaac agcgctaaaa ctaattacac aaccattgcc agcggcgaca tggacagatg    2160
atacaccaac aggatctaat ggtgctctaa gacctggtat ttcttttcat ccaaaactaa    2220
gacctattct attgccaaat aaatctggaa agaaaggaaa ttctgcggat ctaacatctc    2280
cagaaaagat tcaagcgatt atgacatctc tacaagactt caaaattgta ccaattgatc    2340
caacaaagaa tattatggga attgaagtac agaaacact agttcataaa ctaactggaa    2400
agaaagtaac atctaaaaat ggacaaccta ttattccagt attgctacct aaatatattg    2460
gactagatcc agtagcgcct ggagatctaa caatggttat tacacaagat tgtgatactt    2520
gtcattctcc agcgagtttg cctgcggtag tagaaaaata ataattttta tgtcgacctg    2580
cagctaatgt attagttaaa tattaaaact taccacgtaa aacttaaaat ttaaaatgat    2640
atttcattga cagatagatc acacattatg aactttcaag gacttgtgtt aactgacaat    2700
tgcaaaaatc aatgggtcgt tggaccatta ataggaaaag gtggatttgg tagtattat    2760
actactaatg acaataatta tgtagtaaaa atagagccca aagctaacgg atcattattt    2820
accgaacagg catttatac tagagtactt aaaccatccg ttatcgaaga atggaaaaaa    2880
tctcacaata taaagcacgt aggtcttatc acgtgcaagg catttggtct atacaaatcc    2940
attaatgtgg aatatcgatt cttggtaatt aatagattag gtgcagatct agatgcggtg    3000
atcagagcca ataataatag attaccaaaa aggtcggtga tgttgatcgg aatcgaaatc    3060
ttaaatacca tacaatttat gcacgagcaa ggatattctc acggagatat taagcgagt    3120
aatatagtct tggatcaaat agataagaat aaattatatc tagtggatta cggattggtt    3180
tctaaattca tgtcaagctt gtctccctat agtgagtcgt attagagctt ggcgtaatca    3240
tggtcatagc tgtttcctgt gtgaaattgt tatccgctca caattccaca acatacga     3300
gccggaagca taaagtgtaa agcctggggt gcctaatgag tgagctaact cacattaatt    3360
gcgttgcgct cactgcccgc tttcgagtcg ggaaacctgt cgtgccagct gcattaatga    3420
atcggccaac gcgcgggag aggcggtttg cgtattgggc gctcttccgc ttcctcgctc    3480
actgactcgc tgcgctcggt cgttcggctg cggcgagcgg tatcagctca ctcaaaggcg    3540
gtaatacggt tatccacaga atcagggat aacgcaggaa agaacatgtg agcaaaaggc    3600
cagcaaaagg ccaggaaccg taaaaaggcc gcgttgctgg cgttttcga taggctccgc    3660
cccctgacg agcatcacaa aaatcgacgc tcaagtcaga ggtggcgaaa cccgacagga    3720
ctataaagat accaggcgtt tcccctgga agctccctcg tgcgctctcc tgttccgacc    3780
ctgccgctta ccggatacct gtccgccttt ctcccttcgg gaagcgtggc gctttctcat    3840
agctcacgct gtaggtatct cagttcggtg taggtcgttc gctccaagct gggctgtgtg    3900
cacgaacccc ccgttcagcc cgaccgctgc gccttatccg gtaactatcg tcttgagtcc    3960
aacccggtaa gacacgactt atcgccactg gcagcagcca ctggtaacag gattagcaga    4020
gcgaggtatg taggcggtgc tacagagttc ttgaagtgg ggcctaacta cggctacact    4080
agaaggacag tatttggtat ctgcgctctg ctgaagccag ttaccttcgg aaaaagagtt    4140
```

| | |
|---|---:|
| ggtagctctt gatccggcaa acaaaccacc gctggtagcg gtggtttttt tgtttgcaag | 4200 |
| cagcagatta cgcgcagaaa aaaggatct caagaagatc ctttgatctt ttctacgggg | 4260 |
| tctgacgctc agtggaacga aaactcacgt taagggattt tggtcatgag attatcaaaa | 4320 |
| aggatcttca cctagatcct tttaaattaa aaatgaagtt ttaaatcaat ctaaagtata | 4380 |
| tatgagtaaa cttggtctga cagttaccaa tgcttaatca gtgaggcacc tatctcagcg | 4440 |
| atctgtctat ttcgttcatc catagttgcc tgactccccg tcgtgtagat aactacgata | 4500 |
| cgggagggct taccatctgg ccccagtgct gcaatgatac cgcgagaccc acgctcaccg | 4560 |
| gctccagatt tatcagcaat aaaccagcca gccggaaggg ccgagcgcag aagtggtcct | 4620 |
| gcaactttat ccgcctccat ccagtctatt aattgttgcc gggaagctag agtaagtagt | 4680 |
| tcgccagtta atagtttgcg caacgttgtt ggcattgcta caggcatcgt ggtgtcacgc | 4740 |
| tcgtcgtttg gtatggcttc attcagctcc ggttcccaac gatcaaggcg agttacatga | 4800 |
| tcccccatgt tgtgcaaaaa agcggttagc tccttcggtc ctccgatcgt tgtcagaagt | 4860 |
| aagttggccg cagtgttatc actcatggtt atggcagcac tgcataattc tcttactgtc | 4920 |
| atgccatccg taagatgctt ttctgtgact ggtgagtact caaccaagtc attctgagaa | 4980 |
| tagtgtatgc ggcgaccgag ttgctcttgc ccggcgtcaa tacgggataa taccgcgcca | 5040 |
| catagcagaa ctttaaaagt gctcatcatt ggaaaacgtt cttcggggcg aaaactctca | 5100 |
| aggatcttac cgctgttgag atccagttcg atgtaaccca ctcgtgcacc caactgatct | 5160 |
| tcagcatctt ttactttcac cagcgtttct gggtgagcaa aaacaggaag gcaaaatgcc | 5220 |
| gcaaaaaagg aataagggc gacacggaaa tgttgaatac tcatactctt cctttttcaa | 5280 |
| tattattgaa gcatttatca gggttattgt ctcatgagcg gatacatatt tgaatgtatt | 5340 |
| tagaaaaata acaaataggg gttccgcgc acatttcccc gaaaagtgcc acctgacgtc | 5400 |
| taagaaacca ttattatcat gacattaacc tataaaaata ggcgtatcac gaggcccttt | 5460 |
| cgtctcgcgc gtttcggtga tgacggtgaa aacctctgac acatgcagct cccggagacg | 5520 |
| gtcacagctt gtctgtaagc ggatgccggg agcagacaag cccgtcaggg cgcgtcagcg | 5580 |
| ggtgttggcg ggtgtcgggg ctggcttaac tatgcggcat cagagcagat tgtactgaga | 5640 |
| gtgcaccata tgcggtgtga ataccgcac agatgcgtaa ggagaaaata ccgcatcagg | 5700 |
| cgccattcgc cattcaggct gcgcaactgt tgggaagggc gatcggtgcg ggcctcttcg | 5760 |
| ctattacgcc agctggcgaa agggggatgt gctgcaaggc gattaagttg ggtaacgcca | 5820 |
| gggttttccc agtcacgacg ttgtaaaacg acggccagtg aattggattt aggtgacact | 5880 |
| ata | 5883 |

<210> SEQ ID NO 11
<211> LENGTH: 7074
<212> TYPE: DNA
<213> ORGANISM: Ebola virus

<400> SEQUENCE: 11

| | |
|---|---:|
| gaattccctg ggacatacgt atatttctat gatctgtctt atatgaagtc tatacagcga | 60 |
| atagattcag aatttctaca taattatata ttgtacgcta ataagtttaa tctaacactc | 120 |
| cccgaagatt tgtttataat ccctacaaat ttggatattc tatggcgtac aaaggaatat | 180 |
| atagactcgt tcgatattag tacagaaaca tggaataaat tattatccaa ttattatatg | 240 |
| aagatgatag agtatgctaa actttatgta ctaagtccta ttctcgctga ggagttggat | 300 |
| aatttttgaga ggacgggaga attaactagt attgtacaag aagccatttt atctctaaat | 360 |

| | |
|---|---|
| ttacgaatta agatttaaa ttttaaacat aaagatgatg atacgtatat acactttgt | 420 |
| aaaatattat tcggtgtcta aacggaaca aacgctacta tatattatca tagacctcta | 480 |
| acgggatata tgaatatgat ttcagatact atatttgttc ctgtagataa taactaaggc | 540 |
| gcgcctttca ttttgttttt ttctatgcta taaatggtga gcaagggcga ggagctgttc | 600 |
| accggggtgg tgcccatcct ggtcgagctg gacggcgacg taaacggcca caagttcagc | 660 |
| gtgtccggcg agggcgaggg cgatgccacc tacggcaagc tgaccctgaa gttcatctgc | 720 |
| accaccggca agctgcccgt gccctggccc accctcgtga ccaccctgac ctacggcgtg | 780 |
| cagtgcttca gccgctaccc cgaccacatg aagcagcacg acttcttcaa gtccgccatg | 840 |
| cccgaaggct acgtccagga gcgcaccatc ttcttcaagg acgacggcaa ctacaagacc | 900 |
| cgcgccgagg tgaagttcga gggcgacacc ctggtgaacc gcatcgagct gaagggcatc | 960 |
| gacttcaagg aggacggcaa catcctgggg cacaagctgg agtacaacta caacagccac | 1020 |
| aacgtctata tcatggccga caagcagaag aacggcatca aggtgaactt caagatccgc | 1080 |
| cacaacatcg aggacggcag cgtgcagctc gccgaccact accagcagaa cacccccatc | 1140 |
| ggcgacggcc ccgtgctgct gcccgacaac cactacctga gcacccagtc cgccctgagc | 1200 |
| aaagacccca acgagaagcg cgatcacatg gtcctgctgg agttcgtgac cgccgccggg | 1260 |
| atcactctcg gcatgcacga gctgtacaag taagagctcg aggacgggag aattaactag | 1320 |
| tattgtacaa gaagccattt tatctctaaa tttacgaatt aagattttaa attttaaaca | 1380 |
| taaagatgat gatacgtata tacactttgt taaaatatta ttcggtgtct ataacggaac | 1440 |
| aaacgctact atatattatc atagacctct aacgggatat atgaatatga tttcagatac | 1500 |
| tatatttgtt cctgtagata ataactaact cgaggccgct ggtacccaac ctaaaaattg | 1560 |
| aaaataaata caaaggttct tgagggttgt gttaaattga aagcgagaaa taatcataaa | 1620 |
| taagcccggg atgggagtaa ctggaattct acaactacca agagatagat tcaaaagaac | 1680 |
| atcttcttt ctatgggtta taattctatt tcaaagaaca ttttctattc cattgggagt | 1740 |
| aattcataat tctacattgc aagtatctga tgtagataaa ctagtatgta gagataaatt | 1800 |
| gtctagtaca aatcaactaa gatctgtagg attgaatcta gaaggaaatg gtgtagcgac | 1860 |
| agatgttcca tctgtaacaa agagatgggg ttttagatct ggtgtaccac caaaagtagt | 1920 |
| aaattatgaa gcgggagaat gggcggaaaa ttgttataat ctagaaatta agaaaccaga | 1980 |
| tggatctgaa tgtctaccag cggcgccaga tggaattaga ggatttccaa gatgtagata | 2040 |
| tgttcataaa gtatctggaa caggaccatg tgcgggagat tttgcgtttc ataaagaagg | 2100 |
| agcattcttt ctatatgata gactagcgtc tacagtaata tatagaggaa caacatttgc | 2160 |
| ggaaggtgta gtagcttttc taattctacc acaagcgaag aaagatttct ttagttctca | 2220 |
| tccactaaga gaaccagtaa atgcgacaga agatccttct tctggatatt attctactac | 2280 |
| aattagatat caagcgacag gatttggaac aaatgaaaca gaatatctat ttgaagttga | 2340 |
| taatctaaca tatgtacaac tagaaagtag attcacacca caatttctat tgcaattgaa | 2400 |
| tgaaacaata tatgcgtctg gaaagagatc taatacaact ggaaaactaa tttggaaagt | 2460 |
| aaatccagaa attgatacaa caattggaga atgggctttc tgggaaacaa gaagaatttt | 2520 |
| gacaagaaag attagatctg aagaattgtc ttttacagcg gtatctaatg gaccaaagaa | 2580 |
| tatttctgga caatctccag cgagaacttc ttctgatcca gaaacaaata ctacaaatga | 2640 |
| agatcacaaa attatggcgt ctgaaaattc ttctgctatg gtacaagtac attctcaagg | 2700 |
| aagaaaagcg gcggtatctc atctaacaac actagcgact atttctacat ctccacaacc | 2760 |

```
accaacaaca aagactggac cagataatag tacacataat actccagttt ataaactaga    2820
tatttctgaa gcgacacaag ttggacaaca tcatagaaga gcggataatg attctacagc    2880
gtctgataca ccaccagcta caacagctgc tggaccattg aaagcggaaa atacaaatac    2940
ttctaaatct gcggattctc tagatttggc gacaacaact tctcctcaaa attattctga    3000
aacagcggga aataataata ctcatcatca agatactgga gaagaatctg cgtctagtgg    3060
aaaattggga ctaattacaa atacaattgc gggtgtagcg ggattgatta ctggtggaag    3120
aagaactaga agagaagtaa tagttaatgc gcaacctaaa tgtaatccaa atctacatta    3180
ttggacaact caagatgaag gtgctgcgat tggactagct tggattccat attttggacc    3240
tgcggcggaa ggaatatata ctgaaggact aatgcataat caagatggac taatttgtgg    3300
actaagacaa ctagcgaatg aaactacaca agcgctacaa ctattcttga gagcgacaac    3360
agaactaaga acttttagta ttctaaatag aaaagcgatt gatttcttgc tacaaagatg    3420
gggaggaaca tgtcatattc taggaccaga ttgttgtatt gaaccacatg attggacaaa    3480
gaatattaca gacaaaattg atcaaattat tcatgatttt gttgataaaa cactaccaga    3540
tcaaggagat aatgataatt ggtggacagg atggagacaa tggattccag cgggaattgg    3600
agtaacaggt gtaattattg cggttattgc gctattttgt atatgtaaat ttgttttta     3660
ataatttta tgtcgacctg cagtcaaact ctaatgacca catcttttt tagagatgaa      3720
aaattttcca catctccttt tgtagacacg actaaacatt ttgcagaaaa aagtttatta    3780
gtgtttagat aatcgtatac ttcatcagtg tagatagtaa atgtgaacag ataaaggta     3840
ttcttgctca atagattggt aaattccata gaatatatta atcctttctt cttgagatcc    3900
cacatcattt caaccagaga cgttttatcc aatgatttac ctcgtactat accacataca    3960
aaactagatt ttgcagtgac gtcgtatctg gtattcctac caaacaaaat tttactttta    4020
gttcttttag aaaattctaa ggtagaatct ctatttgcca atatgtcatc tatggaatta    4080
ccactagcaa aaaatgatag aaatatatat tgatacatcg cagctggttt tgatctacta    4140
tactttaaaa acgaatcaga ttccataatt gcctgtatat catcagctga aaaactatgt    4200
tttacacgta ttccttcggc atttctttt aatgatatat cttgtttaga caatgataaa      4260
gttatcatgt ccatgagaga cgcgtctccg tatcgtataa atatttcatt agatgttaga    4320
cgcttcatta ggggtatact tctataaggt ttcttaatca gtccatcatt ggttgcgtca    4380
agaacaagct tgtctcccta tagtgagtcg tattagagct tggcgtaatc atggtcatag    4440
ctgtttcctg tgtgaaattg ttatccgctc acaattccac acaacatacg agccggaagc    4500
ataaagtgta aagcctgggg tgcctaatga gtgagctaac tcacattaat tgcgttgcgc    4560
tcactgcccg ctttcgagtc gggaaacctg tcgtgccagc tgcattaatg aatcggccaa    4620
cgcgcgggga gaggcggttt gcgtattggg cgctcttccg cttcctcgct cactgactcg    4680
ctgcgctcgg tcgttcggct gcggcgagcg gtatcagctc actcaaaggc ggtaatacgg    4740
ttatccacag aatcagggga taacgcagga aagaacatgt gagcaaaagg ccagcaaaag    4800
gccaggaacc gtaaaaaggc cgcgttgctg gcgtttttcg ataggctccg ccccctgac    4860
gagcatcaca aaaatcgacg ctcaagtcag aggtggcgaa acccgacagg actataaaga    4920
taccaggcgt ttccccctgg aagctccctc gtgcgctctc ctgttccgac cctgccgctt    4980
accggatacc tgtccgcctt tctcccttcg ggaagcgtgg cgctttctca tagctcacgc    5040
tgtaggtatc tcagttcggt gtaggtcgtt cgctccaagc tgggctgtgt gcacgaaccc    5100
cccgttcagc ccgaccgctg cgccttatcc ggtaactatc gtcttgagtc aacccggta     5160
```

-continued

```
agacacgact tatcgccact ggcagcagcc actggtaaca ggattagcag agcgaggtat      5220
gtaggcggtg ctacagagtt cttgaagtgg tggcctaact acggctacac tagaaggaca      5280
gtatttggta tctgcgctct gctgaagcca gttaccttcg gaaaaagagt tggtagctct      5340
tgatccggca acaaaccac cgctggtagc ggtggttttt ttgtttgcaa gcagcagatt       5400
acgcgcagaa aaaaggatc tcaagaagat cctttgatct tttctacggg gtctgacgct        5460
cagtggaacg aaaactcacg ttaagggatt ttggtcatga gattatcaaa aaggatcttc      5520
acctagatcc ttttaaatta aaaatgaagt tttaaatcaa tctaaagtat atatgagtaa      5580
acttggtctg acagttacca atgcttaatc agtgaggcac ctatctcagc gatctgtcta     5640
tttcgttcat ccatagttgc ctgactcccc gtcgtgtaga taactacgat acgggagggc     5700
ttaccatctg gccccagtgc tgcaatgata ccgcgagacc cacgctcacc ggctccagat     5760
ttatcagcaa taaaccagcc agccggaagg gccgagcgca gaagtggtcc tgcaacttta    5820
tccgcctcca tccagtctat taattgttgc cgggaagcta gagtaagtag ttcgccagtt    5880
aatagtttgc gcaacgttgt tggcattgct acaggcatcg tggtgtcacg ctcgtcgttt    5940
ggtatggctt cattcagctc cggttcccaa cgatcaaggc gagttacatg atcccccatg    6000
ttgtgcaaaa aagcggttag ctccttcggt cctccgatcg ttgtcagaag taagttggcc    6060
gcagtgttat cactcatggt tatggcagca ctgcataatt ctcttactgt catgccatcc    6120
gtaagatgct tttctgtgac tggtgagtac tcaaccaagt cattctgaga atagtgtatg    6180
cggcgaccga gttgctcttg cccggcgtca atacgggata taccgcgcc acatagcaga    6240
actttaaaag tgctcatcat tggaaaacgt tcttcggggc gaaaactctc aaggatctta    6300
ccgctgttga gatccagttc gatgtaaccc actcgtgcac ccaactgatc ttcagcatct    6360
tttactttca ccagcgtttc tgggtgagca aaaacaggaa ggcaaaatgc cgcaaaaaag    6420
ggaataaggg cgacacggaa atgttgaata ctcatactct tccttttcca atattattga    6480
agcatttatc agggttattg tctcatgagc ggatacatat ttgaatgtat ttagaaaaat    6540
aaacaaatag gggttccgcg cacatttccc cgaaaagtgc cacctgacgt ctaagaaacc    6600
attattatca tgacattaac ctataaaaat aggcgtatca cgaggccctt tcgtctcgcg    6660
cgtttcggtg atgacggtga aaacctctga cacatgcagc tcccggagac ggtcacagct    6720
tgtctgtaag cggatgccgg gagcagacaa gcccgtcagg gcgcgtcagc gggtgttggc    6780
gggtgtcggg gctggcttaa ctatgcggca tcagagcaga ttgtactgag agtgcaccat    6840
atgcggtgtg aaataccgca cagatgcgta aggagaaaat accgcatcag cgccattcg    6900
ccattcaggc tgcgcaactg ttgggaaggg cgatcggtgc gggcctcttc gctattacgc    6960
cagctggcga aggggggatg tgctgcaagg cgattaagtt gggtaacgcc agggttttcc    7020
cagtcacgac gttgtaaaac gacggccagt gaattggatt taggtgacac tata           7074
```

<210> SEQ ID NO 12
<211> LENGTH: 5876
<212> TYPE: DNA
<213> ORGANISM: Ebola virus

<400> SEQUENCE: 12

```
gaattcggag tatacgaacc gggaaagaga agatggttaa aaataaagcg agactatttg       60
aacgagggtt ccatggcaga ttctgccgat ttagtagtac taggtgctta ctatggtaaa      120
ggagcaaagg gtggtatcat ggcagtcttt ctaatgggtt gttacgacga tgaatccggt      180
aaatggaaga cggttaccaa gtgttcagga cacgatgata atacgttaag ggagttgcaa      240
```

```
gaccaattaa agatgattaa aattaacaag gatcccaaaa aaattccaga gtggttagta    300
gttaataaaa tctatattcc cgattttgta gtagaggatc caaaacaatc tcagatatgg    360
gaaatttcag gagcagagtt tacatcttcc aagtcccata ccgcaaatgg aatatccatt    420
agatttccta gatttactag gataagagag gataaaacgt ggaaagaatc tactcatcta    480
aacgatttag taaacttgac taaatcttaa tttttatggc gcgcctttca ttttgttttt    540
ttctatgcta taaatggtga gcaagggcga ggagctgttc accggggtgg tgcccatcct    600
ggtcgagctg gacggcgacg taaacggcca caagttcagc gtgtccggcg agggcgaggg    660
cgatgccacc tacggcaagc tgaccctgaa gttcatctgc accaccggca agctgcccgt    720
gccctggccc accctcgtga ccaccctgac ctacggcgtg cagtgcttca gccgctaccc    780
cgaccacatg aagcagcacg acttcttcaa gtccgccatg cccgaaggct acgtccagga    840
gcgcaccatc ttcttcaagg acgacggcaa ctacaagacc cgcgccgagg tgaagttcga    900
gggcgacacc ctggtgaacc gcatcgagct gaagggcatc gacttcaagg aggacggcaa    960
catcctgggg cacaagctgg agtacaacta caacagccac aacgtctata tcatggccga   1020
caagcagaag aacggcatca aggtgaactt caagatccgc cacaacatcg aggacggcag   1080
cgtgcagctc gccgaccact accagcagaa cacccccatc ggcgacggcc ccgtgctgct   1140
gcccgacaac cactacctga gcacccagtc cgccctgagc aaagacccca acgagaagcg   1200
cgatcacatg gtcctgctgg agttcgtgac cgccgccggg atcactctcg gcatgcacga   1260
gctgtacaag taagagctcc ccgattttgt agtagaggat ccaaaacaat ctcagatatg   1320
ggaaatttca ggagcagagt ttacatcttc caagtcccat accgcaaatg gaatatccat   1380
tagatttcct agatttacta ggataagaga ggataaaacg tggaaagaat ctactcatct   1440
aaacgattta gtaaacttga ctaaatctta atttttatct cgaggccgct ggtacccaac   1500
ctaaaaattg aaaataaata caaaggttct tgagggttgt gttaaattga aagcgagaaa   1560
taatcataaa taagcccggg atgaaaagag taacagtacc aacagcgcca ccagcgtatg   1620
cggatatagg atatccaatg tctatgctac ctattaaatc ttctagagcg gtatctggaa   1680
ttcaacaaaa gcaagaagta ctacctggaa tggatacacc atctaattct atgagaccag   1740
tagcggatga taatattgat catacttctc atactccaaa tggtgtagcg tctgctttta   1800
ttctagaagc gacagtaaat gtaatttctg gaccaaaagt actaatgaaa caaattccaa   1860
tttggctacc actaggaatt gcggatcaaa agacatattc ttttgattct acaacagcgg   1920
cgattatgct agcgtcttat acaattacac atttttggaaa agcgaataat ccactagtta   1980
gagtaaatag actaggacaa ggaataccag atcatccact aagactacta agaatgggaa   2040
atcaagcttt tctacaagaa tttgttctac caccagtaca actaccacaa tactttacat   2100
ttgatctaac agcgctaaaa ctagtaacac aaccactacc agcggcgaca tggacagatg   2160
aaactccatc taatctaagt ggtgctctaa gaccaggact atcttttcat ccaaaactaa   2220
gacctgtact actaccagga aagactggaa agaaaggaca tgtatctgat ttgacagcgc   2280
cagacaaaat tcaaacaata gtaaatctaa tgcaagactt caaaattgta ccaattgatc   2340
cagcgaaatc tattattgga attgaagtac cagaactact agttcataaa ttgactggaa   2400
agaaaatgtc tcaaaagaat ggacaaccta ttattccagt actattgcct aaatatattg   2460
gtctagatcc tatttctcct ggagatctaa caatggttat tacaccagat tatgatgatt   2520
gtcattctcc agcgtcttgt tcttatctat ctgaaaagta ataagtcgac ctgcagctaa   2580
tgtattagtt aaatattaaa acttaccacg taaaacttaa aatttaaaat gatatttcat   2640
```

```
tgacagatag atcacacatt atgaactttc aaggacttgt gttaactgac aattgcaaaa    2700
atcaatgggt cgttggacca ttaataggaa aaggtggatt tggtagtatt tatactacta    2760
atgacaataa ttatgtagta aaaatagagc ccaaagctaa cggatcatta tttaccgaac    2820
aggcatttta tactagagta cttaaaccat ccgttatcga agaatggaaa aaatctcaca    2880
atataaagca cgtaggtctt atcacgtgca aggcatttgg tctatacaaa tccattaatg    2940
tggaatatcg attcttggta attaatagat taggtgcaga tctagatgcg gtgatcagag    3000
ccaataataa tagattacca aaaaggtcgg tgatgttgat cggaatcgaa atcttaaata    3060
ccatacaatt tatgcacgag caaggatatt ctcacggaga tattaaagcg agtaatatag    3120
tcttggatca aatagataag aataaattat atctagtgga ttacggattg gtttctaaat    3180
tcatgtcaag cttgtctccc tatagtgagt cgtattagag cttggcgtaa tcatggtcat    3240
agctgtttcc tgtgtgaaat tgttatccgc tcacaattcc acacaacata cgagccggaa    3300
gcataaagtg taaagcctgg ggtgcctaat gagtgagcta actcacatta attgcgttgc    3360
gctcactgcc cgctttcgag tcgggaaacc tgtcgtgcca gctgcattaa tgaatcggcc    3420
aacgcgcggg gagaggcggt ttgcgtattg ggcgctcttc cgcttcctcg ctcactgact    3480
cgctgcgctc ggtcgttcgg ctgcggcgag cggtatcagc tcactcaaag gcggtaatac    3540
ggttatccac agaatcaggg gataacgcag gaaagaacat gtgagcaaaa ggccagcaaa    3600
aggccaggaa ccgtaaaaag gccgcgttgc tggcgttttt cgataggctc cgcccccctg    3660
acgagcatca caaaaatcga cgctcaagtc agaggtggcg aaacccgaca ggactataaa    3720
gataccaggc gtttccccct ggaagctccc tcgtgcgctc tcctgttccg accctgccgc    3780
ttaccggata cctgtccgcc tttctccctt cgggaagcgt ggcgctttct catagctcac    3840
gctgtaggta tctcagttcg gtgtaggtcg ttcgctccaa gctgggctgt gtgcacgaac    3900
cccccgttca gcccgaccgc tgcgccttat ccggtaacta tcgtcttgag tccaacccgg    3960
taagacacga cttatcgcca ctggcagcag ccactggtaa caggattagc agagcgaggt    4020
atgtaggcgg tgctacagag ttcttgaagt ggtggcctaa ctacggctac actagaagga    4080
cagtatttgg tatctgcgct ctgctgaagc cagttacctt cggaaaaaga gttggtagct    4140
cttgatccgg caaacaaacc accgctggta gcggtggttt ttttgtttgc aagcagcaga    4200
ttacgcgcag aaaaaaagga tctcaagaag atcctttgat cttttctacg gggtctgacg    4260
ctcagtggaa cgaaaactca cgttaaggga ttttggtcat gagattatca aaaaggatct    4320
tcacctagat ccttttaaat taaaaatgaa gttttaaatc aatctaaagt atatatgagt    4380
aaacttggtc tgacagttac caatgcttaa tcagtgaggc acctatctca gcgatctgtc    4440
tatttcgttc atccatagtt gcctgactcc ccgtcgtgta gataactacg atacgggagg    4500
gcttaccatc tggccccagt gctgcaatga taccgcgaga cccacgctca ccggctccag    4560
atttatcagc aataaaccag ccagccgaa gggccgagcg cagaagtggt cctgcaactt    4620
tatccgcctc catccagtct attaattgtt gccgggaagc tagagtaagt agttcgccag    4680
ttaatagttt gcgcaacgtt gttggcattg ctacaggcat cgtggtgtca cgctcgtcgt    4740
ttggtatggc ttcattcagc tccggttccc aacgatcaag gcgagttaca tgatccccca    4800
tgttgtgcaa aaaagcggtt agctccttcg gtcctccgat cgttgtcaga agtaagttgg    4860
ccgcagtgtt atcactcatg gttatggcag cactgcataa ttctcttact gtcatgccat    4920
ccgtaagatg cttttctgtg actggtgagt actcaaccaa gtcattctga gaatagtgta    4980
tgcggcgacc gagttgctct tgcccggcgt caatacggga taataccgcg ccacatagca    5040
```

-continued

| | | | |
|---|---|---|---|
| gaactttaaa agtgctcatc attggaaaac gttcttcggg gcgaaaactc tcaaggatct | | | 5100 |
| taccgctgtt gagatccagt tcgatgtaac ccactcgtgc acccaactga tcttcagcat | | | 5160 |
| cttttacttt caccagcgtt tctgggtgag caaaaacagg aaggcaaaat gccgcaaaaa | | | 5220 |
| agggaataag ggcgacacgg aaatgttgaa tactcatact cttccttttt caatattatt | | | 5280 |
| gaagcattta tcagggttat tgtctcatga gcggatacat atttgaatgt atttagaaaa | | | 5340 |
| ataaacaaat aggggttccg cgcacatttc cccgaaaagt gccacctgac gtctaagaaa | | | 5400 |
| ccattattat catgacatta acctataaaa ataggcgtat cacgaggccc tttcgtctcg | | | 5460 |
| cgcgtttcgg tgatgacggt gaaaacctct gacacatgca gctcccggag acggtcacag | | | 5520 |
| cttgtctgta agcggatgcc gggagcagac aagcccgtca gggcgcgtca gcgggtgttg | | | 5580 |
| gcgggtgtcg gggctggctt aactatgcgg catcagagca gattgtactg agagtgcacc | | | 5640 |
| atatgcggtg tgaaataccg cacagatgcg taaggagaaa ataccgcatc aggcgccatt | | | 5700 |
| cgccattcag gctgcgcaac tgttgggaag ggcgatcggt gcgggcctct tcgctattac | | | 5760 |
| gccagctggc gaaagggga tgtgctgcaa ggcgattaag ttgggtaacg ccagggtttt | | | 5820 |
| cccagtcacg acgttgtaaa acgacggcca gtgaattgga tttaggtgac actata | | | 5876 |

<210> SEQ ID NO 13
<211> LENGTH: 7067
<212> TYPE: DNA
<213> ORGANISM: Ebola virus

<400> SEQUENCE: 13

| | | | |
|---|---|---|---|
| gaattccctg ggacatacgt atatttctat gatctgtctt atatgaagtc tatacagcga | | | 60 |
| atagattcag aatttctaca taattatata ttgtacgcta ataagtttaa tctaacactc | | | 120 |
| cccgaagatt tgtttataat ccctacaaat ttggatattc tatggcgtac aaaggaatat | | | 180 |
| atagactcgt tcgatattag tacagaaaca tggaataaat tattatccaa ttattatatg | | | 240 |
| aagatgatag agtatgctaa actttatgta ctaagtccta ttctcgctga ggagttggat | | | 300 |
| aattttgaga ggacgggaga attaactagt attgtacaag aagccatttt atctctaaat | | | 360 |
| ttacgaatta agatttttaaa ttttaaacat aaagatgatg atacgtatat acacttttgt | | | 420 |
| aaaatattat tcggtgtcta taacggaaca aacgctacta tatattatca tagacctcta | | | 480 |
| acgggatata tgaatatgat ttcagatact atatttgttc ctgtagataa taactaaggc | | | 540 |
| gcgcctttca ttttgttttt ttctatgcta taaatggtga gcaagggcga ggagctgttc | | | 600 |
| accggggtgg tgcccatcct ggtcgagctg gacggcgacg taaacggcca aagttcagc | | | 660 |
| gtgtccggcg agggcgaggg cgatgccacc tacggcaagc tgaccctgaa gttcatctgc | | | 720 |
| accaccggca agctgcccgt gccctggccc accctcgtga ccaccctgac ctacggcgtg | | | 780 |
| cagtgcttca gccgctaccc cgaccacatg aagcagcacg acttcttcaa gtccgccatg | | | 840 |
| cccgaaggct acgtccagga gcgcaccatc ttcttcaagg acgacggcaa ctacaagacc | | | 900 |
| cgcgccgagg tgaagttcga gggcgacacc ctggtgaacc gcatcgagct gaagggcatc | | | 960 |
| gacttcaagg aggacggcaa catcctgggg cacaagctgg agtacaacta caacagccac | | | 1020 |
| aacgtctata tcatggccga caagcagaag aacggcatca aggtgaactt caagatccgc | | | 1080 |
| cacaacatcg aggacggcag cgtgcagctc gccgaccact accagcagaa cacccccatc | | | 1140 |
| ggcgacggcc ccgtgctgct gcccgacaac cactacctga gcacccagtc cgccctgagc | | | 1200 |
| aaagacccca acgagaagcg cgatcacatg gtcctgctgg agttcgtgac cgccgccggg | | | 1260 |
| atcactctcg gcatgcacga gctgtacaag taagagctcg aggacgggag aattaactag | | | 1320 |

```
tattgtacaa gaagccattt tatctctaaa tttacgaatt aagattttaa attttaaaca    1380
taaagatgat gatacgtata tacacttttg taaaatatta ttcggtgtct ataacggaac    1440
aaacgctact atatattatc atagacctct aacgggatat atgaatatga tttcagatac    1500
tatatttgtt cctgtagata ataactaact cgaggccgct ggtacccaac ctaaaaattg    1560
aaaataaata caaaggttct tgagggttgt gttaaattga aagcgagaaa taatcataaa    1620
taagcccggg atgggaggac tatctctact acaactacca agagataagt ttagaaaatc    1680
ttctttcttt gtttgggtta taattctatt tcaaaaggcg ttctctatgc cattgggagt    1740
agtaacaaat tctacactag aagtaacaga aattgatcaa ctagtatgta aagatcatct    1800
agcgtctaca gatcaattga aatctgttgg attgaatcta aaggatctg gtgtatctac     1860 agatattcca tctgcgacaa agagatgggg ttttagaagt ggtgtaccac caaaagtagt    1920
atcttatgaa gcgggagaat gggcggaaaa ttgttataat ctagaaatta agaaaccaga    1980
tggatctgaa tgtttgccac caccaccaga tggtgttaga ggatttccaa gatgtagata    2040
tgttcataaa gcgcaaggaa caggaccatg tcctggagat tatgcgtttc ataaagatgg    2100
tgcattcttt ctatatgata gattggcgtc tactgtaata tatagaggtg taaattttgc    2160
ggaaggtgta attgcttttc taattctagc gaaacctaaa gaaacatttc tacaatctcc    2220
accaattaga gaagcggtta attatacaga aaatacttca tcttattatg cgacatctta    2280
tctagaatat gaaattgaaa attttggagc gcaacattct acaactttgt tcaaaattga    2340
taataatact tttgttagac tagatagacc acatacacca caattttgt ttcaattgaa     2400 tgatacaatt catctcacatc aacaactatc taatacaact ggaagattga tttggacact   2460
agatgcgaat attaatgcgg atattggaga atgggctttc tgggaaaata agaagaatct    2520
atctgaacaa ctaagaggag aagaattgtc ttttgaagcg ctatctctaa atgaaactga    2580
agatgatgat gcggcgtcta gtagaattac aaaaggaaga atttctgata gagcgacaag    2640
acaatattct gatctagtac caaagaatcc acctggaatg gttccattgc atattccaga    2700
aggagaaaca acactaccat ctcaaaattc tactgaagga agaagagtat ctgtaaatac    2760
tcaagaaaca attacagaaa cagcggcgac aattattgga acaaatggaa atcatatgca    2820
aatttctact attggaatta gaccatcttc ttctcaaatt ccatcttcta gtccaacaac    2880
agcgccatct ccagaagcgc aaacaccaac aacacataca agtggaccat ctgtaatggc    2940
gacagaagaa cctacaacac caccaggatc ttctccaggt ccaactacag aagcgccaac    3000
tctaactaca ccagaaaata ttacaacagc tgtaaagaca gtactaccac aagaatctac    3060
ttctaatgga ctaattacat ctacagtaac tggaattcta ggatctctag gactaagaaa    3120
gagatctaga agacaaacaa atacaaaagc gactggaaaa tgtaatccaa atctacatta    3180
ttggacagcg caagaacaac ataatgcggc gggaattgct tggattccat attttggacc    3240
aggtgctgaa ggaatatata ctgaaggtct aatgcataat caaaatgcgc tagtatgtgg    3300
actaagacaa ctagcgaatg aaacaactca agcgctacaa ctatttctaa gagcgactac    3360
agaactaaga acatatacaa ttctaaatag aaaagctatt gatttcttgt tgagaagatg    3420
gggaggaaca tgtagaatat tgggaccaga ttgttgtatt gaaccacatg attggacaaa    3480
gaatattact gacaaaatta atcaaattat tcatgacttt attgataatc cactaccaaa    3540
tcaagataat gatgataatt ggtggacagg atggagacaa tggattccag cgggaatagg    3600
aattactgga attattattg cgattatagc gctactatgt gtatgtaaac tactatgtta    3660
ataagtcgac ctgcagtcaa actctaatga ccacatcttt ttttagagat gaaaaatttt    3720
```

```
ccacatctcc ttttgtagac acgactaaac attttgcaga aaaaagttta ttagtgttta    3780
gataatcgta tacttcatca gtgtagatag taaatgtgaa cagataaaag gtattcttgc    3840
tcaatagatt ggtaaattcc atagaatata ttaatccttt cttcttgaga tcccacatca    3900
tttcaaccag agacgtttta tccaatgatt tacctcgtac tataccacat acaaaactag    3960
attttgcagt gacgtcgtat ctggtattcc taccaaacaa aattttactt ttagttcttt    4020
tagaaaattc taaggtagaa tctctatttg ccaatatgtc atctatggaa ttaccactag    4080
caaaaaatga tagaaatata tattgataca tcgcagctgg ttttgatcta ctatactttta   4140
aaaacgaatc agattccata attgcctgta tatcatcagc tgaaaaacta tgttttacac    4200
gtattccttc ggcatttctt tttaatgata tatcttgttt agacaatgat aaagttatca    4260
tgtccatgag agacgcgtct ccgtatcgta taaatatttc attagatgtt agacgcttca    4320
ttaggggtat acttctataa ggtttcttaa tcagtccatc attggttgcg tcaagaacaa    4380
gcttgtctcc ctatagtgag tcgtattaga gcttggcgta atcatggtca tagctgtttc    4440
ctgtgtgaaa ttgttatccg ctcacaattc cacacaacat acgagccgga agcataaagt    4500
gtaaagcctg gggtgcctaa tgagtgagct aactcacatt aattgcgttg cgctcactgc    4560
ccgctttcga gtcgggaaac ctgtcgtgcc agctgcatta atgaatcggc caacgcgcgg    4620
ggagaggcgg tttgcgtatt gggcgctctt ccgcttcctc gctcactgac tcgctgcgct    4680
cggtcgttcg gctgcggcga gcggtatcag ctcactcaaa ggcggtaata cggttatcca    4740
cagaatcagg ggataacgca ggaaagaaca tgtgagcaaa aggccagcaa aaggccagga    4800
accgtaaaaa ggccgcgttg ctggcgtttt tcgataggct ccgcccccct gacgagcatc    4860
acaaaaatcg acgctcaagt cagaggtggc gaaacccgac aggactataa agataccagg    4920
cgtttccccc tggaagctcc ctcgtgcgct ctcctgttcc gaccctgccg cttaccggat    4980
acctgtccgc ctttctccct tcgggaagcg tggcgctttc tcatagctca cgctgtaggt    5040
atctcagttc ggtgtaggtc gttcgctcca agctgggctg tgtgcacgaa ccccccgttc    5100
agcccgaccg ctgcgcctta tccggtaact atcgtcttga gtccaacccg gtaagacacg    5160
acttatcgcc actggcagca gccactggta acaggattag cagagcgagg tatgtaggcg    5220
gtgctacaga gttcttgaag tggtggccta actacggcta cactagaagg acagtatttg    5280
gtatctgcgc tctgctgaag ccagttacct tcggaaaaag agttggtagc tcttgatccg    5340
gcaaacaaac caccgctggt agcggtggtt tttttgtttg caagcagcag attacgcgca    5400
gaaaaaaagg atctcaagaa gatcctttga tcttttctac ggggtctgac gctcagtgga    5460
acgaaaactc acgttaaggg attttggtca tgagattatc aaaaaggatc ttcacctaga    5520
tccttttaaa ttaaaaatga agttttaaat caatctaaag tatatatgag taaacttggt    5580
ctgacagtta ccaatgctta atcagtgagg cacctatctc agcgatctgt ctatttcgtt    5640
catccatagt tgcctgactc cccgtcgtgt agataactac gatacgggag ggcttaccat    5700
ctggccccag tgctgcaatg ataccgcgag acccacgctc accggctcca gatttatcag    5760
caataaacca gccagccgga agggccgagc gcagaagtgg tcctgcaact ttatccgcct    5820
ccatccagtc tattaattgt tgccgggaag ctagagtaag tagttcgcca gttaatagtt    5880
tgcgcaacgt tgttggcatt gctacaggca tcgtggtgtc acgctcgtcg tttggtatgg    5940
cttcattcag ctccggttcc caacgatcaa ggcgagttac atgatccccc atgttgtgca    6000
aaaaagcggt tagctccttc ggtcctccga tcgttgtcag aagtaagttg gccgcagtgt    6060
tatcactcat ggttatggca gcactgcata attctcttac tgtcatgcca tccgtaagat    6120
```

```
gcttttctgt gactggtgag tactcaacca agtcattctg agaatagtgt atgcggcgac    6180
cgagttgctc ttgcccggcg tcaatacggg ataataccgc gccacatagc agaactttaa    6240
aagtgctcat cattggaaaa cgttcttcgg ggcgaaaact ctcaaggatc ttaccgctgt    6300
tgagatccag ttcgatgtaa cccactcgtg cacccaactg atcttcagca tcttttactt    6360
tcaccagcgt ttctgggtga gcaaaaacag gaaggcaaaa tgccgcaaaa aagggaataa    6420
gggcgacacg gaaatgttga atactcatac tcttcctttt tcaatattat tgaagcattt    6480
atcagggtta ttgtctcatg agcggataca tatttgaatg tatttagaaa aataaacaaa    6540
taggggttcc gcgcacattt ccccgaaaag tgccacctga cgtctaagaa accattatta    6600
tcatgacatt aacctataaa aataggcgta tcacgaggcc ctttcgtctc gcgcgtttcg    6660
gtgatgacgg tgaaaacctc tgacacatgc agctcccgga cggtcaca gcttgtctgt     6720
aagcggatgc cgggagcaga caagcccgtc agggcgcgtc agcgggtgtt ggcgggtgtc    6780
ggggctggct taactatgcg gcatcagagc agattgtact gagagtgcac catatgcggt    6840
gtgaaatacc gcacagatgc gtaaggagaa ataccgcat caggcgccat cgccattca     6900
ggctgcgcaa ctgttgggaa gggcgatcgg tgcgggcctc ttcgctatta cgccagctgg    6960
cgaaggggg atgtgctgca aggcgattaa gttgggtaac gccagggttt cccagtcac     7020
gacgttgtaa aacgacggcc agtgaattgg atttaggtga cactata              7067
```

<210> SEQ ID NO 14
<211> LENGTH: 5807
<212> TYPE: DNA
<213> ORGANISM: Marburg virus
<400> SEQUENCE: 14

```
gaattcggag tatacgaacc gggaaagaga agatggttaa aaataaagcg agactatttg      60
aacgagggtt ccatggcaga ttctgccgat ttagtagtac taggtgctta ctatggtaaa     120
ggagcaaagg gtggtatcat ggcagtcttt ctaatgggtt gttacgacga tgaatccggt     180
aaatggaaga cggttaccaa gtgttcagga cacgatgata atacgttaag ggagttgcaa     240
gaccaattaa agatgattaa aattaacaag gatcccaaaa aaattccaga gtggttagta     300
gttaataaaa tctatattcc cgattttgta gtagaggatc caaaacaatc tcagatatgg     360
gaaatttcag gagcagagtt tacatcttcc aagtcccata ccgcaaatgg aatatccatt     420
agatttccta gatttactag gataagagag gataaaacgt ggaaagaatc tactcatcta     480
aacgatttag taaacttgac taaatcttaa tttttatggc gcgcctttca ttttgttttt     540
ttctatgcta taaatggtga gcaagggcga ggagctgttc accggggtgg tgcccatcct     600
ggtcgagctg gacggcgacg taaacggcca caagttcagc gtgtccggcg agggcgaggg     660
cgatgccacc tacggcaagc tgaccctgaa gttcatctgc accaccggca agctgcccgt     720
gccctggccc accctcgtga ccaccctgac ctacggcgtg cagtgcttca gccgctaccc     780
cgaccacatg aagcagcacg acttcttcaa gtccgccatg cccgaaggct acgtccagga     840
gcgcaccatc ttcttcaagg acgacggcaa ctacaagacc cgcgccgagg tgaagttcga     900
gggcgacacc ctggtgaacc gcatcgagct gaagggcatc gacttcaagg aggacggcaa     960
catcctgggg cacaagctgg agtacaacta caacagccac aacgtctata tcatggccga    1020
caagcagaag aacggcatca aggtgaactt caagatccgc cacaacatcg aggacggcag    1080
cgtgcagctc gccgaccact accagcagaa cacccccatc ggcgacggcc ccgtgctgct    1140
gcccgacaac cactacctga gcacccagtc cgccctgagc aaagacccca acgagaagcg    1200
```

```
cgatcacatg gtcctgctgg agttcgtgac cgccgccggg atcactctcg gcatgcacga    1260
gctgtacaag taagagctcc ccgattttgt agtagaggat ccaaaacaat ctcagatatg    1320
ggaaatttca ggagcagagt ttacatcttc caagtcccat accgcaaatg gaatatccat    1380
tagatttcct agatttacta ggataagaga ggataaaacg tggaagaat  ctactcatct    1440 aaacgattta gtaaacttga ctaaatctta attttatct  cgaggccgct ggtacccaac    1500
ctaaaaattg aaaataaata caaggttct  tgagggttgt gttaaattga aagcgagaaa    1560
taatcataaa taagcccggg atggcgtcta gttctaatta taatacttat atgcaatatc    1620
taaatccacc accatatgcg gatcatggtg ctaatcaact aattccagcg gatcaactat    1680
ctaatcaaca tggaattaca ccaaattatg ttggagatct aaatctagat gatcagttta    1740
aaggaaatgt ttgtcatgcg tttacactag aagcgattat tgatatttct gcgtataatg    1800
aaagaacagt aaaaggtgta ccagcttggc taccactagg aattatgtct aattttgaat    1860
atccactagc gcatacagta gcggcgctat tgacaggatc ttatacaatt acacagttta    1920
cacataatgg acaaaagttt gttagagtaa atagactagg aactggaata ccagcgcatc    1980
cactaagaat gctaagagaa ggaaatcaag cttttattca aaatatggtt attccaagaa    2040
atttctctac aaatcagttt acttataatc taactaatct agtactatct gtacaaaagc    2100
taccagatga tgcttggaga ccatctaaag ataaactaat tggaaataca atgcatccag    2160
cgatttctat tcatccaaat ctaccaccaa tagtactacc aactgtaaag aaacaagcgt    2220
atagacaaca taagaatcca aataatggac cactattggc gatttctgga attctacatc    2280
aactaagagt agaaaaggta ccagaaaaga catctttgtt tagaatttct ctaccagcgg    2340
atatgttttc tgtaaaagaa ggaatgatga agaaagagg  agaatcttct ccagtagtat    2400
attttcaagc gccagaaaat tttccattga atggttttaa taatagacaa gtagtactag    2460
cgtatgcgaa tccaacacta tctgcgatat aataagtcga cctgcagcta atgtattagt    2520
taaatattaa aacttaccac gtaaaactta aaatttaaaa tgatatttca ttgacagata    2580
gatcacacat tatgaacttt caaggacttg tgttaactga caattgcaaa atcaatgggg    2640
tcgttggacc attaatagga aaaggtggat ttggtagtat ttatactact aatgacaata    2700
attatgtagt aaaaatagag cccaaagcta acggatcatt atttaccgaa caggcatttt    2760
atactagagt acttaaacca tccgttatcg aagaatggaa aaaatctcac aatataaagc    2820
acgtaggtct tatcacgtgc aaggcatttg gtctatacaa atccattaat gtggaatatc    2880
gattcttggt aattaataga ttaggtgcag atctagatgc ggtgatcaga gccaataata    2940
atagattacc aaaaaggtcg gtgatgttga tcggaatcga aatcttaaat accatacaat    3000
ttatgcacga gcaaggatat tctcacggag atattaaagc gagtaatata gtcttggatc    3060
aaatagataa gaataaatta tatctagtgg attacggatt ggtttctaaa ttcatgtcaa    3120
gcttgtctcc ctatagtgag tcgtattaga gcttggcgta atcatggtca tagctgtttc    3180
ctgtgtgaaa ttgttatccg ctcacaattc cacacaacat acgagccgga agcataaagt    3240
gtaaagcctg gggtgcctaa tgagtgagct aactcacatt aattgcgttg cgctcactgc    3300
ccgctttcga gtcgggaaac ctgtcgtgcc agctgcatta atgaatcggc caacgcgcgg    3360
ggagaggcgg tttgcgtatt gggcgctctt ccgcttcctc gctcactgac tcgctgcgct    3420
cggtcgttcg gctgcggcga gcggtatcag ctcactcaaa ggcggtaata cggttatcca    3480
cagaatcagg gataacgca  ggaaagaaca tgtgagcaaa aggccagcaa aaggccagga    3540
accgtaaaaa ggccgcgttg ctggcgtttt tcgataggct ccgcccccct gacgagcatc    3600
```

```
acaaaaatcg acgctcaagt cagaggtggc gaaacccgac aggactataa agataccagg   3660
cgtttccccc tggaagctcc ctcgtgcgct ctcctgttcc gacccgtgccg cttaccggat   3720 acctgtccgc ctttctccct tcgggaagcg tggcgctttc tcatagctca cgctgtaggt   3780
atctcagttc ggtgtaggtc gttcgctcca agctgggctg tgtgcacgaa ccccccgttc   3840
agcccgaccg ctgcgcctta tccggtaact atcgtcttga gtccaacccg gtaagacacg   3900
acttatcgcc actggcagca gccactggta acaggattag cagagcgagg tatgtaggcg   3960
gtgctacaga gttcttgaag tggtggccta actacggcta cactagaagg acagtatttg   4020
gtatctgcgc tctgctgaag ccagttacct tcggaaaaag agttggtagc tcttgatccg   4080
gcaaacaaac caccgctggt agcggtggtt ttttttgtttg caagcagcag attacgcgca   4140 gaaaaaagg atctcaagaa gatcctttga tcttttctac ggggtctgac gctcagtgga   4200
acgaaaactc acgttaaggg attttggtca tgagattatc aaaaaggatc ttcacctaga   4260
tccttttaaa ttaaaaatga agttttaaat caatctaaag tatatatgag taaacttggt   4320
ctgacagtta ccaatgctta atcagtgagg cacctatctc agcgatctgt ctatttcgtt   4380
catccatagt tgcctgactc cccgtcgtgt agataactac gatacgggag gcttaccat   4440 ctggccccag tgctgcaatg ataccgcgag acccacgctc accggctcca gatttatcag   4500
caataaacca gccagccgga agggccgagc gcagaagtgg tcctgcaact ttatccgcct   4560
ccatccagtc tattaattgt tgccgggaag ctagagtaag tagttcgcca gttaatagtt   4620
tgcgcaacgt tgttggcatt gctacaggca tcgtggtgtc acgctcgtcg tttggtatgg   4680
cttcattcag ctccggttcc caacgatcaa ggcgagttac atgatccccc atgttgtgca   4740
aaaaagcggt tagctccttc ggtcctccga tcgttgtcag aagtaagttg gccgcagtgt   4800
tatcactcat ggttatggca gcactgcata attctcttac tgtcatgcca tccgtaagat   4860
gcttttctgt gactggtgag tactcaacca agtcattctg agaatagtgt atgcggcgac   4920
cgagttgctc ttgcccggcg tcaatacggg ataataccgc gccacatagc agaactttaa   4980
aagtgctcat cattggaaaa cgttcttcgg ggcgaaaact ctcaaggatc ttaccgctgt   5040
tgagatccag ttcgatgtaa cccactcgtg cacccaactg atcttcagca tcttttactt   5100
tcaccagcgt ttctgggtga gcaaaaacag gaaggcaaaa tgccgcaaaa aagggaataa   5160
gggcgacacg gaaatgttga atactcatac tcttcctttt tcaatattat tgaagcattt   5220
atcagggtta ttgtctcatg agcggataca tatttgaatg tatttagaaa aataaacaaa   5280
taggggttcc gcgcacattt ccccgaaaag tgccacctga cgtctaagaa accattatta   5340
tcatgacatt aacctataaa aataggcgta tcacgaggcc ctttcgtctc gcgcgtttcg   5400
gtgatgacgg tgaaaacctc tgacacatgc agctcccgga cggtcaca gcttgtctgt   5460 aagcggatgc cgggagcaga caagcccgtc agggcgcgtc agcgggtgtt ggcgggtgtc   5520
ggggctggct taactatgcg gcatcagagc agattgtact gagagtgcac catatgcggt   5580
gtgaaatacc gcacagatgc gtaaggagaa ataccgcat caggcgccat cgccattca   5640 ggctgcgcaa ctgttgggaa gggcgatcgg tgcgggcctc ttcgctatta cgccagctgg   5700 cgaaggggg atgtgctgca aggcgattaa gttgggtaac gccagggttt tcccagtcac   5760
gacgttgtaa aacgacggcc agtgaattgg atttaggtga cactata          5807
```

<210> SEQ ID NO 15
<211> LENGTH: 7082
<212> TYPE: DNA
<213> ORGANISM: Marburg virus

<400> SEQUENCE: 15

```
gaattccctg ggacatacgt atatttctat gatctgtctt atatgaagtc tatacagcga    60
atagattcag aatttctaca taattatata ttgtacgcta ataagtttaa tctaacactc   120
cccgaagatt tgtttataat ccctacaaat ttggatattc tatggcgtac aaaggaatat   180
atagactcgt tcgatattag tacagaaaca tggaataaat tattatccaa ttattatatg   240
aagatgatag agtatgctaa actttatgta ctaagtccta ttctcgctga ggagttggat   300
aattttgaga ggacgggaga attaactagt attgtacaag aagccatttt atctctaaat   360
ttacgaatta agattttaaa ttttaaacat aaagatgatg atacgtatat acacttttgt   420
aaaatattat tcggtgtcta taacggaaca aacgctacta tatattatca tagacctcta   480
acgggatata tgaatatgat ttcagatact atatttgttc ctgtagataa taactaaggc   540
gcgcctttca ttttgttttt ttctatgcta taaatggtga gcaagggcga ggagctgttc   600
accggggtgg tgcccatcct ggtcgagctg gacggcgacg taaacggcca caagttcagc   660
gtgtccggcg agggcgaggg cgatgccacc tacggcaagc tgaccctgaa gttcatctgc   720
accaccggca agctgcccgt gccctggccc accctcgtga ccaccctgac ctacggcgtg   780
cagtgcttca gccgctaccc cgaccacatg aagcagcacg acttcttcaa gtccgccatg   840
cccgaaggct acgtccagga gcgcaccatc ttcttcaagg acgacggcaa ctacaagacc   900
cgcgccgagg tgaagttcga gggcgacacc ctggtgaacc gcatcgagct gaagggcatc   960
gacttcaagg aggacggcaa catcctgggg cacaagctgg agtacaacta caacagccac  1020
aacgtctata tcatggccga caagcagaag aacggcatca aggtgaactt caagatccgc  1080
cacaacatcg aggacggcag cgtgcagctc gccgaccact accagcagaa cacccccatc  1140
ggcgacggcc ccgtgctgct gcccgacaac cactacctga gcacccagtc cgccctgagc  1200
aaagacccca acgagaagcg cgatcacatg gtcctgctgg agttcgtgac cgccgccggg  1260
atcactctcg gcatgcacga gctgtacaag taagagctcg aggacgggag aattaactag  1320
tattgtacaa gaagccattt tatctctaaa tttacgaatt aagattttaa attttaaaca  1380
taaagatgat gatacgtata tacacttttg taaaatatta ttcggtgtct ataacggaac  1440
aaacgctact atatattatc atagacctct aacgggatat atgaatatga tttcagatac  1500
tatatttgtt cctgtagata taactaact cgaggccgct ggtacccaac ctaaaaattg  1560
aaaataaata caaaggttct tgagggttgt gttaaattga aagcgagaaa taatcataaa  1620
taagcccggg atgtggacaa catgtttctt catttctcta attctaattc aaggaattaa  1680
aacactacca attctagaaa ttgcgtctaa tgatcaacca caaaatgtag attctgtatg  1740
ttctggaaca ctacaaaaga ctgaagatgt acatttgatg ggttttacac tatctggaca  1800
aaaggtagcg gattctccac tagaagcgtc taaaagatgg gcgtttagaa caggtgtacc  1860
accaaagaat gttgaatata cagaaggaga agaagcgaaa acttgttata atatttctgt  1920
aacagatcca tctggaaaat ctctactact agatccacca actaatgtta gagattatcc  1980
aaaatgtaaa acaattcatc atattcaagg acaaaatcca catgcgcaag gaattgcgct  2040
acatctatgg ggagcattct ttctatatga tagaatagcg tctacaacaa tgtatagagg  2100
aaaagttttc actgaaggaa atattgcggc tatgatagta aataagacag ttcacaaaat  2160
gatatttct agacaaggac aaggatatag acatatgaat ctaacatcta caaataaata  2220
ttggacatct tctaatggaa cacaaacaaa tgatacagga tgttttggaa cattgcaaga  2280
atataatagt acaaagaatc aaacatgtgc gccatctaaa actccaccac cacctccaac  2340
```

```
agcgcatcca gaaattaaac ctacatctac accaacagat gcgacaagat tgaatacaac    2400
aaatccaaat tctgatgatg aagatctaac aacatctgga tctggaagtg gagaacaaga    2460
accatataca acaagtgatg cggttacaaa gcaaggacta tcttctacaa tgccaccaac    2520
actatctcca caacctggaa ctccacaaca aggtggaaat aatacaaatc attctcaaga    2580
tgcggcgaca gaactagata atactaatac aactgcgcaa ccaccaatgc catctcataa    2640
tactacaact atttctacta ataatacttc taaacataat ctatctacat tgtctgaacc    2700
acctcaaaat actactaatc ctaatactca atctatggcg actgaaaatg aaaagacttc    2760
tgcgcctcca aagacaactc taccaccaac tgaatctcca acaacagaaa agagtacaaa    2820
taatacaaaa tctccaacta caatggaacc taatacaact aatggacact ttacatctcc    2880
atcttctact cctaattcta caacacaaca tttgatatac tttagaagaa agagatctat    2940
tttgtggaga gaaggagata tgtttccatt tctagatgga ttgattaatg cgccaattga    3000
ttttgatcca gtaccaaata caaagacaat tttcgatgaa tcttcttctt ctggtgcttc    3060
tgcggaagaa gatcaacatg cgtctagtaa tattagtcta acattgtctt atctacctca    3120
tacttctgaa aatactgcgt atagtggaga aaatgagaat gattgtgatg cggaactaag    3180
aatttggagt gtacaagaag atgatctagc ggcgggattg tcttggattc ctttcttcgg    3240
acctggaatt gaaggactat atacagcggg attgattaag aatcagaata atctagtatg    3300
tagactaaga agattggcga atcaaacagc gaaatctcta gaactactac taagagtaac    3360
aactgaagaa agaacattct ctttgattaa tagacatgcg attgattttc tattgacaag    3420
atggggagga acatgtaaag tactaggacc agattgttgt attggaatag aagatctatc    3480
tagaaatatt tcagaacaaa ttgatcaaat taagaaagat gaacaaaagg aaggaactgg    3540
atggggacta ggtggaaaat ggtggacatc tgattgggga gtactaacaa atctaggaat    3600
tctactattg ctatctattg cggtactaat tgcgttgtct tgtatatgta gaattttcac    3660
aaagtatatt ggataataag tcgacctgca gtcaaactct aatgaccaca tcttttttta    3720
gagatgaaaa attttccaca tctccttttg tagacacgac taaacatttt gcagaaaaaa    3780
gtttattagt gtttagataa tcgtatactt catcagtgta gatagtaaat gtgaacagat    3840
aaaaggtatt cttgctcaat agattggtaa attccataga atatattaat cctttcttct    3900
tgagatccca catcatttca accagagacg ttttatccaa tgatttacct cgtactatac    3960
cacatacaaa actagatttt gcagtgacgt cgtatctggt attcctacca aacaaaattt    4020
tacttttagt tcttttagaa aattctaagg tagaatctct atttgccaat atgtcatcta    4080
tggaattacc actagcaaaa aatgatagaa atatatattg atacatcgca gctggttttg    4140
atctactata ctttaaaaac gaatcagatt ccataattgc ctgtatatca tcagctgaaa    4200
aactatgttt tacacgtatt ccttcggcat ttcttttttaa tgatatatct tgtttagaca    4260
atgataaagt tatcatgtcc atgagagacg cgtctccgta tcgtataaat atttcattag    4320
atgttagacg cttcattagg ggtatacttc tataaggttt cttaatcagt ccatcattgg    4380
ttgcgtcaag aacaagcttg tctccctata gtgagtcgta ttagagcttg gcgtaatcat    4440
ggtcatagct gtttcctgtg tgaaattgtt atccgctcac aattccacac aacatacgag    4500
ccggaagcat aaagtgtaaa gcctggggtg cctaatgagt gagctaactc acattaattg    4560
cgttgcgctc actgcccgct ttcgagtcgg gaaacctgtc gtgccagctg cattaatgaa    4620
tcggccaacg cgcggggaga ggcggtttgc gtattgggcg ctcttccgct tcctcgctca    4680
ctgactcgct gcgctcggtc gttcggctgc ggcgagcggt atcagctcac tcaaaggcgg    4740
```

-continued

```
taatacggtt atccacagaa tcaggggata acgcaggaaa gaacatgtga gcaaaaggcc      4800
agcaaaaggc caggaaccgt aaaaaggccg cgttgctggc gtttttcgat aggctccgcc      4860
cccctgacga gcatcacaaa aatcgacgct caagtcagag gtggcgaaac ccgacaggac      4920
tataaagata ccaggcgttt ccccctggaa gctccctcgt gcgctctcct gttccgaccc      4980
tgccgcttac cggatacctg tccgcctttc tcccttcggg aagcgtggcg ctttctcata      5040
gctcacgctg taggtatctc agttcggtgt aggtcgttcg ctccaagctg gctgtgtgc      5100 acgaaccccc cgttcagccc gaccgctgcg ccttatccgg taactatcgt cttgagtcca      5160
acccggtaag acacgactta tcgccactgg cagcagccac tggtaacagg attagcagag      5220
cgaggtatgt aggcggtgct acagagttct tgaagtggtg gcctaactac ggctacacta      5280
gaaggacagt atttggtatc tgcgctctgc tgaagccagt taccttcgga aaaagagttg      5340
gtagctcttg atccggcaaa caaaccaccg ctggtagcgg tggtttttt gtttgcaagc      5400 agcagattac gcgcagaaaa aaggatctca agaagatcc tttgatcttt tctacggggt      5460
ctgacgctca gtggaacgaa aactcacgtt aagggatttt ggtcatgaga ttatcaaaaa      5520
ggatcttcac ctagatcctt ttaaattaaa aatgaagttt taaatcaatc taaagtatat      5580
atgagtaaac ttggtctgac agttaccaat gcttaatcag tgaggcacct atctcagcga      5640
tctgtctatt tcgttcatcc atagttgcct gactccccgt cgtgtagata actacgatac      5700
gggagggctt accatctggc cccagtgctg caatgatacc gcgagaccca cgctcaccgg      5760
ctccagattt atcagcaata aaccagccag ccggaagggc cgagcgcaga agtggtcctg      5820
caactttatc cgcctccatc cagtctatta attgttgccg ggaagctaga gtaagtagtt      5880
cgccagttaa tagtttgcgc aacgttgttg gcattgctac aggcatcgtg gtgtcacgct      5940
cgtcgtttgg tatggcttca ttcagctccg gttcccaacg atcaaggcga gttacatgat      6000
cccccatgtt gtgcaaaaaa gcggttagct ccttcggtcc tccgatcgtt gtcagaagta      6060
agttggccgc agtgttatca ctcatggtta tggcagcact gcataattct cttactgtca      6120
tgccatccgt aagatgcttt tctgtgactg gtgagtactc aaccaagtca ttctgagaat      6180
agtgtatgcg gcgaccgagt tgctcttgcc cggcgtcaat acgggataat accgcgccac      6240
atagcagaac tttaaaagtg ctcatcattg gaaaacgttc ttcggggcga aaactctcaa      6300
ggatcttacc gctgttgaga tccagttcga tgtaacccac tcgtgcaccc aactgatctt      6360
cagcatcttt tactttcacc agcgtttctg ggtgagcaaa aacaggaagg caaaatgccg      6420
caaaaaaggg aataagggcg acacggaaat gttgaatact catactcttc ctttttcaat      6480
attattgaag catttatcag ggttattgtc tcatgagcgg atacatattt gaatgtattt      6540
agaaaaataa acaaataggg gttccgcgca catttccccg aaaagtgcca cctgacgtct      6600
aagaaaccat tattatcatg acattaacct ataaaaatag gcgtatcacg aggccctttc      6660
gtctcgcgcg tttcggtgat gacggtgaaa acctctgaca catgcagctc ccggagacgg      6720
tcacagcttg tctgtaagcg gatgccggga gcagacaagc ccgtcagggc gcgtcagcgg      6780
gtgttggcgg gtgtcgggc tggcttaact atgcggcatc agagcagatt gtactgagag      6840
tgcaccatat gcggtgtgaa ataccgcaca gatgcgtaag gagaaaatac cgcatcaggc      6900
gccattcgcc attcaggctg cgcaactgtt gggaagggcg atcggtgcgg gcctcttcgc      6960
tattacgcca gctggcgaaa gggggatgtg ctgcaaggcg attaagttgg gtaacgccag      7020
ggttttccca gtcacgacgt tgtaaaacga cggccagtga attggattta ggtgacacta      7080
ta                                                                    7082
```

<210> SEQ ID NO 16
<211> LENGTH: 1479
<212> TYPE: DNA
<213> ORGANISM: Lassa virus

<400> SEQUENCE: 16

```
atgggacaaa tagtaacatt cttccaagaa gtaccacatg taattgaaga agtaatgaat    60
attgtactaa ttgcgctatc tgtactagcg gtattgaaag gattgtataa tttcgcgaca   120
tgtggactag taggactagt tacatttcta ctactatgtg aagatcttg tacaacttct   180
ttgtataaag gagtatatga actacaaaca ctagaattga atatggaaac tctaaatatg   240
acaatgcctc tatcatgtac aaagaataat tctcatcatt atattatggt tggaaatgaa   300
acaggactag aactaacact aacaaatact tctattatta atcataaatt ctgtaatcta   360
tctgatgcgc ataagaagaa tctatatgat catgcgctaa tgtctattat ttctacattt   420
catctatcta ttccaaactt taatcaatat gaagctatgt cttgtgactt aatggtgga   480
aagatttctg tacaatataa tctaagtcat tcttatgcgg gagatgcggc gaatcattgt   540
ggaacagtag cgaatggtgt actacaaact ttcatgagaa tggcgtgggg aggatcttat   600
attgcgctag attctggaag aggaaattgg gattgtatta tgacatctta tcaatatcta   660
attattcaga atacaacatg ggaagatcat tgtcaattct ctagaccatc tccaatagga   720
tatctaggac tactatctca aagaacaaga gatatatata ttagtagaag attgctagga   780
actttcacat ggacactatc tgattctgaa ggaaaggata cacctggagg atattgtcta   840
acaagatgga tgctaattga agcggaattg aaatgttttg gaaatactgc ggtagcgaaa   900
tgtaatgaaa agcatgatga agaattttgt gatatgctaa gactatttga ctttaataaa   960
caagcgattc aaagattgaa agcggaagcg caaatgagta ttcaattgat aaataaagcg  1020
gttaatgctt tgattaatga tcaactaatt atgaagaatc atctaagaga tattatggga  1080
attccatatt gtaattatag taaatattgg tatctaaatc atacaacaac tggaagaaca  1140
tctctaccaa aatgttggct agtatctaat ggatcttatc taaatgaaac acatttctct  1200
gatgatattg aacaacaagc ggataatatg attacagaaa tgctacaaaa ggaatatatg  1260
gaaagacaag gaaagacacc actaggattg gtagatctat ttgttttctc tacatctttc  1320
tatctaatta gtatatttct acatctagta aagattccaa cacatagaca tatagtagga  1380
aaatcttgtc aaaaccaca tagattgaat catatgggaa tatgttcttg tggattgtat  1440
aaacaaccag gtgtaccagt taaatggaaa agataataa                         1479
```

<210> SEQ ID NO 17
<211> LENGTH: 303
<212> TYPE: DNA
<213> ORGANISM: Lassa virus

<400> SEQUENCE: 17

```
atgggaaata acaagcgaa agcgccagaa tctaaagatt ctccaagagc gagtctaatt    60
ccagatgcga cacatctagg accacaattt tgtaaatctt gttggtttga aaataaagga   120
ctagtagaat gtaataatca ttatctatgt ctaaattgtc taacactact actatctgta   180
tctaatagat gtccaatatg caaaatgcca ctaccaacaa aactaagacc atctgctgct   240
ccaacagcgc caccaacagg tgctgctgat tctattagac caccaccata ttctccataa   300
taa                                                                 303
```